US011711976B2

(12) United States Patent
Stoessel et al.

(10) Patent No.: US 11,711,976 B2
(45) Date of Patent: Jul. 25, 2023

(54) COMPOUNDS WITH AN ACCEPTOR AND A DONOR GROUP

(71) Applicant: Merck Patent GmbH, Darmstadt (DE)

(72) Inventors: Philipp Stoessel, Frankfurt am Main (DE); Christian Ehrenreich, Darmstadt (DE); Philipp Harbach, Muehltal (DE)

(73) Assignee: MERCK PATENT GMBH, Darmstadt (DE)

( * ) Notice: Subject to any disclaimer, the term of this patent is extended or adjusted under 35 U.S.C. 154(b) by 278 days.

(21) Appl. No.: 16/349,495

(22) PCT Filed: Nov. 13, 2017

(86) PCT No.: PCT/EP2017/078978
§ 371 (c)(1),
(2) Date: May 13, 2019

(87) PCT Pub. No.: WO2018/087346
PCT Pub. Date: May 17, 2018

(65) Prior Publication Data
US 2020/0203624 A1 Jun. 25, 2020

(30) Foreign Application Priority Data

Nov. 14, 2016 (EP) ...................................... 16198684

(51) Int. Cl.
| | |
|---|---|
| *H01L 51/00* | (2006.01) |
| *C09K 11/06* | (2006.01) |
| *C07D 403/10* | (2006.01) |
| *C07D 403/14* | (2006.01) |
| *C07D 251/24* | (2006.01) |
| *C07D 487/04* | (2006.01) |
| *C07D 519/00* | (2006.01) |
| *C07D 405/14* | (2006.01) |
| *C07D 471/04* | (2006.01) |
| *C07D 491/048* | (2006.01) |
| *C07D 413/10* | (2006.01) |
| *C07D 209/86* | (2006.01) |
| *C07D 409/14* | (2006.01) |
| *H10K 85/60* | (2023.01) |
| *H10K 50/11* | (2023.01) |
| *H10K 101/10* | (2023.01) |

(52) U.S. Cl.
CPC ....... *H10K 85/6572* (2023.02); *C07D 209/86* (2013.01); *C07D 251/24* (2013.01); *C07D 403/10* (2013.01); *C07D 403/14* (2013.01); *C07D 405/14* (2013.01); *C07D 409/14* (2013.01); *C07D 413/10* (2013.01); *C07D 471/04* (2013.01); *C07D 487/04* (2013.01); *C07D 491/048* (2013.01); *C07D 519/00* (2013.01); *C09K 11/06* (2013.01); *H10K 85/615* (2023.02); *H10K 85/622* (2023.02); *H10K 85/636* (2023.02); *H10K 85/654* (2023.02); *H10K 85/657* (2023.02); *H10K 85/6574* (2023.02); *H10K 85/6576* (2023.02); *C09K 2211/1018* (2013.01); *H10K 50/11* (2023.02); *H10K 85/626* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 6,221,343 B1 | 4/2001 | Richard et al. | |
| 9,498,043 B2 | 11/2016 | Nishimura et al. | |
| 2011/0015279 A1 | 1/2011 | Doerr et al. | |
| 2011/0184080 A1 | 7/2011 | Schönberger et al. | |
| 2012/0157559 A1 | 6/2012 | Dörr et al. | |
| 2013/0131206 A1 | 5/2013 | Niesten et al. | |
| 2015/0322198 A1* | 11/2015 | Hayer | C08L 65/02 252/500 |
| 2016/0126478 A1 | 5/2016 | Zheng et al. | |
| 2018/0123049 A1* | 5/2018 | Lee | C07D 403/10 |

FOREIGN PATENT DOCUMENTS

| | | |
|---|---|---|
| CN | 101501095 A | 8/2009 |
| CN | 102089341 A | 6/2011 |
| CN | 103080172 A | 5/2013 |
| CN | 104349695 A | 2/2015 |
| CN | 104629076 A | 5/2015 |
| DE | 102017102363 A1 | 8/2018 |
| EP | 1028120 A1 | 8/2000 |
| JP | 2006-135184 A | 5/2006 |
| KR | 10-2014-0120975 A | 10/2014 |
| KR | 10-2016-0030094 A | 3/2016 |
| KR | 2016-0095667 A | 8/2016 |
| KR | 10-2016-0116297 A | 10/2016 |

(Continued)

OTHER PUBLICATIONS

International Search Report for PCT/CN2016/105721 dated Aug. 15, 2017.
Written Opinion of the International Searching Authority for PCT/CN2016/105721 dated Aug. 15, 2017.
Database WPI Week 200646 May 2006 (May 2006), Thomson Scientific, London, GB; AN 2006-447933, XP002778134, 2 pages.
International Preliminary Reporton Patentability received for PCT Patent Application No. PCT/EP2017/078978, dated May 23, 2019, 13 pages (8 pages of English Translation and 5 pages of Original Document).
International Search Report and Written Opinion received for PCT Patent Application No. PCT/EP2017/078978, dated Feb. 22, 2018, 16 pages (7 pages of English Translation and 9 pages of Original Document).

(Continued)

Primary Examiner — Jay Yang
(74) Attorney, Agent, or Firm — Faegre Drinker Biddle & Reath LLP

(57) ABSTRACT

The present invention describes compounds having an acceptor group and a donor group, especially for use in electronic devices. The invention further relates to a process for preparing the compounds of the invention and to electronic devices comprising these.

19 Claims, No Drawings

(56) References Cited

FOREIGN PATENT DOCUMENTS

| | | |
|---|---|---|
| WO | WO-2009118107 A2 | 10/2009 |
| WO | 2013/173845 A1 | 11/2013 |
| WO | 2015/066354 A1 | 5/2015 |
| WO | 2016/138077 A1 | 9/2016 |
| WO | WO-2016/159479 A1 * | 10/2016 |

OTHER PUBLICATIONS

Uoyama et al., "Highly efficient organic light-emitting diodes from delayed fluorescence", nature, 492, 2012, pp. 234-238.

Endo et al., "Thermally Activated Delayed Fluorescence from Sn4 þ-Porphyrin Complexes and Their Application to Organic Light-Emitting Diodes—A Novel Mechanism for Electroluminescence," Advanced Materials, vol. 21, 2009, pp. 4802-4806.

* cited by examiner

COMPOUNDS WITH AN ACCEPTOR AND A DONOR GROUP

CROSS-REFERENCE TO RELATED APPLICATIONS

This application is a national stage application (under 35 U.S.C. § 371) of PCT/EP2017/078978, filed Nov. 13, 2017, which claims benefit of European Application No. 16198684.9, filed Nov. 14, 2016, both of which are incorporated herein by reference in their entirety.

The present invention describes compounds having an acceptor group and a donor group, especially for use in electronic devices. The invention further relates to a process for preparing the compounds of the invention and to electronic devices comprising these compounds.

Light-emitting electronic components are increasingly coming into everyday use as light sources. Their advantages are low energy consumption, a compact design and a much longer lifetime compared to conventional means of lighting. While inorganic light-emitting diodes were the first to be used as means of lighting, organic light-emitting diodes (OLEDs) have also increasingly found use in articles for everyday use, for example in displays for mobile phones. Advantages of the OLEDs over their inorganic equivalents lie in easier processibility. The materials used in OLEDs can be dissolved in suitable solvents. The individual layers of the components can be applied to a substrate, for example, by means of printing methods. It is therefore comparatively simple to produce curved displays. Since the layers are not in crystalline form, OLEDs are flexible compared to LEDs based on inorganic compounds and can therefore also be applied to flexible substrates for the production of flexible screens. OLEDs themselves emit light and therefore do not require any backlighting, as required in the case of liquid-crystal displays (LCDs) for instance. It is thus possible to make screens based on OLEDs very thin. A further advantage exhibited by displays based on OLEDs is very high contrast, since non-excited OLEDs do not emit any light, i.e. are completely black. In terms of light yield, great advances have been achieved, and so it is now possible to convert the energy used to induce electronic states of the OLED virtually completely to light.

OLEDs are formed from multiple layers. First of all, an anode is applied to a substrate, which is preferably transparent, for example a glass plate or a transparent polymer film. Indium tin oxide (ITO) is usually used here to obtain a transparent anode. Then a hole transport layer (HTL) is applied to the anode. In order to facilitate the transfer of holes from the anode to the hole transport layer, i.e. to lower the injection barrier for holes, an interlayer composed of PEDOT/PSS (poly(3,4-ethylenedioxythiophene) doped with polystyrenesulfonate) is often first applied to the anode before the hole transport layer is then applied. The hole transport layer is then followed by an emitter layer (EL) containing or based on a dye in a proportion of, for example, 5% to 10% by weight. To the latter may then be applied an electron transport layer (ETL). Finally, under high vacuum, a cathode consisting of a metal or an alloy having a low electron work function, for example calcium, aluminium, barium, ruthenium, magnesium/silver alloy, is applied by vapour deposition. As a protective layer and to reduce the injection barrier for electrons, it is also possible to apply a very thin layer of lithium fluoride, caesium fluoride or silver between the cathode and ETL. The structure of the OLEDs is thus relatively complex and entails multiple operating steps. Moreover, the materials used are sensitive to moisture and oxygen, and so the structure has to be encapsulated in order to ensure that the OLED will be able to function over a prolonged period.

Electrons are injected into the layer structure from the cathode and holes from the anode as charge carriers. Electrons and holes drift toward one another and in the emitter layer in order to form a bound state which is referred to as an exciton. In the recombination of the charge carriers, singlet and triplet excitons are formed in a ratio of 1:3. The decay of the exciton provides the energy for the excitation of the dye molecule. The excited state can then return to the ground state and in so doing emit a photon. In the case of emission from the singlet state, which is referred to as fluorescence, only a maximum of 25% of the excitons generated lead to emission, while the radiationless transitions that proceed from the triplet state are lost in the form of heat. The transition from the triplet state $T_1$ to the singlet state $S_0$ is highly spin-forbidden and is therefore not available for emission of light.

In the case of triplet emission, which is referred to as phosphorescence, it is theoretically possible by means of triplet harvesting to utilize all excitons and emit them as light. In this case, the additionally induced singlet state at an energy above the triplet state is fully relaxed to the triplet state by intersystem crossing.

Triplet emitters used are usually transition metal complexes in which the metal is chosen from the third period of the transition elements, for example iridium, platinum or else gold. As a result of the high spin-orbit coupling of the central noble metal ions, the triplet-singlet transition which is strictly forbidden for optical transitions is allowed and the emission lifetime of a few μs which is suitable for use in OLEDs is achieved. With growing current densities and the resulting population of a majority or all triplet states $T_1$ of the emitter molecules, however, saturation effects arise and, as a result, charge carrier streams can no longer be utilized fully for population of excited states, meaning that ohmic losses arise and the efficiency of the emitter falls ("roll-off" characteristics).

Singlet emitters have a much shorter emission lifetime in the region of nanoseconds, and so roll-off effects occur to a much lesser degree, if at all. The efficiency of the emitters or the quantum yield can be increased by utilizing triplet states as well for the emission of light. For this purpose, however, the energy difference between the highest occupied triplet state $T_1$ and the lowest excited singlet state $S_1$ has to be small, such that thermal repopulation of the singlet state $S_1$ from the triplet state $T_1$ is possible at room temperature. Moreover, strong spin-orbit coupling has to be enabled, such that intersystem crossing enables the spin-forbidden $T_1 \rightarrow S_1$ transition. The emission lifetime for this transition should be in the region of less than 1 μs, for example about 100 to 600 ns.

In singlet harvesting, as in the case of triplet harvesting, it is thus the lowest excited singlet state which is populated. However, the emission is not from the lowest triplet state $T_1$ but via thermal repopulation from the lowest excited singlet state $S_1$, such that the excitation energy that would otherwise be lost is almost completely available to the triplet state for the emission of light.

This process is referred to as thermally activated delayed fluorescence (TADF) and is described, for example, by B. H. Uoyama et al., Nature 2012, Vol. 492, 234. In order to enable this process, a comparatively small singlet-triplet separation $\Delta E(S_1-T_1)$ of less than about 2000 cm$^{-1}$, for example, is needed in the emitter. In order to open up the $T_1 \rightarrow S_1$ transition which is spin-forbidden in principle, as well as the emitter, it is possible to provide a further compound in the matrix that has strong spin-orbit coupling, such that intersystem crossing is enabled via the spatial proximity and the interaction which is thus possible between the molecules, or the spin-orbit coupling is generated by means of a metal atom present in the emitter.

Suitable emitters are in particular molecules which exhibit high charge transfer character, for example copper compounds. A highly luminescent compound that exhibits thermally activated delayed fluorescence thus has to be configured such that it has a very small separation $\Delta E(S_1-T_1)$ coupled with relatively short decay rates of $>10^8$ s$^{-1}$, such that there is a decline in competing decay pathways where there is no emission of light.

A further light-emitting electronic component which has been developed is organic light-emitting electrical cells (OLECs, also called LECs or LEECs). OLECs were described for the first time by Ouibing Pei et al., Science, 1995, 296, 1086-1088, where the underlying principles are also elucidated.

By comparison with OLEDs, OLECs have a simpler structure and are also simpler to produce. For instance, OLECs can have a smaller number of layers compared to OLEDs. In addition, the active layer can be thicker in OLECs, and so it is possible to use simpler processes for producing the active, light-emitting layer. The active light-emitting layer in OLECs can have a thickness of several micrometres up to several tens of micrometres. Application of the active layer can therefore be accomplished using processes such as inkjet printing, screen printing or spray coating, which are also suitable for inexpensive mass production. By comparison with OLEDs, OLECs exhibit lower sensitivity to irregularities of the substrate surface and to defects in the active layer. OLECs therefore have better suitability for production of large-area light-emitting devices.

An OLEC comprises two electrodes and an active layer arranged between the cathode and anode. The active layer comprises a light-emitting organic semiconductor and an electrolyte which provides mobile ions. In order to enable the exit of light, at least one of the electrodes should be transparent.

Light-emitting organic semiconductors used may be conjugated copolymers or ionic transition metal complexes as also used in OLEDs, for example. Illustrative transition metal complexes are tris(2-phenylpyridine)iridium (Ir(ppy)$_3$) or tris(8-hydroxyquinoline)aluminium (Alq$_3$). Small molecules offer the advantage that they are easier to process, since they can more easily be dissolved in a suitable solvent. However, in the processing of these solutions, the difficulty of poor film-forming properties can arise.

The ability of the organic semiconductor to emit light is determined by the energy of the highest occupied molecular orbital (HOMO) and of the lowest unoccupied molecular orbital (LUMO) and their relative positions. In the case of organic semiconductors, however, HOMO and LUMO can be adjusted in terms of their energy by introducing side chains in the molecule or preparing copolymers from different organic semiconductors, such that different organic semiconductors are present in the copolymer chain. In this way, it is also possible to influence the solubility of the organic semiconductor and the film-forming properties thereof. However, the interaction between the orbitals by which the position of the energy states is determined is also affected by the geometry of the polymer and the relative position with respect to other molecules. In the case of films which are produced from solutions, therefore, a change in the solvent can affect the position of the HOMO and LUMO, such that the emission of an organic light-emitting component has a relatively broad spectrum owing to the amorphous character of the film.

Most metals have a relatively high work function, and for that reason there is considerable expenditure of energy at the electrodes in order to inject electrons from the electrode material into the organic semiconductor. In the case of use of alkali metals or alkaline earth metals, these metals do have a low work function, such that the energy differential between the cathode and the LUMO of the organic semiconductor is reduced. However, these metals are very reactive toward oxygen and water, and so the production of the electronic components is complex.

In the case of organic light-emitting electrochemical cells, mobile ions are utilized in order to enable the transfer of charge from the electrode into the active layer. If a voltage is applied between the cathode and anode, positive ions accumulate at the cathode and negative ions at the anode, such that an electrical double layer is formed. The electrical double layers are very thin, which means that a high electrical field gradient builds up at the interface to the electrode irrespective of the layer thickness of the active layer. If there is a sufficiently great potential difference between the electrodes, the electrical double layer enables efficient injection of charge carriers into the HOMO or LUMO of the organic semiconductor. The injection of charge carriers is compensated for by an opposing movement of charged ions. The injection of electrons at the cathode therefore brings about an accumulation of positive ions and hence causes n-doping. The extraction of electrons at the anode or the injection of holes at the anode is correspondingly compensated for by negatively charged ions and brings about p-doping. The electrochemical doping facilitates the transport of electrons or holes within the organic semiconductor. In the case of thicker active layers too that bring about a greater electrode separation, it is therefore possible to bring about effective charge transport with a small potential difference.

The electrochemically doped regions grow in the direction of one another until they ultimately meet, and pn recombination is brought about in a very thin undoped layer. However, there is a crucial difference in the mechanism of charge transport in OLECs and OLEDs. While the charges in OLECs are transported with the aid of mobile ions, the charge is transported in OLEDs by hopping of electrons/holes from more or less stationary molecules. In addition, OLEDs often contain further layers (for example electron and hole transport layers) having different materials. The OLEC, by contrast, in production, requires merely the provision of a single homogeneous active layer since the layers for the electron and hole transport form automatically in the active layer after application of a potential difference between the electrodes. By comparison with OLEDs, therefore, the function of the OLEC does not depend on the work function of the electrodes. Thus, both electrodes can be produced from the same material. It is thus also possible to produce a completely metal-free OLEC.

OLEDs are diodes having a forward and reverse direction for the charge transport, meaning that the current-voltage curves are unsymmetric. OLECs are essentially an electrolytic cell. After application of a potential difference, the electrolyte is oxidized at the anode and reduced at the cathode.

OLECs are typically produced with a single solution comprising light-emitting and charge-transporting conjugated polymers, for example polyphenylene-vinylene polymers, polythiophene polymers or polyfluorene polymers, and an electrolyte system comprising mobile ionic dopants, for example lithium triflate, and compounds that form the electrolyte, for example polyethylene oxide.

Light-emitting electrochemical cells are known, for example, from WO 2013/173845.

If a singlet emitter is used as the dye, analogously to the processes as described above for OLEDs, the energy released in triplet transitions is lost in the form of heat. Since only about 25% of the recombinations of charge carriers lead to singlet excitons, this means that 75% of all charge carriers which are injected into the active layer are lost to generation of light. The efficiency in relation to the light yield is thus unsatisfactory in LECs of this kind. It is known in the prior art that OLEDs are distinctly superior to the OLECs with regard to lifetime and efficiency.

One problem addressed by the invention was therefore that of providing organic electroluminescent devices (OLEDs, PLEDs) or organic light-emitting electrochemical cells (OLECs) which achieve a high light yield with the electrical energy used and overcome the disadvantages known from the prior art.

A further problem addressed by the present invention is that of providing compounds which are suitable for use in an organic electronic device, especially in an organic electroluminescent device or an organic electrochemical cell, and which lead to good device properties when used in this device, and that of providing the corresponding electronic device.

More particularly, the problem addressed by the present invention is that of providing compounds which lead to a high lifetime, good efficiency and low operating voltage. Particularly the properties of the matrix materials too have an essential influence on the lifetime and efficiency of the organic electroluminescent device.

A further problem addressed by the present invention can be considered that of providing compounds suitable for use in a phosphorescent or fluorescent OLED, especially as a matrix material. It is a particular object of the present invention to provide matrix materials suitable for red-, yellow- and green-phosphorescing OLEDs and possibly also for blue-phosphorescing OLEDs.

Moreover, the compounds should be processible in a very simple manner, and especially exhibit good solubility and film formation. For example, the compounds should exhibit elevated oxidation stability and an improved glass transition temperature.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, particular compounds that are described in detail hereinafter solve these problems and eliminate the disadvantage from the prior art. The use of the compounds leads to very good properties of organic electronic devices, especially of organic electroluminescent devices, especially with regard to lifetime, efficiency and operating voltage. The present invention therefore provides electronic devices, especially organic electroluminescent devices or organic light-emitting electrochemical cells, comprising compounds of this kind, and also the corresponding preferred embodiments.

The present invention therefore provides a compound comprising at least one structure of the following formula (I):

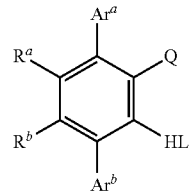

Formula (I)

where the symbols used are as follows:

Q is an acceptor group comprising an aromatic or heteroaromatic ring system which has 5 to 60 aromatic ring atoms and may be substituted by one or more $R^1$ radicals;

HL is a donor group;

$Ar^a$, $Ar^b$ is the same or different and is an aromatic or heteroaromatic ring system which has 5 to 60 aromatic, preferably 5 to 40 aromatic, ring atoms and may be substituted by one or more $R^1$ radicals;

$R^a$, $R^b$ is the same or different and is H, D, F, Cl, Br, I, $B(OR^1)_2$, CHO, $C(=O)R^1$, $CR^1=C(R^1)_2$, CN, $C(=O)OR^1$, $C(=O)N(R^1)_2$, $Si(R^1)_3$, $N(R^1)_2$, $NO_2$, $P(=O)(R^1)_2$, $OSO_2R^1$, $OR^1$, $S(=O)R^1$, $S(=O)_2R^1$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^1$ radicals, where one or more nonadjacent $CH_2$ groups may be replaced by —$R^1C=CR^1$—, —C≡C—, $S_i(R^1)_2$, $Ge(R^1)_2$, $Sn(R^1)_2$, C=O, C=S, C=Se, $C=NR^1$, $NR^1$, $P(=O)(R^1)$, —C(=O)O—, —C(=O)$NR^1$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic, preferably 5 to 40 aromatic, ring atoms and may be substituted in each case by one or more $R^1$ radicals, or an aryloxy or heteroaryloxy group which has 5 to 60 aromatic, preferably 5 to 40 aromatic, ring atoms and may be substituted by one or more $R^1$ radicals, or an aralkyl or heteroaralkyl group which has 5 to 60 aromatic, preferably 5 to 40 aromatic, ring atoms and may be substituted by one or more $R^1$ radicals, or a diarylamino group, diheteroarylamino group or arylheteroarylamino group which has 10 to 40 aromatic ring atoms and may be substituted by one or more $R^1$ radicals; or a combination of these systems; at the same time, the $R^a$ and $R^b$ together or with the $Ar^a$ or $Ar^b$ group may form a mono- or polycyclic, aliphatic, heteroaliphatic, aromatic or heteroaromatic ring system;

$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by —$R^2C=CR^2$—, —C≡C—, $Si(R^2)_2$, $Ge(R^2)_2$, $Sn(R^2)_2$, C=O, C=S, C=Se, $C=NR^2$, $NR^2$, $P(=O)(R^2)$, —C(=O)O—, —C(=O)$NR^2$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic, preferably 5 to 40 aromatic, ring atoms and may be substituted in each case by one or more $R^2$ radicals, or an aryloxy or heteroaryloxy group which has 5 to 60 aromatic, preferably 5 to 40 aromatic, ring atoms and may be substituted by one or more $R^2$ radicals, or an aralkyl or heteroaralkyl group which has 5 to 60 aromatic, preferably 5 to 40 aromatic, ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more, preferably adjacent $R^1$ radicals together may form a mono- or polycyclic, aliphatic, heteroaliphatic, aromatic or heteroaromatic ring system;

$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by —$R^3C=CR^3$—, —C≡C—, $S_1(R^3)_2$, $Si(R^3)_2$, $Ge(R^3)_2$, $Sn(R^3)_2$, C=O, C=S, C=Se, C=$NR^3$, $NR^3$, $P(=O)(R^3)$, —C(=O)O—, —C(=O)$NR^3$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic, preferably 5 to 40 aromatic, ring atoms and may be substituted in each case by one or more $R^3$ radicals, or an aryloxy or heteroaryloxy group which has 5 to 60 aromatic, preferably 5 to 40 aromatic, ring atoms and may be substituted by one or more $R^3$ radicals, or an aralkyl or heteroaralkyl group which has 5 to 60 aromatic, preferably 5 to 40 aromatic, ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more, preferably adjacent $R^2$ substituents together may also form a mono- or polycyclic, aliphatic, heteroaliphatic, aromatic or heteroaromatic ring system;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more, preferably adjacent $R^3$ substituents together may also form a mono- or polycyclic, aliphatic, heteroaliphatic, aromatic or heteroaromatic ring system.

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

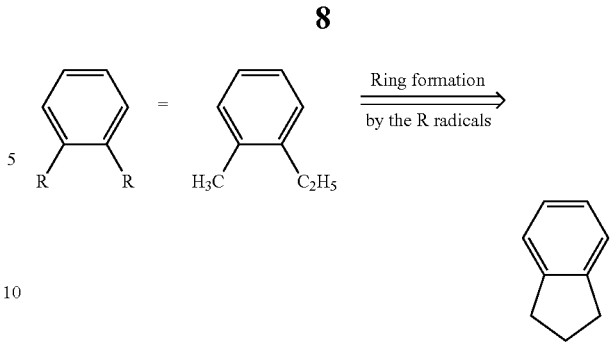

In addition, however, the abovementioned wording shall also be understood to mean that, if one of the two radicals is hydrogen, the second radical binds to the position to which the hydrogen atom was bonded, forming a ring. This shall be illustrated by the following scheme:

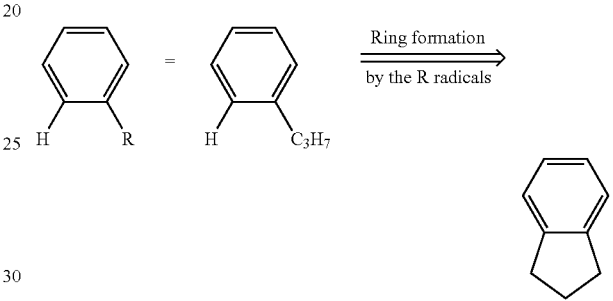

A fused aryl group, a fused aromatic ring system or a fused heteroaromatic ring system in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge. Corresponding definitions apply to heteroaryl groups and to fused ring systems which may but need not also contain heteroatoms.

An aryl group in the context of this invention contains 6 to 60 carbon atoms, preferably 6 to 40 carbon atoms; a heteroaryl group in the context of this invention contains 2 to 60 carbon atoms, preferably 2 to 40 carbon atoms, and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60, preferably 6 to 40, carbon atoms in the ring system. A heteroaromatic ring system in the context of this invention contains 1 to 60, preferably 1 to 40, carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5 to 60, preferably 5-40, aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred configuration, compounds of the invention can be represented by structures of formula (I). Preferably, compounds comprising structures of formula (I) have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

The HL group represents a donor group, this concept being known in the specialist field, especially in relation to TADF materials.

The donor group D (also called donor substituent) in the present case is understood to mean a group which is an electron donor group. What is meant by a donor group is well known to those skilled in the art. It is preferable when the donor group has a positive inductive effect (+I) and/or a positive mesomeric effect (+M). The determination of the parameters with the aid of the Hammett equation is well known to those skilled in the art. Suitable donor substituents are especially diaryl- or -heteroarylamino groups and carbazole groups or carbazole derivatives, such as indenocarbazoles or indolocarbazoles. These groups may also have further substitution.

In a further embodiment, the donor group is selected from arylamino groups, preferably di- or triarylamino groups, heteroarylamino groups, preferably di- or triheteroarylamino groups, carbazole groups, preference being given to carbazole groups.

It may preferably be the case that the donor group HL comprises a group and preferably is a group selected from the formulae (H-1) to (H-3)

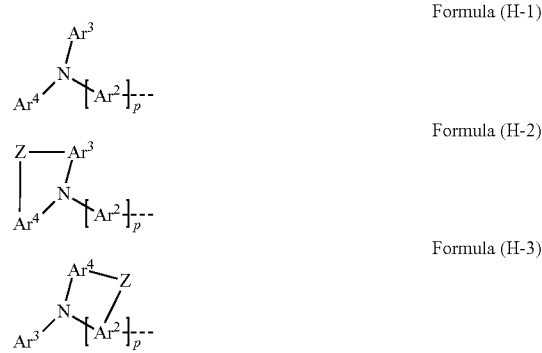

Formula (H-1)

Formula (H-2)

Formula (H-3)

where the dotted bond marks the attachment position and

Ar$^2$, Ar$^3$, Ar$^4$ are each independently an aryl group having 6 to 40 carbon atoms or a heteroaryl group having 3 to 40 carbon atoms, each of which may be substituted by one or more R$^1$ radicals;

p is 0, 1, 2, 3, 4, 5 or 6, preferably 0, 1, 2 or 3 and more preferably 0, 1 or 2 and Z is CR$^1_2$, SiR$^1_2$, C=O, N—Ar$^1$, BR$^1$, PR$^1$, POR$^1$, SO, SO$_2$, Se, O or S, preferably CR$^1_2$, N—Ar$^1$, O or S, where the R$^1$ radical has the definition given in claim 1 and Ar$^1$ represents an aromatic or heteroaromatic ring system which has 5 to 60 aromatic, preferably 5 to 40 aromatic, ring atoms and may be substituted in each case by one or more R$^1$ radicals, an aryloxy group which has 5 to 60 aromatic, preferably 5 to 40 aromatic, ring atoms and may be substituted in each case by one or more R$^1$ radicals, or an aralkyl group which has 5 to 60 aromatic, preferably 5 to 40 aromatic, ring atoms and may be substituted in each case by one or more R$^1$ radicals, where it is optionally possible for two or more, preferably adjacent R$^1$ substituents to form a mono- or polycyclic, aliphatic, heteroaliphatic, aromatic or heteroaromatic ring system which may be substituted by one or more R$^2$ radicals.

It may additionally be the case that the donor group HL comprises a group and preferably is a group selected from the formulae (H-4) to (H-26)

Formula (H-4)

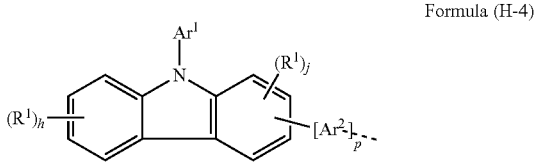

Formula (H-5)

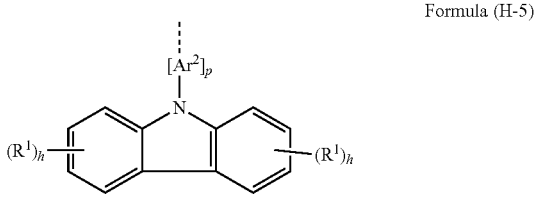

Formula (H-6)

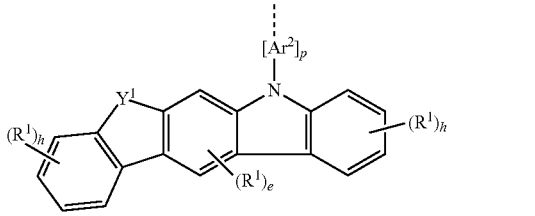

Formula (H-7)

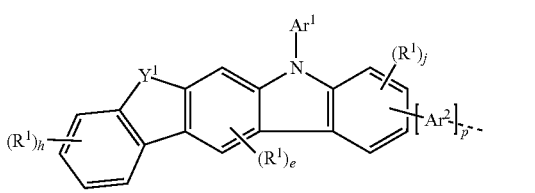

Formula (H-8)

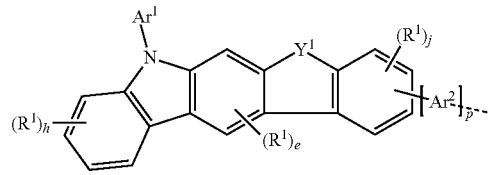

Formula (H-9)

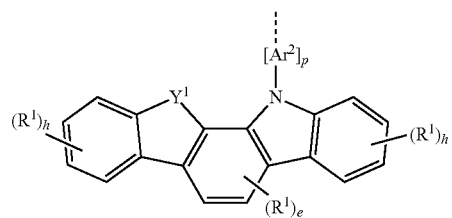

Formula (H-10)

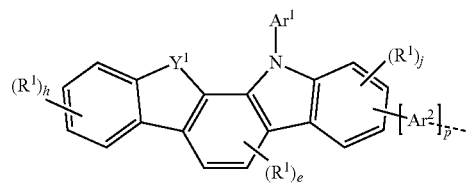

Formula (H-11)

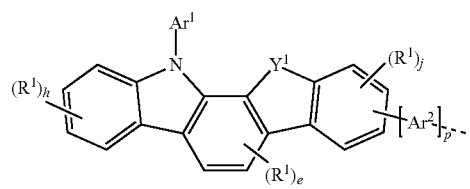

Formula (H-12)

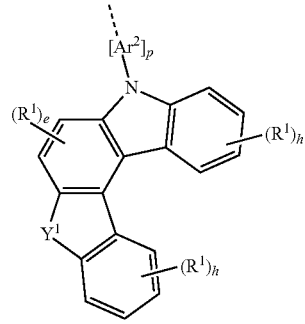

Formula (H-13)

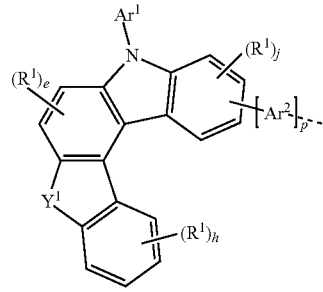

-continued
Formula (H-14)
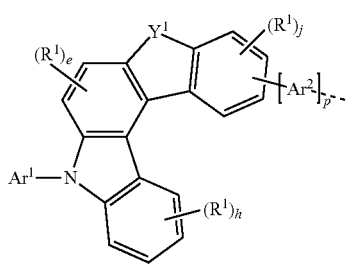
Formula (H-15)
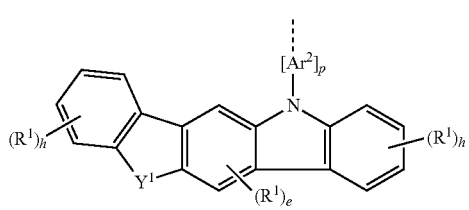
Formula (H-16)
Formula (H-17)
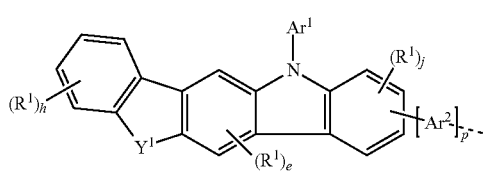
Formula (H-18)
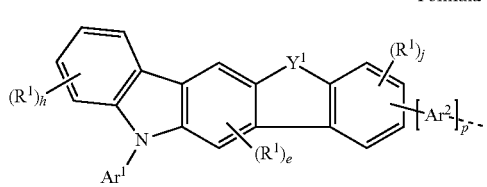
Formula (H-19)
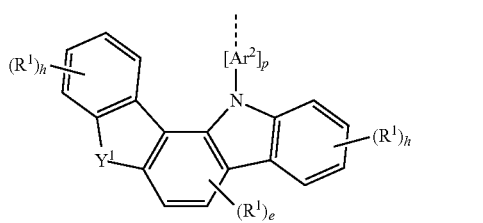
Formula (H-20)
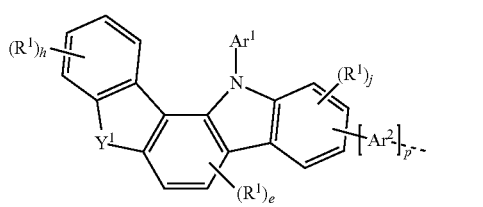
-continued
Formula (H-21)
Formula (H-22)
Formula (H-23)
Formula (H-24)
Formula (H-25)
Formula (H-26)
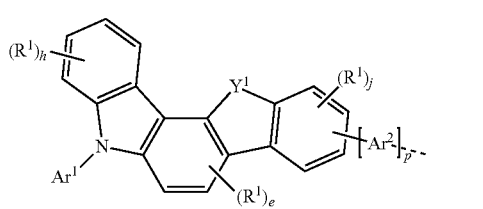
where $Y^1$ represents O, S, $C(R^1)_2$ or $NAr^1$, the dotted bond marks the attachment position, e is 0, 1 or 2, j is 0, 1, 2 or 3, h is 0, 1, 2, 3 or 4, p is 0, 1, 2, 3, 4, 5 or 6, preferably 0, 1, 2 or 3 and more preferably 0, 1 or 2, $Ar^1$ and $Ar^2$ have the definition given above, especially for formula (H-1) or (H-2), and R¹ has the definition given above, especially for formula (I).

Of the groups (H-1) to (H-26), preference is given to carbazole groups, especially the groups (H-4) to (H-26).

Preferably, the Ar² group in the formulae (H-1) to (H-26) may be a connecting structure of the formula (LAr-1)

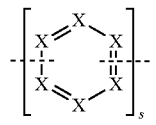

Formula (LAr-1)

where X is the same or different at each instance and is N or $CR^1$, preferably $CR^1$, or C if a group binds to X; the dotted bond marks the attachment position and s is 0, 1, 2, 3, 4, 5 or 6, preferably 0, 1, 2 or 3, more preferably 0, 1 or 2 and especially preferably 0 or 1, where the R¹ radical has the definition given above, especially for formula (I). Preferably, the two attachment positions of the group shown in formula (LAr-1) are in para positions. It is further preferable that the index p in formula (H-1) to (H-26) is 1 and the index s in formula (LAr-1) is 0, 1, 2, 3, 4, 5 or 6, preferably 0, 1, 2 or 3, more preferably 0, 1 or 2 and especially preferably 0 or 1.

Preferably, not more than two X groups in formula (LAr-1) per ring are N. More preferably, the connecting structure of the formula (LAr-1) comprises not more than two nitrogen atoms, more preferably not more than one nitrogen atom and especially preferably no nitrogen atom. Furthermore, preference is given to compounds which are characterized in that, in formula (LAr-1), at least four X per ring and preferably all X are $CR^1$, where preferably at most 4, more preferably at most 3 and especially preferably at most 2 of the $CR^1$ groups that X represents are not the CH group. More preferably, the connecting structure of the formula (LAr-1) comprises not more than two R¹ radicals that are not H, more preferably not more than one and especially none.

The Q group in formula (I) represents an acceptor group comprising an aromatic or heteroaromatic ring system which has 5 to 60 aromatic ring atoms and may be substituted by one or more R¹ radicals. Acceptor groups having this property are widely known in the specialist field, especially in relation to TADF materials. It is preferable when the acceptor group has a negative inductive effect (−I) and/or a negative mesomeric effect (−M). The determination of the parameters with the aid of the Hammett equation is also well known to those skilled in the art. Suitable acceptor substituents are especially electron-deficient heteroaryl groups and aryl group substituted by electron-withdrawing substituents, where these groups may also have further substitution. Examples of preferred electron-deficient heteroaryl groups are selected from the group consisting of triazines, pyrimidines, phosphine oxides and ketones.

Furthermore, surprising advantages are exhibited by compounds comprising at least one structure of formula (I) or preferred embodiments thereof in which the acceptor group Q comprises at least one structure selected from the group of the pyridines, pyrimidines, pyrazines, pyridazines, triazines, quinazolines, quinoxalines, quinolines, isoquinolines, imidazoles and/or benzimidazoles, particular preference being given to pyrimidines, triazines and quinazolines.

In a preferred configuration of the present invention, it may be the case that the acceptor group is a group that can be represented by the formula (QL)

$Q^1\text{-}L^1\text{-}$  Formula (QL)

in which L¹ represents a bond or an aromatic or heteroaromatic ring system which has 5 to 60 aromatic, preferably 5 to 40 aromatic, ring atoms and may be substituted by one or more R¹ radicals, and Q¹ is an electron-withdrawing group, where R¹ has the definition given above, especially for formula (I).

Preferably, the L¹ group is a connecting structure of the formula (LAr-2)

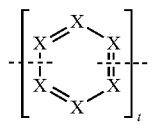

Formula (LAr-2)

where X is the same or different at each instance and is N or $CR^1$, preferably $CR^1$, or C if a group binds to X;

the dotted bond marks the attachment position and t is 0, 1, 2, 3, 4, 5 or 6, preferably 0, 1, 2 or 3, more preferably 0, 1 or 2 and especially preferably 0 or 1, where R¹ has the definition set out above, especially for formula (I).

Preferably, the two attachment positions of the connecting structure shown in formula (LAr-2) are in para positions.

Preferably, not more than two X groups in formula (LAr-2) per ring are N. More preferably, the connecting structure of the formula (LAr-2) comprises not more than two nitrogen atoms, more preferably not more than one nitrogen atom and especially preferably no nitrogen atom. Furthermore, preference is given to compounds which are characterized in that, in formula (LAr-2), at least four X per ring and preferably all X are $CR^1$, where preferably at most 4, more preferably at most 3 and especially preferably at most 2 of the $CR^1$ groups that X represents are not the CH group. More preferably, the connecting structure of the formula (LAr-2) comprises not more than two R¹ radicals that are not H, more preferably not more than one and especially none.

It may further be the case that the index p in formula (H-1) to (H-26) is 0, 1 or 2 and the index t in formula (LAr-2) is 0, 1 or 2. Preferably, the index s in formula (LAr-1) may be 0, 1 or 2 and the index t in formula (LAr-2) may be 0, 1 or 2. It may further be the case that the difference between the index s in formula (LAr-1) and the index t in formula (LAr-2) is not more than 2, preferably not more than 1 and especially preferably 0.

Preferred compounds of formula (I) comprise at least one donor group of formulae (H-1) to (H-26) where the Ar² group is a connecting structure of the formula (LAr-1), and at least one acceptor group of formula (QL) where L¹ can be represented by a connecting structure of the formula (LAr-2) in which the index s in formula (LAr-1) and the index t in formula (LAr-2) have the following values:

| Compound | Index s in formula (LAr-1) | Index t in formula (LAr-2) |
|---|---|---|
| Formula (I-1) | 0 | 0 |
| Formula (I-2) | 1 | 1 |
| Formula (I-3) | 2 | 2 |

| Compound | Index s in formula (LAr-1) | Index t in formula (LAr-2) |
|---|---|---|
| Formula (I-4) | 0 | 1 |
| Formula (I-5) | 1 | 0 |
| Formula (I-6) | 1 | 2 |
| Formula (I-7) | 2 | 1 |
| Formula (I-8) | 3 | 3 |
| Formula (I-9) | 3 | 2 |
| Formula (I-10) | 2 | 3 |
| Formula (I-11) | 0 | 2 |
| Formula (I-12) | 2 | 0 |
| Formula (I-13) | 3 | 1 |
| Formula (I-14) | 1 | 3 |

In a further configuration, it may be the case that the Q group detailed inter alia in the formula (I) or the electron-withdrawing $Q^1$ group represents a heteroaromatic ring system, where the ring atoms comprise 1 to 4 nitrogen atoms and the ring system may be substituted by one or more $R^1$ radicals, but is preferably unsubstituted, where $R^1$ has the definition detailed above, especially for formula (I).

Furthermore, preference is given to compounds which are characterized in that the acceptor group Q in formula (I) or the electron-withdrawing $Q^1$ group is a heteroaromatic ring system having at least two fused rings which may be substituted by one or more $R^1$ radicals, but is preferably unsubstituted, where the ring atoms of the at least two fused rings comprise at least one nitrogen atom and preferably at least two nitrogen atoms, where $R^1$ has the definition set out above, especially for formula (I).

It may further be the case that the Q group detailed inter alia in the formula or the electron-withdrawing $Q^1$ group represents a heteroaromatic ring system having 9 to 14 and preferably 10 ring atoms, which may be substituted by one or more $R^1$ radicals, where $R^1$ has the definition detailed above, especially for formula (I), but is preferably unsubstituted.

Preferably, the Q group detailed inter alia in the formula (I) or the $Q^1$ group detailed in formula (QL) may be selected from structures of the formulae (Q-1), (Q-2), (Q-3), (Q-4), (Q-5), (Q-6), (Q-7), (Q-8), (Q-9) and/or (Q-10)

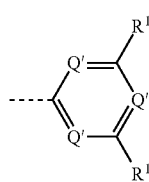

Formula (Q-1)

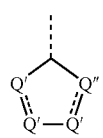

Formula (Q-2)

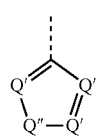

Formula (Q-3)

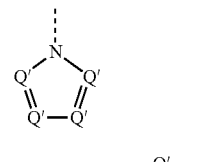

Formula (Q-4)

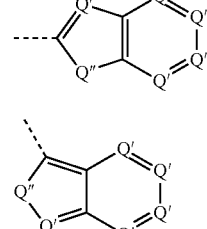

Formula (Q-5)

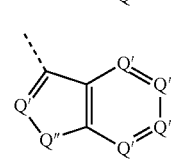

Formula (Q-6)

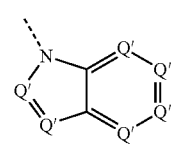

Formula (Q-7)

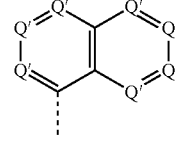

Formula (Q-8)

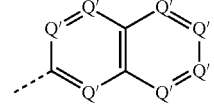

Formula (Q-9)

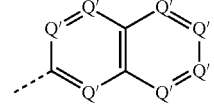

Formula (Q-10)

where the dotted bond marks the attachment position,
Q' is the same or different at each instance and represents $CR^1$ or N, and
Q" represents $NR^1$, O or S;
where at least one Q' is N and/or at least one Q" is $NR^1$ and
$R^1$ is as defined in claim 1.

Preferably, Q in formula (I) or the $Q^1$ group detailed in formula (QL) is selected from structures of the formulae (Q-11), (Q-12), (Q-13), (Q-14) and/or (Q-15)

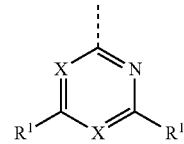

Formula (Q-11)

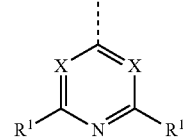

Formula (Q-12)

Formula (Q-13)

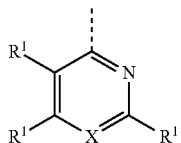

Formula (Q-14)

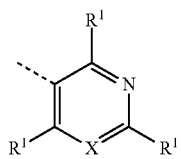

Formula (Q-15)

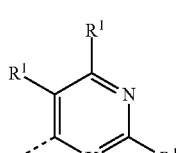

where the symbol $R^1$ has the definition given for formula (I) inter alia, X is N or $CR^1$ and the dotted bond marks the attachment position, where X preferably represents a nitrogen atom.

In a further embodiment, the Q group detailed inter alia in formula (I) or the $Q^1$ group detailed inter alia in formula (QL) may be selected from structures of the formulae (Q-16), (Q-17), (Q-18), (Q-19), (Q-20), (Q-21) and/or (Q-22)

Formula (Q-16)

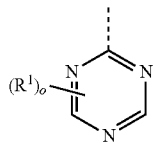

Formula (Q-17)

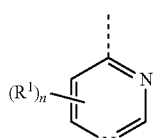

Formula (Q-18)

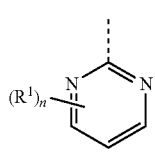

Formula (Q-19)

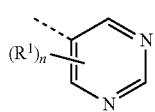

Formula (Q-20)

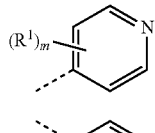

Formula (Q-21)

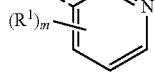

Formula (Q-22)

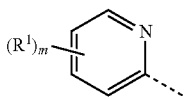

in which the symbol $R^1$ has the definition detailed above for formula (I) inter alia, the dotted bond marks the attachment position and m is 0, 1, 2, 3 or 4, preferably 0, 1 or 2, n is 0, 1, 2 or 3, preferably 0, 1 or 2, and o is 0, 1 or 2, preferably 1 or 2. Preference is given here to the structures of the formulae (Q-16), (Q-17), (Q-18) and (Q-19).

In a further embodiment, the Q group detailed inter alia in formula (I) or the $Q^1$ group detailed inter alia in formula (QL) may be selected from structures of the formulae (Q-23), (Q-24) and/or (Q-25)

Formula (Q-23)

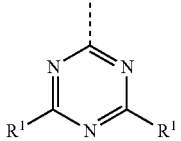

Formula (Q-24)

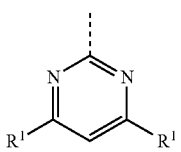

Formula (Q-25)

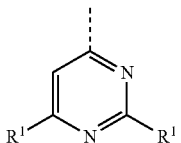

in which the symbol $R^1$ has the definition set out above for formula (I) inter alia, and the dotted bond marks the attachment position.

In a further embodiment, the Q group detailed inter alia in formula (I) or the $Q^1$ group detailed inter alia in formula (QL) may be selected from structures of the formulae (Q-26), (Q-27), (Q-28), (Q-29) and/or (Q-30)

Formula (Q-26)

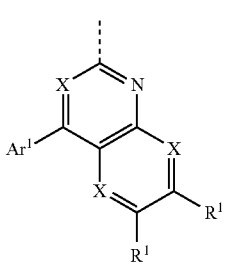

Formula (Q-27)

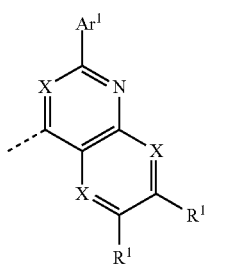

Formula (Q-28)

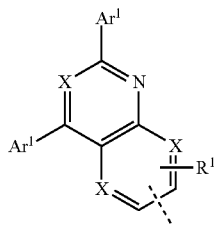

Formula (Q-29)

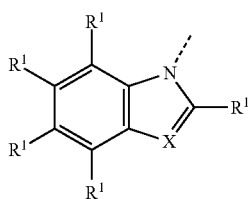

Formula (Q-30)

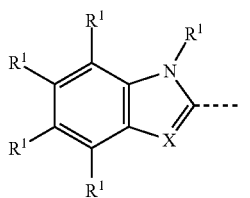

Formula (Q-31)

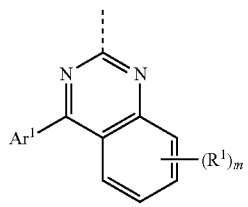

Formula (Q-32)

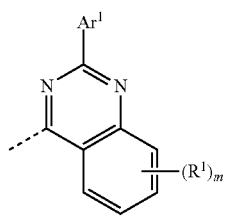

Formula (Q-33)

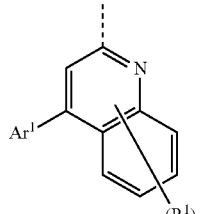

Formula (Q-34)

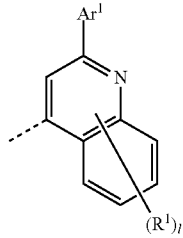

Formula (Q-35)

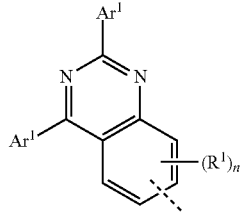

Formula (Q-36)

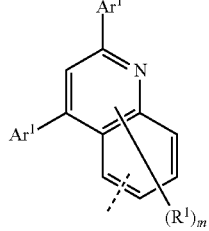

Formula (Q-37)

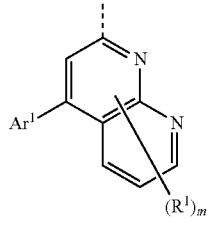

where X is N or $CR^1$, the symbol $R^1$ has the definition given above for formula (I) inter alia, the dotted bond marks the attachment position, where X preferably represents a nitrogen atom and $Ar^1$ represents an aromatic or heteroaromatic ring system which has 5 to 60 aromatic, preferably 5 to 40 aromatic, ring atoms and may be substituted in each case by one or more $R^1$ radicals, an aryloxy group which has 5 to 60 aromatic, preferably 5 to 40 aromatic, ring atoms and may be substituted by one or more $R^1$ radicals, or an aralkyl group which has 5 to 60 aromatic, preferably 5 to 40 aromatic, ring atoms and may be substituted in each case by one or more $R^1$ radicals, where it is optionally possible for two or more, preferably adjacent $R^1$ substituents to form a mono- or polycyclic, aliphatic, heteroaliphatic, aromatic or heteroaromatic ring system, preferably a mono- or polycyclic aliphatic ring system, which may be substituted by one or more $R^2$ radicals.

Preferably, the Q group detailed inter alia in the formula (I) or the $Q^1$ group detailed inter alia in formula (QL) may be selected from structures of the formulae (Q-31), (Q-32), (Q-33), (Q-34), (Q-35), (Q-36), (Q-37), (Q-38), (Q-39), (Q-40), (Q-41), (Q-42), (Q-43) and/or (Q-44)

Formula (Q-38)

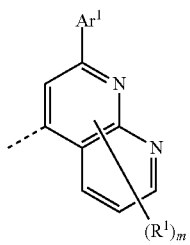

Formula (Q-39)

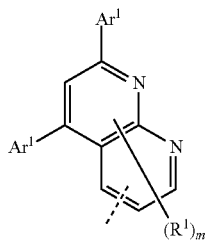

Formula (Q-40)

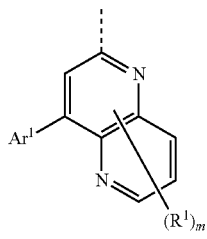

Formula (Q-41)

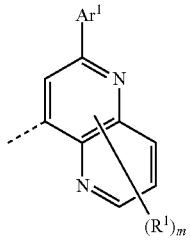

Formula (Q-42)

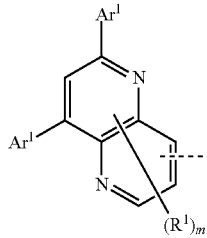

Formula (Q-43)

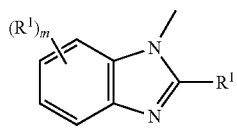

Formula (Q-44)

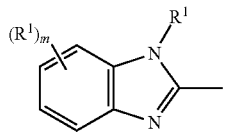

in which the symbols Ar¹ have the definition set out above for formula (Q-26), (Q-27), (Q-28), (Q-29) or (Q-30) inter alia and R¹ has the definition set out above for formula (I) inter alia, the dotted bond represents the attachment position and m is 0, 1, 2, 3 or 4, preferably 0, 1 or 2, n is 0, 1, 2 or 3, preferably 0 or 1, and l is 0, 1, 2, 3, 4 or 5, preferably 0, 1 or 2.

Preferably, the symbol $Ar^1$ represents an aryl or heteroaryl radical, such that an aromatic or heteroaromatic group of an aromatic or heteroaromatic ring system is bonded directly, i.e. via an atom of the aromatic or heteroaromatic group, to the respective atom of the further group, for example the carbon or nitrogen atom of the (Q-26) to (Q-42) groups shown above.

In a further preferred embodiment of the invention, $Ar^1$ is the same or different at each instance and is an aromatic or heteroaromatic ring system having 6 to 24 aromatic ring atoms, preferably 6 to 18 aromatic ring atoms, and is more preferably an aromatic ring system having 6 to 12 aromatic ring atoms or a heteroaromatic ring system which has 6 to 13 aromatic ring atoms and may be substituted in each case by one or more $R^1$ radicals, but is preferably unsubstituted, where $R^1$ may have the definition given above, especially in formula (I).

Advantageously, $Ar^1$ in the formulae (Q-26) to (Q-42) represents an aromatic ring system which has 6 to 12 aromatic ring atoms and may be substituted by one or more $R^1$ radicals, but is preferably unsubstituted, where $R^1$ may have the definition detailed above, especially for formula (I).

Preferably, the $R^1$ radicals in the formulae (Q-1) to (Q-44) do not form a fused ring system with the ring atoms of the heteroaryl group to which the $R^1$ radicals are bonded. This includes the formation of a fused ring system with possible $R^2$, $R^3$ substituents which may be bonded to the $R^1$ radicals.

Preferably, the $R^2$ radicals do not form a fused ring system with the ring atoms of the aryl group or heteroaryl group $Ar^1$ to which the $R^2$ radicals in the formulae (Q-26) to (Q-42) may be bonded. This includes the formation of a fused ring system with possible $R^3$ substituents which may be bonded to the $R^2$ radicals.

In a preferred embodiment, it may be the case that the electron-withdrawing $Q^1$ group is an aromatic or heteroaromatic ring system having 5 to 60, preferably having 5 to 40 and more preferably having 6 to 24 aromatic ring atoms, especially preferably having 6 to 18 aromatic ring atoms, and having one or more electron-withdrawing substituents. Preferably, the electron-withdrawing substituent has a Hammett constant, σ, of not less than zero. Very preferably, the Hammett constant of the electron-withdrawing substituent is not less than 0.2, more preferably not less than 0.4 and most preferably not less than 0.55. Further details regarding the definition and determination of the Hammett constant are well known to the person skilled in the art from the basics of organic chemistry and are disclosed in standard textbooks. The Hammett constant and the determination thereof for the purposes of the present invention are as defined in chapter 9 of Jerry March, Advanced Organic Chemistry, John Wiley & Sons, Fourth Edition, 1992.

Examples of suitable aromatic or heteroaromatic ring systems having one or more electron-withdrawing substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1- or 2-naphthyl, anthracenyl, each of which may be substituted by one or more $R^2$ radicals, particular preference being given to spirobifluorene, fluorene, dibenzofuran, dibenzothiophene, anthracene, phenanthrene, triphenylene groups. Of the groups mentioned, phenyl radicals having one or more electron-withdrawing substituents are especially preferred.

The preferred electron-withdrawing substituents include F, fluorinated alkyl groups, $CF_3$, $C_nF_{2n+1}$, $C(=O)OR^1$, $C(=O)N(R^1)_2$, $B(OR^1)_2$, $NO_2$, CHO, $C(=O)R^1$, $P(=O)(R^1)_2$, $S(=O)R^1$, $S(=O)_2R^1$ and/or CN, preference being given to $CF_3$, $C_nF_{2n+1}$, $C(=O)OR^1$, $C(=O)N(R^1)_2$, $NO_2$, CHO, $C(=O)R^1$, $S(=O)R^1$, $S(=O)_2R^1$ and/or CN, and particular preference to CN, F, fluorinated alkyl groups, $CF_3$, $C_nF_{2n+1}$. The electron-withdrawing $Q^1$ group may preferably have two or more electron-withdrawing substituents, where these may be the same or different.

Preferably, the symbol $Ar^a$ and/or $Ar^b$ represents an aryl or heteroaryl radical, such that an aromatic or heteroaromatic group of an aromatic or heteroaromatic ring system is bonded directly to the respective atom of the further group, i.e. via an atom of the aromatic or heteroaromatic group.

In a further preferred embodiment of the invention, the symbol $Ar^a$ and/or $Ar^b$ is the same or different and is an aromatic or heteroaromatic ring system having 6 to 24 aromatic ring atoms, preferably 6 to 18 aromatic ring atoms, and is more preferably an aromatic ring system having 6 to 12 aromatic ring atoms or a heteroaromatic ring system which has 6 to 13 aromatic ring atoms and may be substituted in each case by one or more $R^1$ radicals, but is preferably unsubstituted, where $R^1$ may have the definition given above, especially in formula (I).

Advantageously, each symbol $Ar^a$ and/or $Ar^b$ in formula (I) independently represents an aromatic ring system which has 6 to 12 aromatic ring atoms and may be substituted by one or more $R^1$ radicals, but is preferably unsubstituted, where $R^1$ may have the definition detailed above, especially for formula (I). Especially preferably, each of $Ar^a$ and/or $Ar^b$ in formula (I) represents a phenyl ring which may be substituted by one or more $R^1$ radicals, but is preferably unsubstituted.

Especially preferably, the $Ar^a$ and/or $Ar^b$ group in formula (I) is different from a donor group as per symbol HL. It may additionally be the case that the $Ar^a$ group in formula (I) is different from a donor group as per symbol HL. It may further be the case that the $Ar^b$ group in formula (I) is different from a donor group as per symbol HL. Particularly preferably, both the $Ar^a$ and the $Ar^b$ groups in formula (I) are different from a donor group as per symbol HL.

Especially preferably, the $Ar^a$ and/or $Ar^b$ group in formula (I) is different from an acceptor group as per symbol Q. It may additionally be the case that the $Ar^a$ group in formula (I) is different from an acceptor group as per symbol Q. It may further be the case that the $Ar^b$ group in formula (I) is different from an acceptor group as per symbol Q. Particularly preferably, both the $Ar^a$ and the $Ar^b$ groups in formula (I) are different from an acceptor group as per symbol Q.

Preferably, the $R^a$, $R^b$ substituents in formula (I) are selected from the group consisting of F, CN, $N(Ar^1)_2$, $C(=O)Ar^1$, $P(=O)(Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^2$ radicals, where one or more nonadjacent $CH_2$ groups may be replaced by O and where one or more hydrogen atoms may be replaced by D or F, an aromatic or heteroaromatic ring system which has 5 to 40 aromatic ring atoms and may be substituted in each case by one or more $R^2$ radicals, but is preferably unsubstituted, or an aralkyl or heteroalkyl group which has 5 to 25 aromatic ring atoms and may be substituted by one or more $R^2$ radicals; at the same time, it is optionally possible for two $R^1$ substituents bonded to the same carbon atom or to adjacent carbon atoms to form a monocyclic or polycyclic, aliphatic, aromatic or heteroaromatic ring system which may be substituted by one or more $R^1$ radicals; where $Ar^1$ may have the definition set out for formula (H-1) to (H-26) or/and formula (Q-26), (Q-27), (Q-28), (Q-29) or (Q-30), where the preferences set out here are applicable in this definition too. Preferably, $Ar^1$ is the same or different at each instance and represents an aryl or heteroaryl group which has 5 to 24 and preferably 5 to 12 aromatic ring atoms, and which may be substituted in each case by one or more $R^2$ radicals, but is preferably unsubstituted.

Preferably, the symbol $R^a$ and/or $R^b$ represents an aryl or heteroaryl radical, such that an aromatic or heteroaromatic group of an aromatic or heteroaromatic ring system is bonded directly to the respective atom of the further group, i.e. via an atom of the aromatic or heteroaromatic group.

In a further preferred embodiment of the invention, the symbol $R^a$ and/or $R^b$ is in each case independently an aromatic or heteroaromatic ring system having 5 to 24 aromatic ring atoms, preferably 6 to 18 aromatic ring atoms, and is more preferably an aromatic ring system having 6 to 12 aromatic ring atoms or a heteroaromatic ring system which has 5 to 13 aromatic ring atoms and may be substituted in each case by one or more $R^1$ radicals, but is preferably unsubstituted, where $R^1$ may have the definition given above, especially in formula (I).

Advantageously, each symbol $R^a$ and/or $R^b$ in formula (I) independently represents an aromatic ring system which has 6 to 12 aromatic ring atoms and may be substituted by one or more $R^1$ radicals, but is preferably unsubstituted, where $R^1$ may have the definition detailed above, especially for formula (I). Especially preferably, each of $Ar^a$ and/or $Ar^b$ in formula (I) represents a phenyl ring which may be substituted by one or more $R^1$ radicals, but is preferably unsubstituted.

Especially preferably, the $R^a$ and/or $R^b$ group in formula (I) is different from a donor group as per symbol HL. It may additionally be the case that the $R^a$ group in formula (I) is different from a donor group as per symbol HL. It may further be the case that the $R^b$ group in formula (I) is different from a donor group as per symbol HL. Particularly preferably, both the $R^a$ and the $R^b$ groups in formula (I) are different from a donor group as per symbol HL.

Especially preferably, the $R^a$ and/or $R^b$ group in formula (I) is different from an acceptor group as per symbol Q. It may additionally be the case that the $R^a$ group in formula (I) is different from an acceptor group as per symbol Q. It may further be the case that the $R^b$ group in formula (I) is different from an acceptor group as per symbol Q. Particularly preferably, both the $R^a$ and the $R^b$ groups in formula (I) are different from an acceptor group as per symbol Q.

More preferably, the symbols $Ar^a$, $Ar^b$, $R^a$ and $R^b$ in formula (I) are each independently an aromatic or heteroaromatic ring system having preferably 5 to 24 aromatic ring atoms, more preferably having 6 to 18 aromatic ring atoms, each of which may be substituted by one or more $R^1$ radicals, but is preferably unsubstituted. More preferably, the symbols $Ar^a$, $Ar^b$, $R^a$ and $R^b$ in formula (I) are each independently an aromatic ring system having 6 to 12 aromatic ring atoms or a heteroaromatic ring system having 5 to 13 heteroaromatic ring atoms, each of which may be substituted by one or more $R^1$ radicals, but is preferably unsubstituted, where $R^1$ may have the definition detailed above, especially in formula (I). Especially preferably, symbols $Ar^a$, $Ar^b$, $R^a$ and $R^b$ in formula (I) each represent a phenyl ring which may be substituted by one or more R¹ radicals, but is preferably unsubstituted.

It is possible here for two or more of the symbols Ar$^a$, Ar$^b$, R$^a$ and/or R$^b$ in formula (I) to be joined by a ring closure, where the joining can more preferably be effected by a bond between the respective Ar$^a$, Ar$^b$, R$^a$ and/or R$^b$ groups in formula (I).

When X is CR¹ or when the aromatic and/or heteroaromatic groups are substituted by R¹ substituents, these R¹ substituents are preferably selected from the group consisting of H, D, F, CN, N(Ar¹)$_2$, C(=O)Ar¹, P(=O)(Ar¹)$_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more R² radicals, where one or more nonadjacent CH$_2$ groups may be replaced by O and where one or more hydrogen atoms may be replaced by D or F, an aromatic or heteroaromatic ring system which has 5 to 24 aromatic ring atoms and may be substituted in each case by one or more R² radicals, but is preferably unsubstituted, or an aralkyl or heteroaralkyl group which has 5 to 25 aromatic ring atoms and may be substituted by one or more R² radicals; at the same time, it is optionally possible for two R¹ substituents bonded to the same carbon atom or to adjacent carbon atoms to form a monocyclic or polycyclic, aliphatic, aromatic or heteroaromatic ring system which may be substituted by one or more R¹ radicals; where Ar¹ may have the definition set out for formula (H-1) to (H-26) or/and formula (Q-26), (Q-27), (Q-28), (Q-29) or (Q-30), where the preferences set out here are applicable in this definition too.

More preferably, these R¹ substituents are selected from the group consisting of H, D, F, CN, N(Ar¹)$_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more R² radicals, but is preferably unsubstituted, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more nonaromatic R¹ radicals, but is preferably unsubstituted; at the same time, it is optionally possible for two R¹ substituents bonded to the same carbon atom or to adjacent carbon atoms to form a monocyclic or polycyclic aliphatic ring system which may be substituted by one or more R² radicals, but is preferably unsubstituted, where Ar¹ may have the definition set out above.

Most preferably, the R¹ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic R² radicals, but is preferably unsubstituted.

Preferably, the R¹ radicals do not form a fused ring system with the ring atoms of the aryl group or of the heteroaryl group to which the R¹ radicals are bonded. This includes the formation of a fused ring system with possible R², R³ substituents which may be bonded to the R¹ radicals.

It may preferably be the case that the Ar$^a$, Ar$^b$, Ar¹, Ar², Ar³, Ar⁴, R$^a$, R$^b$ and/or R¹ group in the structures of formula (I), (H-1) to (H-26), (LAr-1), (LAr-2) and/or (Q-1) to (Q-44) is selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, 1- or 2-naphthyl, anthracenyl, preferably 9-anthracenyl, phenanthrenyl and/or triphenylenyl, each of which may be substituted by one or more R² radicals, but are preferably unsubstituted, particular preference being given to phenyl, spirobifluorene, fluorene, dibenzofuran, dibenzothiophene, anthracene, phenanthrene, triphenylene groups.

It may further be the case that, in a structure of formula (I), (H-1) to (H-26), (LAr-1), (LAr-2) and/or (Q-1) to (Q-44), at least one Ar$^a$, Ar$^b$, Ar¹, Ar³, Ar⁴, R$^a$, R$^b$ and/or R¹ radical comprises a group and is preferably a group selected from the formulae (R¹-1) to (R¹-86):

Formula (R¹-1)

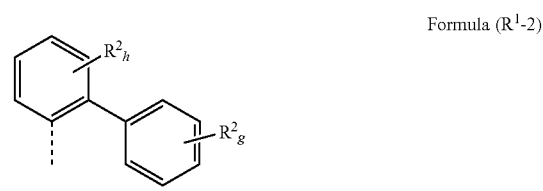

Formula (R¹-2)

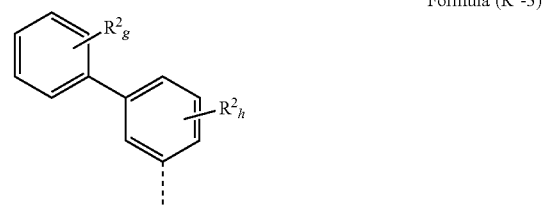

Formula (R¹-3)

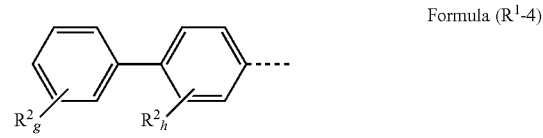

Formula (R¹-4)

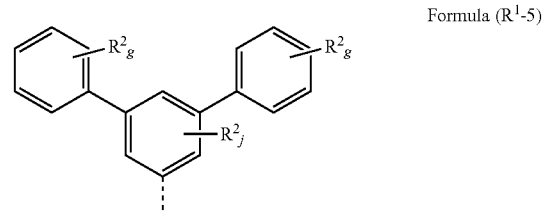

Formula (R¹-5)

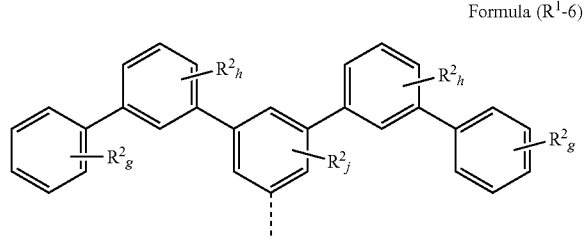

Formula (R¹-6)

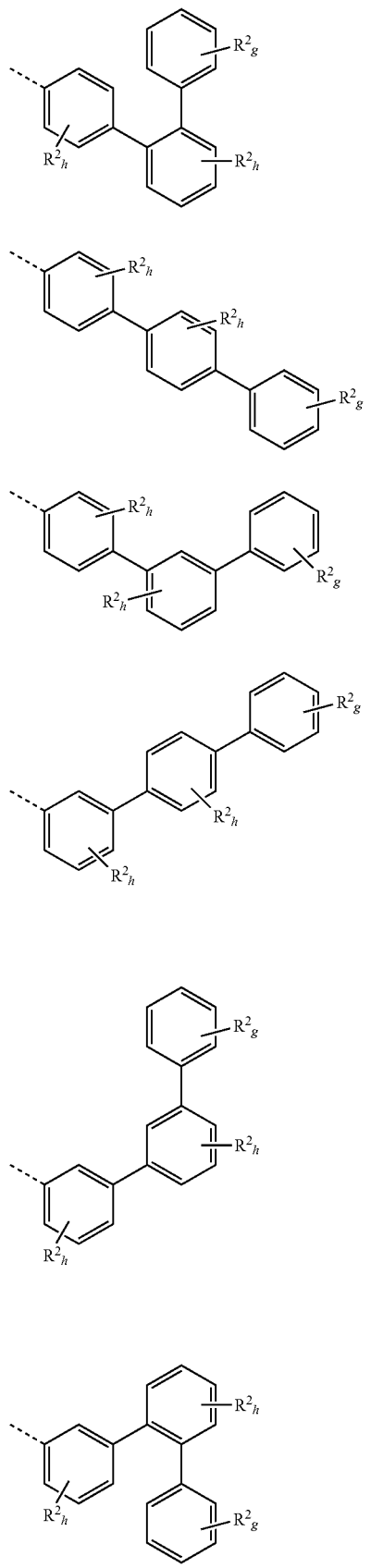
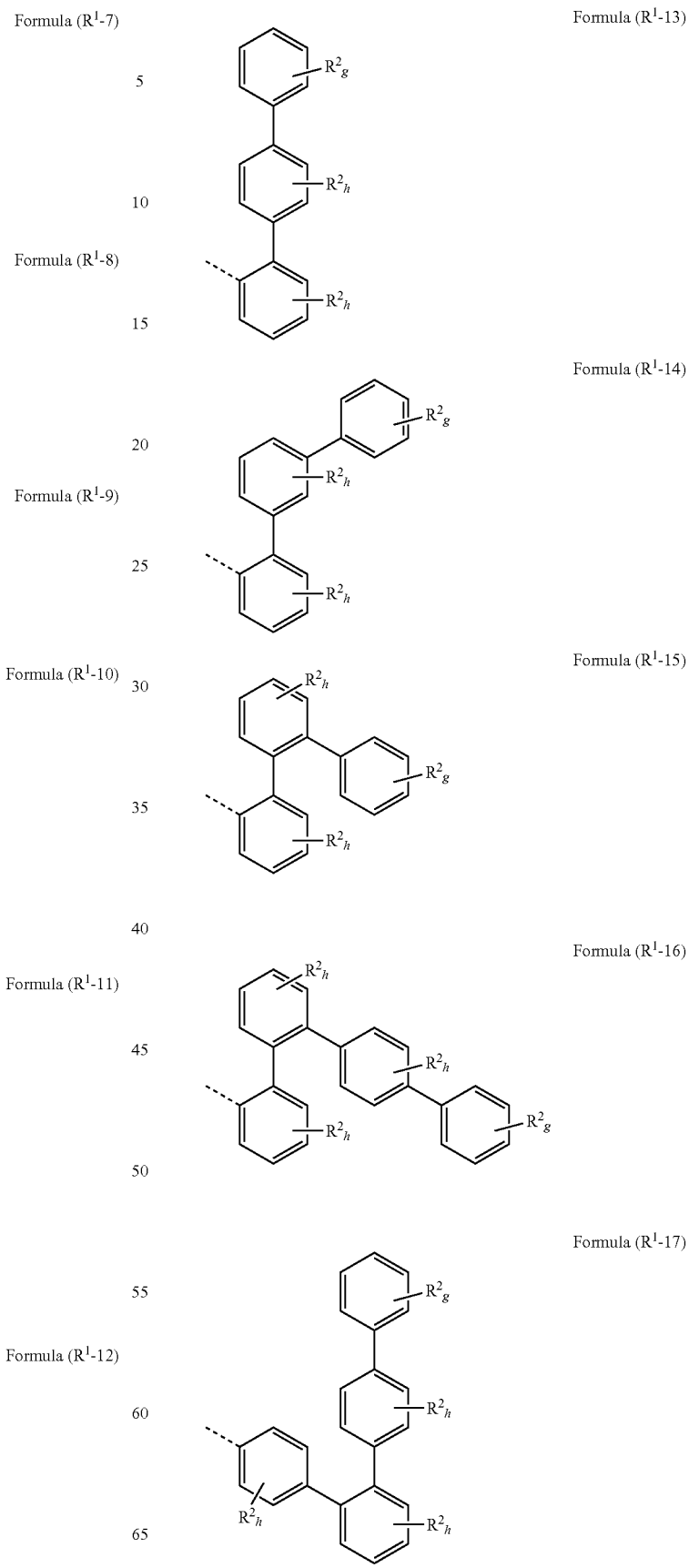

Formula (R¹-18)
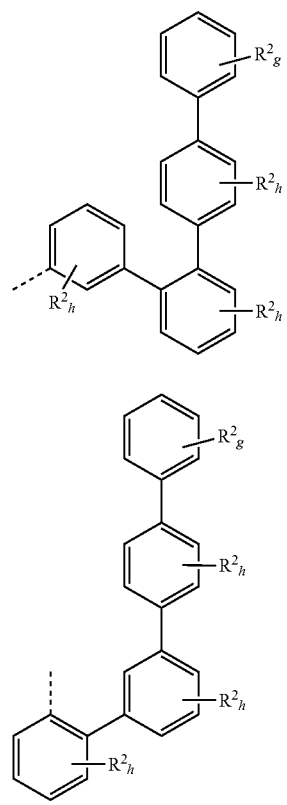
Formula (R¹-19)
Formula (R¹-20)
Formula (R¹-21)
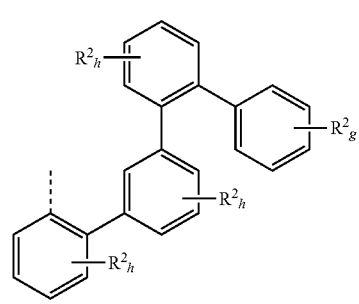
Formula (R¹-22)
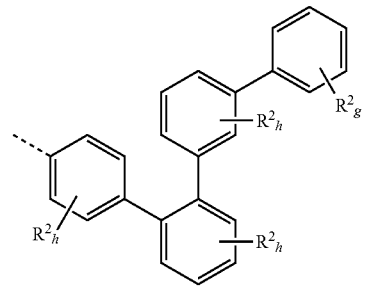
Formula (R¹-23)
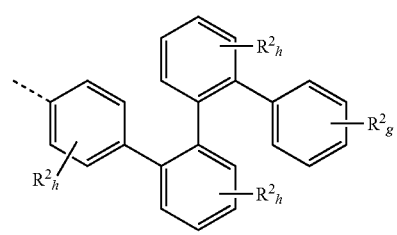
Formula (R¹-24)
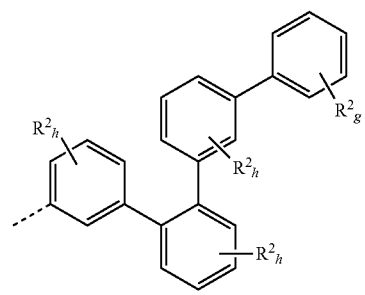
Formula (R¹-25)
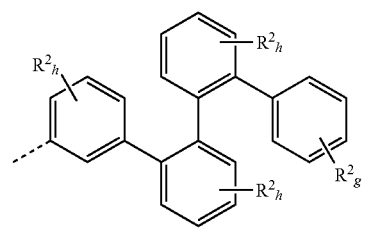
Formula (R¹-26)
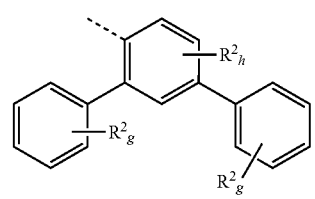
Formula (R¹-27)
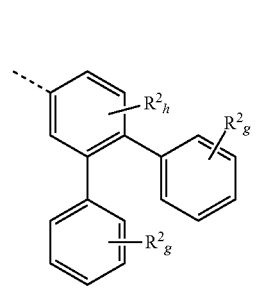

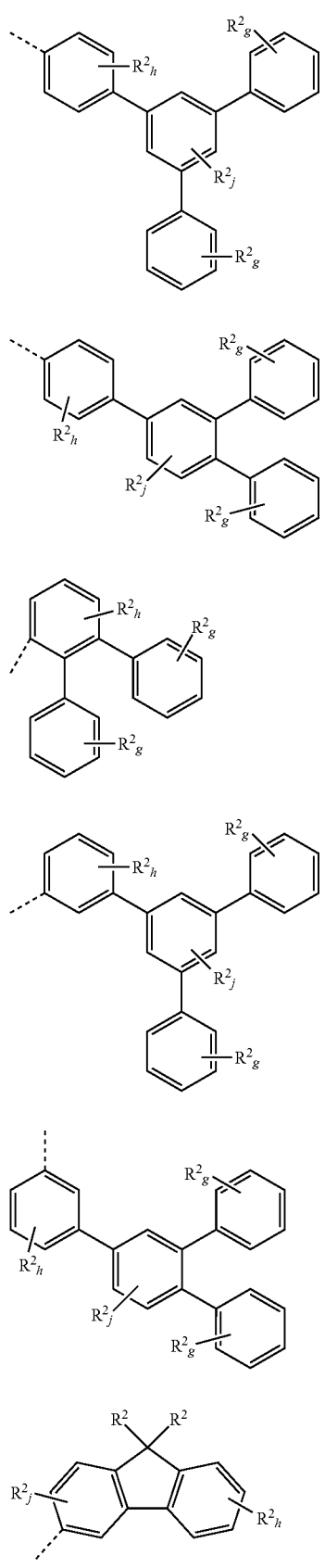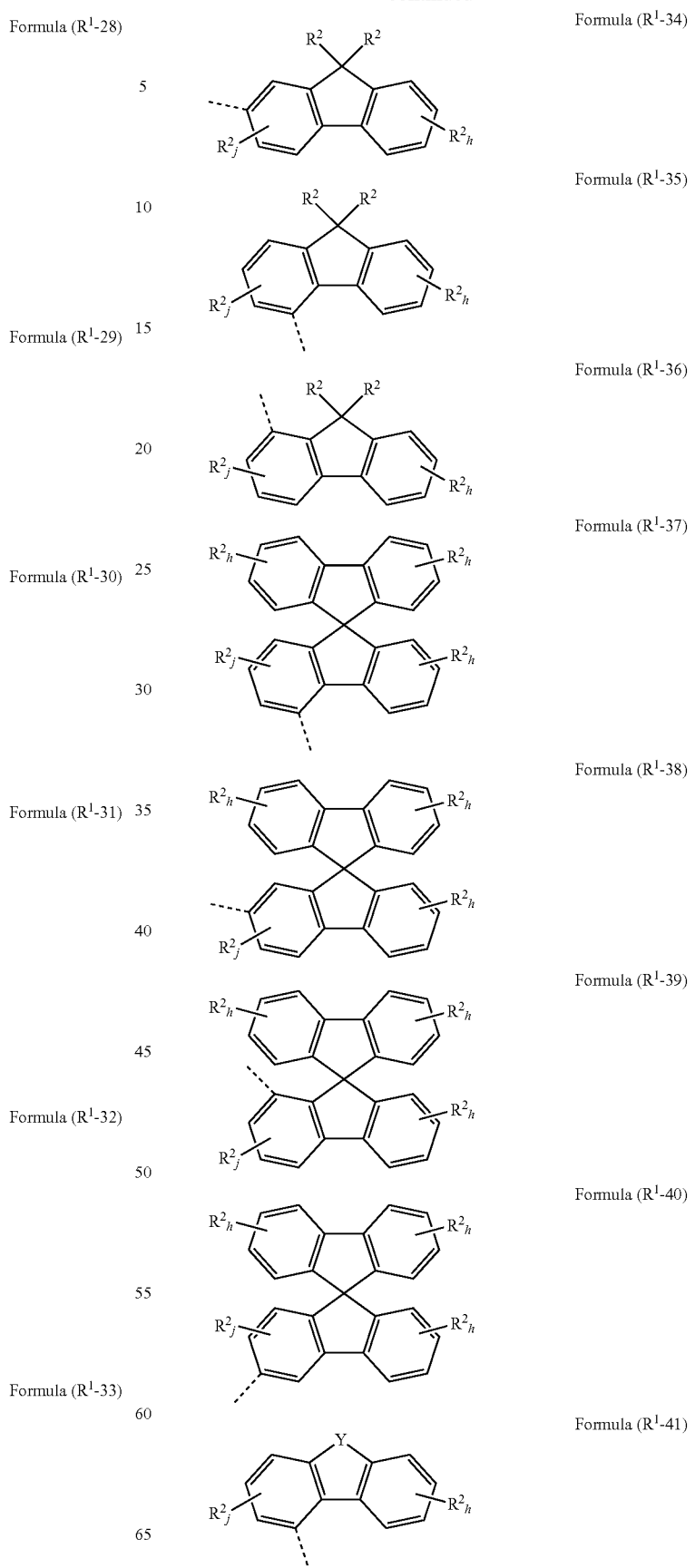

Formula (R¹-42)

Formula (R¹-43)

Formula (R¹-44)

Formula (R¹-45)

Formula (R¹-46)

Formula (R¹-47)

Formula (R¹-48)

Formula (R¹-49)

Formula (R¹-50)

Formula (R¹-51)

Formula (R¹-52)

Formula (R¹-53)

Formula (R¹-54)

Formula (R¹-55)

Formula (R¹-56)
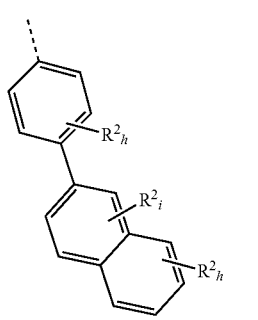
Formula (R¹-57)
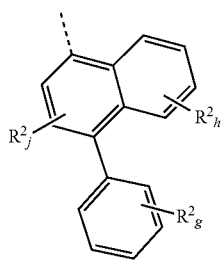
Formula (R¹-58)
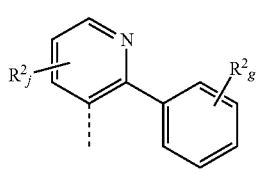
Formula (R¹-59)
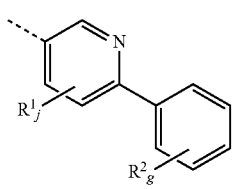
Formula (R¹-60)
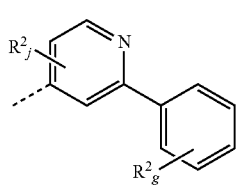
Formula (R¹-61)
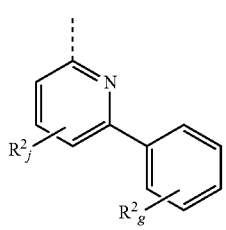
Formula (R¹-62)
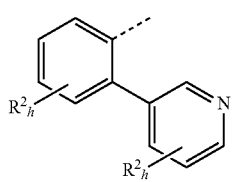
Formula (R¹-63)
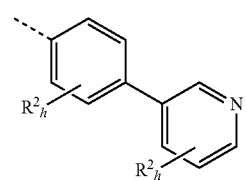
Formula (R¹-64)
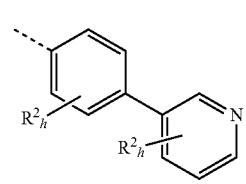
Formula (R¹-65)
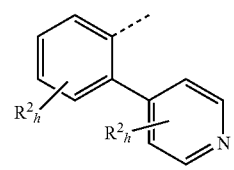
Formula (R¹-66)
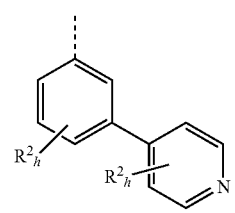
Formula (R¹-67)
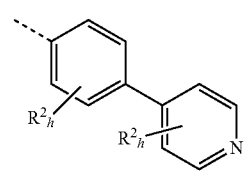
Formula (R¹-68)
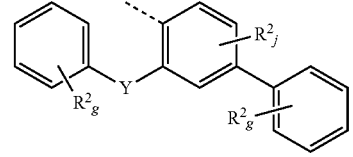
Formula (R¹-69)
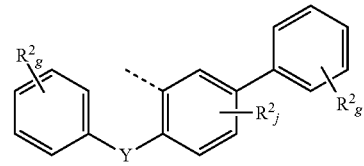
Formula (R¹-70)
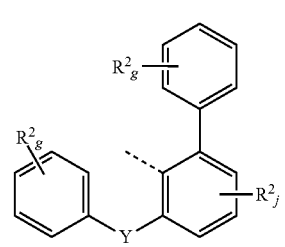

-continued
Formula (R¹-71)
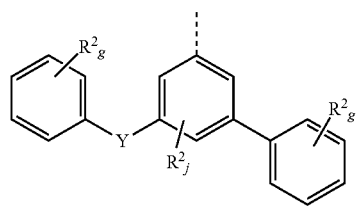
Formula (R¹-72)
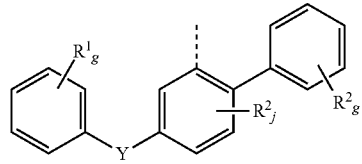
Formula (R¹-73)
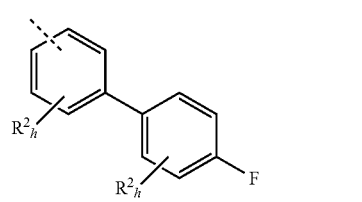
Formula (R¹-74)
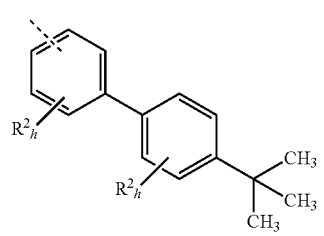
Formula (R¹-75)
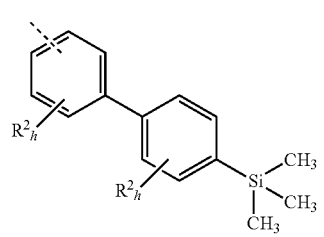
Formula (R¹-76)
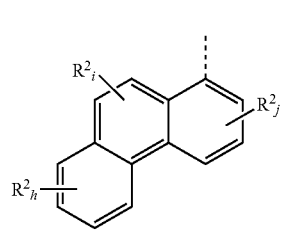
Formula (R¹-77)
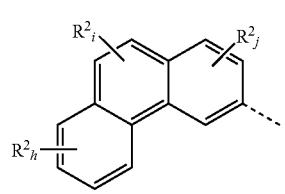
-continued
Formula (R¹-78)
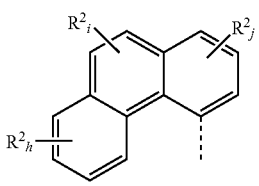
Formula (R¹-79)
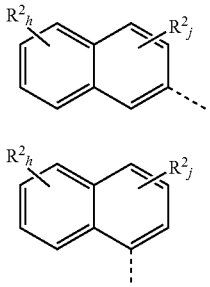
Formula (R¹-80)
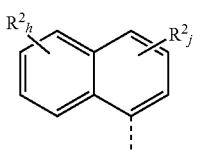
Formula (R¹-81)
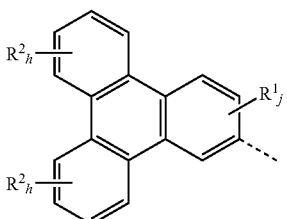
Formula (R¹-82)
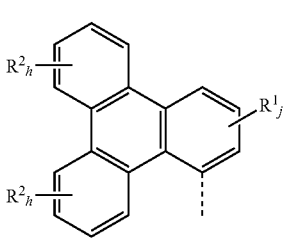
Formula (R¹-83)
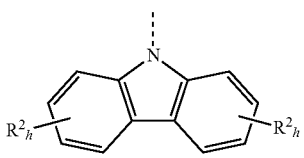
Formula (R¹-84)
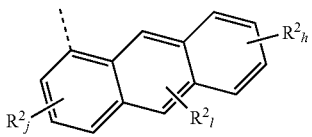
Formula (R¹-85)
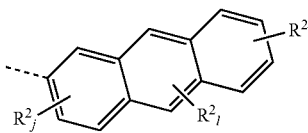
Formula (R¹-86)
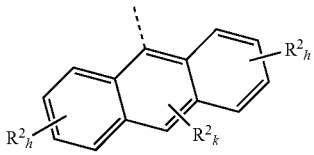

where the symbols used are as follows:

Y is O, S or $NR^2$, preferably O or S;

at each instance is independently 0, 1 or 2;

at each instance is independently 0, 1, 2 or 3;

h at each instance is independently 0, 1, 2, 3 or 4;

g at each instance is independently 0, 1, 2, 3, 4 or 5;

$R^2$ may have the definition given above, especially for formula (I), and the dotted bond marks the attachment position. Preference is given here to the groups of the formulae R1-1 to R1-54 and particular preference to groups of the formulae R1-1, R1-3, R1-5, R1-6, R1-15, R1-29, R1-34, R1-35, R1-45, R1-46, R1-47 and/or R1-48.

It may preferably be the case that the sum total of the indices i, j, h and g in the structures of the formula ($R^1$-1) to ($R^1$-86) is not more than 3 in each case, preferably not more than 2 and more preferably not more than 1.

Preferably, the $R^2$ radicals in the formulae ($R^1$-1) to ($R^1$-86) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

Preferably, the $L^1$ group may form through-conjugation with the $Q^1$ group and the aromatic radical to which the $L^1$ group of formula (I) or (QL) is bonded. Through-conjugation of the aromatic or heteroaromatic systems is formed as soon as direct bonds are formed between adjacent aromatic or heteroaromatic rings. A further bond between the aforementioned conjugated groups, for example via a sulfur, nitrogen or oxygen atom or a carbonyl group, is not detrimental to conjugation. In the case of a fluorene system, the two aromatic rings are bonded directly, where the $sp^3$-hybridized carbon atom in position 9 does prevent fusion of these rings, but conjugation is possible since this spa-hybridized carbon atom in position 9 does not necessarily lie between the $Q^1$ group and the aromatic radical to which the $L^1$ group of formula (I) or (QL) is bonded. In contrast, in the case of a second spirobifluorene structure, through-conjugation can be formed if the bond between the $Q^1$ group and the aromatic radical of the formula (I) is via the same phenyl group in the spirobifluorene structure or via phenyl groups in the spirobifluorene structure that are bonded directly to one another and are in one plane. If the bond between the $Q^1$ group and the aromatic radical of the formula (I) is via different phenyl groups in the second spirobifluorene structure bonded via the $sp^3$-hybridized carbon atom in position 9, the conjugation is interrupted. Preferably, the $Ar^2$ radicals, for example in formulae (H-1) to (H-26), also form through-conjugation with the groups to which the $Ar^2$ radicals are bonded. In addition, the connecting structures of the formula (LAr-1) and/or (LAr-2) form through-conjugation with the groups to which the connecting structures of the formula (LAr-1) and/or (LAr-2) are bonded.

In a further preferred embodiment of the invention, $L^1$ or the $Ar^2$ group is an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (I). More preferably, $L^1$ or the $Ar^2$ group is an aromatic ring system having 6 to 10 aromatic ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formula (I).

Further preferably, the symbol $L^1$ or the $Ar^2$ group detailed in the formulae (H-1) to (H-26) that are detailed in the structures of formula (QL) inter alia is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded directly, i.e. via an atom of the aromatic or heteroaromatic group, to the respective atom of the further group.

It may additionally be the case that the symbol $L^1$ detailed in the structures of formula (QL) inter alia or the $Ar^2$ group detailed in the formulae (H-1) to (H-26) comprises an aromatic ring system having not more than two fused aromatic and/or heteroaromatic rings, preferably not having any fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems $L^1$ or $Ar^2$ are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, pyrenyl, triazinyl, imidazolyl, benzimidazolyl, benzoxazolyl, benzothiazolyl, 1-, 2-, 3- or 4-carbazolyl, 1- or 2-naphthyl, anthracenyl, preferably 9-anthracenyl, phenanthrenyl and/or triphenylenyl, each of which may be substituted by one or more $R^2$ radicals, but are preferably unsubstituted, particular preference being given to phenyl, spirobifluorene, fluorene, dibenzofuran, dibenzothiophene, anthracene, phenanthrene, triphenylene groups.

It may further be the case that the $Ar^2$ group in the structure of formulae (H-1) to (H-26) and/or the $L^1$ group in formula (QL) is a bond or a group selected from the formulae ($L^1$-1) to ($L^1$-108) or the structure of the formula (LAr-1) or (LAr-2) represents a bond or forms a group selected from the formulae ($L^1$-1) to ($L^1$-108)

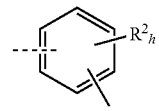

Formula ($L^1$-1)

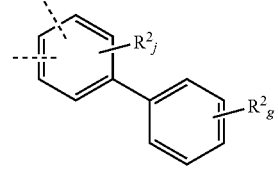

Formula ($L^1$-2)

Formula (L¹-3)
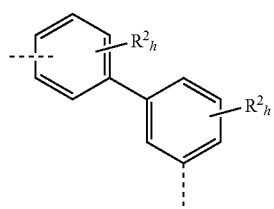
Formula (L¹-4)
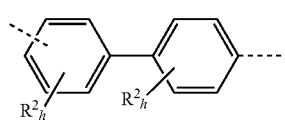
Formula (L¹-5)
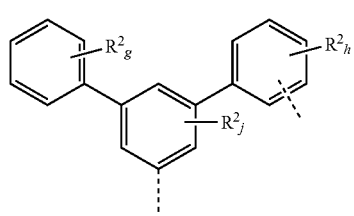
Formula (L¹-6)
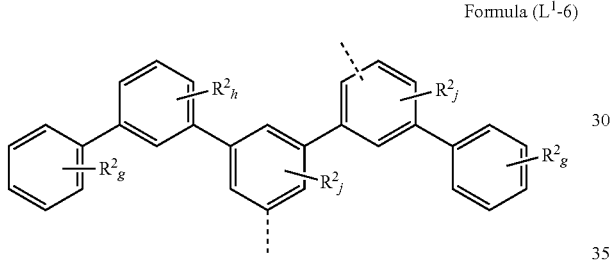
Formula (L¹-7)
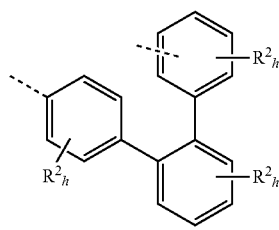
(Formula (L¹-8))
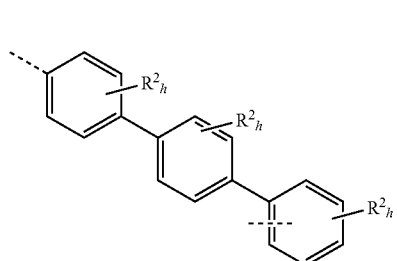
Formula (L¹-9)
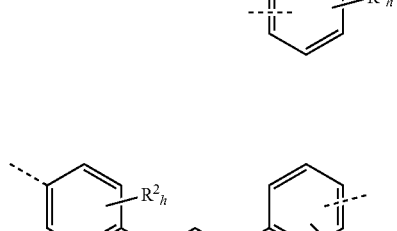
Formula (L¹-10)
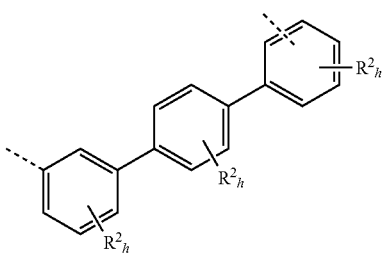
Formula (L¹-11)
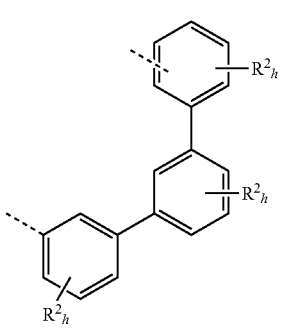
Formula (L¹-12)
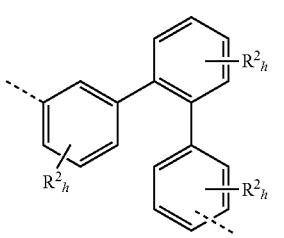
Formula (L¹-13)
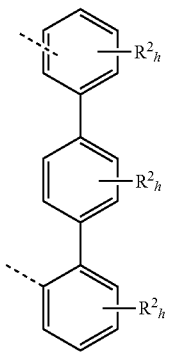
Formula (L¹-14)
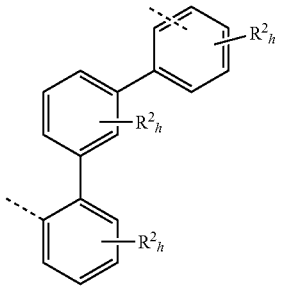

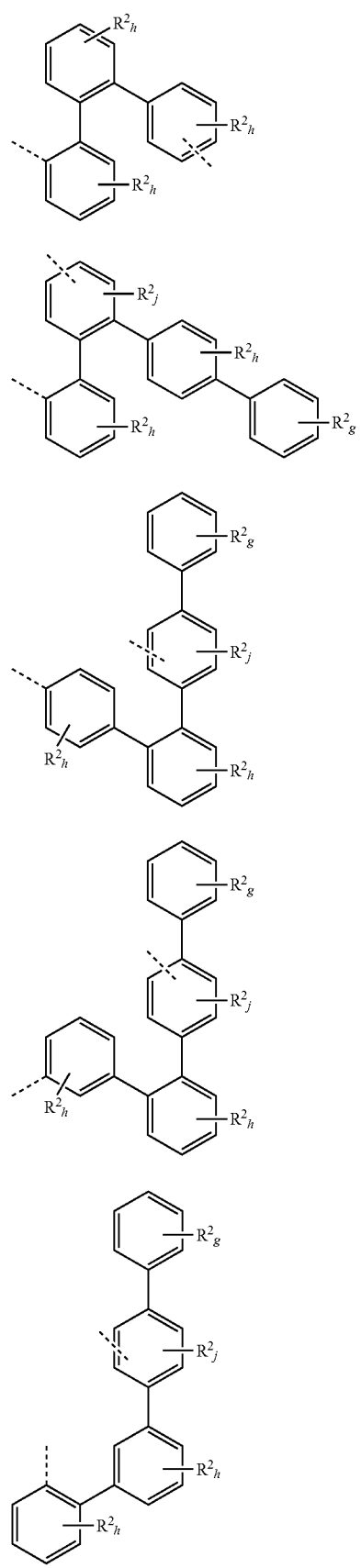
Formula (L¹-15)
Formula (L¹-16)
Formula (L¹-17)
Formula (L¹-18)
Formula (L¹-19)
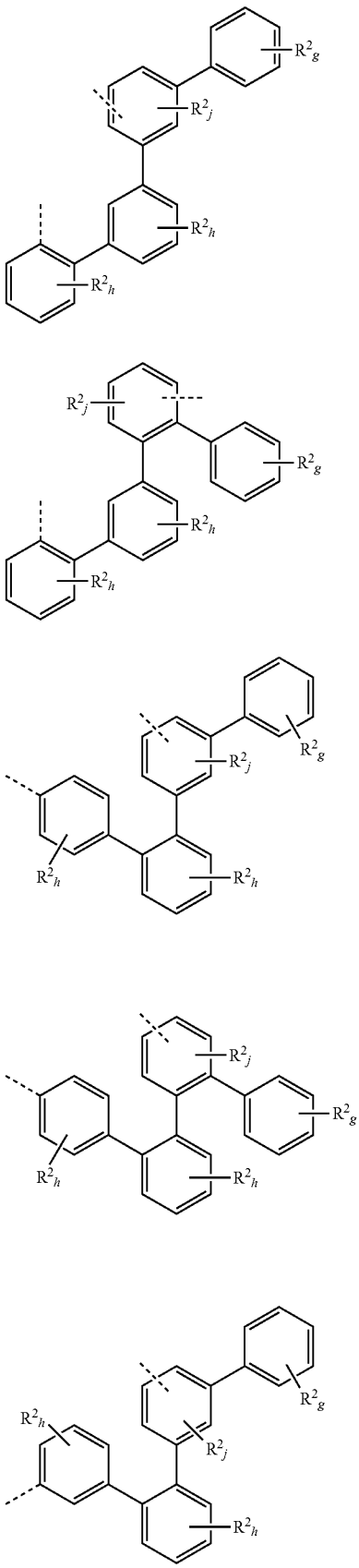
Formula (L¹-20)
Formula (L¹-21)
Formula (L¹-22)
Formula (L¹-23)
Formula (L¹-24)

Formula (L¹-25)
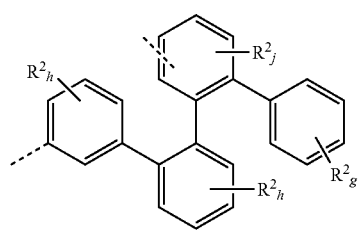
Formula (L¹-26)
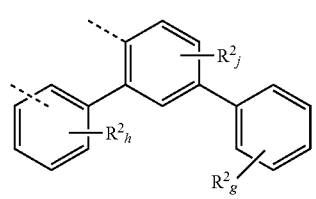
Formula (L¹-27)
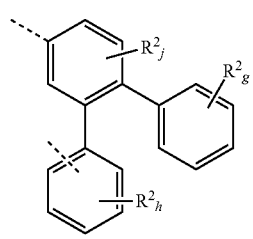
Formula (L¹-28)
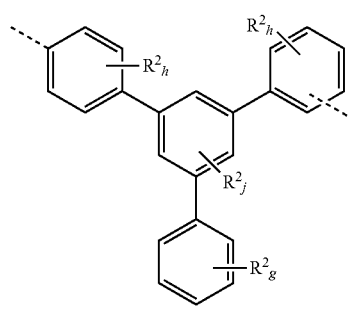
Formula (L¹-29)
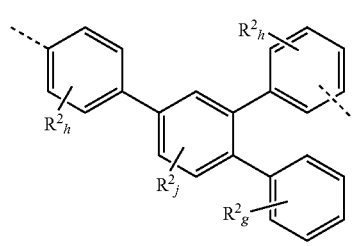
Formula (L¹-30)
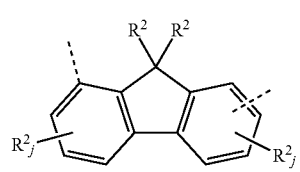
Formula (L¹-31)
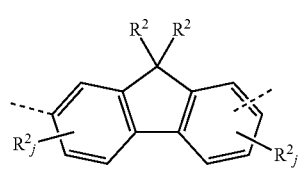
Formula (L¹-32)
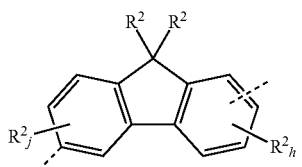
Formula (L¹-33)
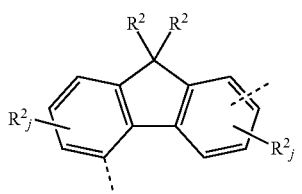
Formula (L¹-34)
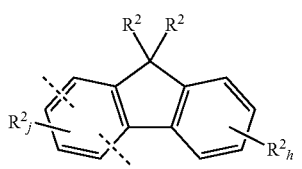
Formula (L¹-35)
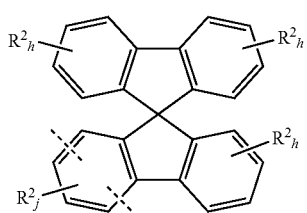
Formula (L¹-36)
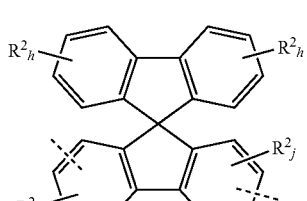
Formula (L¹-37)
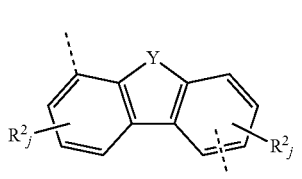
Formula (L¹-38)
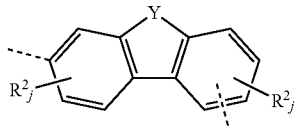
Formula (L¹-39)
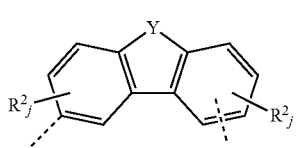

-continued
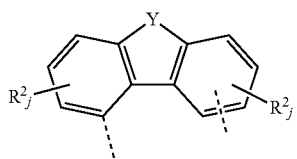
Formula (L¹-40)
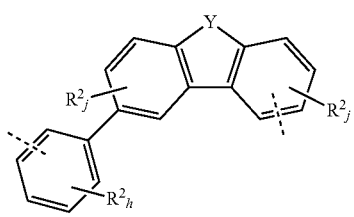
Formula (L¹-41)
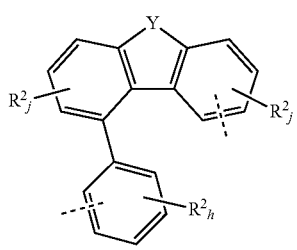
Formula (L¹-42)
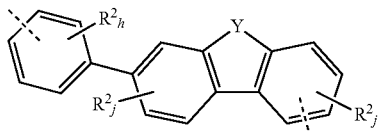
Formula (L¹-43)
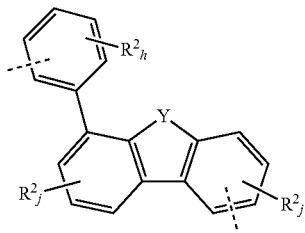
Formula (L¹-44)
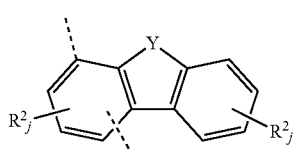
Formula (L¹-45)
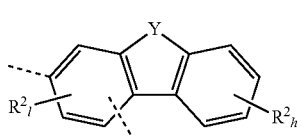
Formula (L¹-46)
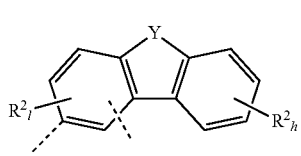
Formula (L¹-47)
-continued
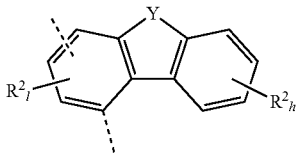
Formula (L¹-48)
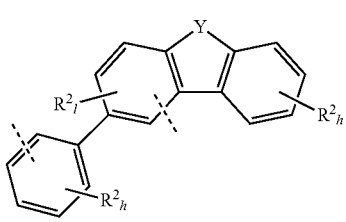
Formula (L¹-49)
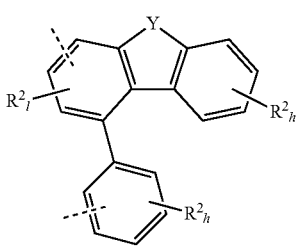
Formula (L¹-50)
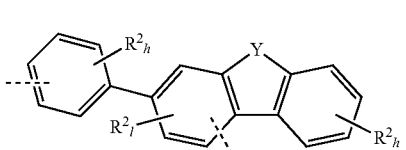
Formula (L¹-51)
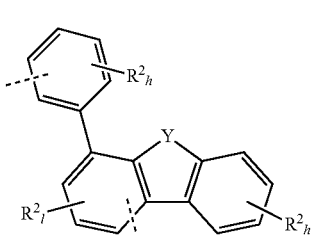
Formula (L¹-52)
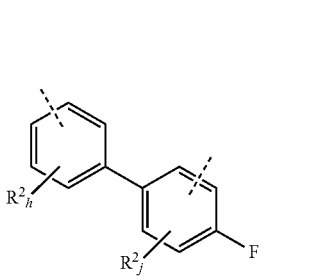
Formula (L¹-53)
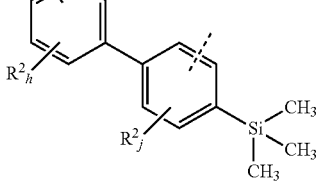
Formula (L¹-54)

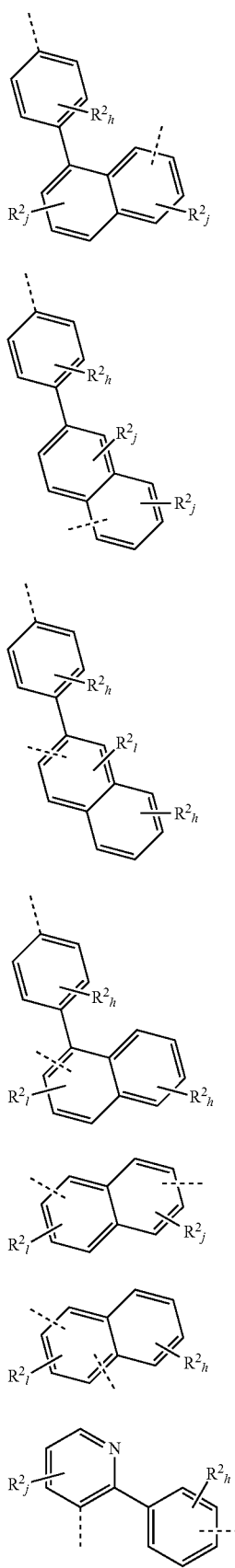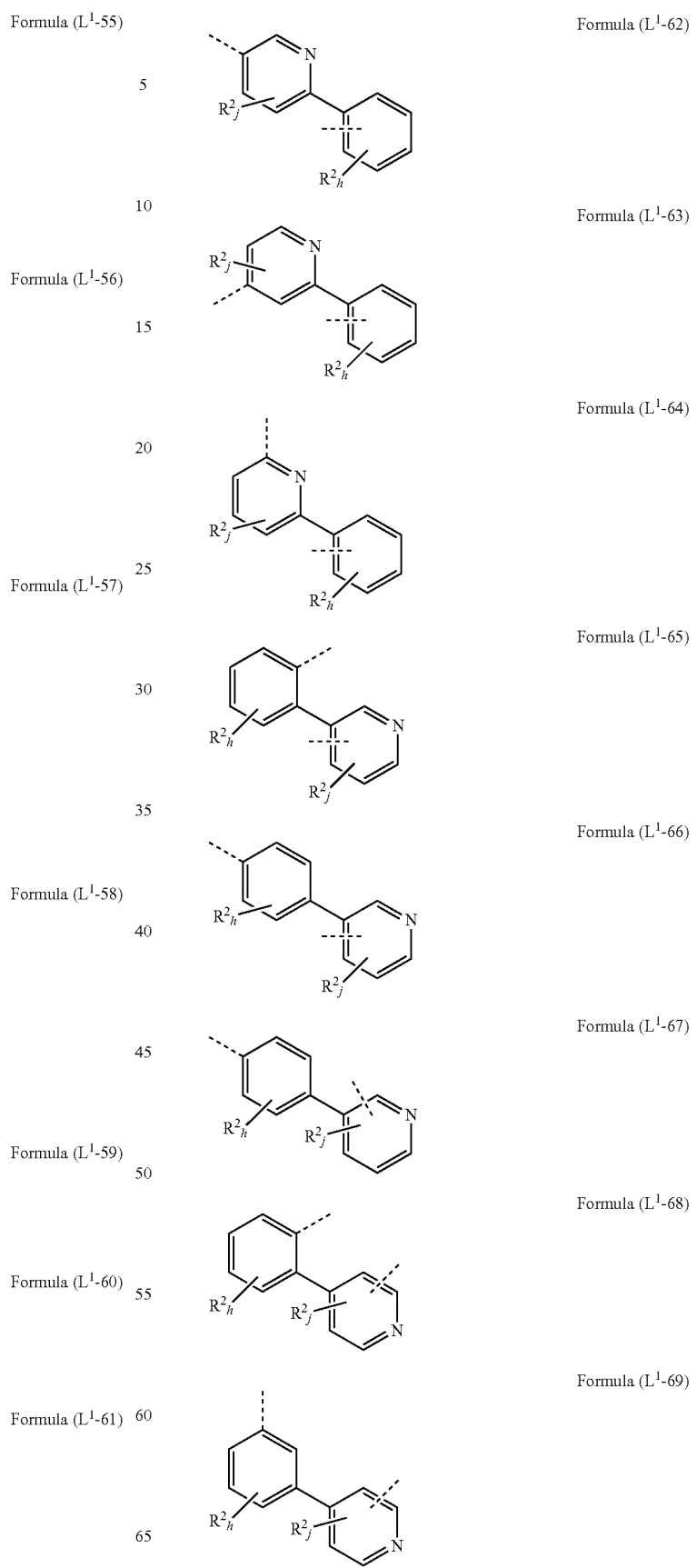

-continued

Formula (L¹-70)

Formula (L¹-71)

Formula (L¹-72)

Formula (L¹-73)

Formula (L¹-74)

Formula (L¹-75)

Formula (L¹-76)

Formula (L¹-77)

Formula (L¹-78)

Formula (L¹-79)

-continued

Formula (L¹-80)

Formula (L¹-81)

Formula (L¹-82)

Formula (L¹-83)

Formula (L¹-84)

Formula (L¹-85)

Formula (L¹-86)

Formula (L¹-87)

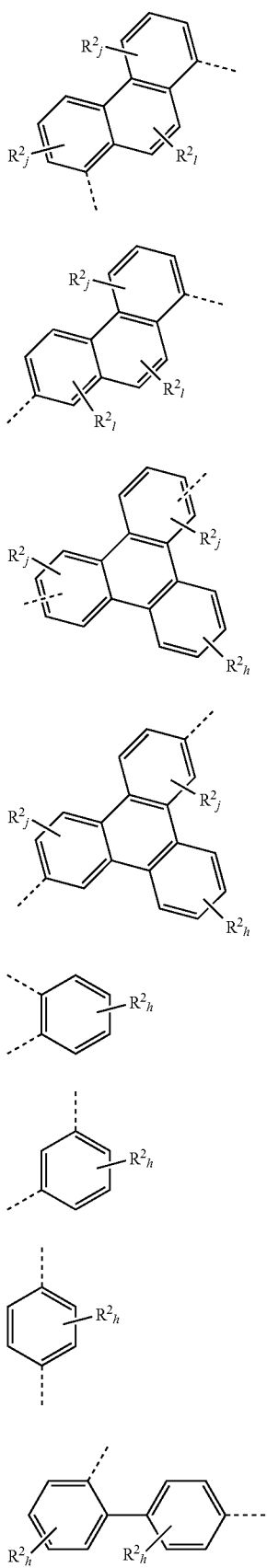
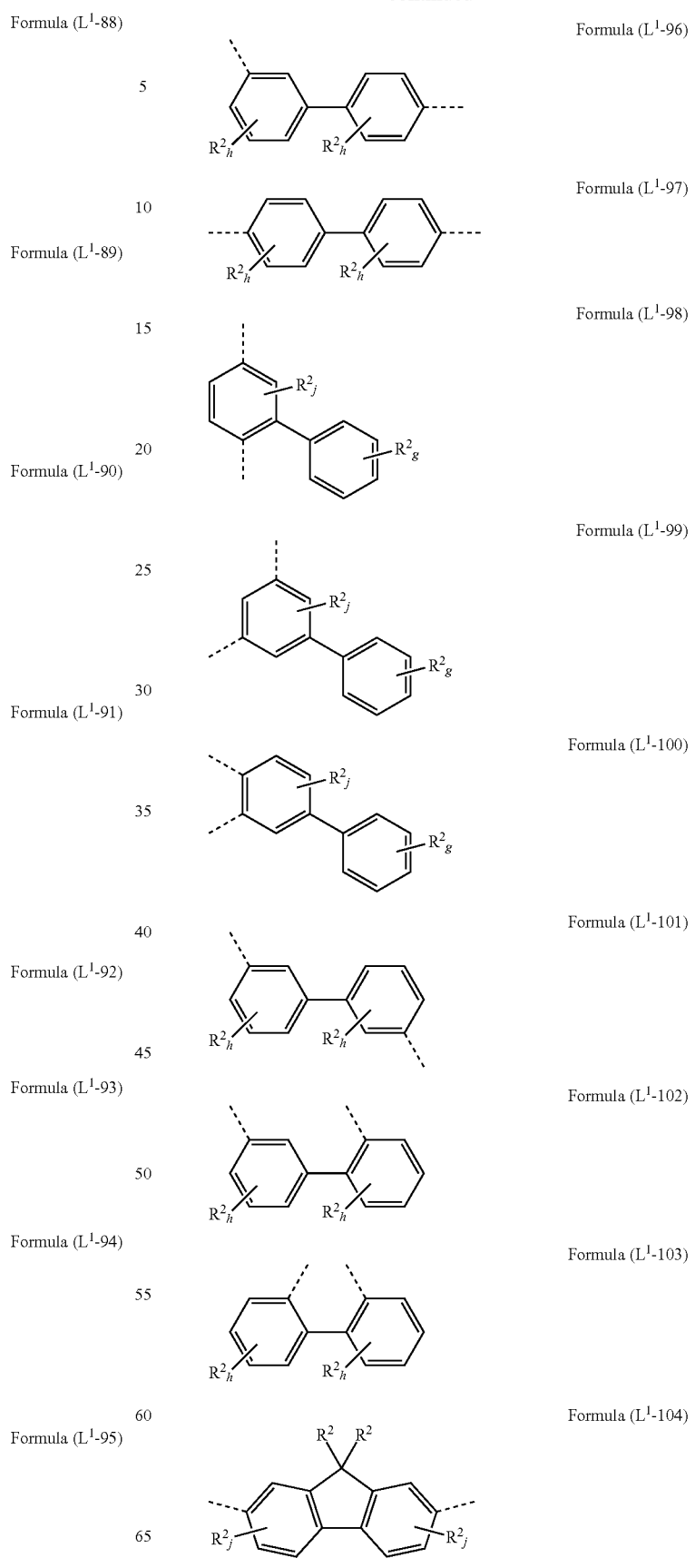

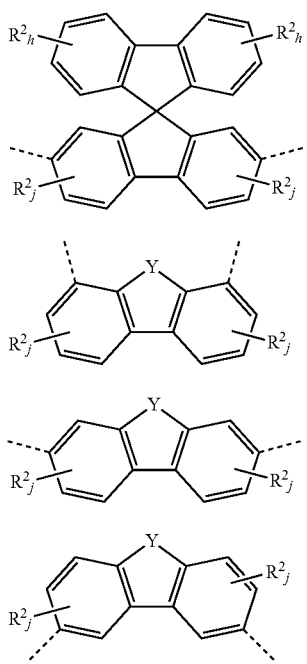

Formula (L¹-105)

Formula (L¹-106)

Formula (L¹-107)

Formula (L¹-108)

where the dotted bonds in each case mark the attachment positions, the index k at each instance is independently 0 or 1, the index l at each instance is independently 0, 1 or 2, the index j at each instance is independently 0, 1, 2 or 3; the index h at each instance is independently 0, 1, 2, 3 or 4, the index g at each instance is independently is 0, 1, 2, 3, 4 or 5; the symbol Y is O, S or NR², preferably 0 or S; and the symbol R² has the definition given above, especially for formula (I).

It may preferably be the case that the sum total of the indices k, l, g, h and j in the structures of the formula (L¹-1) to (L¹-108) is at most 3 in each case, preferably at most 2 and more preferably at most 1.

Preferred compounds according to the invention comprise an L¹ or Are group which represents a bond or which is selected from one of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103). Advantageously, the sum total of the indices k, l, g, h and j in the structures of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103), may in each case be not more than 3, preferably not more than 2 and more preferably not more than 1.

Preferably, the R² radicals in the formulae (L¹-1) to (L¹-108) do not form a fused aromatic or heteroaromatic ring system, and preferably do not form any fused ring system, with the ring atoms of the aryl group or heteroaryl group to which the R² radicals are bonded. This includes the formation of a fused ring system with possible R³ substituents which may be bonded to the R² radicals.

In a further preferred embodiment of the invention, R², for example in a structure of formula (I) and preferred embodiments of this structure or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

In a further preferred embodiment of the invention, R³, for example in a structure of formula (I) and preferred embodiments of this structure or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

When the compound of the invention is substituted by aromatic or heteroaromatic $R^1$ or $R^2$ groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

Particular preference is given to compounds of the invention having the following properties:

| $Ar^a$ and $Ar^b$ | $R^a$ and $R^b$ | Acceptor group (QL) | | Donor group |
|---|---|---|---|---|
| | | $Q^1$ | $L^1$ | |
| $R^1$-1 to $R^1$-86 | $R^1$-1 to $R^1$-86 | Q-1 to Q-44 | bond | H-1 to H-44 |
| $R^1$-1 to R1-82 | $R^1$-1 to $R^1$-82 | Q-1 to Q-44 | bond | H-1 to H-44 |
| $R^1$-1 to $R^1$-54 | $R^1$-1 to $R^1$-54 | Q-1 to Q-44 | bond | H-1 to H-44 |
| $R^1$-1 | $R^1$-1 | Q-1 to Q-44 | bond | H-1 to H-44 |
| $R^1$-1 to $R^1$-86 | $R^1$-1 to $R^1$-86 | Q-1 to Q-44 | L-1 | H-1 to H-44 |
| $R^1$-1 to $R^1$-82 | $R^1$-1 to $R^1$-82 | Q-1 to Q-44 | L-1 | H-1 to H-44 |
| $R^1$-1 to $R^1$-54 | $R^1$-1 to $R^1$-54 | Q-1 to 0-44 | L-1 | H-1 to H-44 |
| $R^1$-1 | $R^1$-1 | Q-1 to Q-44 | L-1 | H-1 to H-44 |

Particular preference is given to compounds of the invention comprising at least one donor group of formulae (H-1) to (H-26) where the $Ar^2$ group is a connecting structure of the formula (LAr-1), and at least one acceptor group of formula (QL) where $L^1$ can be represented by a connecting structure of the formula (LAr-2), where the following additional properties are fulfilled:

| $Ar^a$ and $Ar^b$ | $R^a$ and $R^b$ | Index s in formula (LAr-1) | Index t in formula (LAr-2) |
|---|---|---|---|
| $R^1$-1 to $R^1$-86 | $R^1$-1 to $R^1$-86 | 0, 1 or 2 | 0 |
| $R^1$-1 to $R^1$-86 | $R^1$-1 to $R^1$-86 | 0, 1 or 2 | 1 |

| Ar$^a$ and Ar$^b$ | R$^a$ and R$^b$ | Index s in formula (LAr-1) | Index t in formula (LAr-2) |
|---|---|---|---|
| R$^1$-1 to R$^1$-86 | R$^1$-1 to R$^1$-86 | 0, 1 or 2 | 2 |
| R$^1$-1 to R$^1$-86 | R$^1$-1 to R$^1$-86 | 0 | 0, 1 or 2 |
| R$^1$-1 to R$^1$-86 | R$^1$-1 to R$^1$-86 | 1 | 0, 1 or 2 |
| R$^1$-1 to R$^1$-86 | R$^1$-1 to R$^1$-86 | 2 | 0, 1 or 2 |
| R$^1$-1 to R$^1$-82 | R$^1$-1 to R$^1$-82 | 0 | 0 |
| R$^1$-1 to R$^1$-82 | R$^1$-1 to R$^1$-82 | 1 | 1 |
| R$^1$-1 to R$^1$-82 | R$^1$-1 to R$^1$-82 | 2 | 2 |
| R$^1$-1 to R$^1$-82 | R$^1$-1 to R$^1$-82 | 0 | 1 |
| R$^1$-1 to R$^1$-82 | R$^1$-1 to R$^1$-82 | 1 | 2 |
| R$^1$-1 to R$^1$-82 | R$^1$-1 to R$^1$-82 | 2 | 3 |
| R$^1$-1 to R$^1$-82 | R$^1$-1 to R$^1$-82 | 1 | 0 |
| R$^1$-1 to R$^1$-82 | R$^1$-1 to R$^1$-82 | 2 | 2 |
| R$^1$-1 to R$^1$-82 | R$^1$-1 to R$^1$-82 | 3 | 2 |
| R$^1$-1 | R$^1$-1 | 0, 1 or 2 | 0 |
| R$^1$-1 | R$^1$-1 | 0, 1 or 2 | 1 |
| R$^1$-1 | R$^1$-1 | 0, 1 or 2 | 2 |
| R$^1$-1 | R$^1$-1 | 0 | 0, 1 or 2 |
| R$^1$-1 | R$^1$-1 | 1 | 0, 1 or 2 |
| R$^1$-1 | R$^1$-1 | 2 | 0, 1 or 2 |
| R$^1$-1 | R$^1$-1 | 0 | 0 |
| R$^1$-1 | R$^1$-1 | 1 | 1 |
| R$^1$-1 | R$^1$-1 | 2 | 2 |
| R$^1$-1 | R$^1$-1 | 0 | 1 |
| R$^1$-1 | R$^1$-1 | 1 | 2 |
| R$^1$-1 | R$^1$-1 | 2 | 3 |
| R$^1$-1 | R$^1$-1 | 1 | 0 |
| R$^1$-1 | R$^1$-1 | 2 | 1 |
| R$^1$-1 | R$^1$-1 | 3 | 2 |

In the tables set out above, the assignment that Ar$^a$ and Ar$^b$ is R$^1$-1 to R$^1$-86 means that both the Ar$^a$ group and the Ar$^b$ group is selected from the radicals of the above-detailed formulae R$^1$-1 to R$^1$-86, preferably R$^1$-1. The assignment of R$^a$ and R$^b$ means that both the R$^a$ group and the R$^b$ group are selected from the radicals of the above-detailed formulae R$^1$-1 to R$^1$-86, preferably R$^1$-1. The further assignments apply correspondingly.

Examples of suitable compounds of the invention are the structures of the following formulae 1 to 51 shown below:

Formula 1

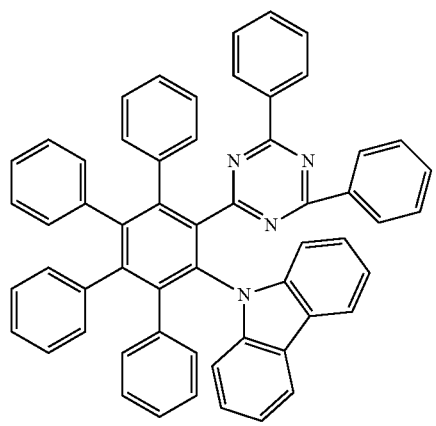

Formula 2

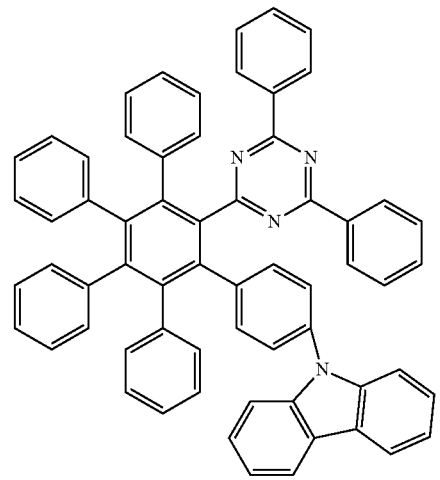

Formula 3

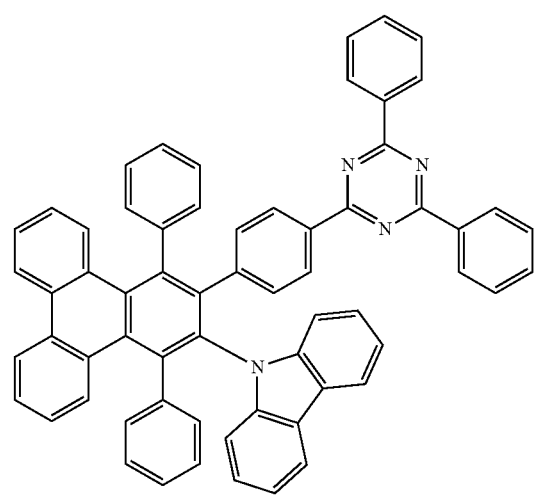

Formula 4

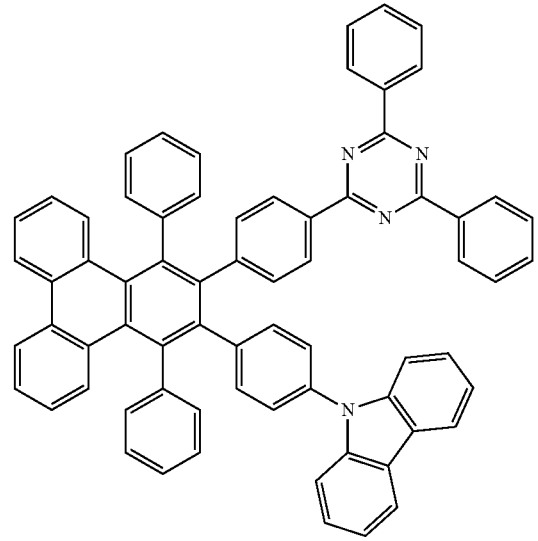

Formula 5
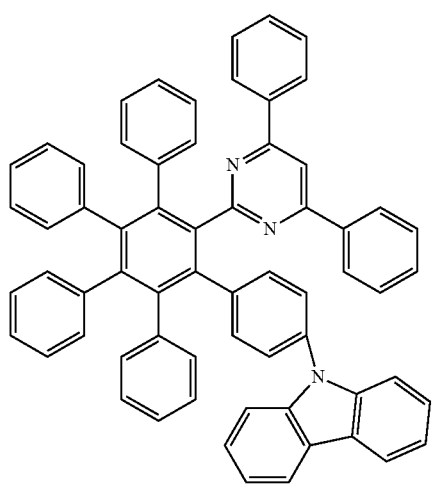
Formula 6
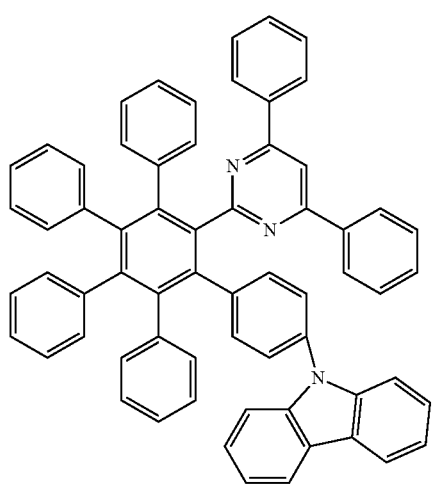
Formula 7
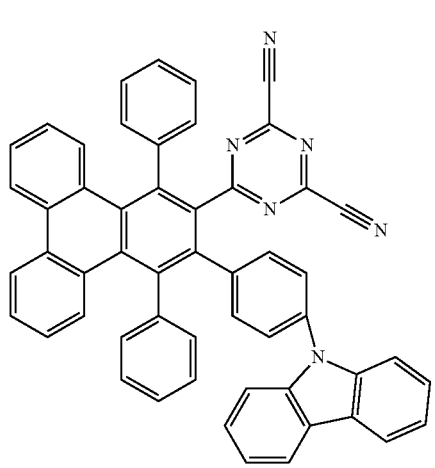
Formula 8
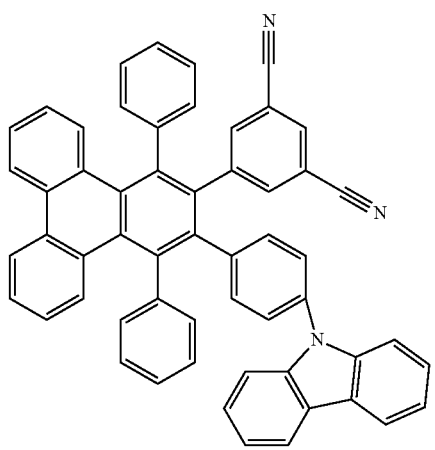
Formula 9
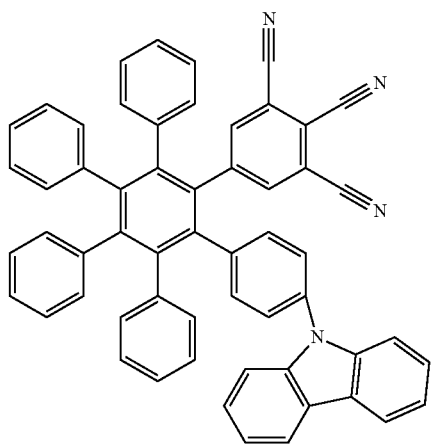
Formula 10
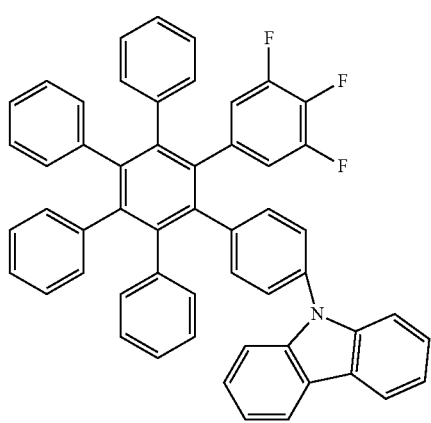

Formula 11
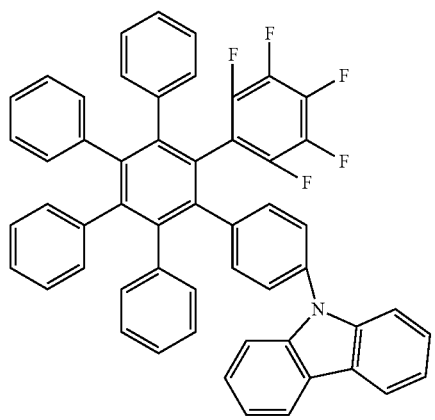
Formula 12
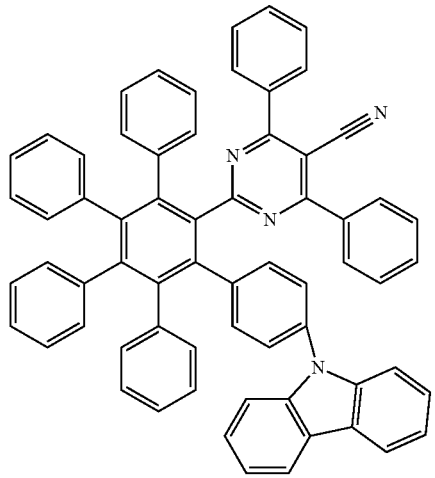
Formula 13
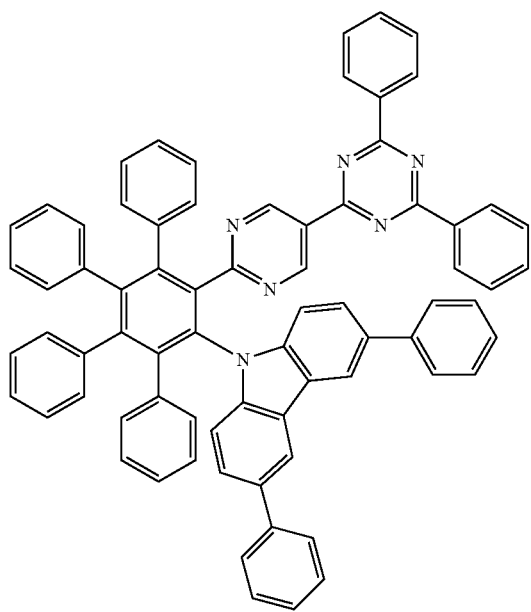
Formula 14
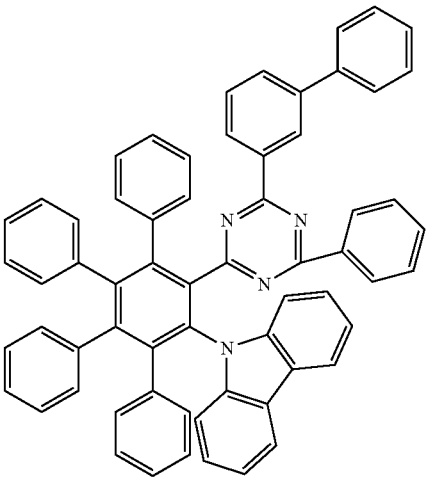
Formula 15
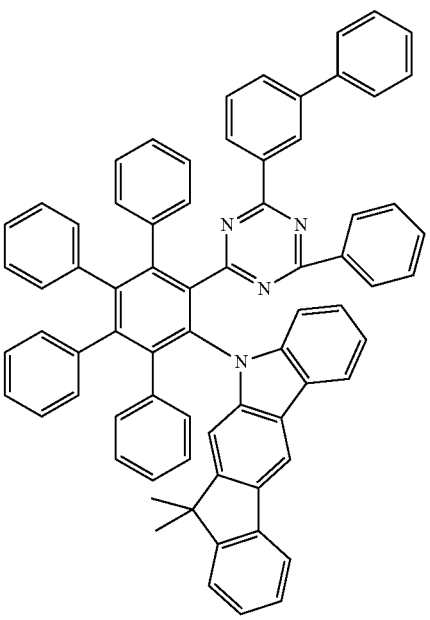
Formula 16
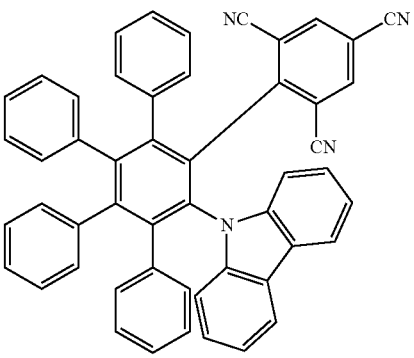

Formula 17
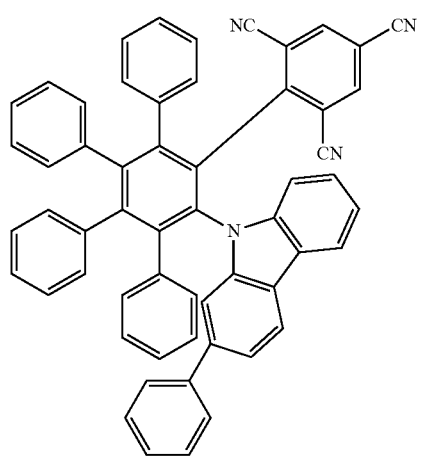
Formula 18
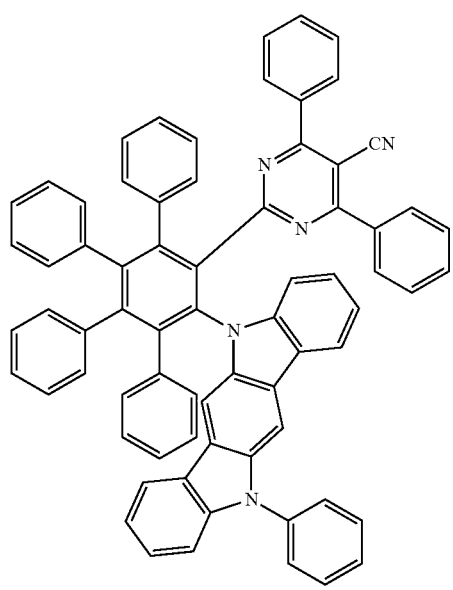
Formula 19
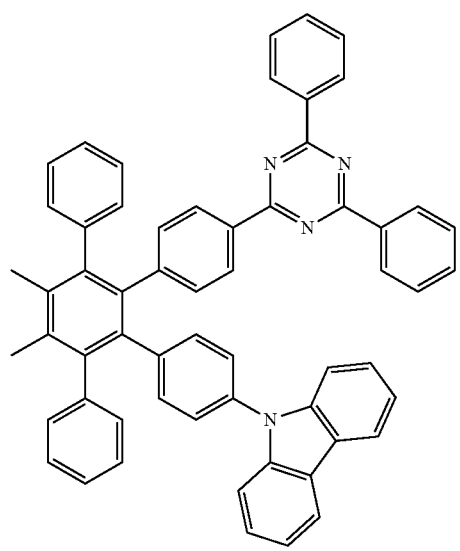
Formula 20
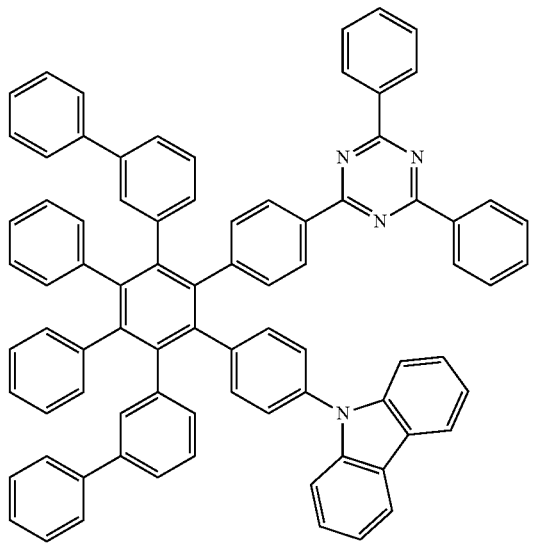
Formula 21
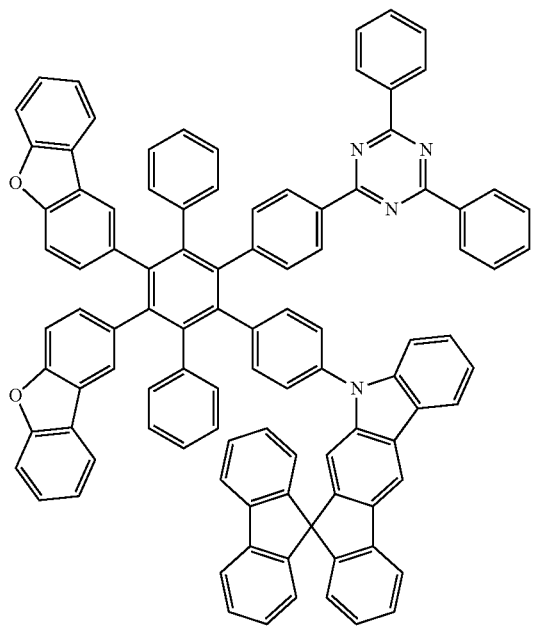

Formula 22
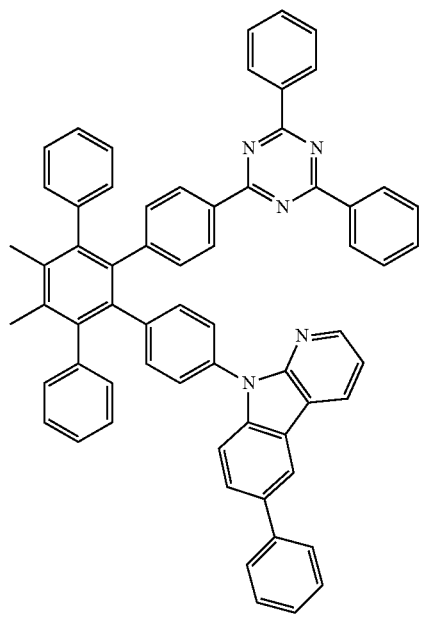
Formula 23
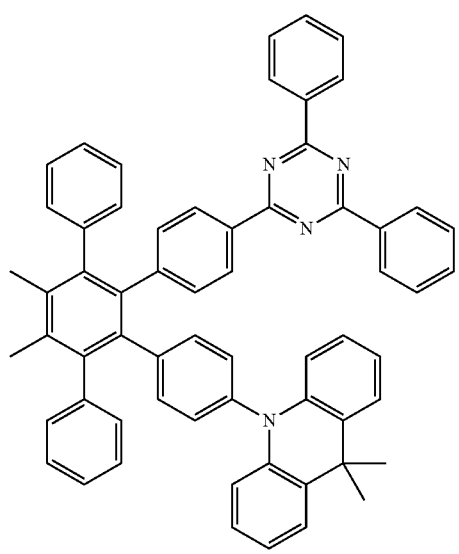
Formula 24
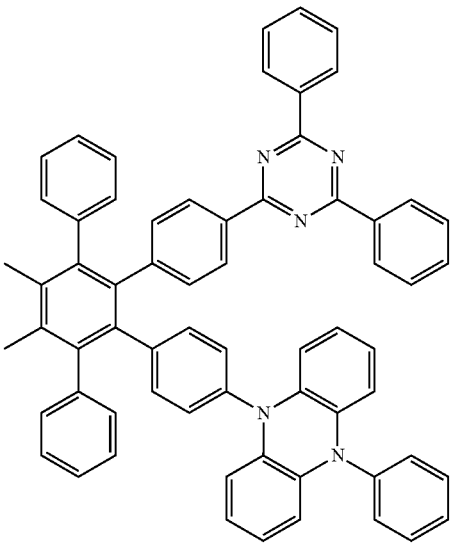
Formula 25
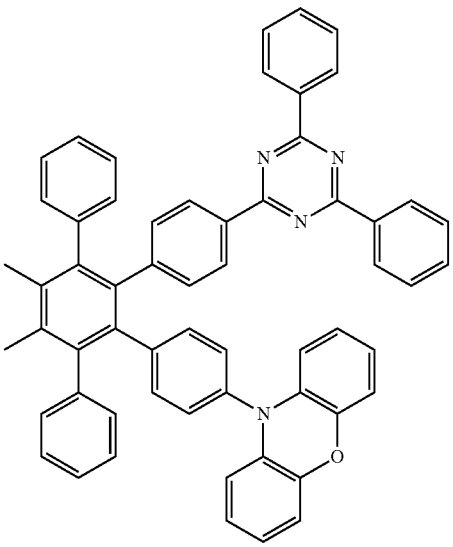

Formula 26
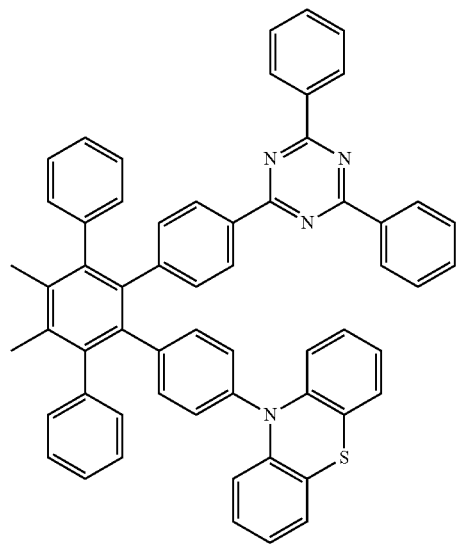
Formula 27
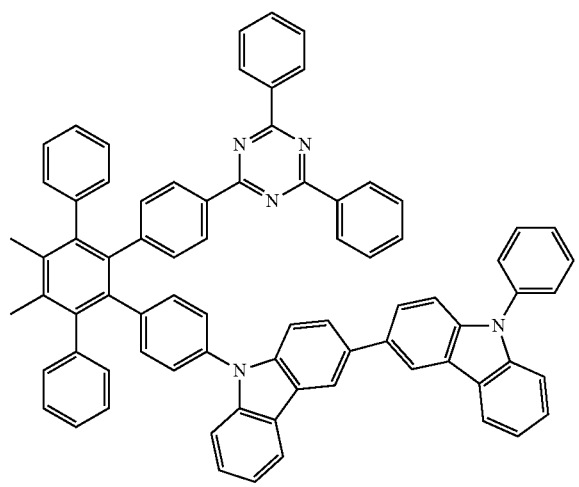
Formula 28
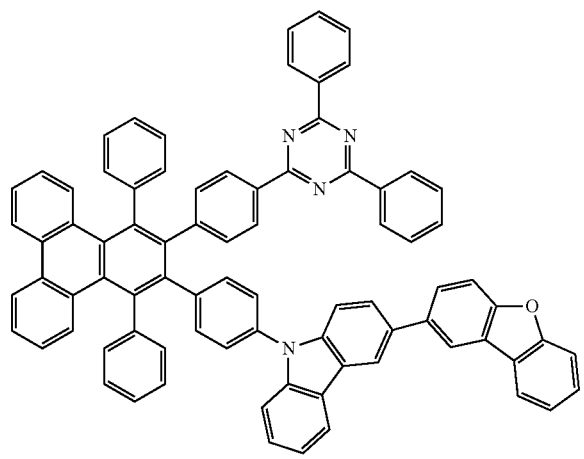
Formula 29
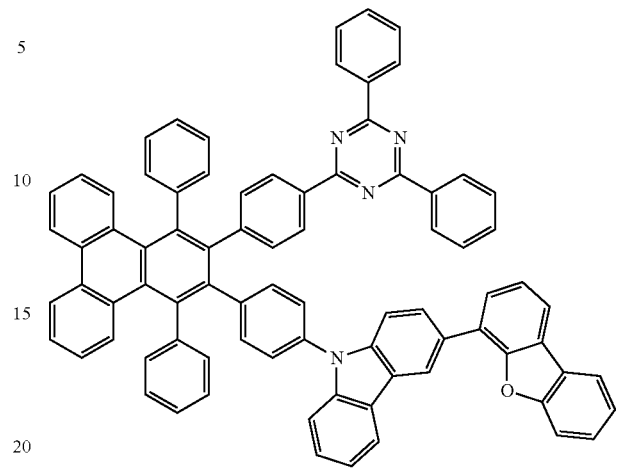
Formula 30
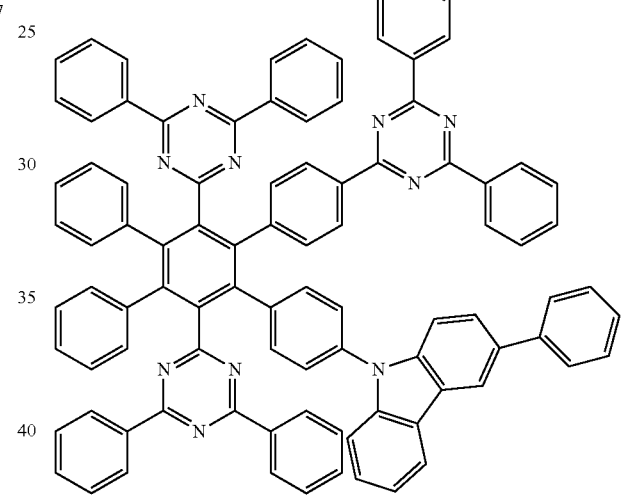
Formula 31
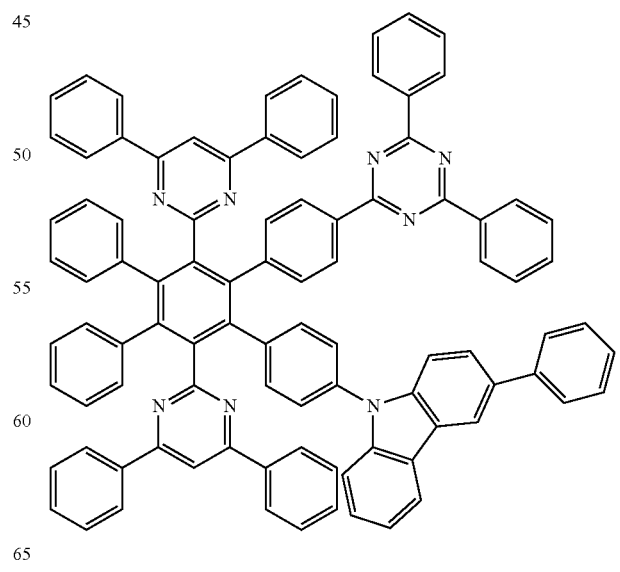

Formula 32
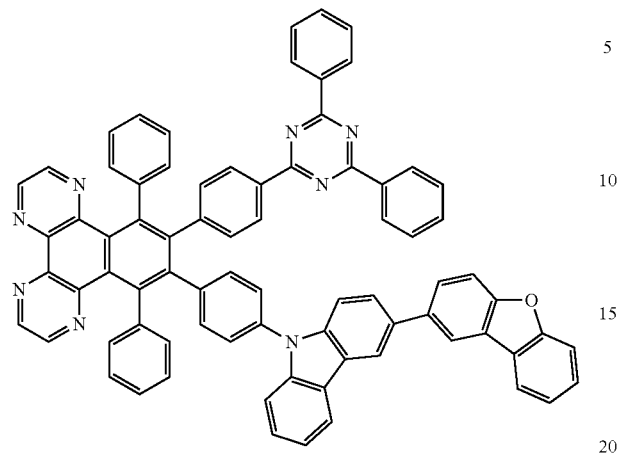
Formula 33
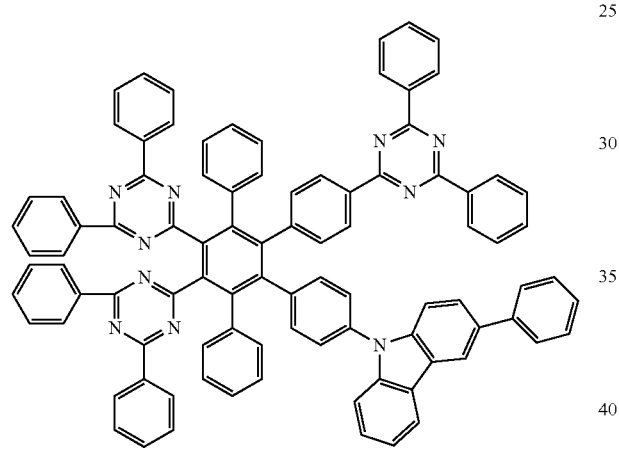
Formula 34
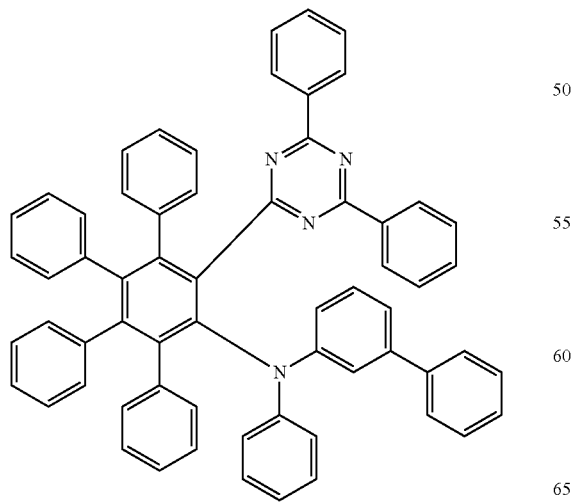
Formula 35
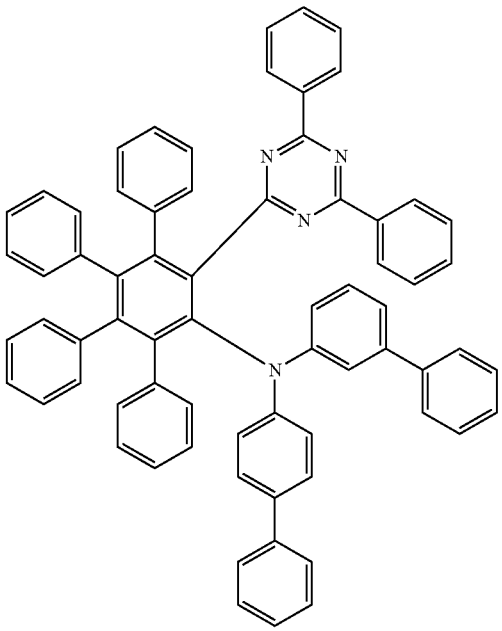
Formula 36
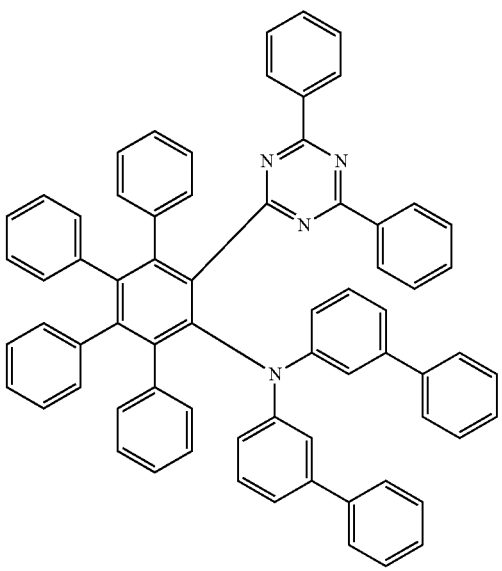

Formula 37
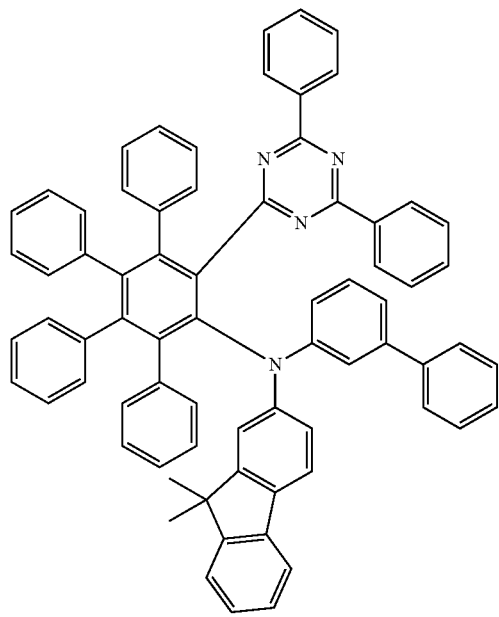
Formula 38
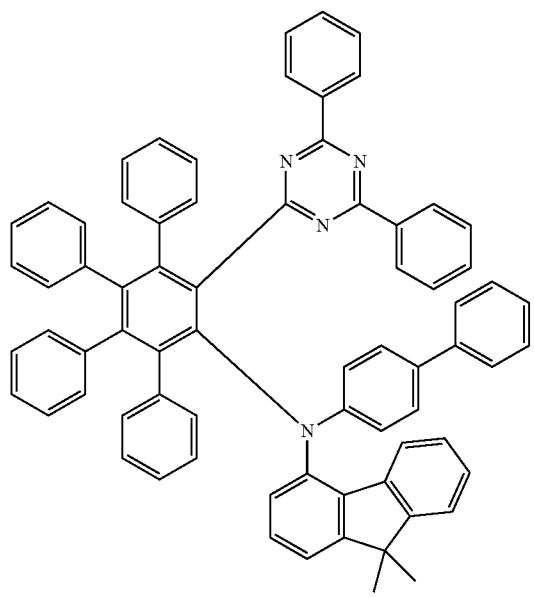
Formula 39
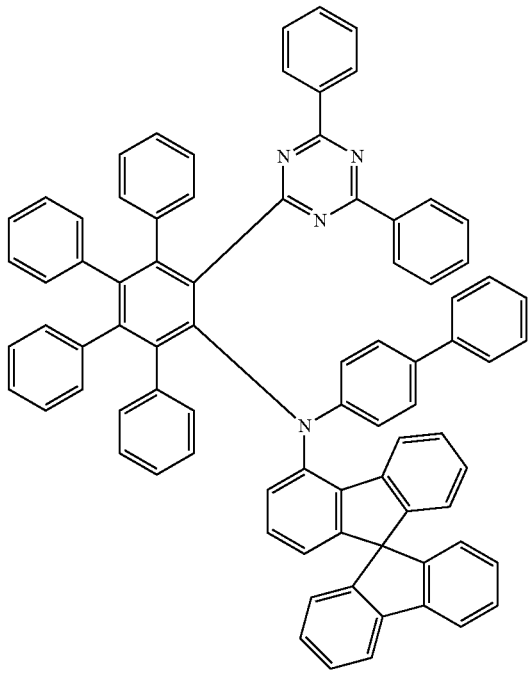
Formula 40
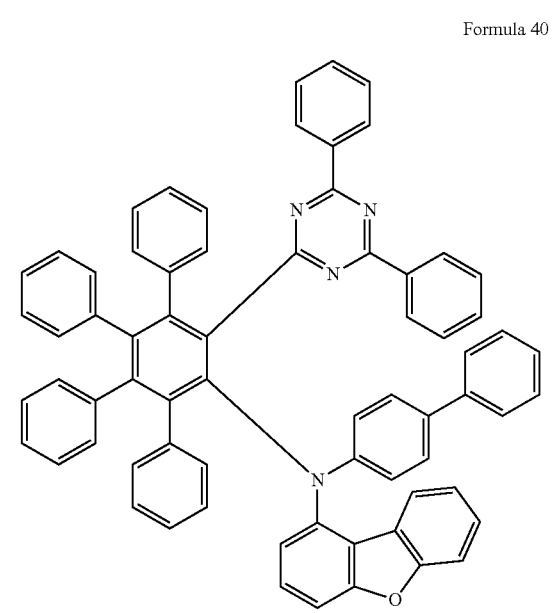

Formula 41
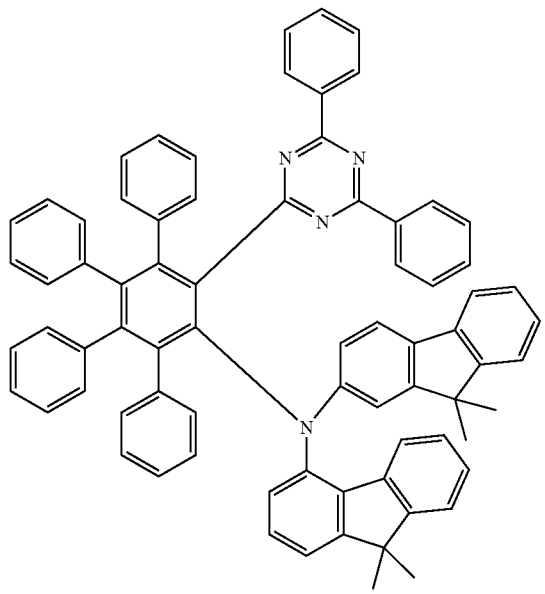
Formula 42
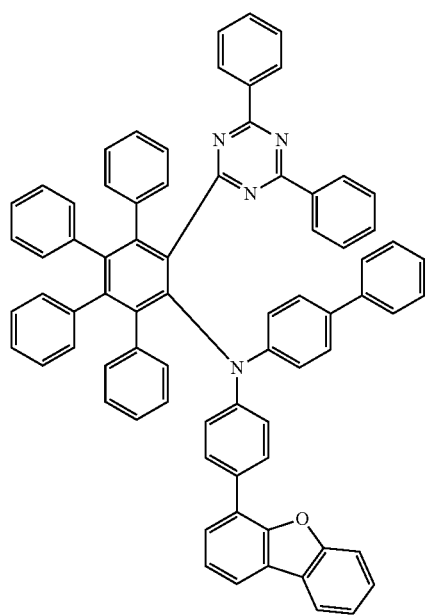
Formula 43
Formula 44

Formula 45
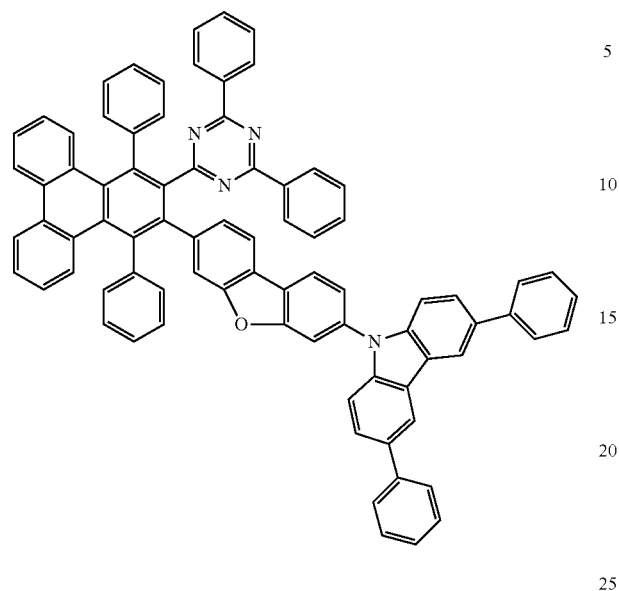
Formula 46
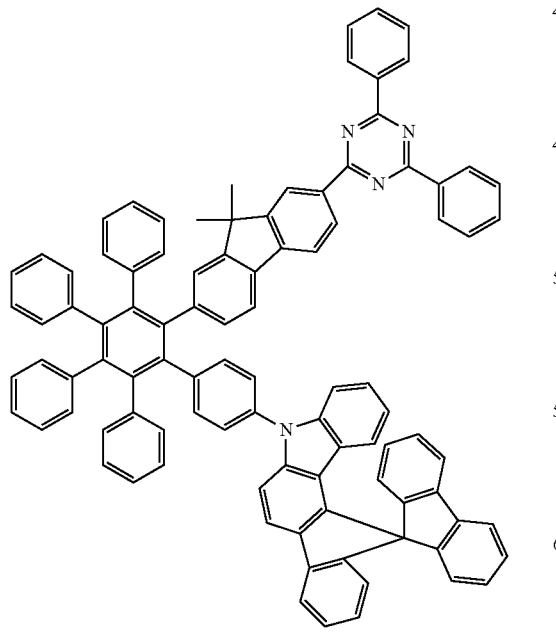
Formula 47
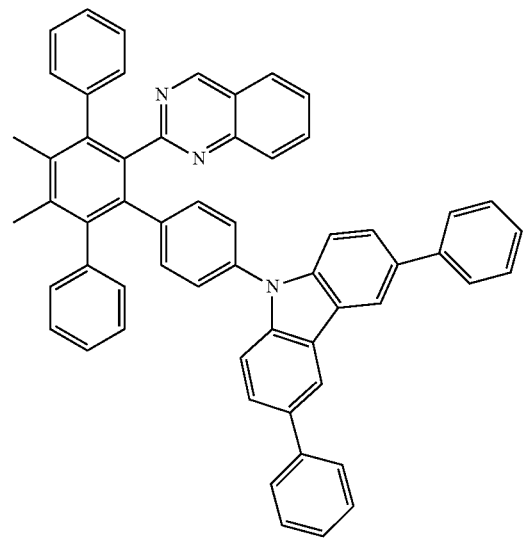
Formula 48
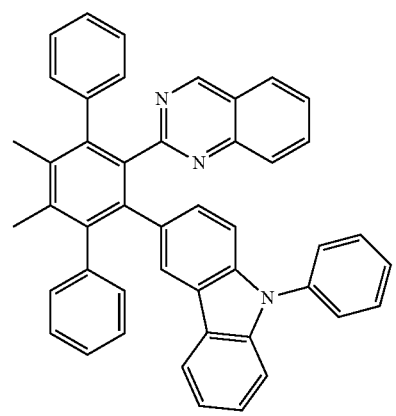
Formula 49
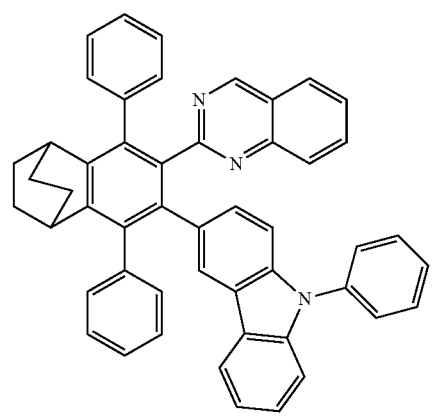

Formula 50

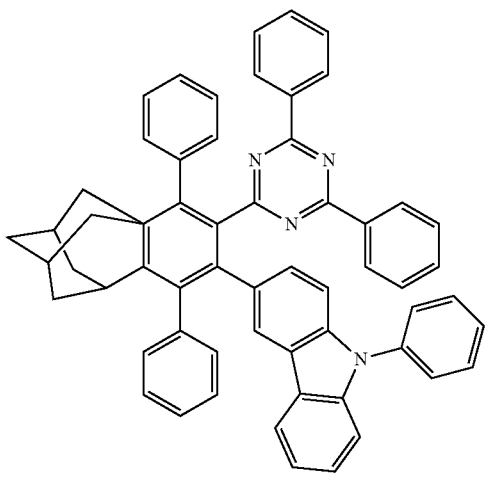

Formula 51

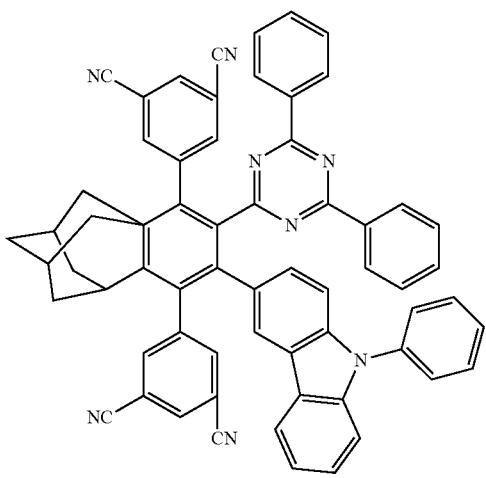

Preferred embodiments of compounds of the invention are recited specifically in the examples, these compounds being usable alone or in combination with further compounds for all purposes of the invention.

Provided that the conditions specified in claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds comprising at least one structure of formula (I), in which a compound comprising at least one donor group is joined to an acceptor group in a coupling reaction.

Suitable compounds having a donor group are in many cases commercially available, and the starting compounds detailed in the examples are obtainable by known processes, and so reference is made thereto.

Preferably, a cyclopentadienone derivative can be reacted with an alkyne derivative, which can be effected in a Diels-Alder reaction. The Diels-Alder product then reacts with elimination of CO to give a compound of the invention.

This reaction is advantageous especially if the $Ar^a$, $Ar^b$, $R^a$ and $R^b$ groups represent aryl or heteroaryl groups.

It is possible here to obtain corresponding alkyne derivatives of compounds that preferably comprise a donor group and/or an acceptor group by reaction of compounds containing corresponding reactive groups with aromatic or heteroaromatic alkyne compounds. Coupling reactions suitable for this purpose, for example Suzuki coupling, are common knowledge, and the reaction known as the Sonogashira reaction has been found to be particularly useful for this purpose. The reaction conditions for a Suzuki coupling or a Sonogashira reaction are widely known in the technical field, and the examples give valuable pointers in this connection.

The reactive reactant compounds for use as reactant for a Suzuki coupling or a Sonogashira reaction can be obtained, for example, by known halogenations, preferably brominations, from known aryl or heteroaryl compounds.

These compounds can be reacted with further aryl compounds by known coupling reactions, the necessary conditions for this purpose being known to the person skilled in the art, and detailed specifications in the examples give support to the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

It is possible by these processes, if necessary followed by purification, for example recrystallization or sublimation, to obtain the compounds of the invention comprising structures of formula (I) in high purity, preferably more than 99% (determined by means of $^1$H NMR and/or HPLC).

The compounds of the invention may also have suitable substituents, for example relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in a sufficient concentration, in order to be able to process the compounds from solution. These soluble compounds are of particularly good suitability for processing from solution, for example by printing methods. In addition, it should be emphasized that the compounds of the invention comprising at least one structure of the formula (I) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (I) or compounds of the invention, wherein one or more bonds of the compounds of the invention or of the structures of the formula (I) to the polymer, oligomer or dendrimer are present. According to the linkage of the structures of the formula (I) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the general formula (I) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (–)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, especially a phosphorescent dopant, and/or a further matrix material. This further compound may also be polymeric.

The present invention therefore still further provides a composition comprising a compound of the invention and at least one further organically functional material. Functional materials are generally the organic or inorganic materials introduced between the anode and cathode. Preferably, the organically functional material is selected from the group consisting of fluorescent emitters, phosphorescent emitters, host materials, electron transport materials, electron injection materials, hole conductor materials, hole injection materials, electron blocker materials, hole blocker materials, wide band gap materials and n-dopants.

The present invention therefore also relates to a composition comprising at least one compound comprising structures of formula (I) or the preferred embodiments recited above and hereinafter and at least one matrix material. The matrix material is also referred to as host material. In this context, the compound of the invention may have properties of a matrix material or of an emitter. If the compound comprising structures of formula (I) or the preferred embodiments recited above and hereinafter is used as matrix material, a host material other than the compounds of the invention will especially also be used herein as further matrix material. According to a particular aspect of the present invention, the further matrix material has hole-transporting properties.

The matrix material may especially be selected according to the nature of the electronic device, especially of the use of the compound of the invention. If the compound of the invention is used, for example, as emitter, for example in organic electroluminescent devices or organic light-emitting electrochemical cells, the host material preferably has a greater energy gap than the compound comprising structures of formula (I) which is used in accordance with the invention as fluorescent TADF material.

Preferably, the host material acts as electron or hole conductor or as a combined electron/hole conductor.

In one embodiment, the absorption spectrum of the compound of the invention used as fluorescent TADF material overlaps with the photoluminescence spectrum of the at least one host material, such that an energy transition is possible between the compound of the invention and the at least one host material. In principle, it is possible to use host materials as known or customary for employment in OLECs or OLEDs.

In one embodiment, the host material is a hole- or electron-transporting material.

In one embodiment, the host material has a lowest triplet state $T_1^H$ having an energy higher than the energy of the lowest triplet state $T_1$ of the uncharged organic luminescent compound.

Suitable host materials are selected, for example, from anthracenes, benzanthracenes, indenofluorenes, fluorenes, spiro-bifluorenes, phenanthrenes, dehydrophenanthrenes, dehydrofluorenes, thiophenes, triazines, carbazoles, indenocarbazoles, indolocarbazoles, pyrimidines, lactams, benzophenones, triarylamines, quinazolines and imidazoles.

Very preferred host materials are selected from indenofluorenes, fluorenes, spiro-bifluorenes, phenanthrenes, dehydrophenanthrenes, dehydrofluorenes, thiophenes, triazines, carbazoles, indenocarbazoles, indolocarbazoles, pyrimidines, lactams, benzophenones, triarylamines, quinazolines and imidazoles.

In one embodiment the composition comprises four or fewer host materials, in a further embodiment three or fewer host materials, and in a further embodiment one or two host materials.

Particularly preferred host materials are selected from the group of the oligoarylenes, for example 2,2',7,7'-tetraphenylspirobifluorene which is described in EP 676461, or dinaphthylanthracene. Preference is given to oligoarylenes comprising fused aromatic groups, for example phenanthrene, tetracene, coronene, chrysene, fluorene, spirofluorene, perylene, phthaloperylene, naphthaloperylene, decacyclene, rubrene, oligoarylenevinylenes, for example 4,4'-bis(2,2-diphenylethenyl)-1,1'-biphenyl (DPVBi) or 4,4-bis-2,2-diphenylvinyl-1,1-spirobiphenyl (spiro-DPVBi), as described in EP 676461.

Further suitable host materials are polypodal metal complexes as described, for example, in WO 2004/081017, for example metal complexes with 8-hydroxyquinoline, such as aluminium(III) tris(8-hydroxyquinoline) (Alq$_3$), or bis-(2-methyl-8-quinolinolato)-4-(phenylphenolinolato)aluminium, imidazole chelate compounds as described in US 2007/0092753 A1, and also quinoline-metal complexes, aminoquinoline-metal complexes, benzoquinoline-metal complexes, hole-transporting materials as described, for example, in WO 2004/058911, electron-transporting materials, especially ketones, phosphine oxides, sulfoxides as described, for example, in WO 2005/084081 and WO 2005/08408, atropisomers as described in WO 2006/048268, boronic acid derivatives as described, for example, in WO 2006/117052, or benzanthracenes as described in DE 102007024850.

Further suitable host materials are oligoarylenes such as naphthalene, anthracene, benzanthracene and pyrene, and also atropisomers of these compounds, ketones, phosphine oxides and sulfoxides. Preferably, the host material is selected from the class of the oligoarylenes, especially naphthalene, anthracene, benzanthracene and pyrene. An oligoaryl compound in the context of this invention is understood to mean a compound comprising at least three aryl or arylene groups joined to one another.

Further suitable host materials are selected from compounds of the formula (HM-1):

$Ar^5$—$(Ar^6)_p$—$Ar^7$     Formula (HM-1)

where:

$Ar^5, Ar^6, Ar^7$ are the same or different at each instance and are an aryl or heteroaryl group having 5 to 30 aromatic ring atoms, which may also be mono- or polysubstituted, p=1, 2 or 3;

where the sum total of the π electrons in the $Ar^5$, $Ar^6$, $Ar^7$ groups is at least 30 when p=1 and at least 36 if p=2 and at least 42 if p=3.

Within the host materials of the formula (HM-1), $Ar^6$ is preferably anthracene which may be substituted by one or more $R^1$ radicals, where the $Ar^5$ and $Ar^7$ groups are bonded at positions 9 and 10 in a further embodiment. More preferably, at least one of the $Ar^5$ and $Ar^7$ groups is a fused aryl group which is preferably selected from the group of 1- or 2-naphthyl, 2-, 3- or 9-phenanthrenyl or 2-, 3-, 4-, 5-, 6- or 7-benzanthracenyl, each of which may be mono- or polysubstituted by $R^1$. $R^1$ here is as defined above.

Suitable anthracene compounds are described, for example, in US 2007/0092753 A1 and US 2007/0252517 A1, for example 2-(4-methylphenyl)-9,10-di(2-naphthyl)anthracene, 9-(2-naphthyl)-10-(1,1'-biphenyl)anthracene and 9,10-bis[4-(2,2-diphenylethenyl)phenyl]anthracene, 9,10-diphenylanthracene, 9,10-bis(phenylethynyl)anthracene and 1,4-bis(9'-ethynylanthracenyl)benzene. Preference is also given to host materials having at least two anthracene groups (US 2008/0193796 A1), for example 10,10'-bis[1,1',4',1"]terphenyl-2-yl-9,9'-bisanthracenyl.

Further suitable host materials are derivatives of arylamines, styrylamines, fluorescein, perinone, phthaloperinone, naphthaloperinone, diphenylbutadiene, tetraphenylbutadiene, cyclopentadienes, tetraphenylcyclopentadiene, pentaphenylcyclopentadiene, coumarin, oxadiazole, bisbenzoxazoline, oxazone, pyridine, pyrazine, imines, benzothiazoles, benzoxazoles, benzimidazoles (US 2007/0092753 A1), for example 2,2',2"-(1,3,5-phenylene)tris[1-phenyl-1H-benzimidazole], aldazines, stilbenes, styrylarylene derivatives, for example 9,10-bis[4-(2,2-diphenylethenyl)phenyl]anthracene, and distyrylarylene derivatives (U.S. Pat. No. 5,121,029), diphenylethylene, vinylanthracene, diaminocarbazole, pyran, thiopyran, diketopyrrolopyrrole, polymethine, merocyanine, acridone, quinacridone, cinnamic esters and fluorescent dyes.

In a preferred embodiment, arylamine and styrylamine derivatives are used as host materials, for example 4,4'-bis[N-(1-naphthyl)-N-(2-naphthyl)amino]biphenyl (TNB).

Oligoarylenes suitable as host materials are described, for example, in US 2003/0027016 A1, U.S. Pat. No. 7,326,371 B2, US 2006/043858 A, U.S. Pat. No. 7,326,371 B2, US 2003/0027016 A1, WO 2007/114358, WO 2008/145239, JP 3148176 B2, EP 1009044, US 2004/018383, WO 2005/061656 A1, EP 0681019B1, WO 2004/013073A1, U.S. Pat. No. 5,077,142, WO 2007/065678, and US 2007/0205412 A1.

Compounds particularly preferred as host material are shown in the following formulae (HM-2) to (HM-8):

Formula (HM-2)

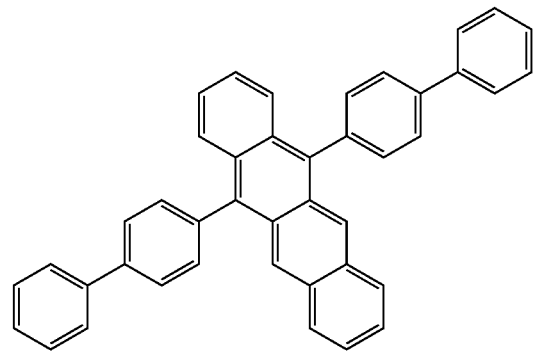

Formula (HM-3)

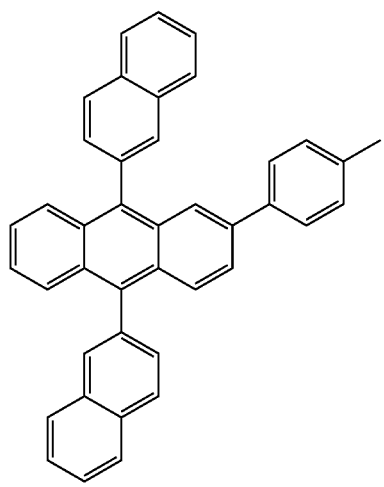

Formula (HM-4)

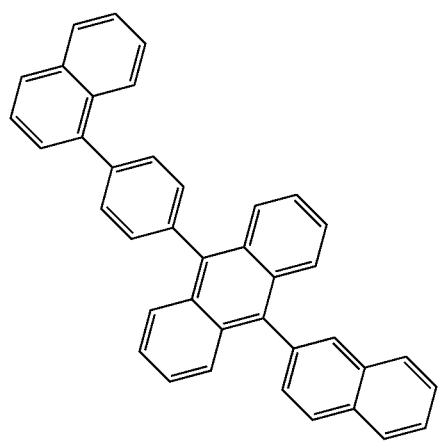

Formula (HM-5)

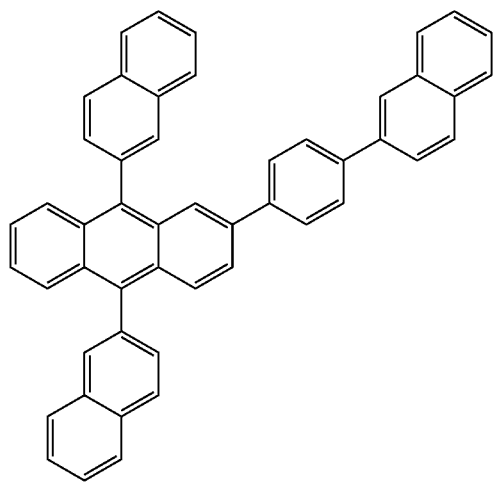

Formula (HM-6)

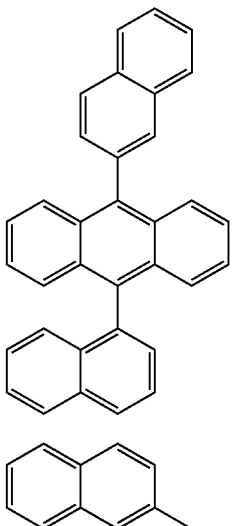

Formula (HM-7)

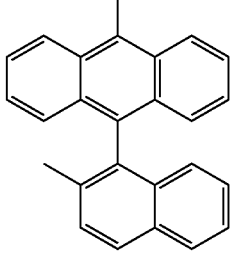

Formula (HM-8)

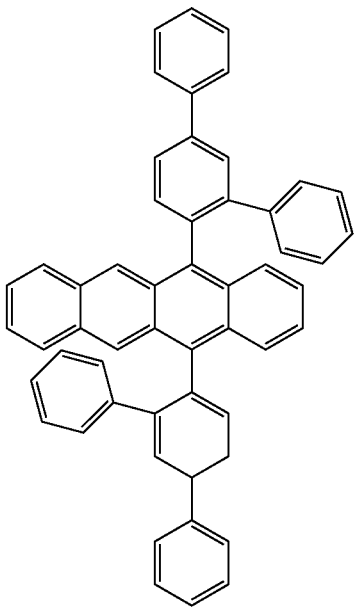

Further suitable host materials are spirobifluorene and derivatives thereof, for example spiro-DPVBi which is described in EP 0676461, or indenofluorene which is described in U.S. Pat. No. 6,562,485.

The combination of compounds of the invention which are used as emitters or as TADF material with the aforementioned host materials, in order to form an emitting layer in an OLEC, can be correspondingly supplemented with an electrolyte which provides mobile ions, as known from the prior art as described particularly in the introductory part of this application.

The present invention further provides a composition comprising at least one compound comprising at least one structure of formula (I) or the preferred embodiments recited above and hereinafter and at least one wide band gap material, a wide band gap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

$$HOMO(eV)=((HEh*27.212)-0.9899)/1.1206$$

$$LUMO(eV)=((LEh*27.212)-2.0041)/1.385$$

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09W" (Gaussian Inc.) and Q-Chem 4.1 (Q-Chem, Inc.).

In addition, a compound of the invention can be used as matrix material in combination with an emitter.

Therefore, the present invention also relates to a composition comprising at least one compound having structures of formula (I) or the preferred embodiments recited above and hereinafter and at least one fluorescent emitter, the term "fluorescent emitters" also being understood to mean fluorescent dopants. It may preferably be the case that the weight ratio of fluorescent emitter to compound, oligomer, polymer or dendrimer according to the present invention is in the range from 0.1% to 50% by weight, 1% to 20% by weight and 3% to 15% by weight.

The present invention also relates to a composition comprising at least one compound comprising structures of formula (I) or the preferred embodiments recited above and hereinafter and at least one phosphorescent emitter, the term "phosphorescent emitters" also being understood to mean phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2016/124304, WO 2016/015815, WO 2016/000803, WO 2015/117718, WO 2015/104045 and WO 2015/036074. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

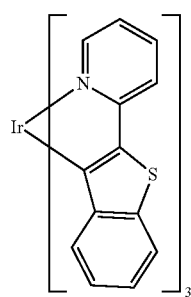
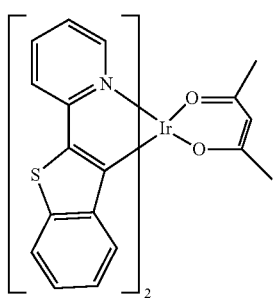
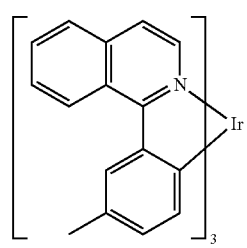
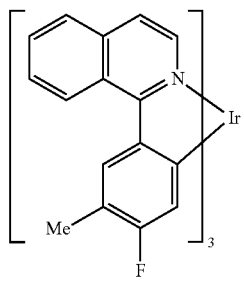
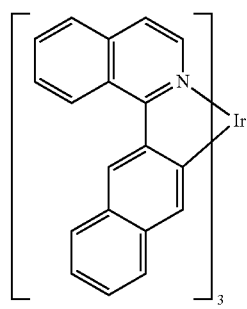
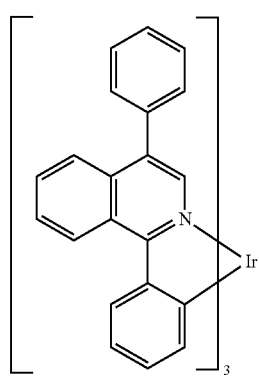
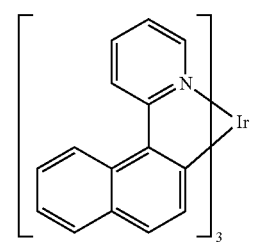
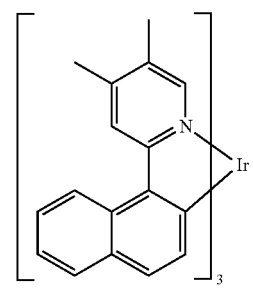
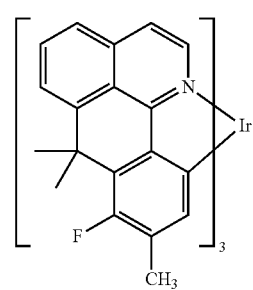
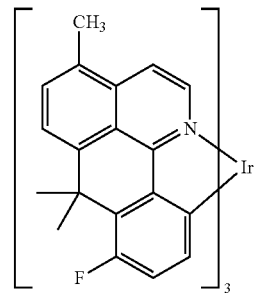

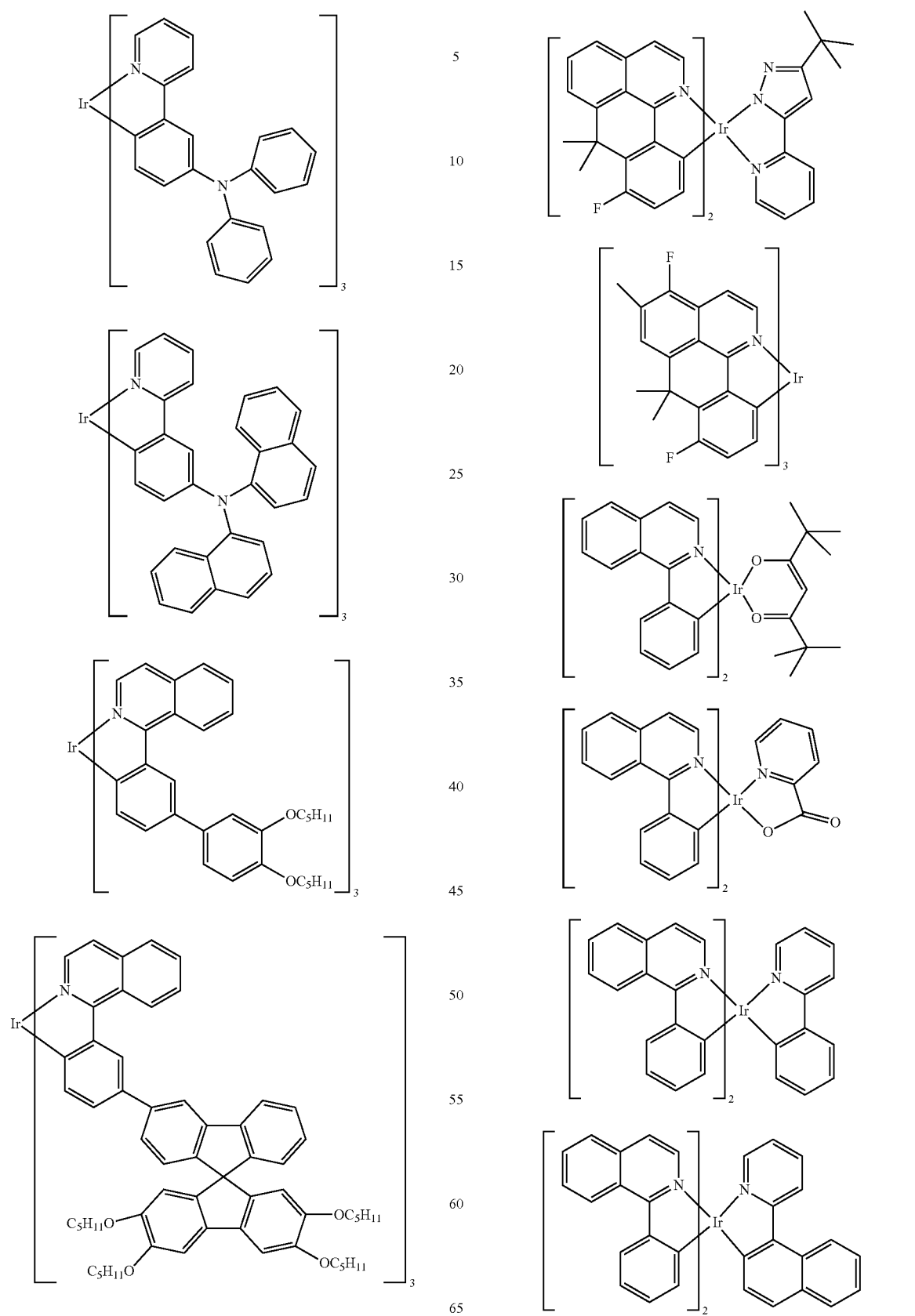

93
-continued
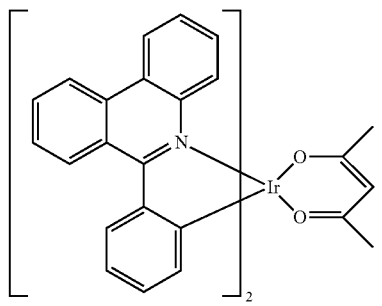
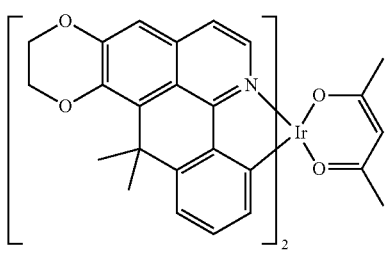
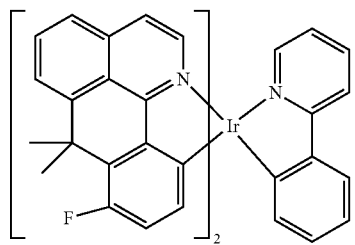
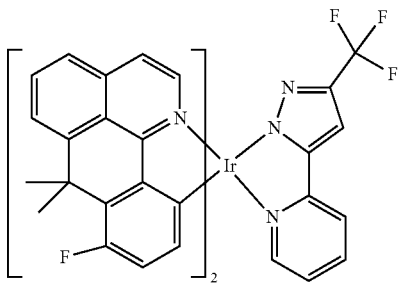
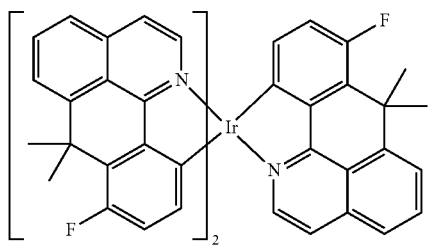
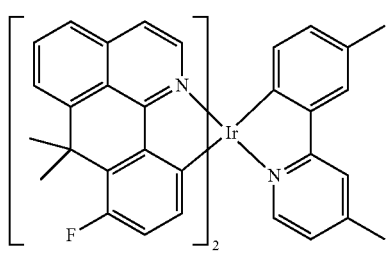
94
-continued
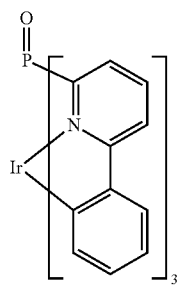
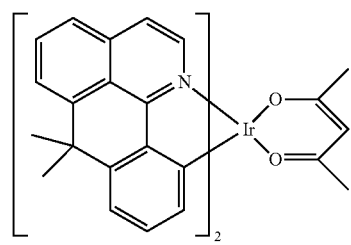
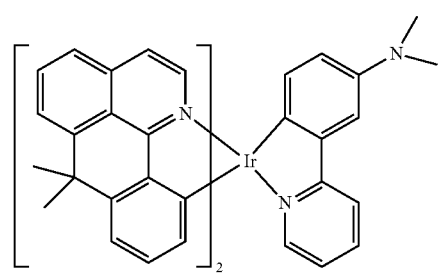
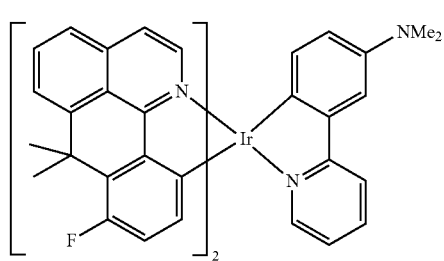
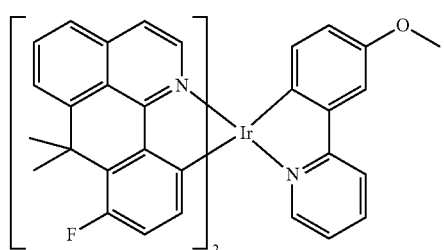
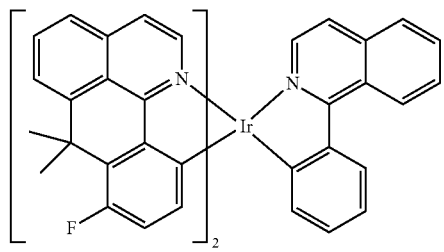

95
-continued
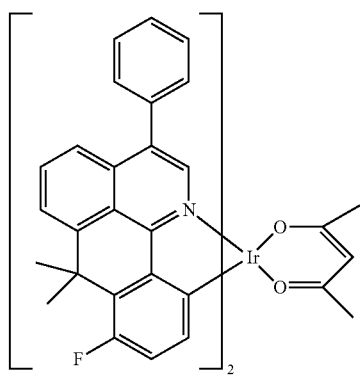
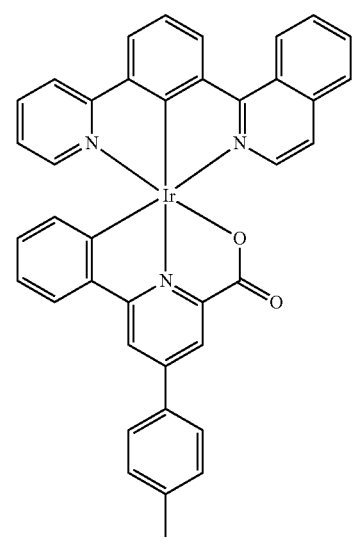
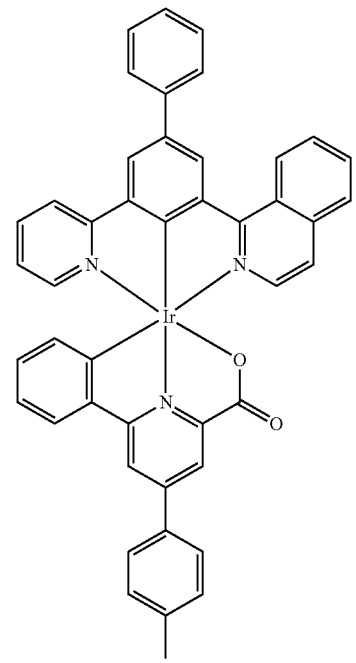
96
-continued
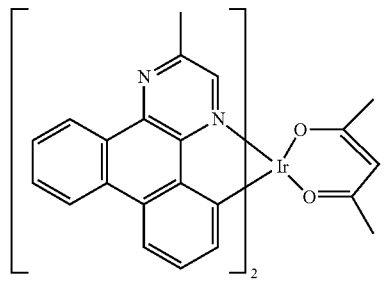
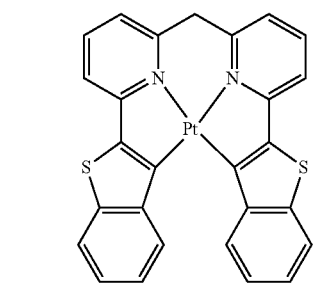
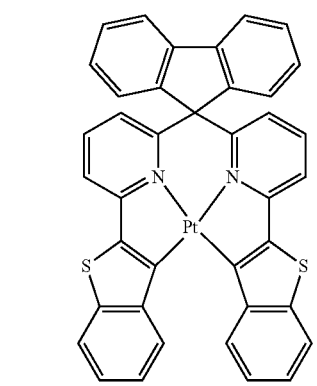
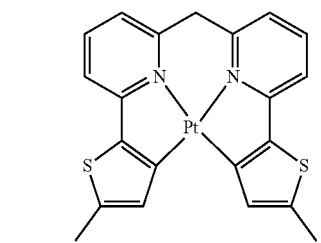
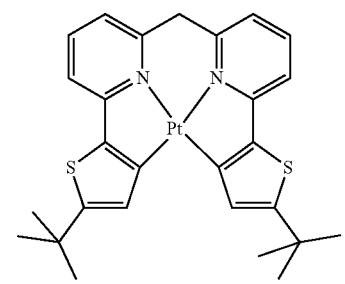

97
-continued
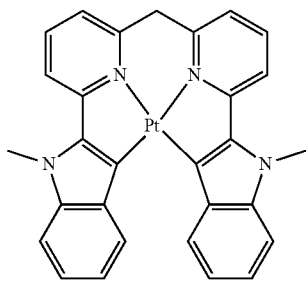
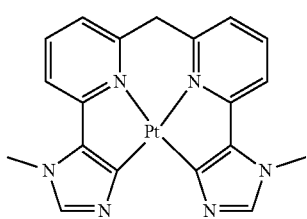
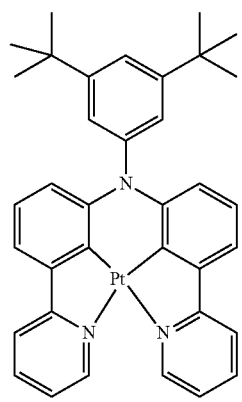
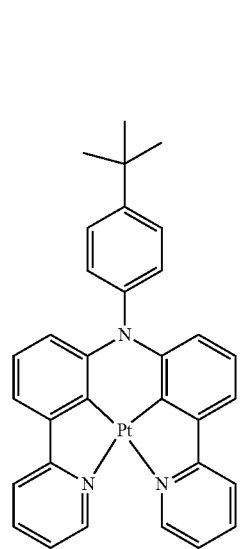
98
-continued
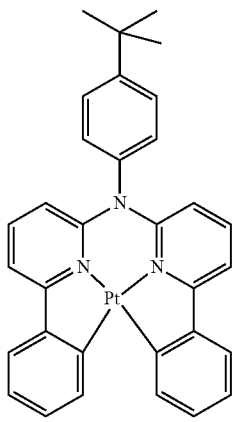
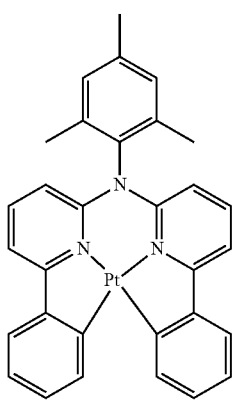
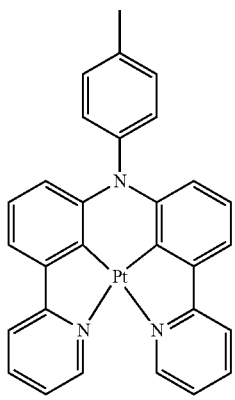

99
-continued
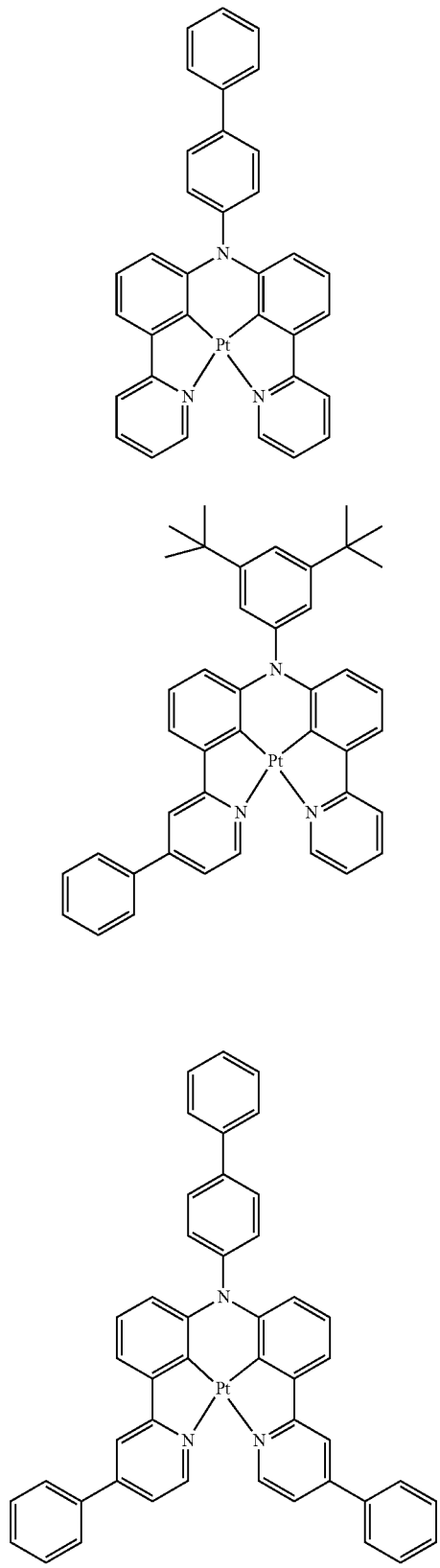
100
-continued
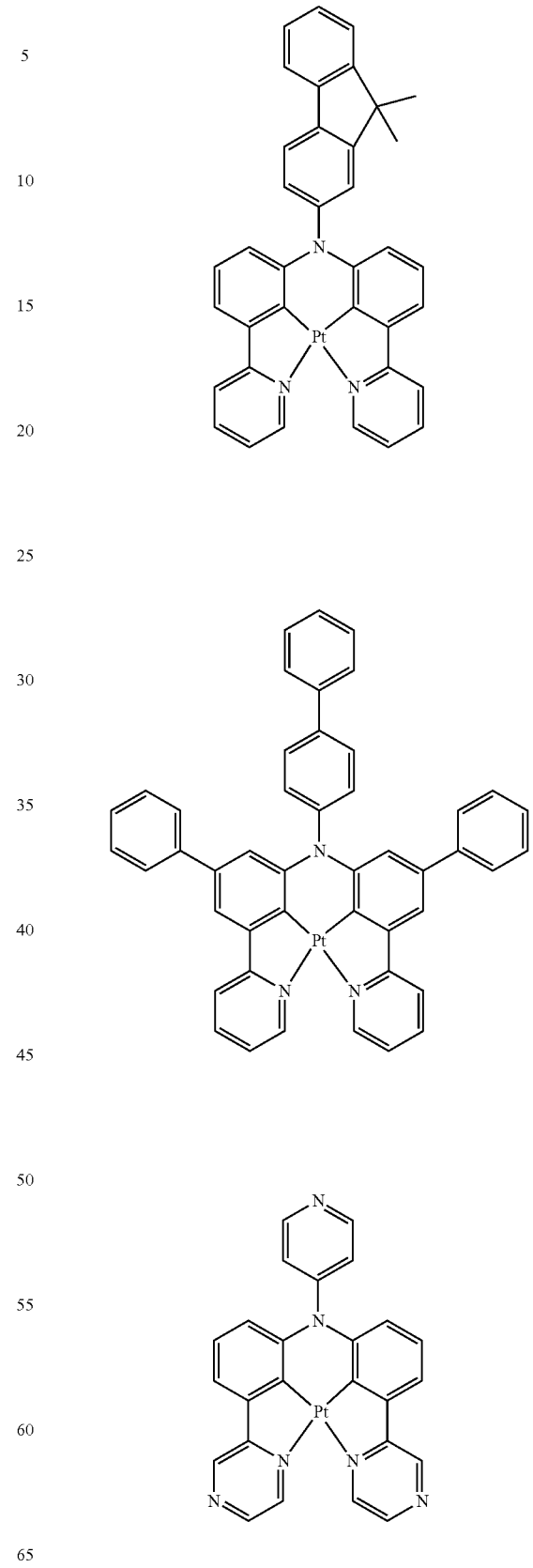

| 101 -continued | 102 -continued |
|---|---|
| 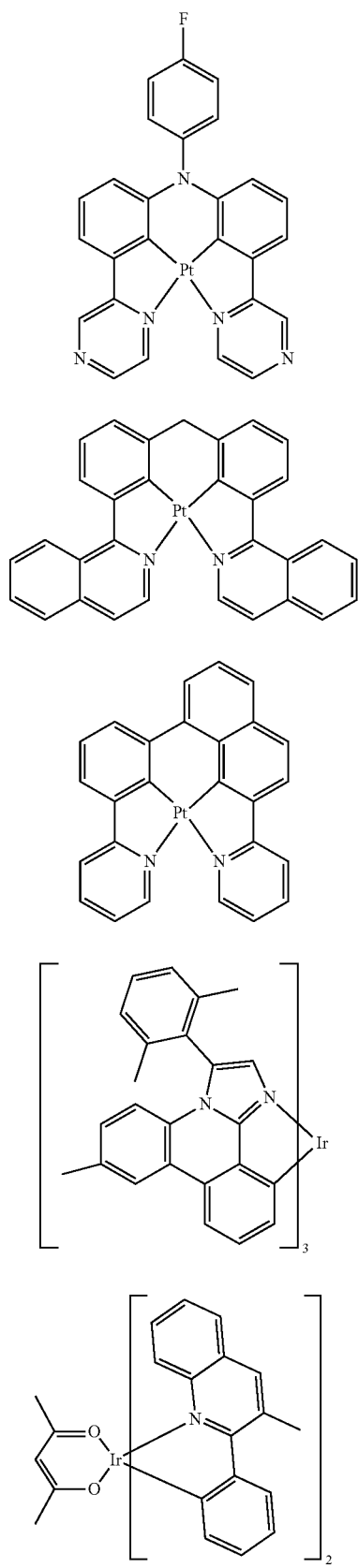 | 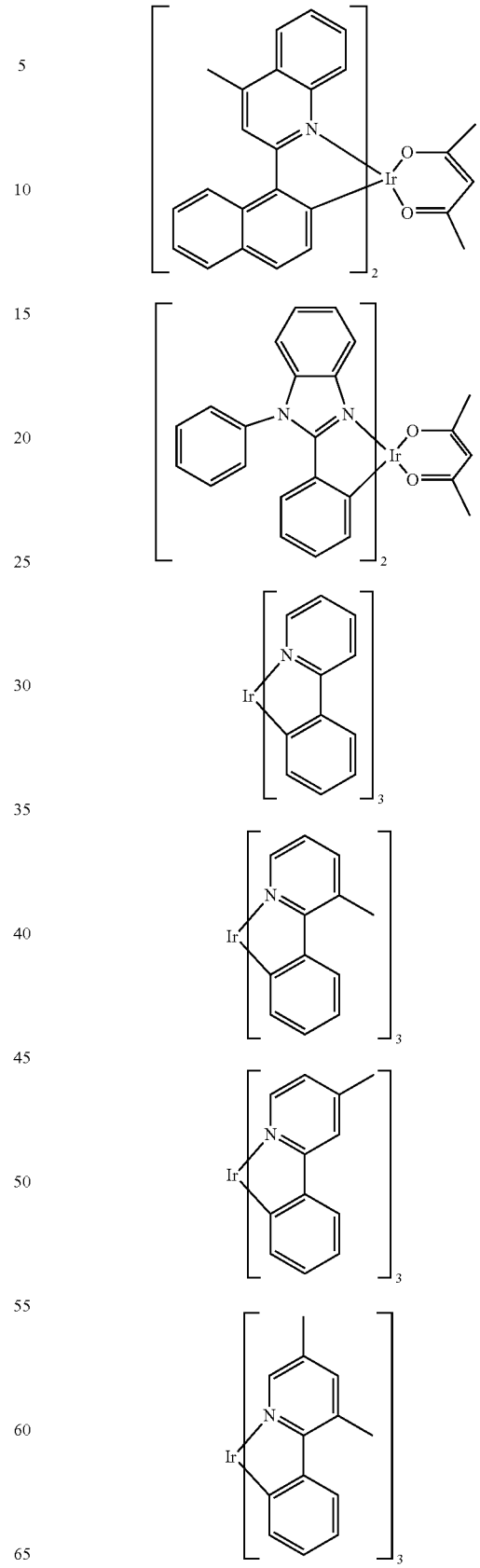 |

103
-continued
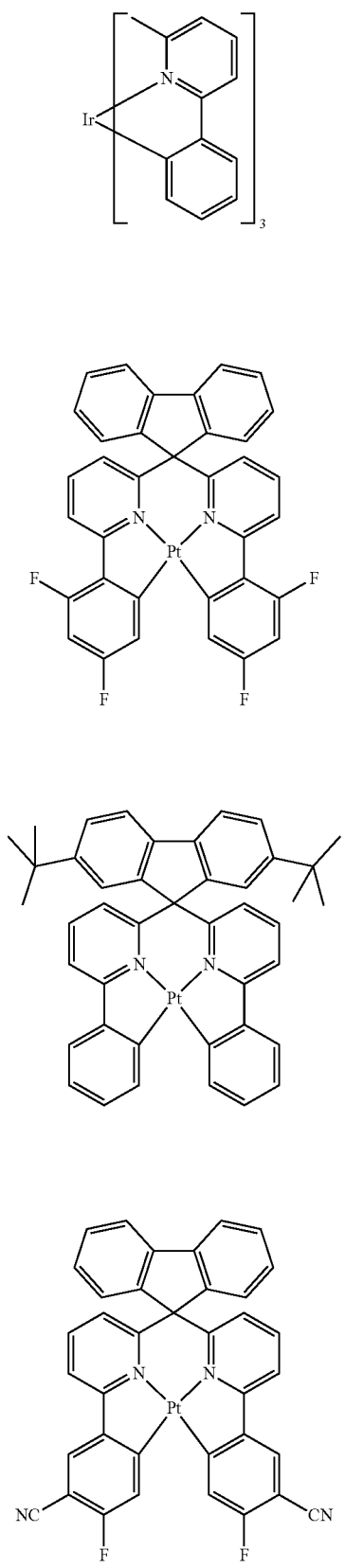
104
-continued
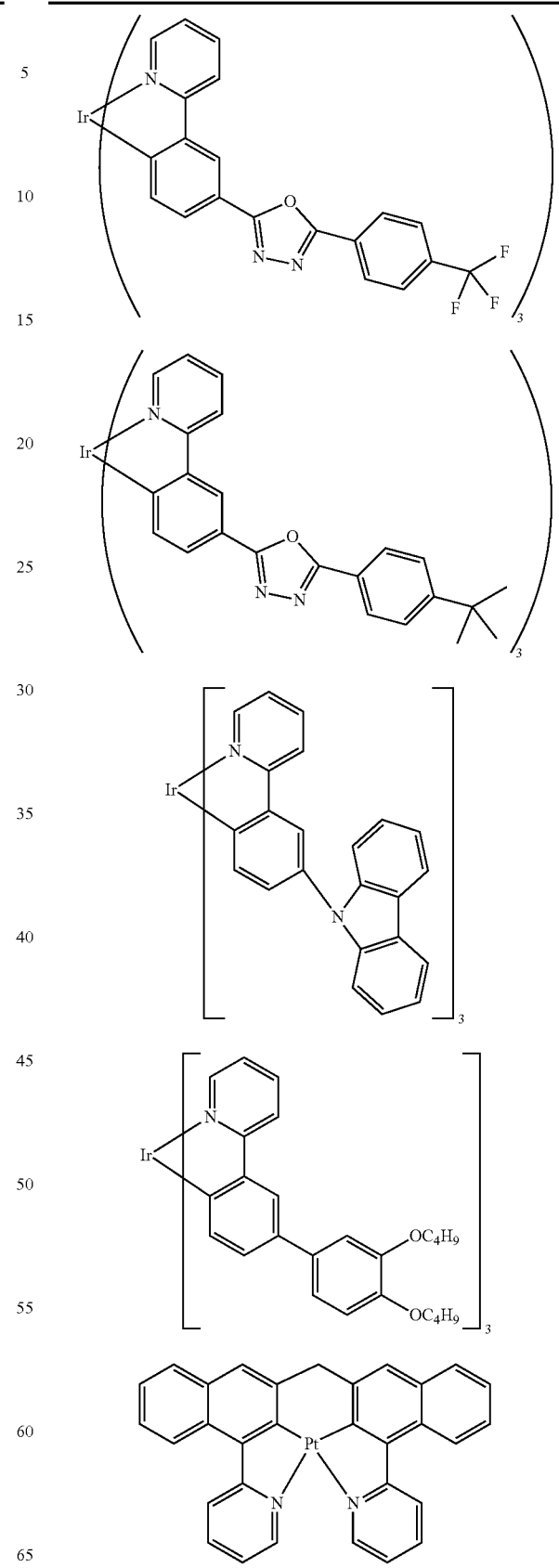

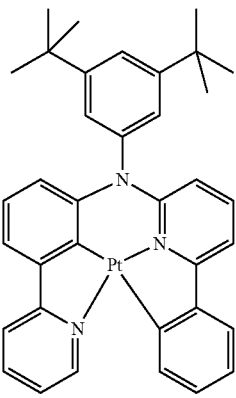
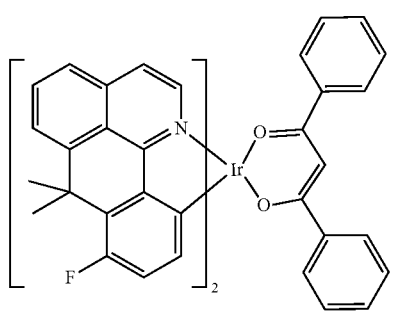
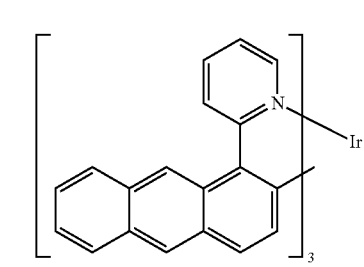
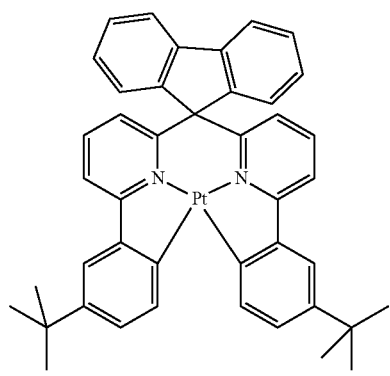
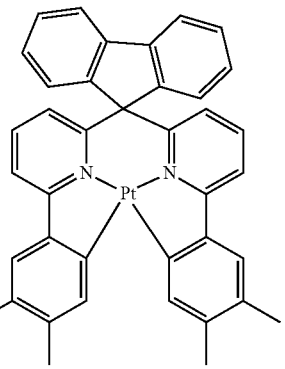
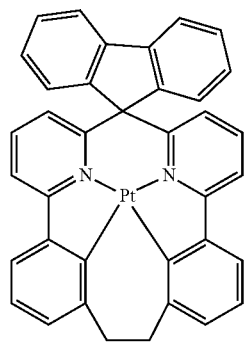
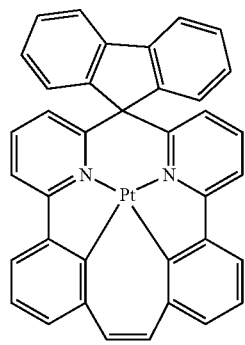
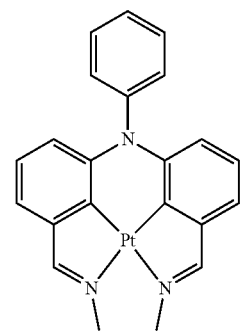

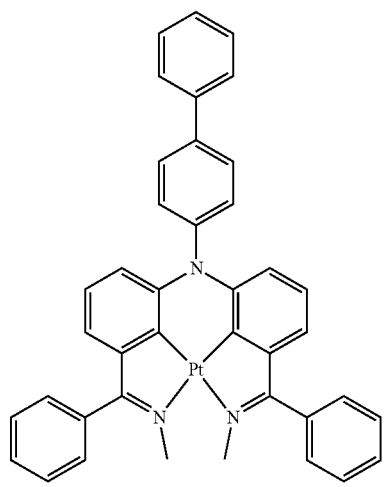
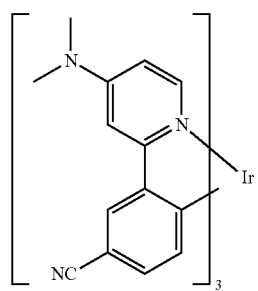
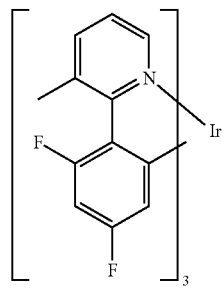
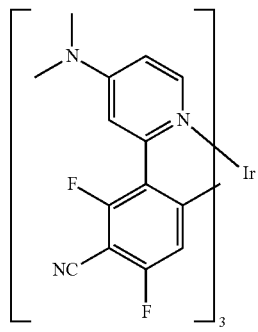
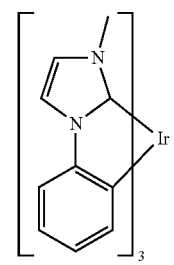
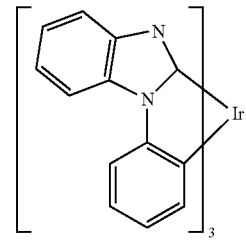
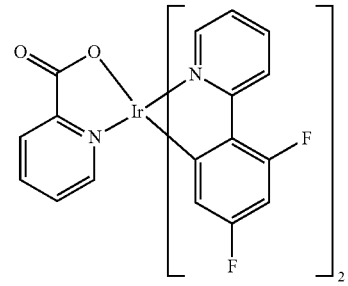
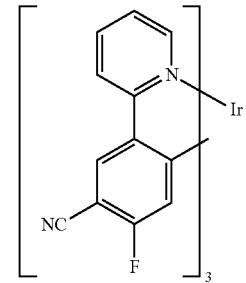
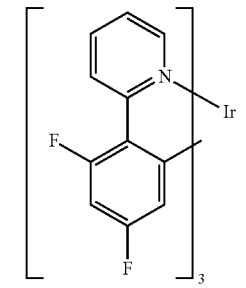

| 109 -continued | 110 -continued |
|---|---|
| 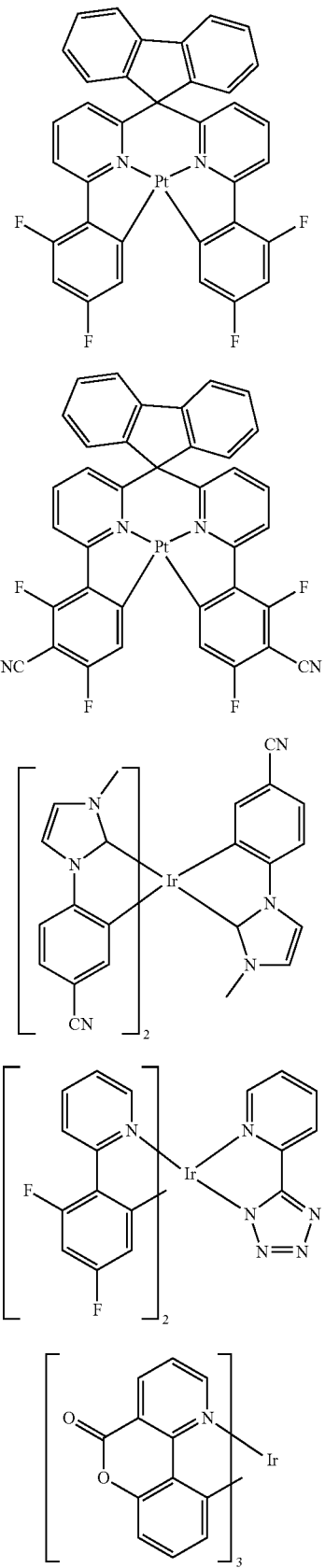 | 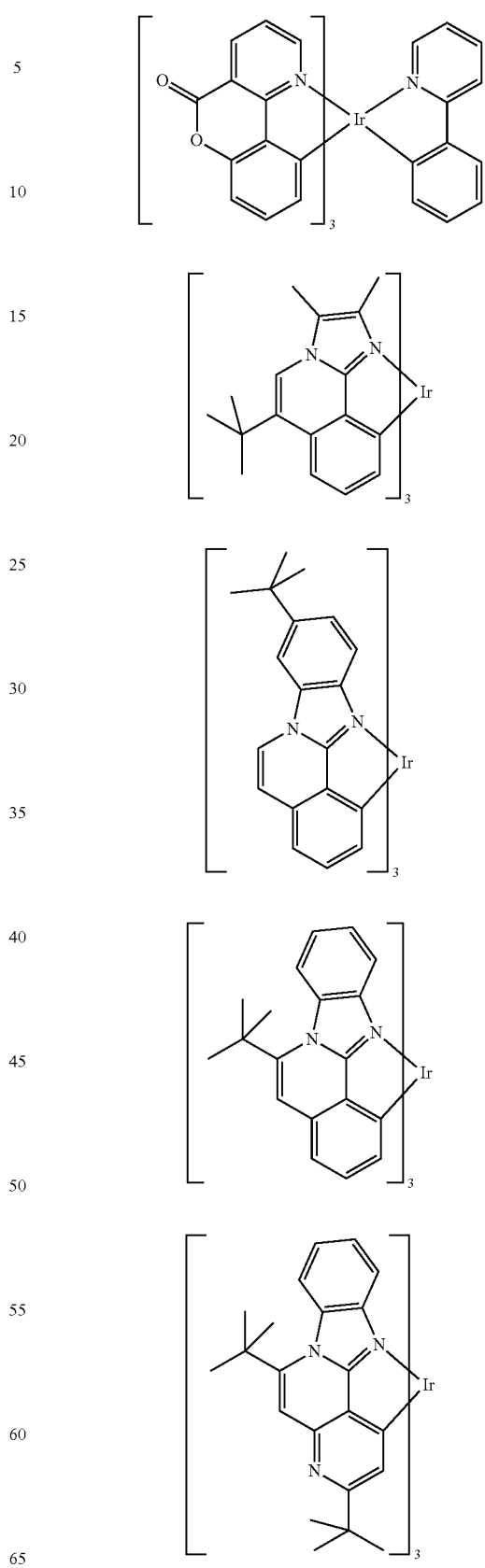 |

111
-continued
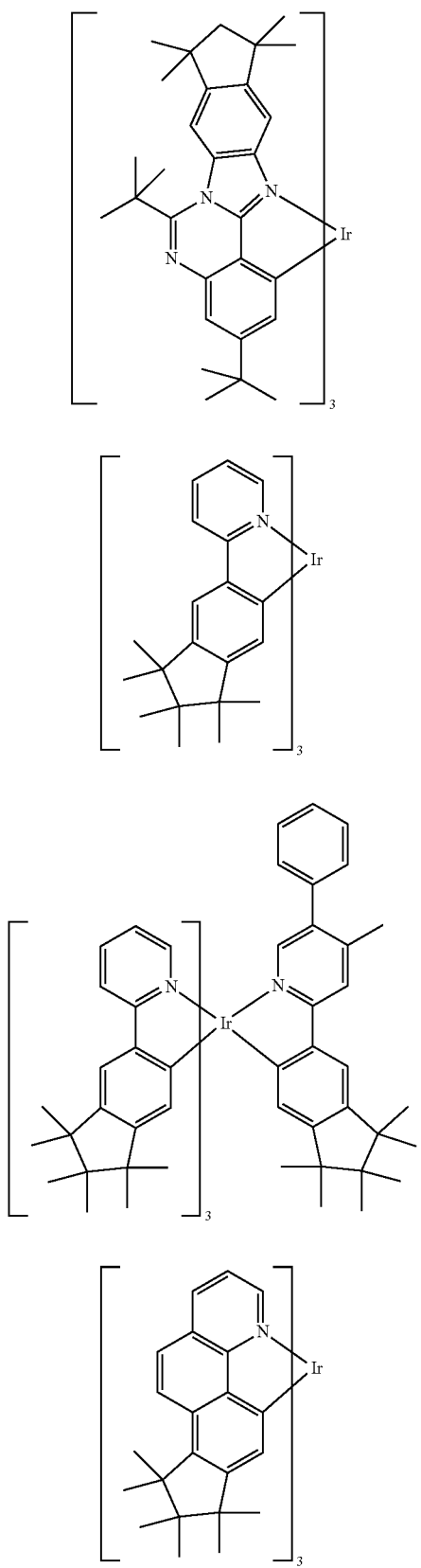
112
-continued
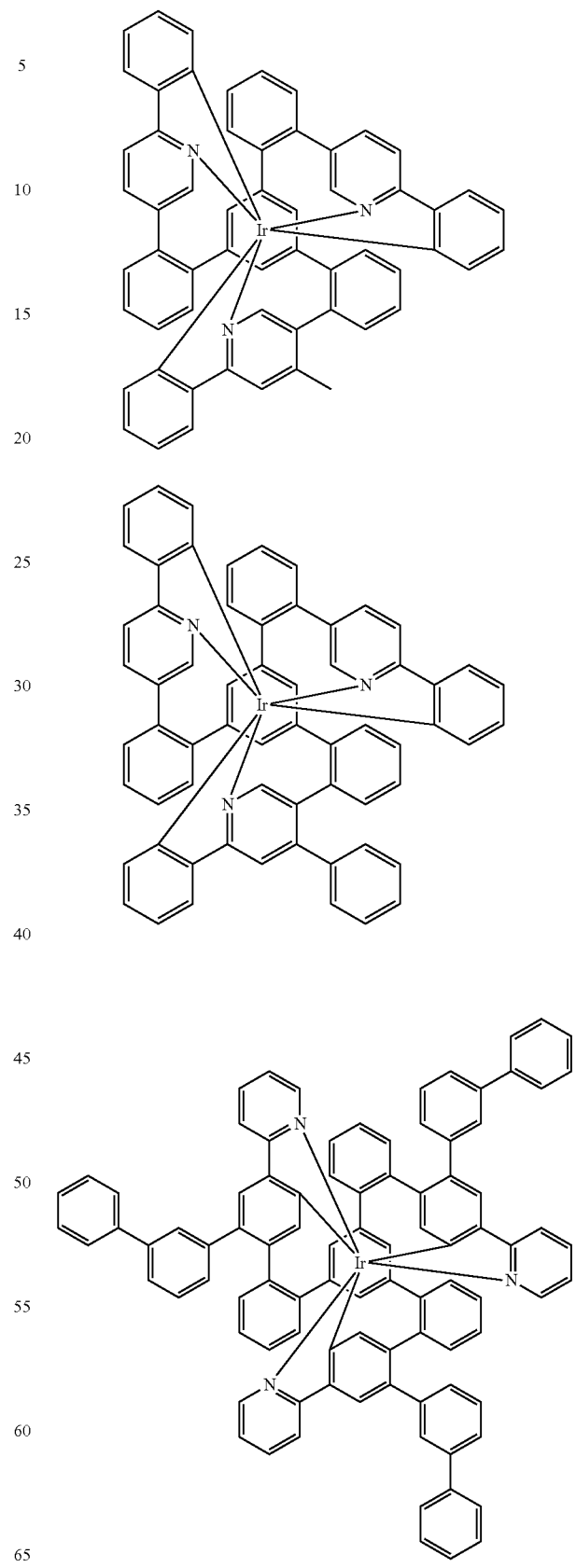

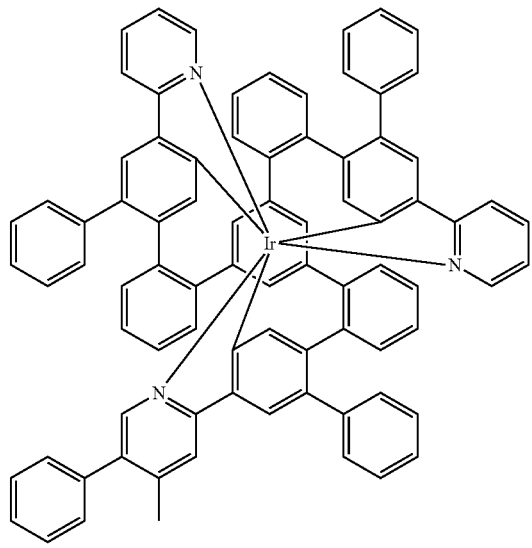
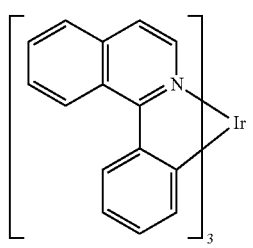
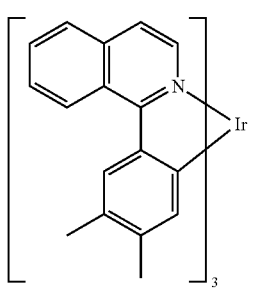
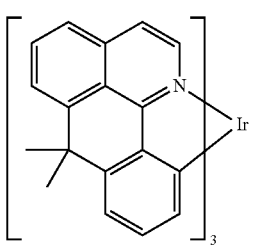
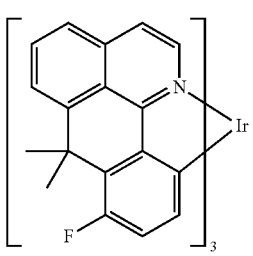
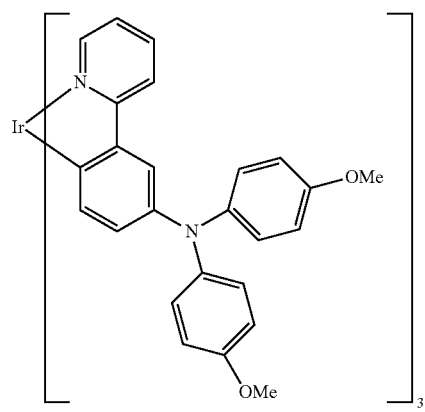
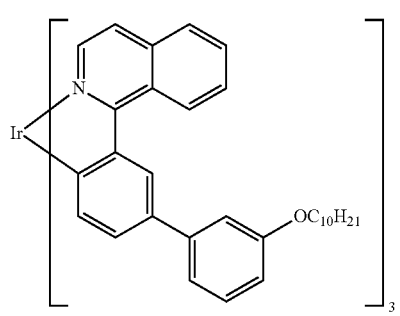
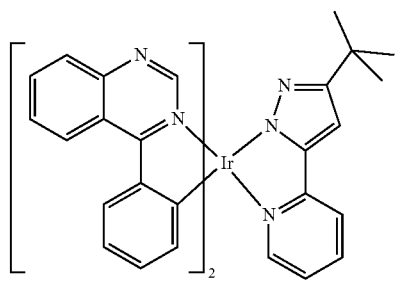
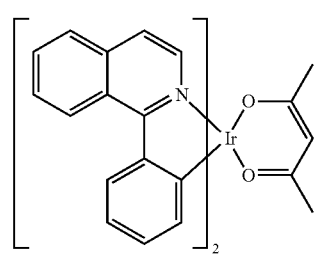
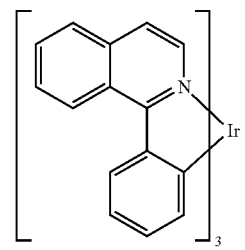

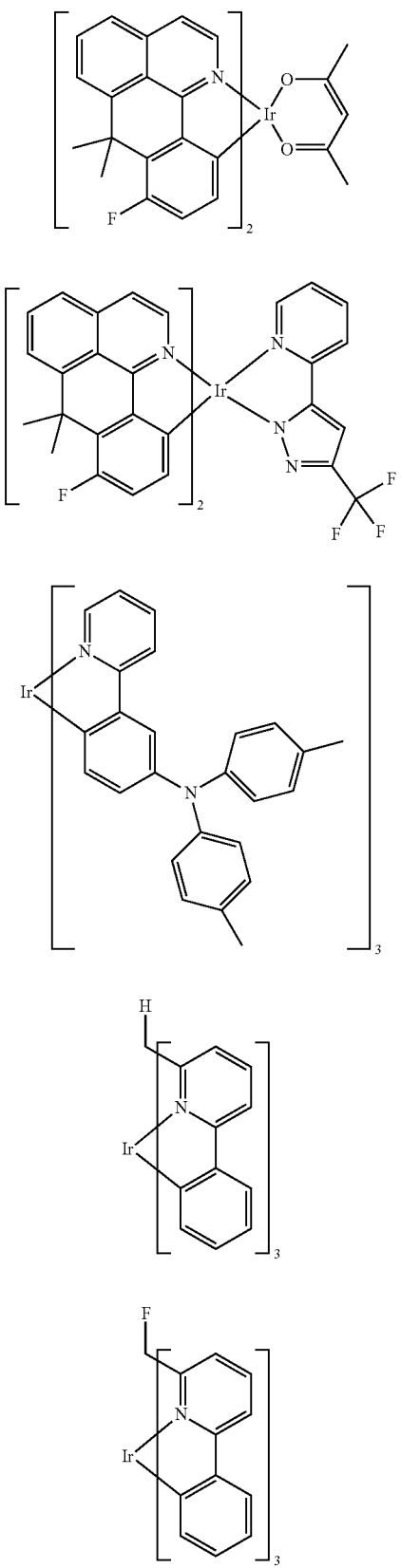
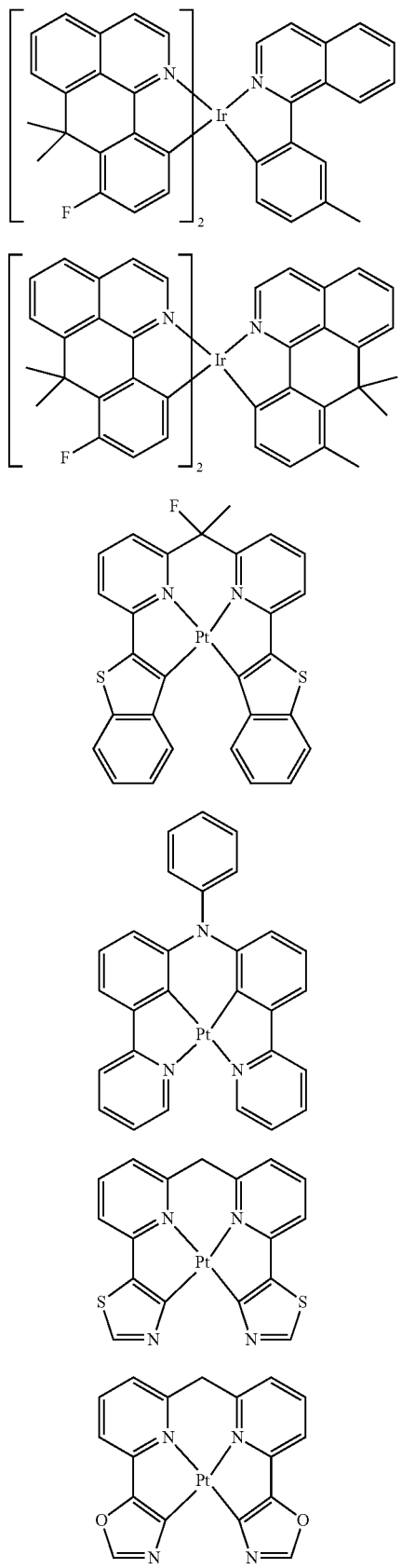

117
-continued
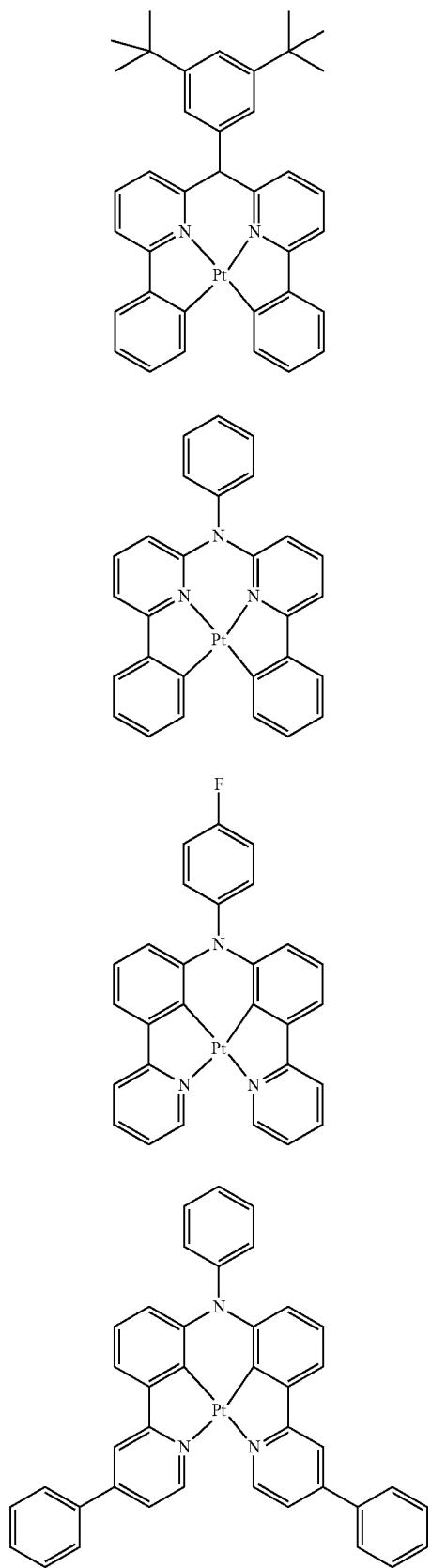
118
-continued
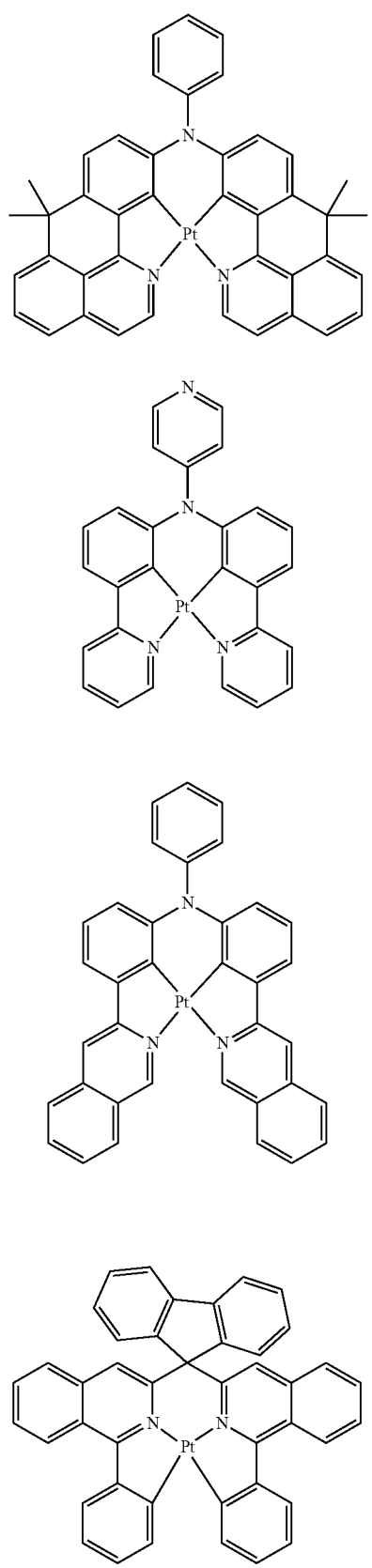

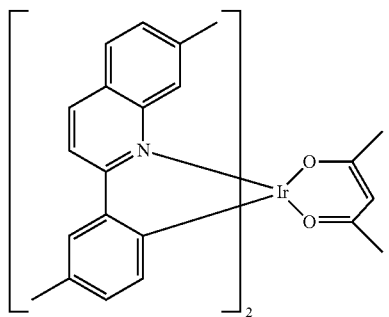
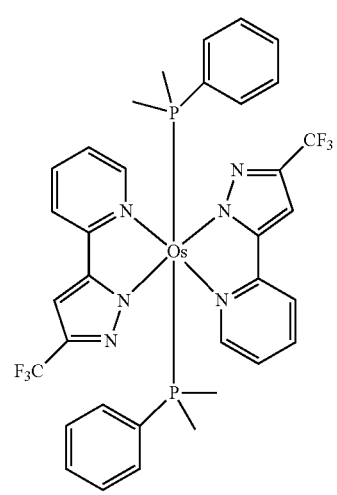
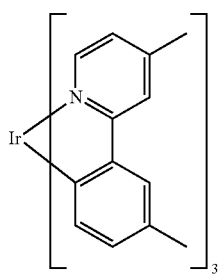
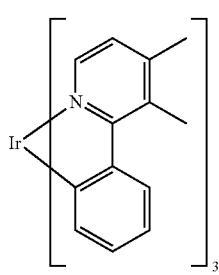
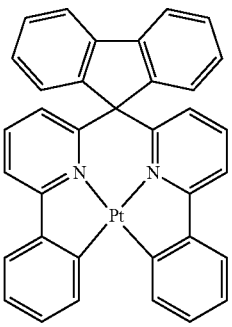
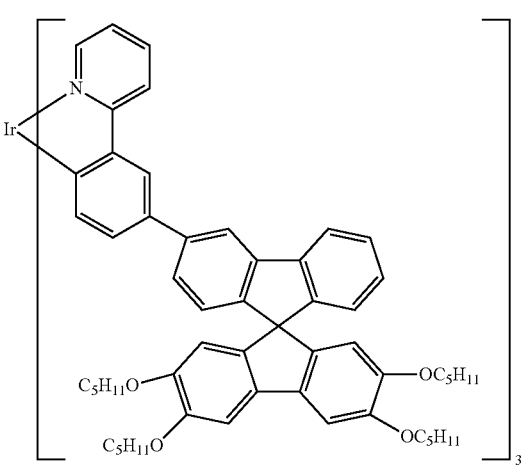
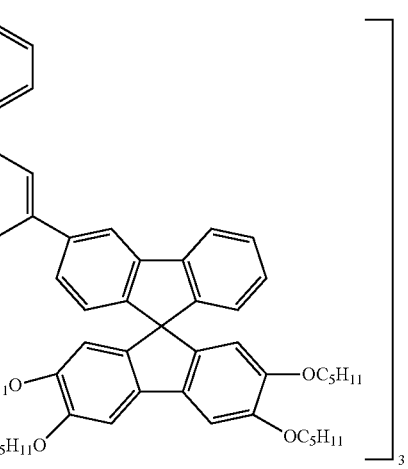
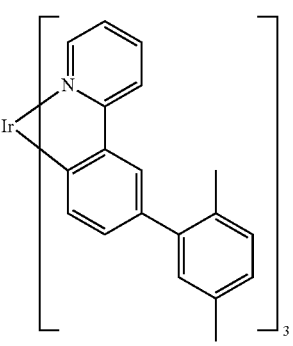
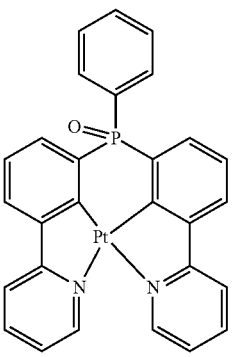

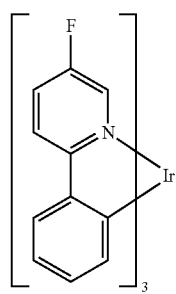
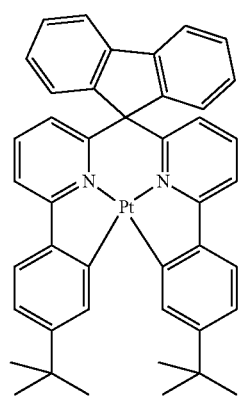
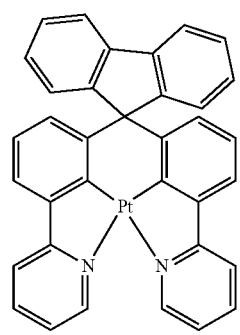
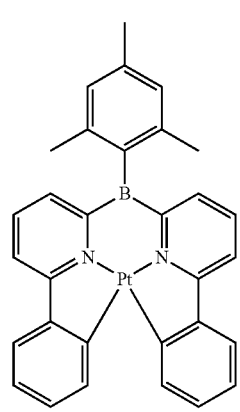
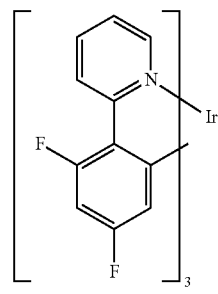
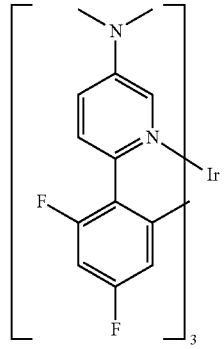
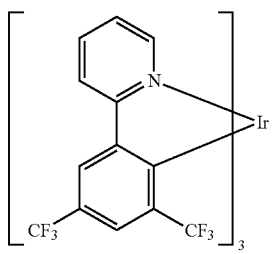
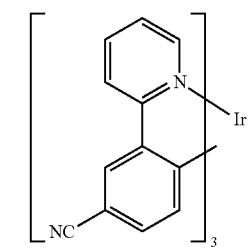
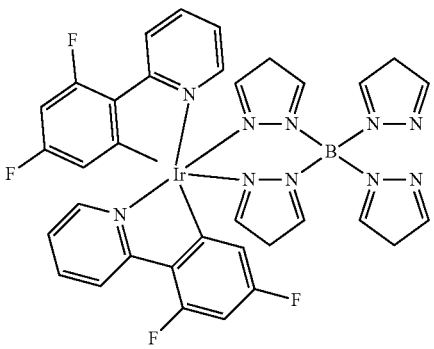

123
-continued
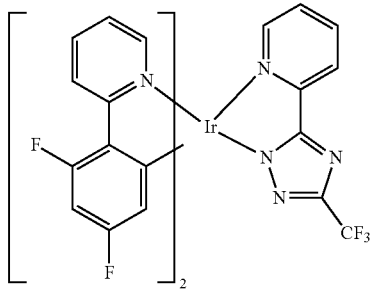
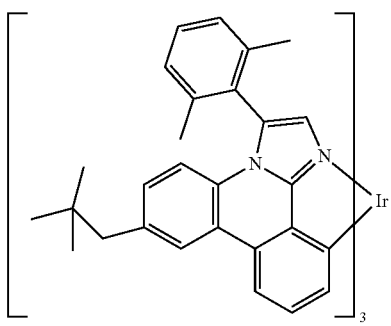
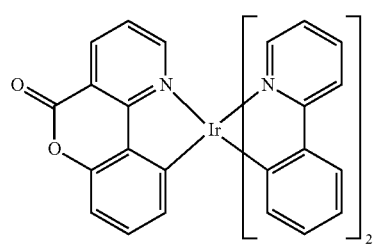
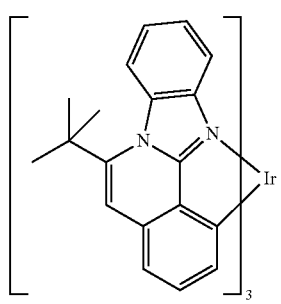
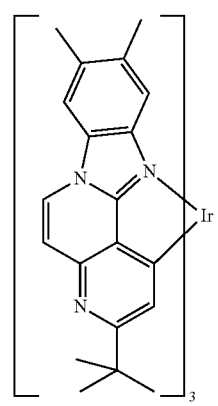
124
-continued
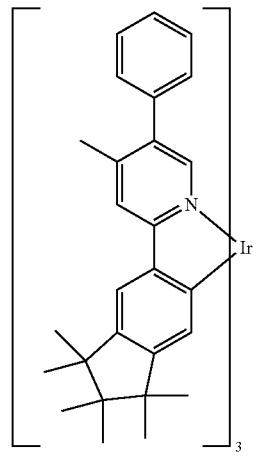
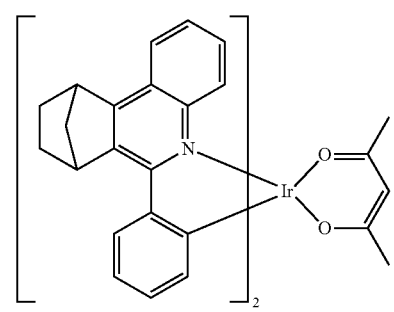
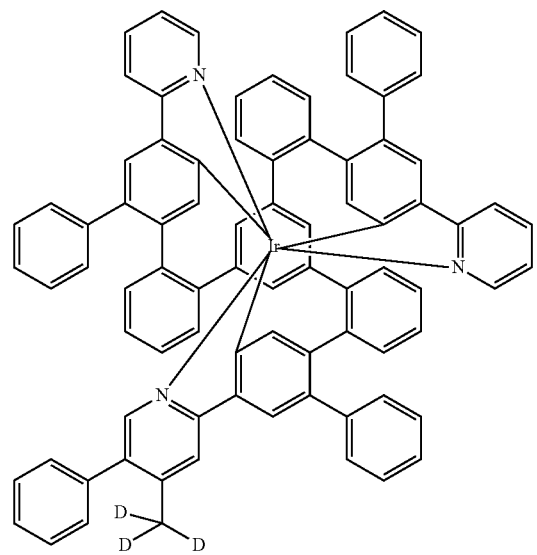

-continued

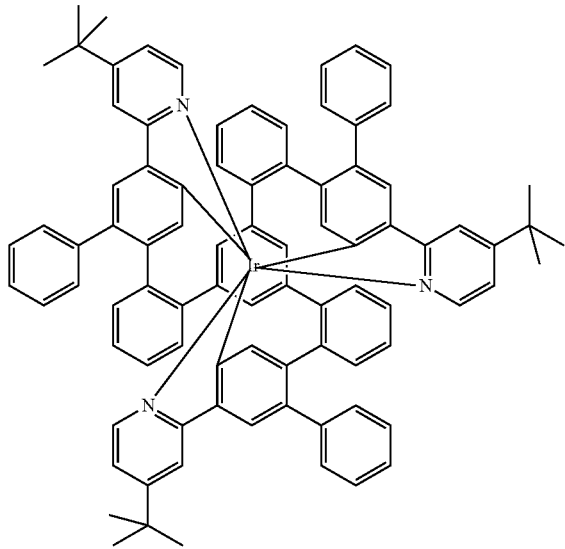

The above-described compound comprising structures of the formula (I) or the above-detailed preferred embodiments can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one intervening layer containing at least one compound comprising structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), preferably organic light-emitting electrochemical cells (OLECs), organic laser diodes (O-lasers) and organic plasmon emitting devices (D. M. Koller et al., Nature Photonics 2008, 1-4), preferably organic electroluminescent devices (OLEDs, PLEDs) or organic light-emitting electrochemical cells (OLECs), especially phosphorescent OLEDs or organic light-emitting electrochemical cells OLECs, containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as MoO₃ or WO₃ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) or the above-detailed preferred embodiments as matrix material, preferably as electron-conducting matrix material, in one or more emitting layers, preferably in combination with a further matrix material, preferably a hole-conducting matrix material. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer. An emitting layer comprises at least one emitting compound.

Suitable matrix materials which can be used in combination with the compounds of formula (I) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, or 4-spirocarbazole derivatives, for example according to WO 2014/094963 or the as yet unpublished application EP 14002104.9. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (I), in a preferred embodiment, as matrix material in an emission layer of an organic electronic device, especially in an organic electroluminescent device, for example in an OLED or OLEO. In this case, the matrix material containing compound comprising structures of formula (I) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) or the preferred embodiments recited above and below are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device or an organic electrochemical cell, comprising one or more compounds of the invention and/or at least one oligomer, polymer or dendrimer of the invention in one or more emitting layers, as matrix material.

The present invention additionally provides an electronic device, preferably an organic electroluminescent device or an organic electrochemical cell, comprising one or more compounds of the invention and/or at least one oligomer, polymer or dendrimer of the invention in one or more emitting layers, as emitter material.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapour deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapour deposition. For example, it is possible to apply an emitting layer comprising a compound of the invention comprising structures of formula (I) and a matrix material from solution, and to apply a hole blocker layer and/or an electron transport layer thereto by vapour deposition under reduced pressure.

These methods are known in general terms to those skilled in the art and can be applied without difficulty to electronic devices, especially organic electroluminescent devices comprising compounds of the invention comprising structures of formula (I) or the above-detailed preferred embodiments.

The electronic devices of the invention, especially organic electroluminescent devices, are notable for one or more of the following surprising advantages over the prior art:

1. Electronic devices, especially organic electroluminescent devices and very particularly organic light-emitting diodes or organic light-emitting electrochemical cells, comprising compounds, oligomers, polymers or dendrimers having structures of formula (I) or the preferred embodiments recited above and hereinafter, especially as electron-conducting materials, have a very good lifetime.
2. Electronic devices, especially organic electroluminescent devices and very particularly organic light-emitting diodes or organic light-emitting electrochemical cells, comprising compounds, oligomers, polymers or dendrimers having structures of formula (I) or the preferred embodiments recited above and hereinafter, as electron-conducting materials, electron injection materials and/or host materials, have excellent efficiency. More particularly, efficiency is much higher compared to analogous compounds containing no structural unit of formula (I). In this context, compounds, oligomers, polymers or dendrimers of the invention having structures of formula (I) or the preferred embodiments recited above and hereinafter bring about a low operating voltage when used in electronic devices. In this context, these compounds especially bring about low roll-off, i.e. a small drop in power efficiency of the device at high luminances.
3. The compounds, oligomers, polymers or dendrimers of the invention having structures of formula (I) or the preferred embodiments recited above and hereinafter exhibit very high stability (for example redox stability, thermal stability and photochemical stability) and lead to compounds having a very long lifetime.
4. With compounds, oligomers, polymers or dendrimers having structures of formula (I) or the preferred embodiments recited above and hereinafter, it is possible to avoid the formation of optical loss channels in electronic devices, especially organic electroluminescent devices and very particularly organic light-emitting diodes or organic light-emitting electrochemical cells. As a result, these devices feature a high PL efficiency and hence high EL efficiency of emitters, and excellent energy transmission of the matrices to dopants.
5. The use of compounds, oligomers, polymers or dendrimers having structures of formula (I) or the preferred embodiments recited above and hereinafter in layers of electronic devices, especially organic electroluminescent devices and very particularly organic light-emitting diodes or organic light-emitting electrochemical cells, leads to high mobility of the electron conductor structures.
6. Compounds, oligomers, polymers or dendrimers having structures of formula (I) or the preferred embodiments recited above and below feature excellent thermal stability, and compounds having a molar mass of less than about 1200 g/mol have good sublimability.
7. Compounds, oligomers, polymers or dendrimers having structures of formula (I) or the preferred embodiments recited above and hereinafter have excellent glass film formation.
8. Compounds, oligomers, polymers or dendrimers having structures of formula (I) or the preferred embodiments recited above and hereinafter form very good films from solutions.
9. The compounds, oligomers, polymers or dendrimers comprising structures of formula (I) or the preferred embodiments recited above and hereinafter have a surprisingly high triplet level $T_1$, this being particularly true of compounds which are used as electron-conducting materials.

These abovementioned advantages are not accompanied by a deterioration in the further electronic properties.

The compounds and mixtures of the invention are suitable for use in an electronic device. An electronic device is understood to mean a device containing at least one layer containing at least one organic compound. The component may also comprise inorganic materials or else layers formed entirely from inorganic materials.

The present invention therefore further provides for the use of the compounds or mixtures of the invention in an electronic device, especially in an organic electroluminescent device.

The present invention still further provides for the use of a compound of the invention and/or of an oligomer, polymer or dendrimer of the invention in an electronic device as TADF material, host material, hole conductor material, electron injection material and/or electron transport material, preferably as TADF material, host material, hole conductor material and/or electron transport material.

The present invention still further provides an electronic device comprising at least one of the above-detailed compounds or mixtures of the invention. In this case, the preferences detailed above for the compound also apply to the electronic devices. Particular preference is given to an electronic device selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), preferably organic light-emitting electrochemical cells (OLECs), organic laser diodes (O-lasers) and organic plasmon emitting devices (D. M. Koller et al., *Nature Photonics* 2008, 1-4), preferably organic electroluminescent devices (OLEDs, PLEDs) or organic light-emitting electrochemical cells (OLECs), especially phosphorescent or fluorescent OLEDs or fluorescent OLECs.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In addition, it is possible to use the compounds of the invention in an electron transport layer.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (I) or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

Synthesis of the Synthons

Example S1

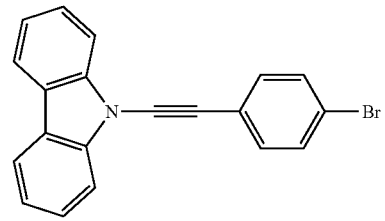 [SMILES: Brc1ccc(C#Cn2c3ccccc3c3ccccc32)cc1]

Procedure analogous to A. Sagadevan, et al., Green Chemistry, 17(2), 1113-1119; 2015. To a well-stirred mixture of 16.7 g (100 mmol) of carbazole [86-74-8], 34.6 g (250 mmol) of potassium carbonate, 2.5 g (10 mmol) of copper(II) sulfate pentahydrate [7758-99-8], 3.6 g (20 mmol) of phenanthroline, 300 ml of toluene and 50 g of glass beads are added 33.8 g (130 mmol) of 1-bromo-4-(2-bromethynyl)benzene [934-94-1], and then the mixture is stirred at 80° C. for 16 h. After cooling, the mixture is filtered through a Celite bed, the latter is washed through and the filtrate is concentrated to dryness. The residue is purified by flash chromatography (CombiFlash Torrent from Axel Semrau). Yield: 23.2 g (67 mmol), 67%; purity: 95% by $^1$H NMR.

Example S100

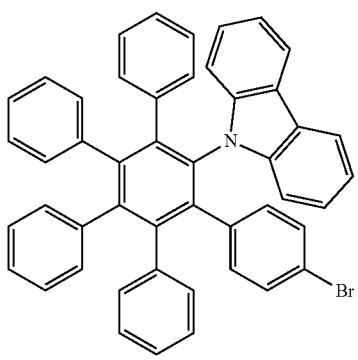 [SMILES: Brc1ccc(-c2c(-c3ccccc3)c(-c3ccccc3)c(-c3ccccc3)c(-c3ccccc3)c2-n2c3ccccc3c3ccccc32)cc1]

A mixture of 34.6 g (100 mmol) of S1, 38.5 g (100 mmol) of 2,3,4,5-tetraphenyl-2,4-cyclopentadien-1-one [479-33-4] and 130 ml of diphenyl ether is heated to 265° C. for 24 h. After cooling and removal of the diphenyl ether under reduced pressure, the residue is extracted by boiling with 300 ml of ethanol, and the solids are filtered off with suction, washed three times with 100 ml each time of EtOH and dried under reduced pressure. The residue is purified by flash chromatography (CombiFlash Torrent from Axel Semrau). Yield: 51.4 g (73 mmol), 73%; purity: 98% by $^1$H NMR.

In an analogous manner, it is possible to prepare the following compounds using S1, i.e. 1-bromo-4-[2-(4-chlorophenyl)ethynyl]benzene [832744-28-2], as dienophile:

| Ex. | Diene | Product | Yield |
|---|---|---|---|
| S101 | | | 54% |
| S102 | 38268-11-0 S1 | | 56% |

-continued

| Ex. | Diene | Product | Yield |
|---|---|---|---|
| S103 | 5660-91-3 S1 | | 52% |
| S104 | 23414-46-2 | | 63% |
| S105 | 412268-65-6 | | 43% |
| S106 | 1607433-47-5 | | 55% |

-continued
| Ex. | Diene | Product | Yield |
|---|---|---|---|
| S107 | 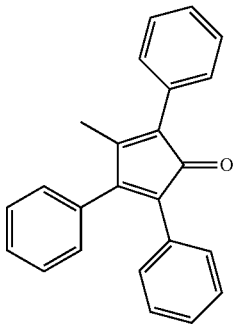<br>107319-64-2 | 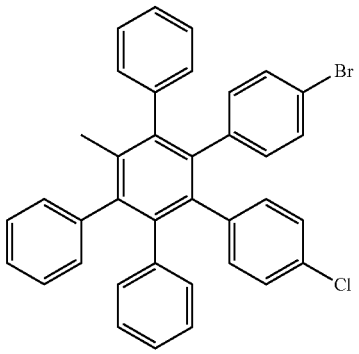 [SMILES: Cc1c(-c2ccccc2)c(-c2ccccc2)c(-c2ccc(Cl)cc2)c(-c2ccc(Br)cc2)c1-c1ccccc1]<br><br>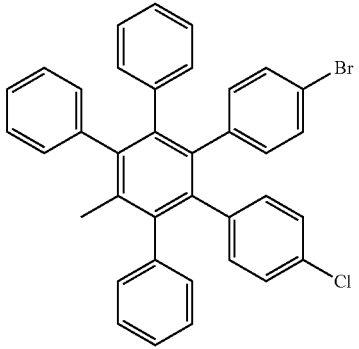<br>isomer mixture | 53% |
| S108 | 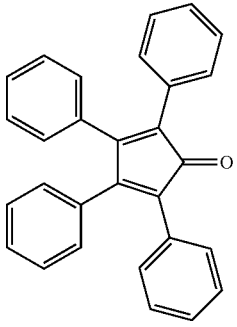<br>479-33-4 | 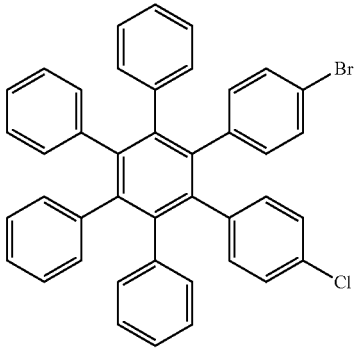 [SMILES: Clc1ccc(-c2c(-c3ccccc3)c(-c3ccccc3)c(-c3ccccc3)c(-c3ccccc3)c2-c2ccc(Br)cc2)cc1] | 67% |
| S109 | 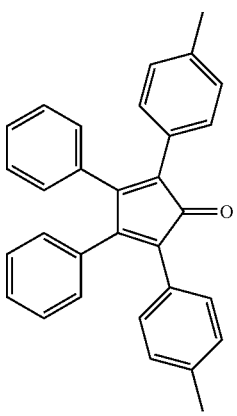<br>38268-18-7 | 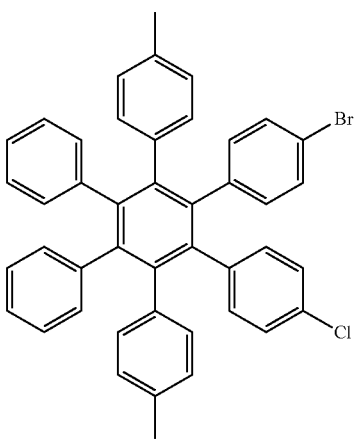 [SMILES: Cc1ccc(-c2c(-c3ccccc3)c(-c3ccccc3)c(-c3ccc(C)cc3)c(-c3ccc(Br)cc3)c2-c2ccc(Cl)cc2)cc1] | 60% |

-continued

| Ex. | Diene | Product | Yield |
|---|---|---|---|
| S110 | 356074-64-1 | | 63% |
| S111 | 106821-16-3 | | 68% |
| S112 | 5660-91-3<br>S1 | | 73% |

-continued
| Ex. | Diene | Product | Yield |
|---|---|---|---|
| S113 | 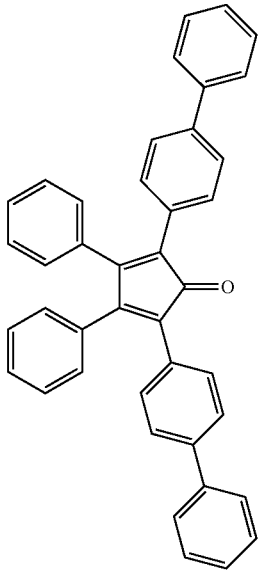<br>19059-92-8 | 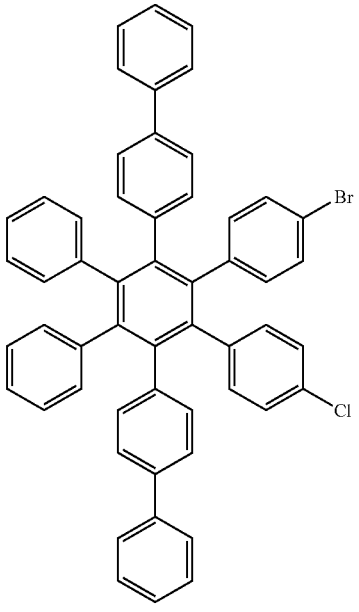 [SMILES: Clc1ccc(-c2c(-c3ccc(Br)cc3)c(-c3ccc(-c4ccccc4)cc3)c(-c3ccccc3)c(-c3ccccc3)c2-c2ccc(-c3ccccc3)cc2)cc1] | 69% |
| S114 | 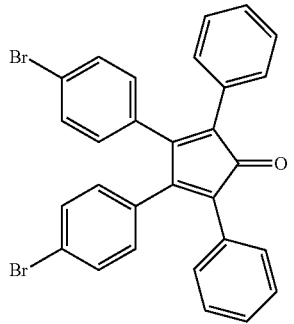<br>38268-11-0 | 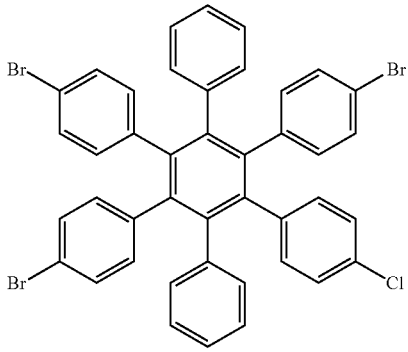 [SMILES: Clc1ccc(-c2c(-c3ccccc3)c(-c3ccc(Br)cc3)c(-c3ccc(Br)cc3)c(-c3ccccc3)c2-c2ccc(Br)cc2)cc1] | 57% |
| S115 | 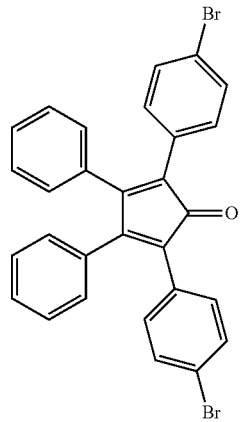<br>54523-24-9 | 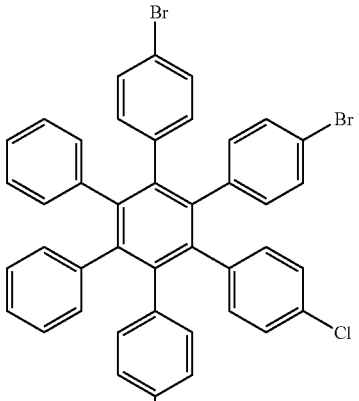 | 53% |

| Ex. | Diene | Product | Yield |
|---|---|---|---|
| S116 | 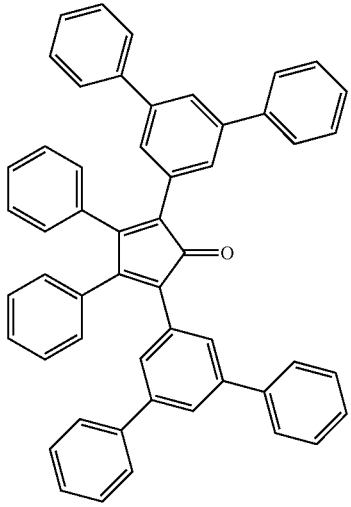<br>297154-31-2 | 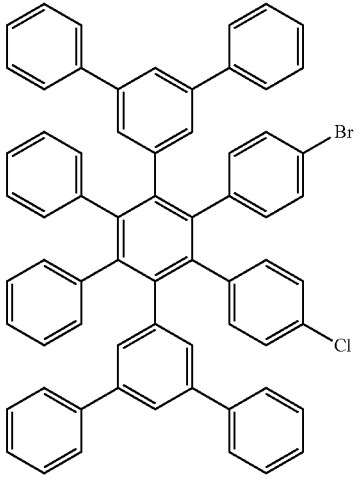 [SMILES: Clc1ccc(-c2c(-c3ccc(Br)cc3)c(-c3cc(-c4ccccc4)cc(-c4ccccc4)c3)c(-c3ccccc3)c(-c3ccccc3)c2-c2cc(-c3ccccc3)cc(-c3ccccc3)c2)cc1] | 62% |
| S117 | 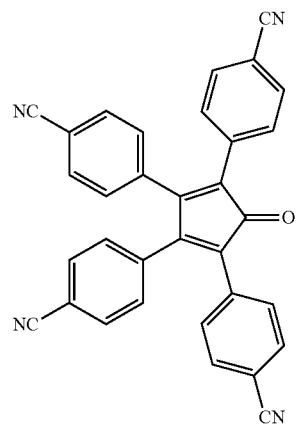<br>1465020-42-1 | 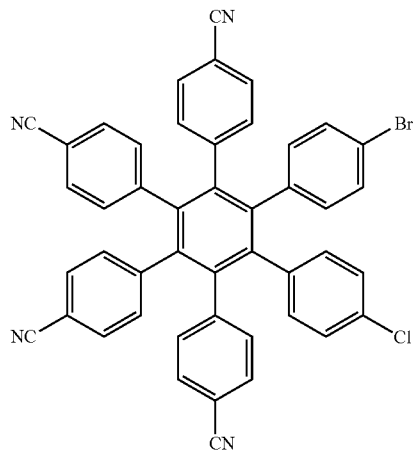 [SMILES: N#Cc1ccc(-c2c(-c3ccc(Cl)cc3)c(-c3ccc(Br)cc3)c(-c3ccc(C#N)cc3)c(-c3ccc(C#N)cc3)c2-c2ccc(C#N)cc2)cc1] | 43% |
| S118 | 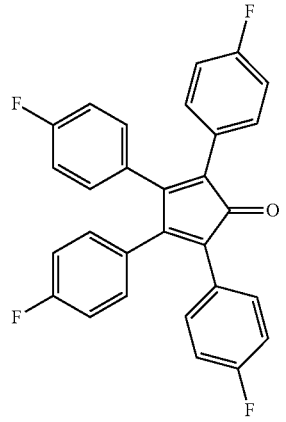<br>163132-55-6 | 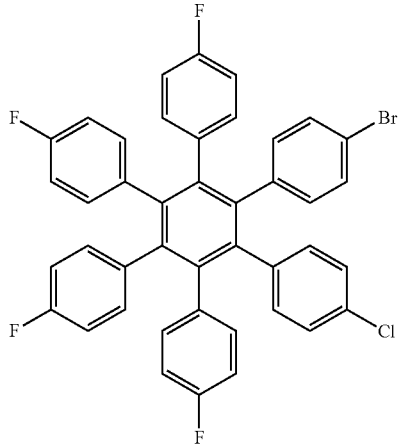 [SMILES: Fc1ccc(-c2c(-c3ccc(F)cc3)c(-c3ccc(F)cc3)c(-c3ccc(Br)cc3)c(-c3ccc(Cl)cc3)c2-c2ccc(F)cc2)cc1] | 66% |

-continued
| Ex. | Diene | Product | Yield |
|---|---|---|---|
| S119 | 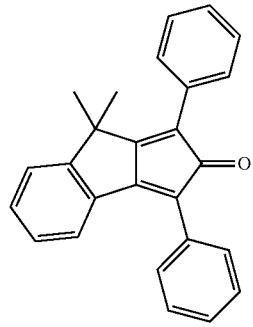<br>132665-86-2 | 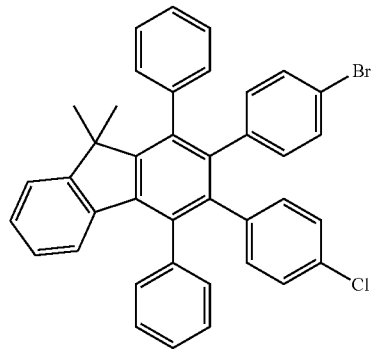 [SMILES: CC1(C)c2ccccc2-c2c(-c3ccccc3)c(-c3ccc(Cl)cc3)c(-c3ccc(Br)cc3)c(-c3ccccc3)c21]<br><br>isomer mixture | 60% |
| S120 | 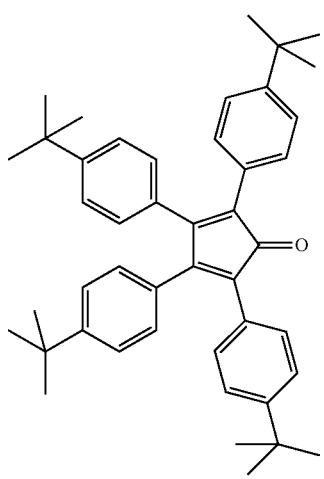<br>196505-83-6 | 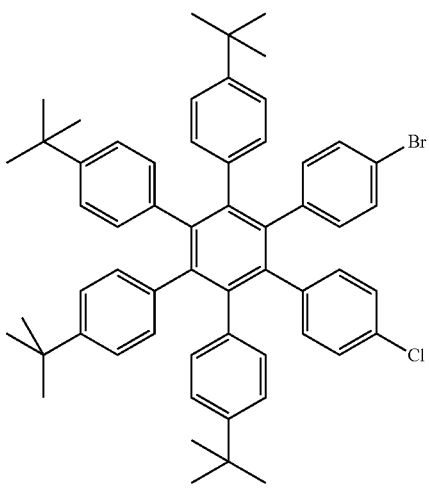 [SMILES: CC(C)(C)c1ccc(-c2c(-c3ccc(Cl)cc3)c(-c3ccc(Br)cc3)c(-c3ccc(C(C)(C)C)cc3)c(-c3ccc(C(C)(C)C)cc3)c2-c2ccc(C(C)(C)C)cc2)cc1] | 67% |

-continued
| Ex. | Diene | Product | Yield |
|---|---|---|---|
| S121 | 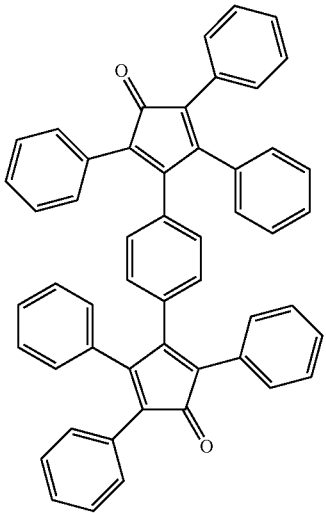3432-73-3 | 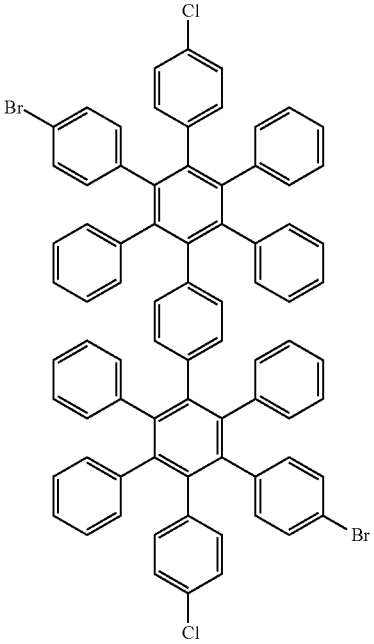 | 61% |
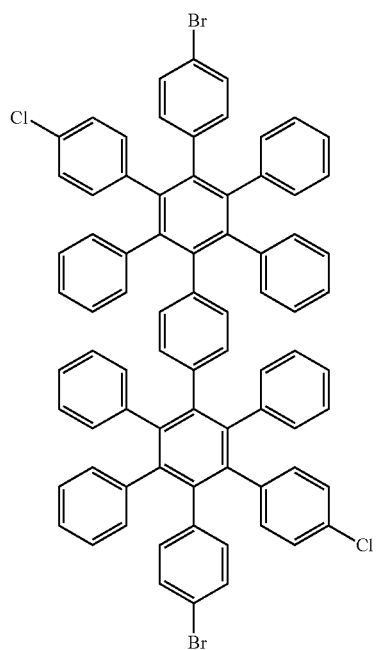

| Ex. | Diene | Product | Yield |
|---|---|---|---|
| | | 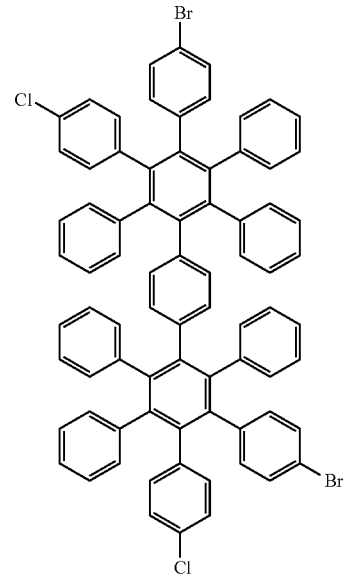 [SMILES: Clc1ccc(-c2c(-c3ccccc3)c(-c3ccccc3)c(-c3ccc(-c4c(-c5ccccc5)c(-c5ccccc5)c(-c5ccc(Cl)cc5)c(-c5ccc(Br)cc5)c4-c4ccccc4)cc3)c(-c3ccccc3)c2-c2ccc(Br)cc2)cc1]isomer mixture | |
| S122 | 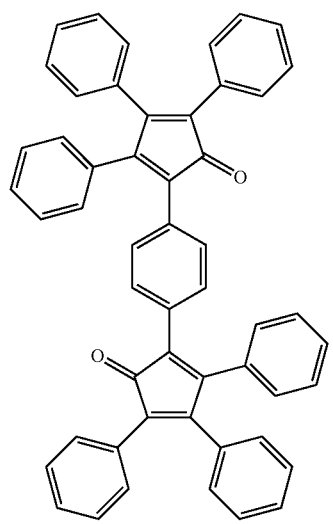1018691-33-2 | 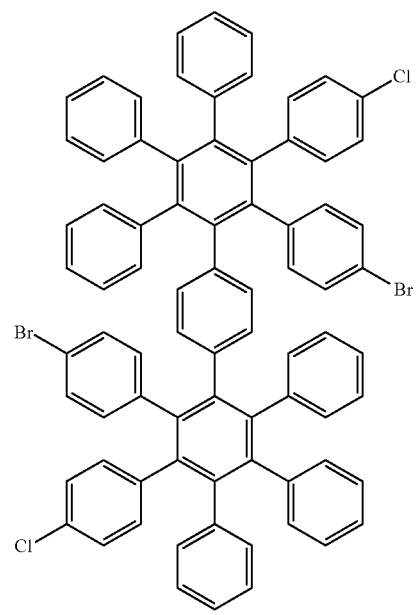 [SMILES: Clc1ccc(-c2c(-c3ccccc3)c(-c3ccccc3)c(-c3ccccc3)c(-c3ccc(-c4c(-c5ccccc5)c(-c5ccccc5)c(-c5ccccc5)c(-c5ccc(Cl)cc5)c4-c4ccc(Br)cc4)cc3)c2-c2ccc(Br)cc2)cc1] | 63% |

-continued
| Ex. | Diene | Product | Yield |
|---|---|---|---|
| | | 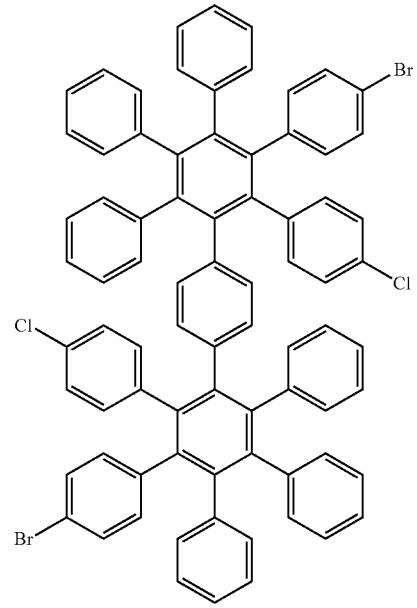 [SMILES: Clc1ccc(-c2c(-c3ccc(Br)cc3)c(-c3ccccc3)c(-c3ccccc3)c(-c3ccccc3)c2-c2ccc(-c3c(-c4ccccc4)c(-c4ccccc4)c(-c4ccccc4)c(-c4ccc(Br)cc4)c3-c3ccc(Cl)cc3)cc2)cc1] | |
| | | 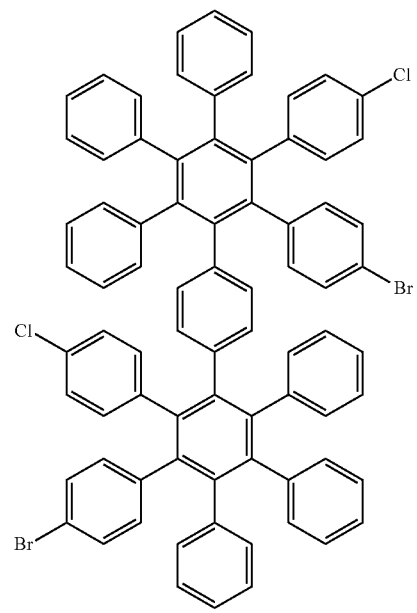isomer mixture | |

-continued
| Ex. | Diene | Product | Yield |
|---|---|---|---|
| S123 | 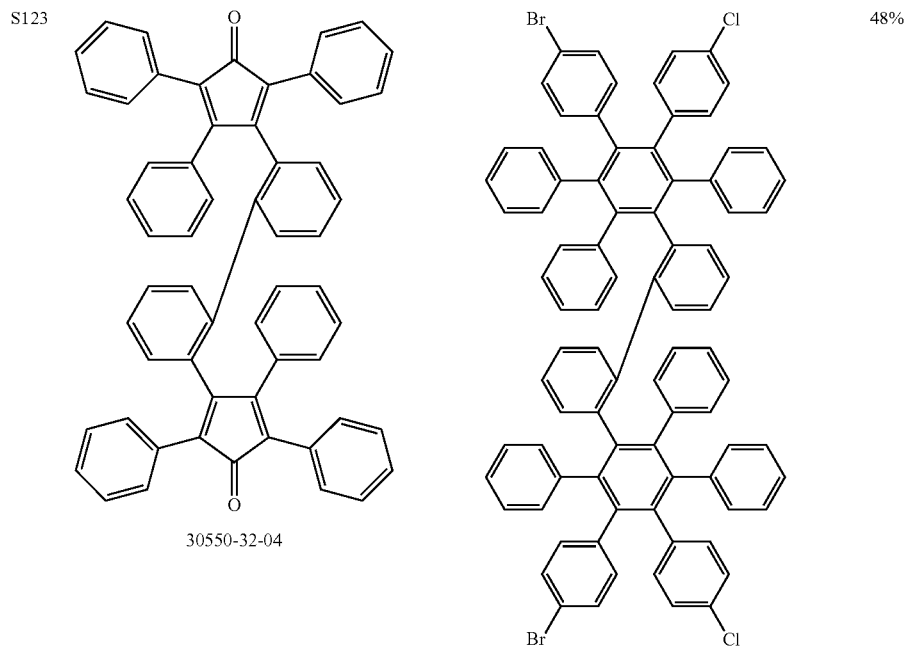  30550-32-04 |  | 48% |
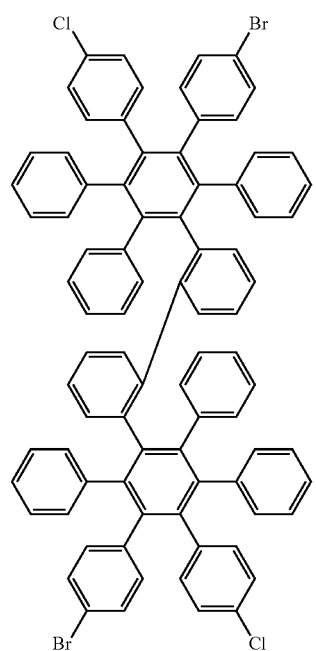 [SMILES: Clc1ccc(-c2c(-c3ccccc3)c(-c3ccccc3)c(-c3ccccc3-c3ccccc3-c3c(-c4ccccc4)c(-c4ccccc4)c(-c4ccc(Cl)cc4)c(-c4ccc(Br)cc4)c3-c3ccccc3)c(-c3ccccc3)c2-c2ccc(Br)cc2)cc1]

| Ex. | Diene | Product | Yield |
|---|---|---|---|

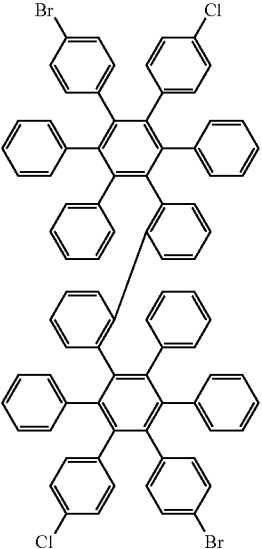

isomer mixture

Example S200: Buchwald Coupling

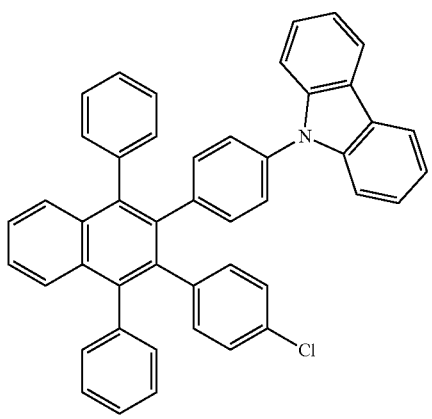 [SMILES: Clc1ccc(-c2c(-c3ccc(-n4c5ccccc5c5ccccc54)cc3)c(-c3ccccc3)c3ccccc3c2-c2ccccc2)cc1]

A mixture of 54.6 g (100 mmol) of S104, 16.7 g (100 mmol) of carbazole [86-74-8], 41.5 g (300 mmol) of potassium carbonate, 50 g of glass beads, 700 ml of toluene, 405 mg (2 mmol) of tri-Cert-butylphosphine and 225 mg (1 mmol) of palladium acetate is heated under reflux with good stirring for 24 h. After cooling, the salts are filtered off with suction through a Celite bed in the form of a toluene slurry, the bed is washed through three times with 100 ml each time of warm toluene, and the filtrate is washed once with 500 ml of water and once with 300 ml of sodium chloride solution and dried over magnesium sulfate. The solids obtained after the desiccant has been filtered off and the solvent has been removed are chromatographed (silica gel, dichloromethane) and then recrystallized from dimethylacetamide (DMAC). Yield: 46.1 g (73 mmol), 73%; purity: 97% by $^1$H NMR.

In an analogous manner, it is possible to prepare the following compounds, using 120 mmol of sodium tert-butoxide rather than potassium carbonate for couplings with secondary amines

| Ex. | Reactants | Product | Yield |
|---|---|---|---|
| S201 | S104<br>122-39-4 | 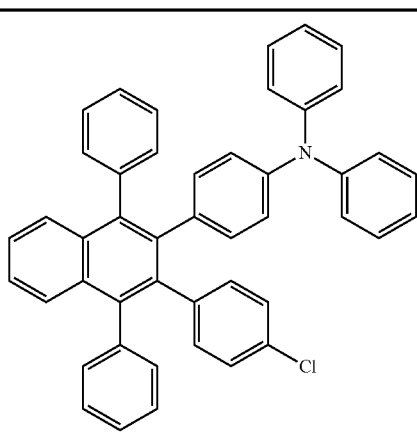 | 58% |

US 11,711,976 B2
157                                                                 158
-continued
| Ex. | Reactants | Product | Yield |
|---|---|---|---|
| S202 | S104<br>1421789-16-3 | 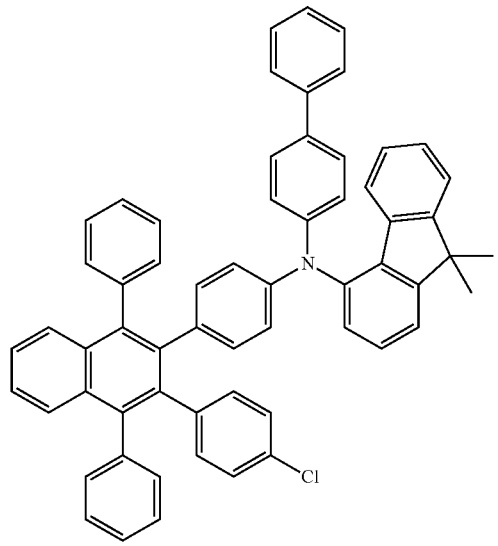 [SMILES: CC1(C)c2ccccc2-c2c(N(c3ccc(-c4ccccc4)cc3)c3ccc(-c4c(-c5ccc(Cl)cc5)c(-c5ccccc5)c5ccccc5c4-c4ccccc4)cc3)cccc21] | 70% |
| S203 | S104<br>205-25-4 | 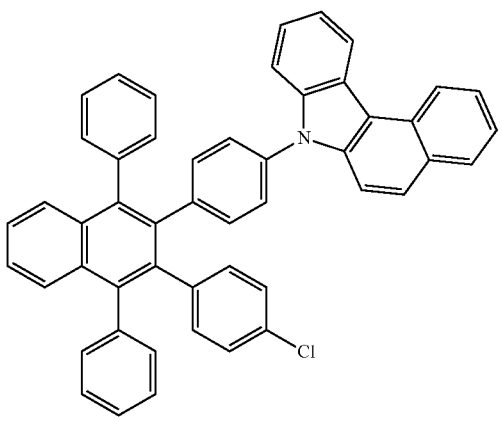 [SMILES: Clc1ccc(-c2c(-c3ccc(-n4c5ccccc5c5c6ccccc6ccc54)cc3)c(-c3ccccc3)c3ccccc3c2-c2ccccc2)cc1] | 68% |
| S204 | S105<br>56525-79-2 | 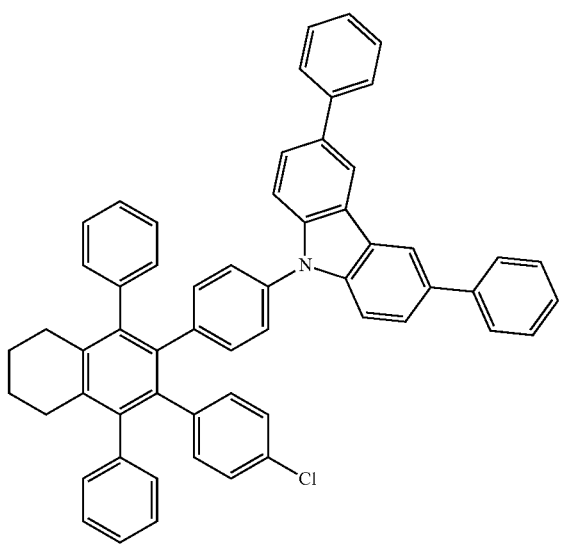 [SMILES: Clc1ccc(-c2c(-c3ccccc3)c3c(c(-c4ccccc4)c2-c2ccc(-n4c5ccc(-c6ccccc6)cc5c5cc(-c6ccccc6)ccc54)cc2)CCCC3)cc1] | 67% |

| Ex. | Reactants | Product | Yield |
|---|---|---|---|
| S205 | S106<br>1257220-47-5 | 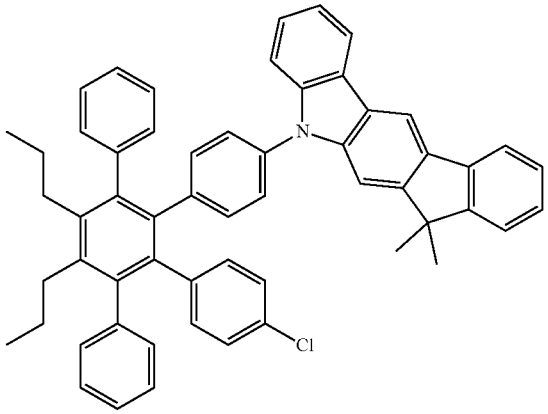 [SMILES: CCCc1c(CCC)c(-c2ccccc2)c(-c2ccc(-n3c4ccccc4c4cc5c(cc43)C(C)(C)c3ccccc3-5)cc2)c(-c2ccc(Cl)cc2)c1-c1ccccc1] | 72% |
| S206 | S107<br>1466521-76-5 | 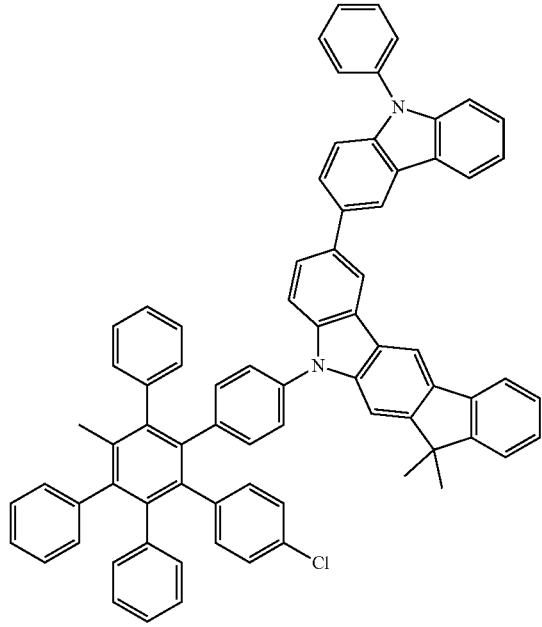 [SMILES: Cc1c(-c2ccccc2)c(-c2ccccc2)c(-c2ccc(Cl)cc2)c(-c2ccc(-n3c4ccc(-c5ccc6c(c5)c5ccccc5n6-c5ccccc5)cc4c4cc5c(cc43)C(C)(C)c3ccccc3-5)cc2)c1-c1ccccc1] | 49% |

| Ex. | Reactants | Product | Yield |
|---|---|---|---|
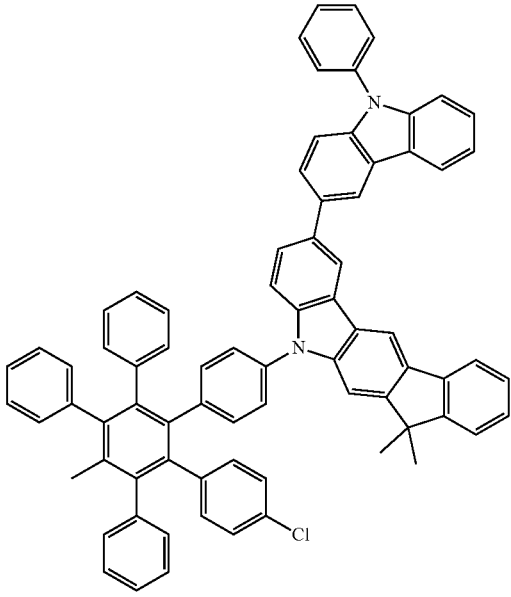
isomer mixture
| | | | |
|---|---|---|---|
| S207 | S108<br>1257247-94-1 | | 59% |
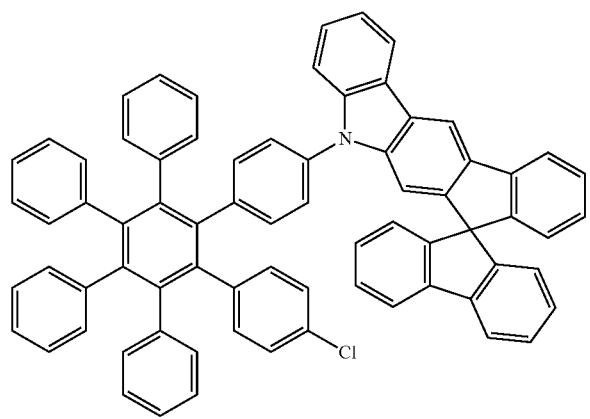 [SMILES: Clc1ccc(-c2c(-c3ccccc3)c(-c3ccccc3)c(-c3ccccc3)c(-c3ccccc3)c2-c2ccc(-n3c4ccccc4c4cc5c(cc43)C3(c4ccccc4-c4ccccc43)c3ccccc3-5)cc2)cc1]

-continued

| Ex. | Reactants | Product | Yield |
|---|---|---|---|
| S208 | S108<br>1431284-23-9 | | 55% |
| S209 | S108<br>1316311-27-9 | | 60% |
| S210 | S109<br>1024598-06-8 | | 38% |

| Ex. | Reactants | Product | Yield |
|---|---|---|---|
| S211 | S110
1199350-22-5 | | 70% |
| S212 | S111
1382955-10-3 | | 64% |

| Ex. | Reactants | Product | Yield |
|---|---|---|---|
| S213 | S111<br>1060735-14-9 | 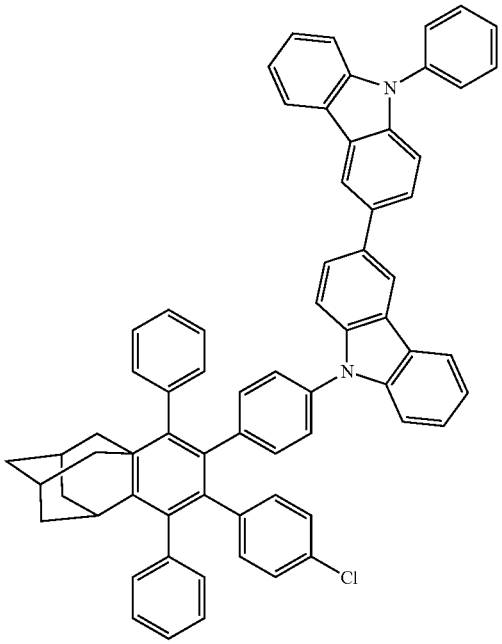 | 60% |
| S214 | S112<br>1609088-05-2 | 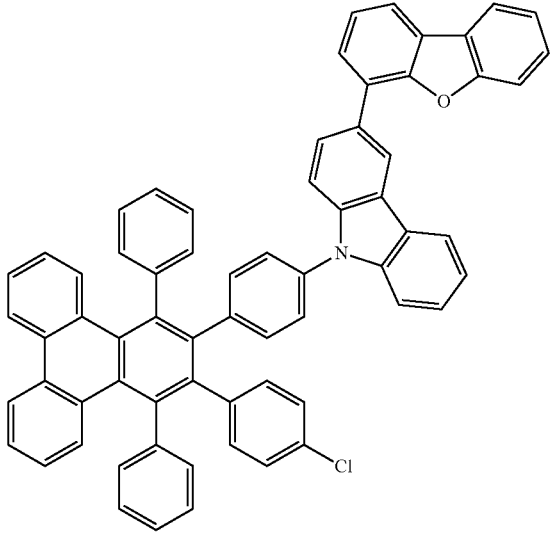 [SMILES: Clc1ccc(-c2c(-c3ccc(-n4c5ccccc5c5cc(-c6cccc7c6oc6ccccc67)ccc54)cc3)c(-c3ccccc3)c3c4ccccc4c4ccccc4c3c2-c2ccccc2)cc1] | 59% |

-continued
| Ex. | Reactants | Product | Yield |
|---|---|---|---|
| S215 | S113<br>244-76-8 | 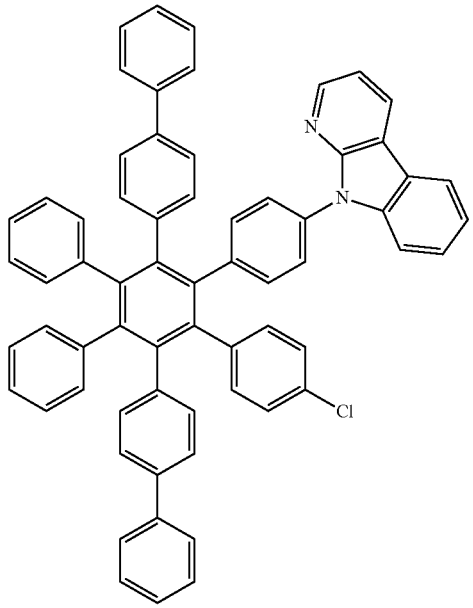 [SMILES: Clc1ccc(-c2c(-c3ccc(-c4ccccc4)cc3)c(-c3ccccc3)c(-c3ccccc3)c(-c3ccc(-c4ccccc4)cc3)c2-c2ccc(-n3c4ccccc4c4cccnc43)cc2)cc1] | 68% |
| S216 | S114<br>88590-00-5 | 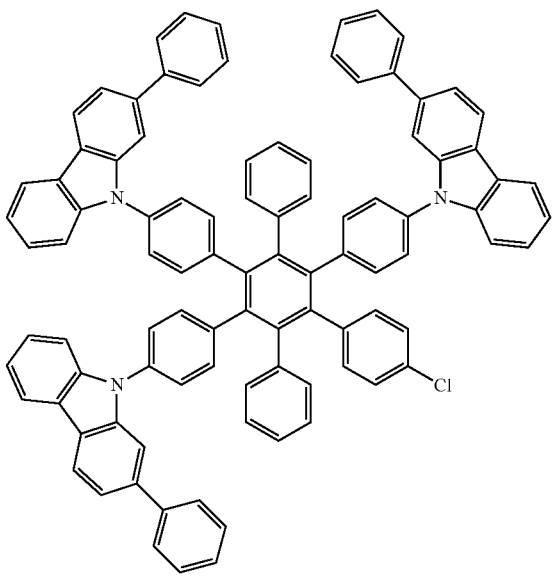 | 45% |
300 mmol 88590-00-5
6 mmol P-tBu₃/3 mmol Pd(ac)₂

-continued

| Ex. | Reactants | Product | Yield |
|---|---|---|---|
| S217 | S115<br>244-63-3 | | 48% |
| | | 300 mmol 244-63-3<br>6 mmol P-tBu₃/3 mmol Pd(ac)₂ | |
| S218 | S116<br>1365647-82-0 | | 58% |
| S219 | S117<br>135-67-1 | | 62% |

-continued
| Ex. | Reactants | Product | Yield |
|---|---|---|---|
| S220 | S118<br>1799501-71-5 | 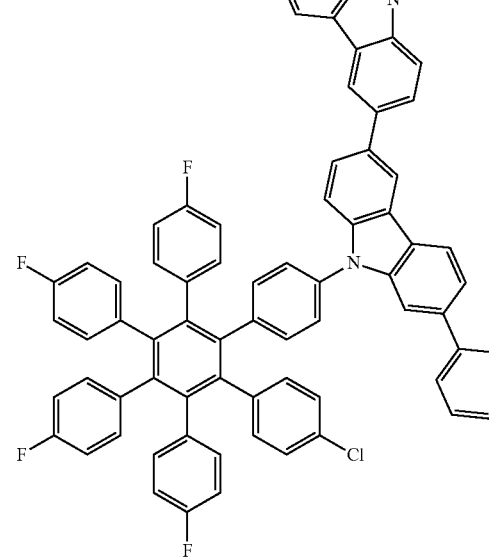 | 60% |
| S221 | S119<br>955959-89-4 | 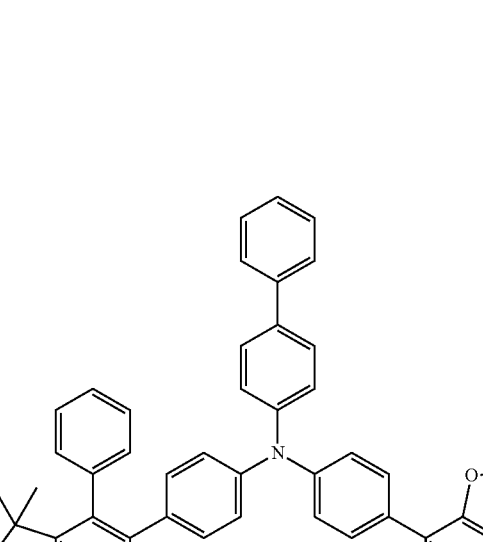 | 49% |

| Ex. | Reactants | Product | Yield |
|---|---|---|---|
| | | 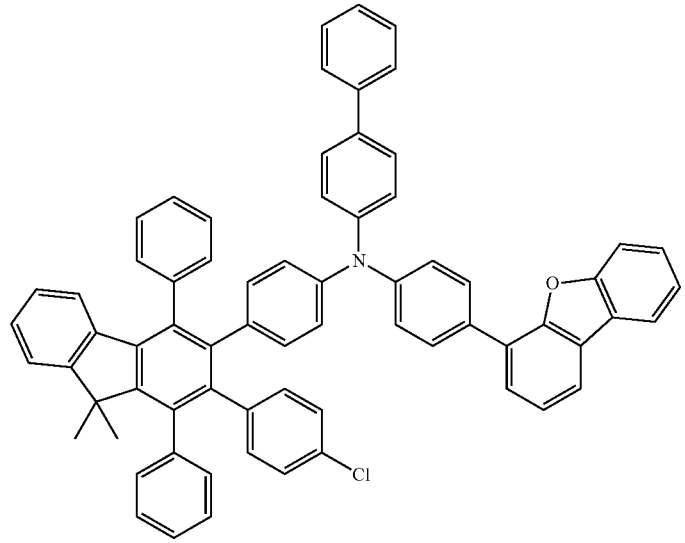 [SMILES: CC1(C)c2ccccc2-c2c(-c3ccccc3)c(-c3ccc(Cl)cc3)c(-c3ccc(N(c4ccc(-c5ccccc5)cc4)c4ccc(-c5cccc6c5oc5ccccc56)cc4)cc3)c(-c3ccccc3)c21]<br>isomer mixture | |
| S222 | S120<br>1346669-46-2 | 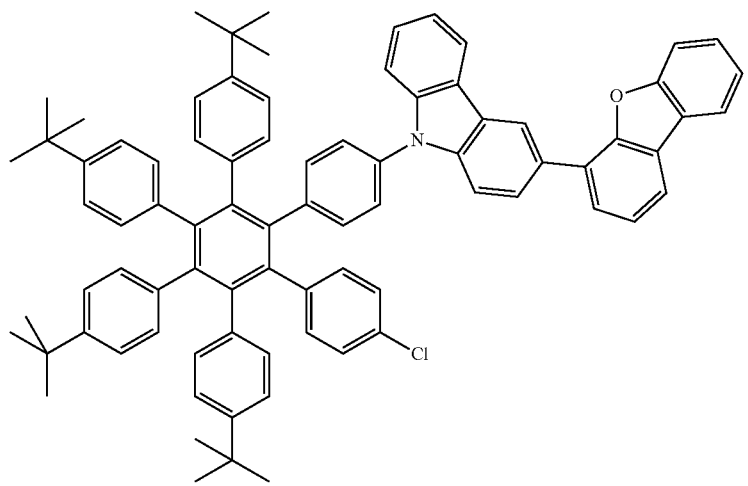 [SMILES: CC(C)(C)c1ccc(-c2c(-c3ccc(Cl)cc3)c(-c3ccc(-n4c5ccccc5c5cc(-c6cccc7c6oc6ccccc67)ccc54)cc3)c(-c3ccc(C(C)(C)C)cc3)c(-c3ccc(C(C)(C)C)cc3)c2-c2ccc(C(C)(C)C)cc2)cc1] | 55% |

| Ex. | Reactants | Product | Yield |
|---|---|---|---|
| S223 | S121<br>1364890-88-9 | 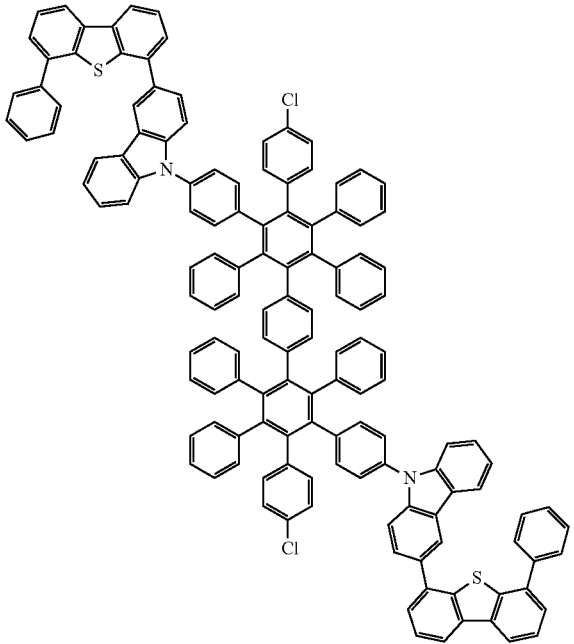 [SMILES: Clc1ccc(-c2c(-c3ccccc3)c(-c3ccccc3)c(-c3ccc(-c4c(-c5ccccc5)c(-c5ccccc5)c(-c5ccc(Cl)cc5)c(-c5ccc(-n6c7ccccc7c7cc(-c8cccc9c8sc8c(-c%10ccccc%10)cccc89)ccc76)cc5)c4-c4ccccc4)cc3)c(-c3ccccc3)c2-c2ccc(-n3c4ccccc4c4cc(-c5cccc6c5sc5c(-c7ccccc7)cccc56)ccc43)cc2)cc1]<br>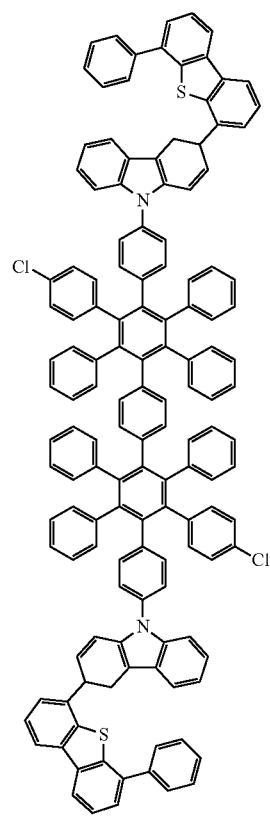 [SMILES: Clc1ccc(-c2c(-c3ccccc3)c(-c3ccc(-c4c(-c5ccccc5)c(-c5ccccc5)c(-c5ccc(-n6c7c(c8ccccc86)CC(c6cccc8c6sc6c(-c9ccccc9)cccc68)C=C7)cc5)c(-c5ccc(Cl)cc5)c4-c4ccccc4)cc3)c(-c3ccccc3)c(-c3ccccc3)c2-c2ccc(-n3c4c(c5ccccc53)CC(c3cccc5c3sc3c(-c6ccccc6)cccc35)C=C4)cc2)cc1] | 47% |

| Ex. | Reactants | Product | Yield |
|---|---|---|---|
| | | 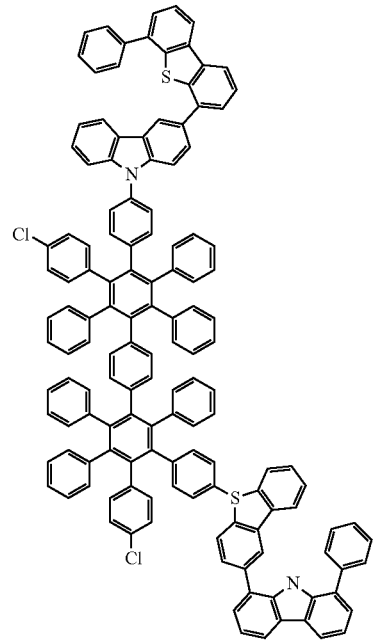200 mmol 1364890-88-9<br>4 mmol P-tBu₃/2 mmol Pd(ac)₂<br>isomer mixture | |
| S224 | S122<br>1807860-07-6 | 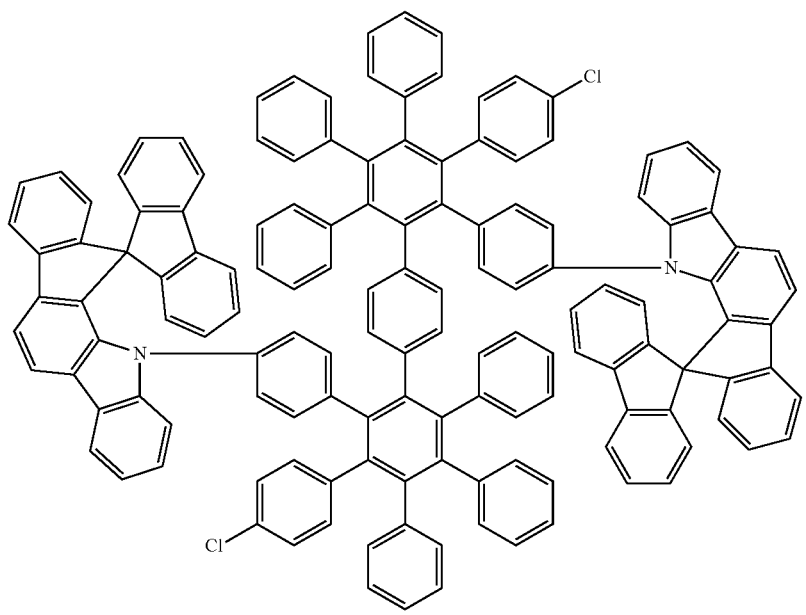 [SMILES: Clc1ccc(-c2c(-c3ccccc3)c(-c3ccccc3)c(-c3ccccc3)c(-c3ccc(-c4c(-c5ccccc5)c(-c5ccccc5)c(-c5ccccc5)c(-c5ccc(Cl)cc5)c4-c4ccc(-n5c6ccccc6c6ccc7c(c65)C5(c6ccccc6-c6ccccc65)c5ccccc5-7)cc4)cc3)c2-c2ccc(-n3c4ccccc4c4ccc5c(c43)C3(c4ccccc4-c4ccccc43)c3ccccc3-5)cc2)cc1] | 51% |

| Ex. | Reactants | Product | Yield |
|---|---|---|---|
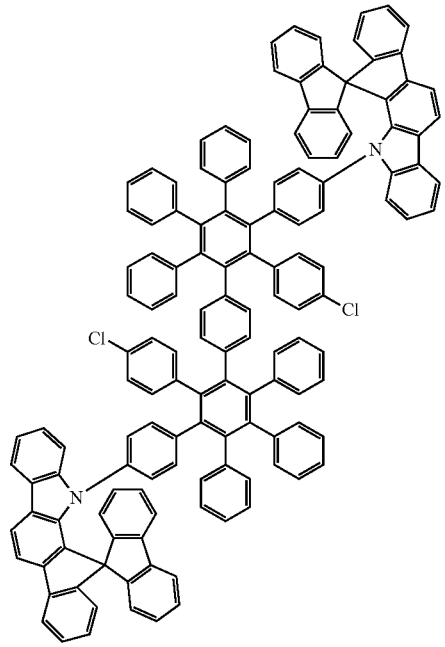 [SMILES: Clc1ccc(-c2c(-c3ccc(-c4c(-c5ccccc5)c(-c5ccccc5)c(-c5ccccc5)c(-c5ccc(-n6c7ccccc7c7ccc8c(c76)C6(c7ccccc7-c7ccccc76)c6ccccc6-8)cc5)c4-c4ccc(Cl)cc4)cc3)c(-c3ccccc3)c(-c3ccccc3)c(-c3ccccc3)c2-c2ccc(-n3c4ccccc4c4ccc5c(c43)C3(c4ccccc4-c4ccccc43)c3ccccc3-5)cc2)cc1]
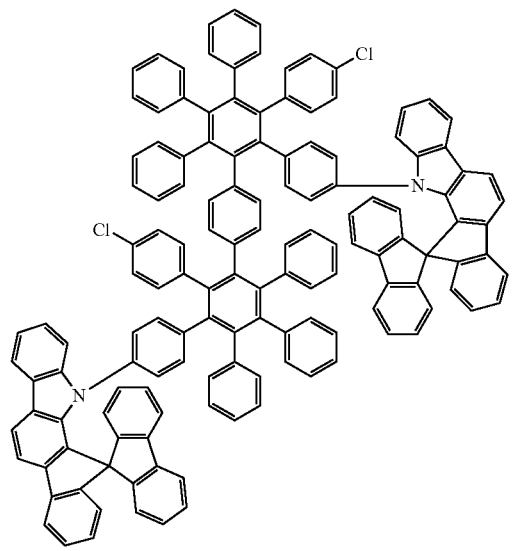
200 mmol 1807860-07-6
4 mmol P-tBu₃/2 mmol Pd(ac)₂
isomer mixture

| Ex. | Reactants | Product | Yield |
|---|---|---|---|
| S225 | S123<br>1372775-52-4 | 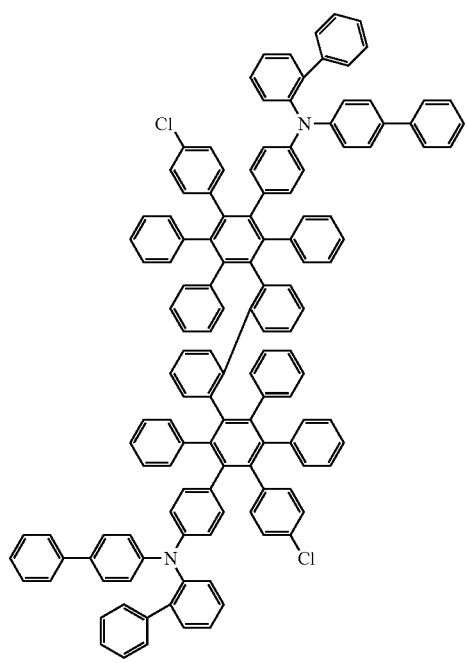 [SMILES: Clc1ccc(-c2c(-c3ccccc3)c(-c3ccccc3)c(-c3ccccc3-c3ccccc3-c3c(-c4ccccc4)c(-c4ccccc4)c(-c4ccc(Cl)cc4)c(-c4ccc(N(c5ccc(-c6ccccc6)cc5)c5ccccc5-c5ccccc5)cc4)c3-c3ccccc3)c(-c3ccccc3)c2-c2ccc(N(c3ccc(-c4ccccc4)cc3)c3ccccc3-c3ccccc3)cc2)cc1] | 45% |

| Ex. | Reactants | Product | Yield |
|---|---|---|---|

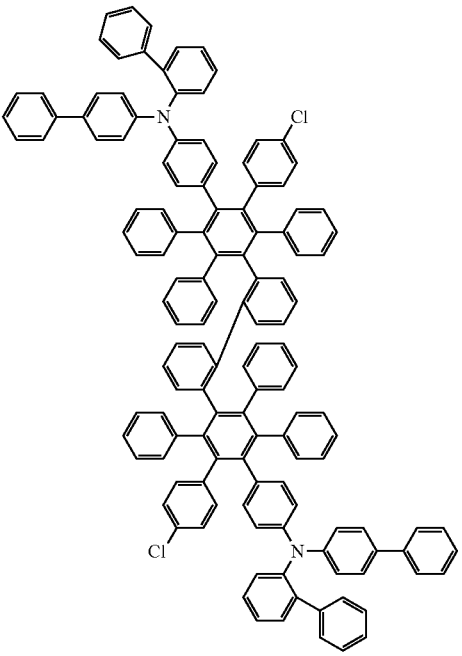

200 mmol 1372775-52-4
4 mmol P-tBu₃/2 mmol Pd(ac)₂
isomer mixture

Example S300: Borylation

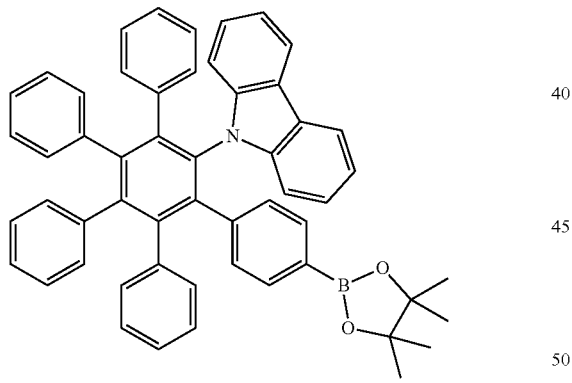

To a mixture of 70.3 g (100 mmol) of S100, 26.7 g (105 mmol) of 4,4,4',4',5,5,5',5'-octamethyl-2,2'-bi(1,3,2-dioxaborolane) [73183-34-3], 29.5 g (300 mmol) of anhydrous potassium acetate, 50 g of glass beads (diameter 3 mm) and 700 ml of dioxane are added 543 mg (1.3 mmol) of S-Phos [657408-07-6] and 225 mg (1 mmol) of palladium(II) acetate, and the mixture is heated to 90° C. with good stirring for 16 h. After cooling, the mixture is filtered through a Celite bed in the form of a dioxane slurry, the bed is washed through with 300 ml of dioxane, the filtrate is concentrated to dryness, the residue is taken up in 500 ml of toluene, and the solution is washed three times with 100 ml each time of water and once with 200 ml of saturated sodium chloride solution and then dried over magnesium sulfate. The foam obtained after the desiccant has been filtered off and the solvent has been removed is recrystallized from ethyl acetate/methanol. Yield: 65.2 g (87 mmol), 87%; purity: 95% by $^1$H NMR.

In an analogous manner, it is possible to prepare the following compounds:
| Ex. | Reactant | Product | Yield |
|---|---|---|---|
| S301 | S101 | 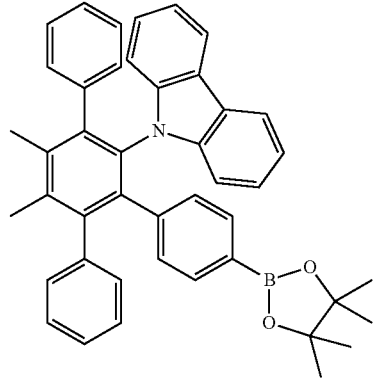 | 89% |
| S302 | S102 | 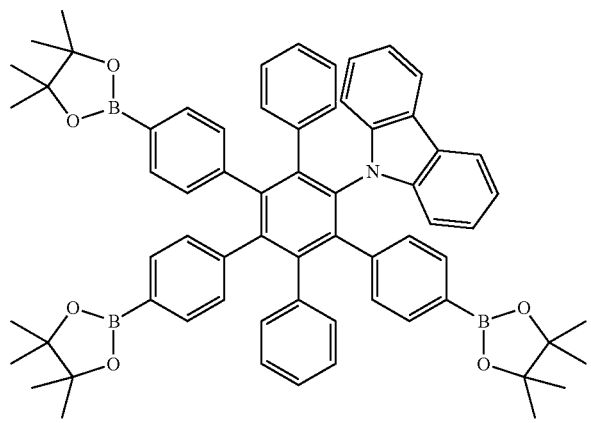<br>315 mmol 73183-34-3 | 90% |
| S303 | S103 | 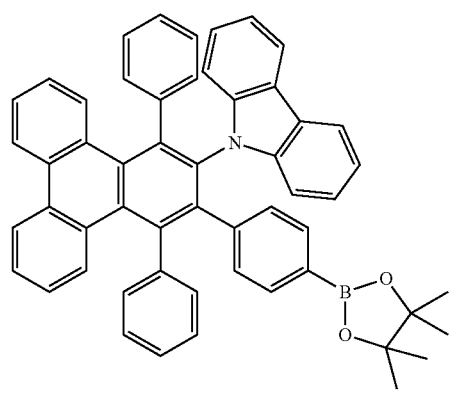 [SMILES: CC1(C)OB(c2ccc(-c3c(-n4c5ccccc5c5ccccc54)c(-c4ccccc4)c4c5ccccc5c5ccccc5c4c3-c3ccccc3)cc2)OC1(C)C] | 85% |

| Ex. | Reactant | Product | Yield |
|---|---|---|---|
| S304 | S201 | 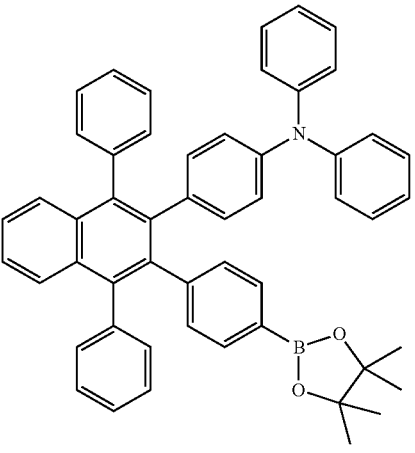 [SMILES: CC1(C)OB(c2ccc(-c3c(-c4ccc(N(c5ccccc5)c5ccccc5)cc4)c(-c4ccccc4)c4ccccc4c3-c3ccccc3)cc2)OC1(C)C] | 86% |
| S305 | S202 | 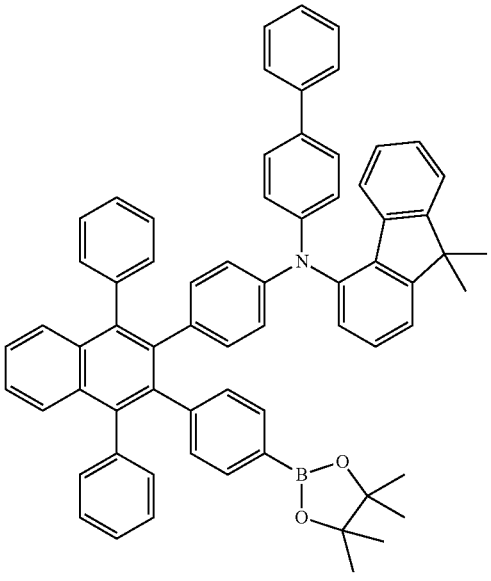 [SMILES: CC1(C)c2ccccc2-c2c(N(c3ccc(-c4ccccc4)cc3)c3ccc(-c4c(-c5ccc(B6OC(C)(C)C(C)(C)O6)cc5)c(-c5ccccc5)c5ccccc5c4-c4ccccc4)cc3)cccc21] | 83% |
| S306 | S203 | 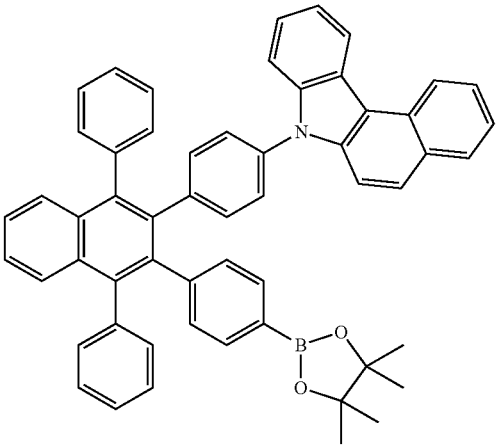 [SMILES: CC1(C)OB(c2ccc(-c3c(-c4ccc(-n5c6ccccc6c6c7ccccc7ccc65)cc4)c(-c4ccccc4)c4ccccc4c3-c3ccccc3)cc2)OC1(C)C] | 90% |

-continued

| Ex. | Reactant | Product | Yield |
|---|---|---|---|
| S307 | S204 | | 86% |
| S308 | S205 | | 87% |

| Ex. | Reactant | Product | Yield |
|---|---|---|---|
| S309 | S206 | 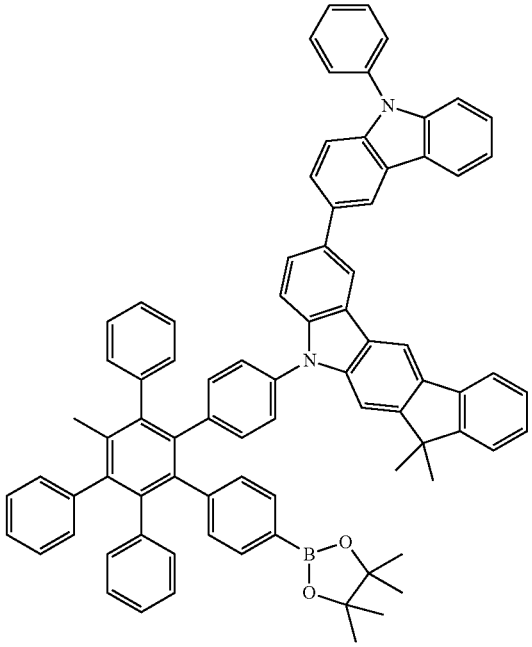 [SMILES: Cc1c(-c2ccccc2)c(-c2ccccc2)c(-c2ccc(B3OC(C)(C)C(C)(C)O3)cc2)c(-c2ccc(-n3c4ccc(-c5ccc6c(c5)c5ccccc5n6-c5ccccc5)cc4c4cc5c(cc43)C(C)(C)c3ccccc3-5)cc2)c1-c1ccccc1] | 73% |
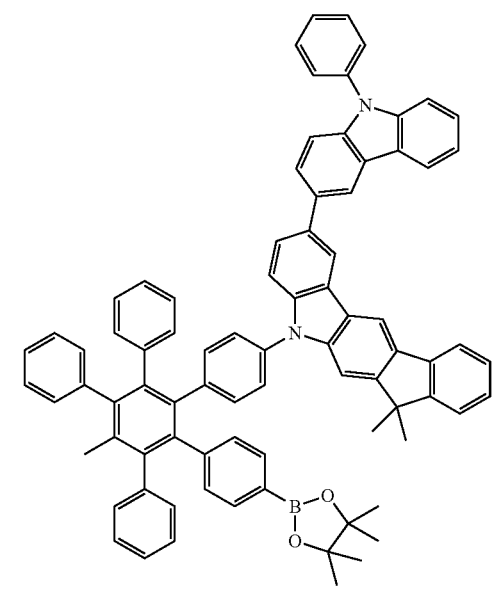
isomer mixture

| Ex. | Reactant | Product | Yield |
|---|---|---|---|
| S310 | S207 | | 79% |
| S311 | S208 | | 80% |
| S312 | S209 | | 85% |

| Ex. | Reactant | Product | Yield |
|---|---|---|---|
| S313 | S210 | 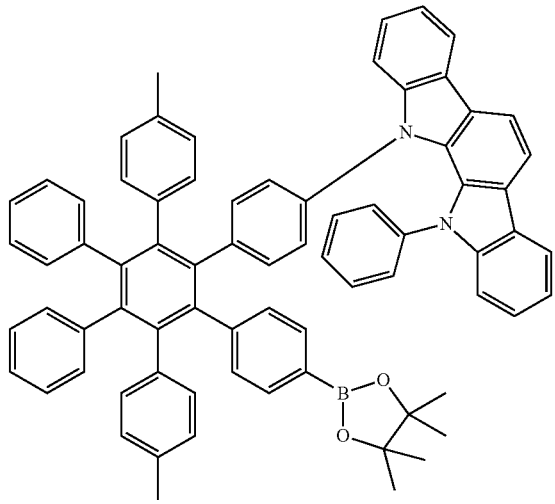 [SMILES: Cc1ccc(-c2c(-c3ccccc3)c(-c3ccccc3)c(-c3ccc(C)cc3)c(-c3ccc(-n4c5ccccc5c5ccc6c7ccccc7n(-c7ccccc7)c6c54)cc3)c2-c2ccc(B3OC(C)(C)C(C)(C)O3)cc2)cc1] | 85% |
| S314 | S211 | 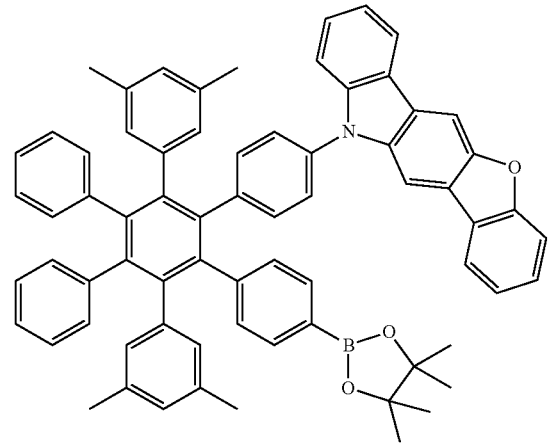 [SMILES: Cc1cc(C)cc(-c2c(-c3ccccc3)c(-c3ccccc3)c(-c3cc(C)cc(C)c3)c(-c3ccc(-n4c5ccccc5c5cc6oc7ccccc7c6cc54)cc3)c2-c2ccc(B3OC(C)(C)C(C)(C)O3)cc2)c1] | 87% |
| S315 | S212 | 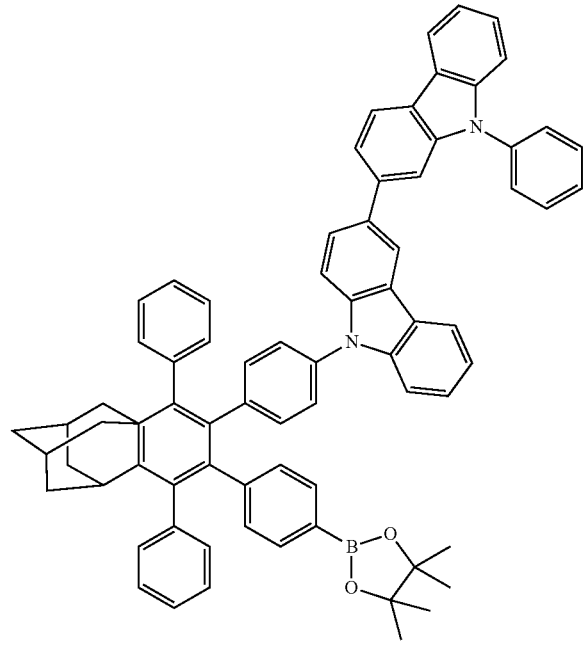 | 86% |

| Ex. | Reactant | Product | Yield |
|---|---|---|---|
| S316 | S213 | 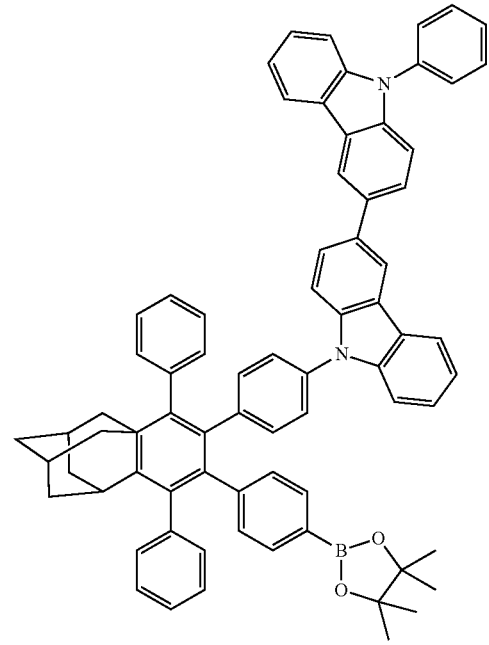 | 88% |
| S317 | S214 | 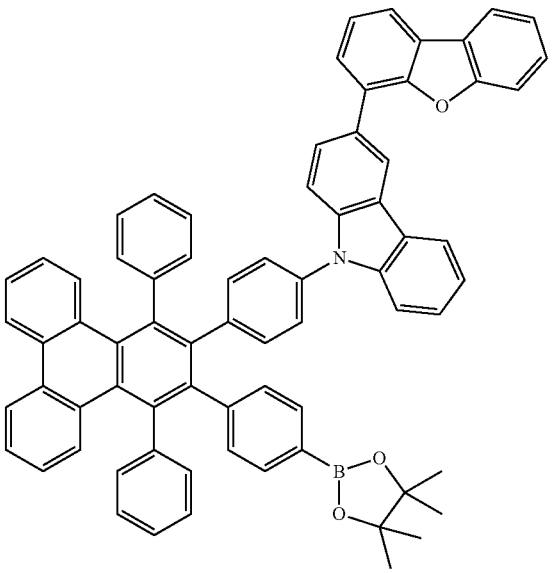 [SMILES: CC1(C)OB(c2ccc(-c3c(-c4ccc(-n5c6ccccc6c6cc(-c7cccc8c7oc7ccccc78)ccc65)cc4)c(-c4ccccc4)c4c5ccccc5c5ccccc5c4c3-c3ccccc3)cc2)OC1(C)C] | 79% |

| Ex. | Reactant | Product | Yield |
|---|---|---|---|
| S318 | S215 | 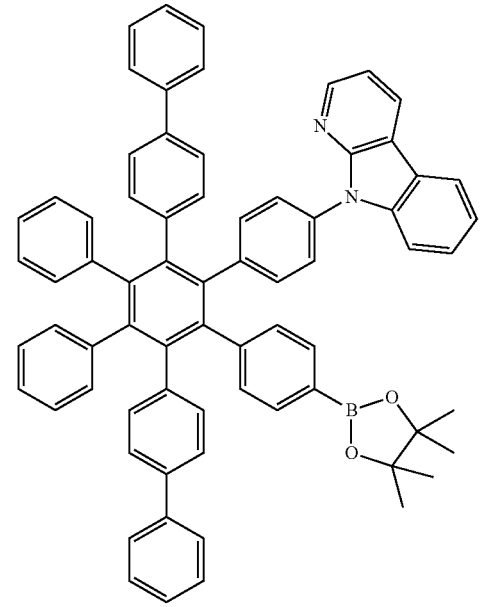 [SMILES: CC1(C)OB(c2ccc(-c3c(-c4ccc(-c5ccccc5)cc4)c(-c4ccccc4)c(-c4ccccc4)c(-c4ccc(-c5ccccc5)cc4)c3-c3ccc(-n4c5ccccc5c5cccnc54)cc3)cc2)OC1(C)C] | 81% |
| S319 | S216 | 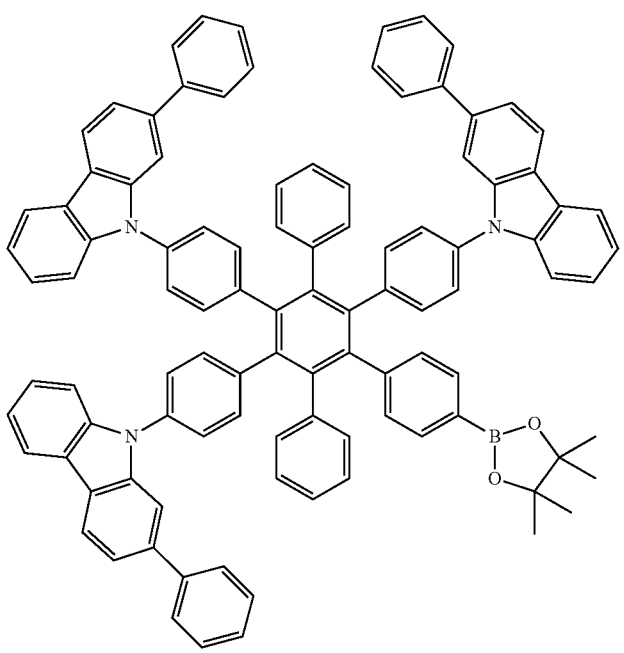 [SMILES: CC1(C)OB(c2ccc(-c3c(-c4ccccc4)c(-c4ccc(-n5c6ccccc6c6ccc(-c7ccccc7)cc65)cc4)c(-c4ccc(-n5c6ccccc6c6ccc(-c7ccccc7)cc65)cc4)c(-c4ccccc4)c3-c3ccc(-n4c5ccccc5c5ccc(-c6ccccc6)cc54)cc3)cc2)OC1(C)C] | 90% |

-continued
| Ex. | Reactant | Product | Yield |
|---|---|---|---|
| S320 | S217 | 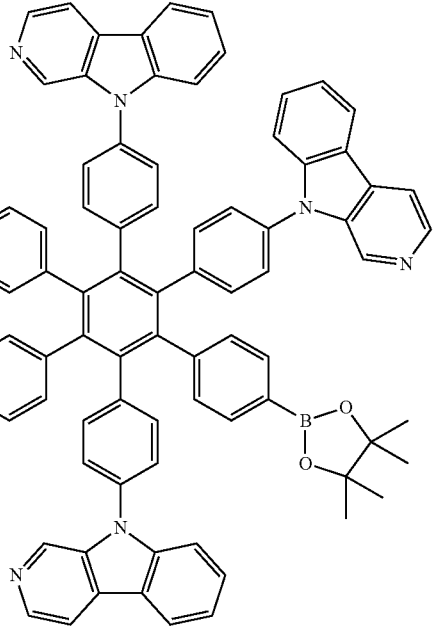 | 80% |
| S321 | S218 | 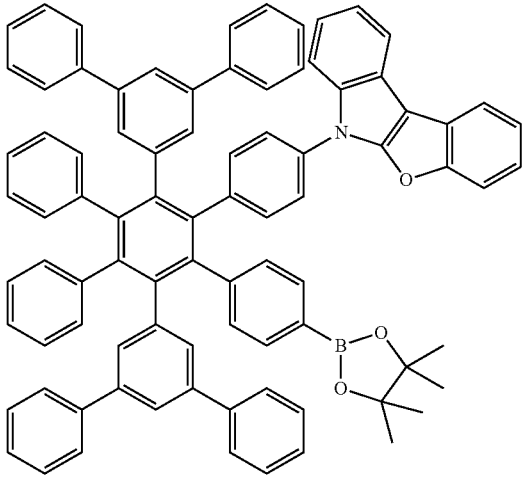 [SMILES: CC1(C)OB(c2ccc(-c3c(-c4ccc(-n5c6ccccc6c6c7ccccc7oc65)cc4)c(-c4cc(-c5ccccc5)cc(-c5ccccc5)c4)c(-c4ccccc4)c(-c4ccccc4)c3-c3cc(-c4ccccc4)cc(-c4ccccc4)c3)cc2)OC1(C)C] | 88% |
| S322 | S219 | 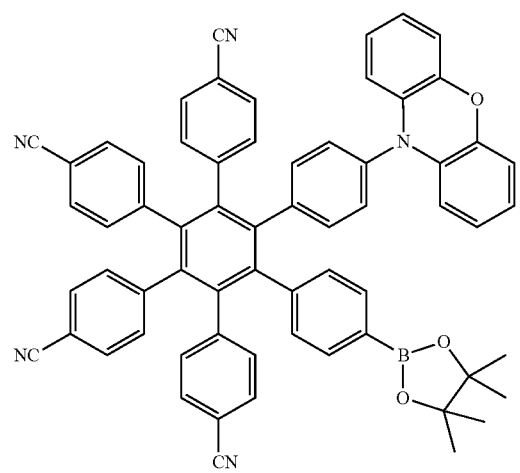 [SMILES: CC1(C)OB(c2ccc(-c3c(-c4ccc(C#N)cc4)c(-c4ccc(C#N)cc4)c(-c4ccc(C#N)cc4)c(-c4ccc(C#N)cc4)c3-c3ccc(N4c5ccccc5Oc5ccccc54)cc3)cc2)OC1(C)C] | 74% |

| Ex. | Reactant | Product | Yield |
|---|---|---|---|
| S323 | S220 | 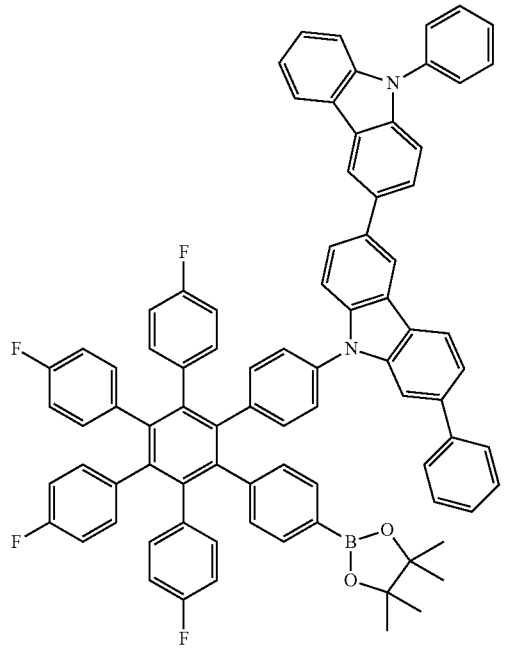 [SMILES: CC1(C)OB(c2ccc(-c3c(-c4ccc(F)cc4)c(-c4ccc(F)cc4)c(-c4ccc(F)cc4)c(-c4ccc(F)cc4)c3-c3ccc(-n4c5ccc(-c6ccc7c(c6)c6ccccc6n7-c6ccccc6)cc5c5ccc(-c6ccccc6)cc54)cc3)cc2)OC1(C)C] | 82% |
| S324 | S221 | 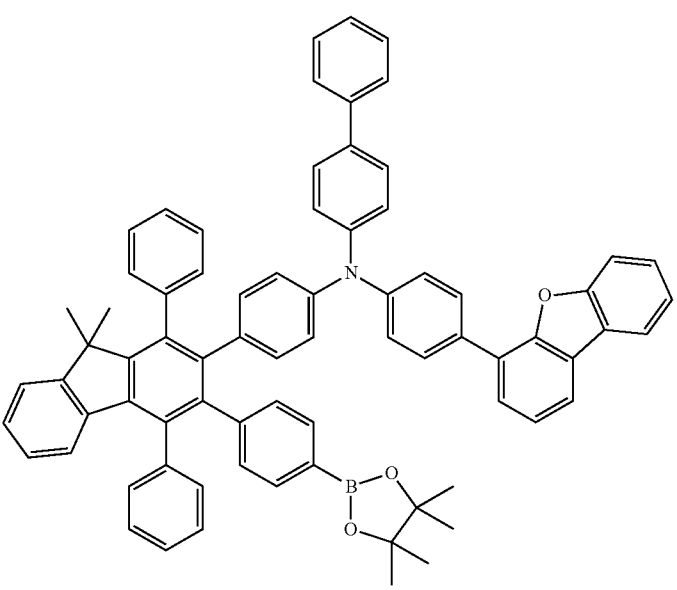 [SMILES: CC1(C)c2ccccc2-c2c(-c3ccccc3)c(-c3ccc(B4OC(C)(C)C(C)(C)O4)cc3)c(-c3ccc(N(c4ccc(-c5ccccc5)cc4)c4ccc(-c5cccc6c5oc5ccccc56)cc4)cc3)c(-c3ccccc3)c21] | 76% |

-continued
| Ex. | Reactant | Product | Yield |
|---|---|---|---|
| | | 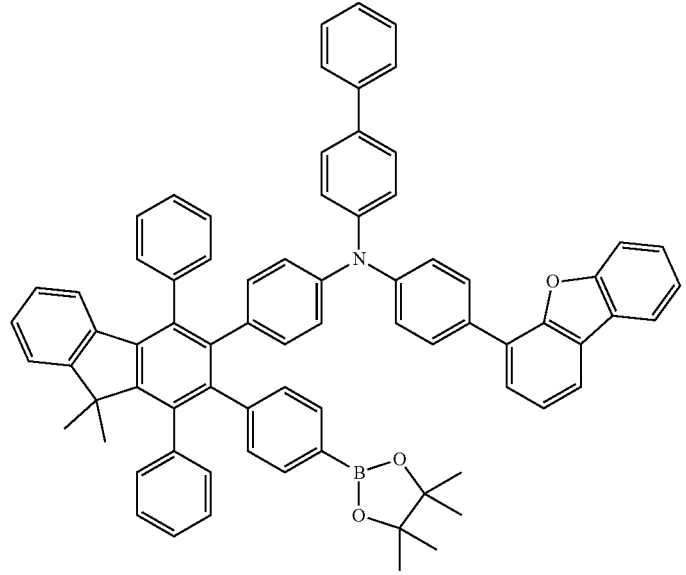
isomer mixture | |
| S325 | S222 | 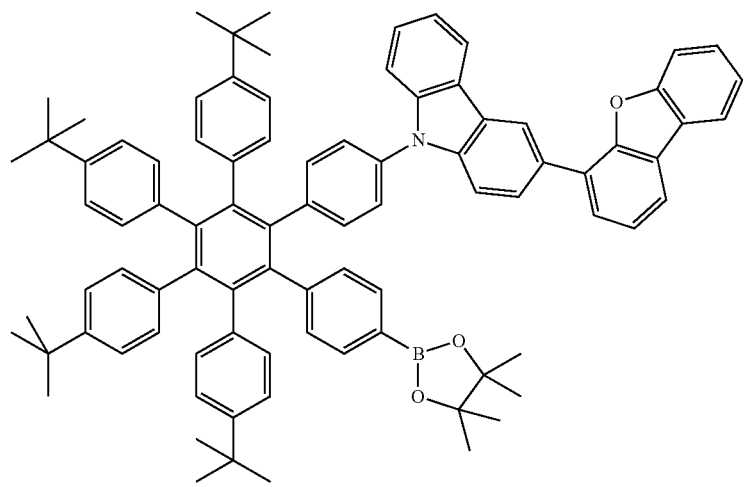 [SMILES: CC(C)(C)c1ccc(-c2c(-c3ccc(B4OC(C)(C)C(C)(C)O4)cc3)c(-c3ccc(-n4c5ccccc5c5cc(-c6cccc7c6oc6ccccc67)ccc54)cc3)c(-c3ccc(C(C)(C)C)cc3)c(-c3ccc(C(C)(C)C)cc3)c2-c2ccc(C(C)(C)C)cc2)cc1] | 69% |

| Ex. | Reactant | Product | Yield |
|---|---|---|---|
| S326 | S223 | 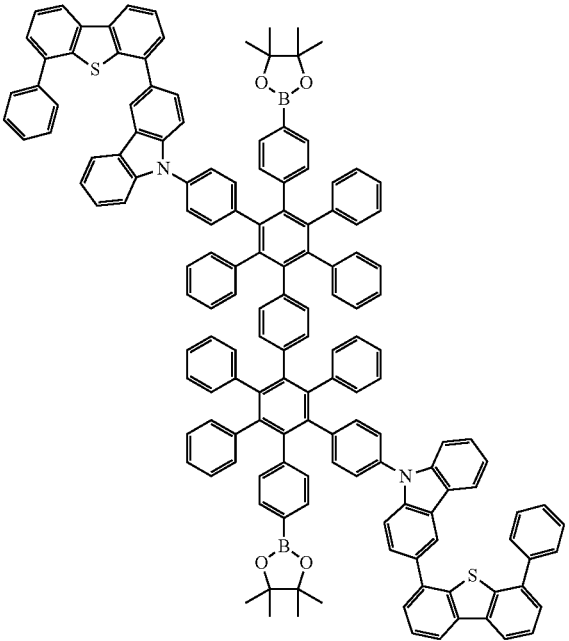 [SMILES: CC1(C)OB(c2ccc(-c3c(-c4ccccc4)c(-c4ccccc4)c(-c4ccc(-c5c(-c6ccccc6)c(-c6ccccc6)c(-c6ccc(B7OC(C)(C)C(C)(C)O7)cc6)c(-c6ccc(-n7c8ccccc8c8cc(-c9cccc%10c9sc9c(-c%11ccccc%11)cccc9%10)ccc87)cc6)c5-c5ccccc5)cc4)c(-c4ccccc4)c3-c3ccc(-n4c5ccccc5c5cc(-c6cccc7c6sc6c(-c8ccccc8)cccc67)ccc54)cc3)cc2)OC1(C)C] | |

| Ex. | Reactant | Product | Yield |
|---|---|---|---|
| | | 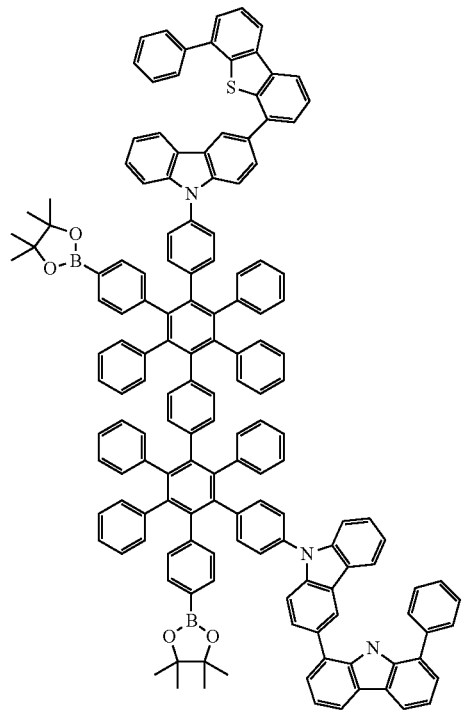isomer mixture<br>210 mmol 73183-34-3 | |
| S327 | S224 | 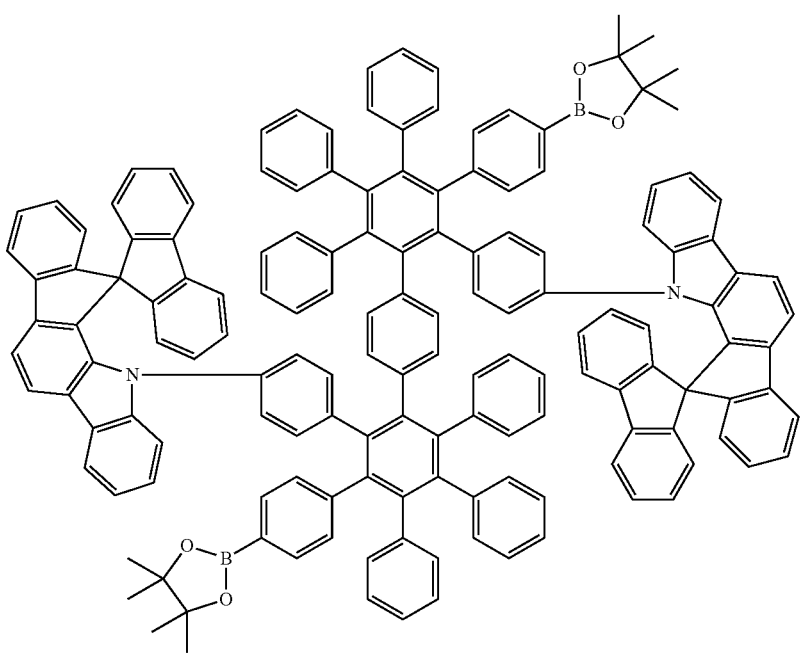 [SMILES: CC1(C)OB(c2ccc(-c3c(-c4ccccc4)c(-c4ccccc4)c(-c4ccccc4)c(-c4ccc(-c5c(-c6ccccc6)c(-c6ccccc6)c(-c6ccccc6)c(-c6ccc(B7OC(C)(C)C(C)(C)O7)cc6)c5-c5ccc(-n6c7ccccc7c7ccc8c(c76)C6(c7ccccc7-c7ccccc76)c6ccccc6-8)cc5)cc4)c3-c3ccc(-n4c5ccccc5c5ccc6c(c54)C4(c5ccccc5-c5ccccc54)c4ccccc4-6)cc3)cc2)OC1(C)C] | 67% |

| Ex. | Reactant | Product | Yield |
|---|---|---|---|
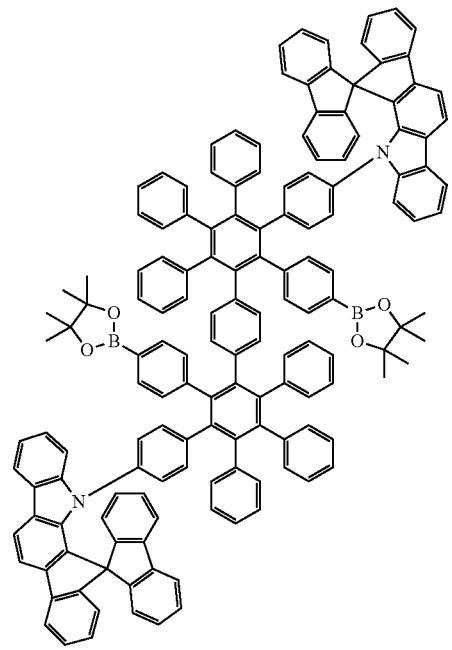 [SMILES: CC1(C)OB(c2ccc(-c3c(-c4ccc(-c5c(-c6ccccc6)c(-c6ccccc6)c(-c6ccccc6)c(-c6ccc(-n7c8ccccc8c8ccc9c(c87)C7(c8ccccc8-c8ccccc87)c7ccccc7-9)cc6)c5-c5ccc(B6OC(C)(C)C(C)(C)O6)cc5)cc4)c(-c4ccccc4)c(-c4ccccc4)c(-c4ccccc4)c3-c3ccc(-n4c5ccccc5c5ccc6c(c54)C4(c5ccccc5-c5ccccc54)c4ccccc4-6)cc3)cc2)OC1(C)C]
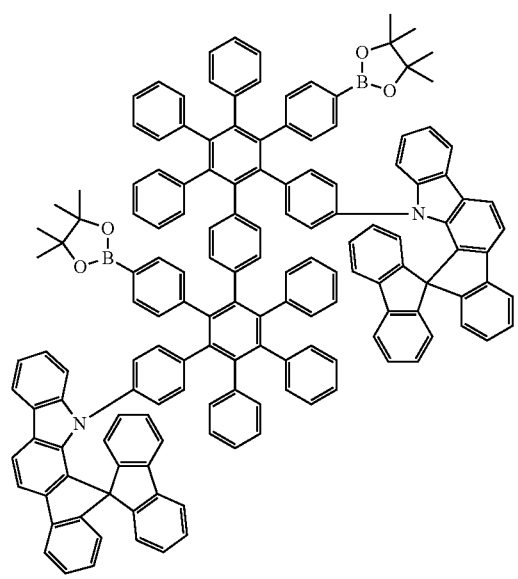
isomer mixture
210 mmol 73183-34-3

| Ex. | Reactant | Product | Yield |
|---|---|---|---|
| S328 | S225 | 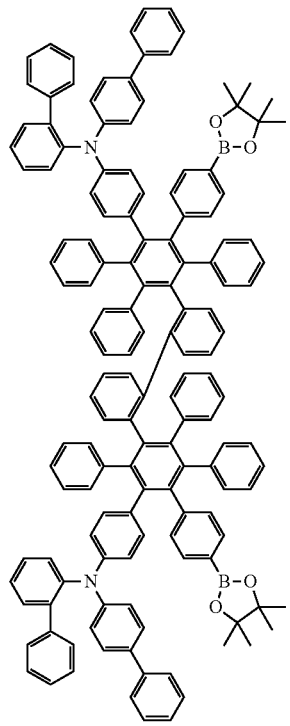 [SMILES: CC1(C)OB(c2ccc(-c3c(-c4ccccc4)c(-c4ccccc4)c(-c4ccccc4-c4ccccc4-c4c(-c5ccccc5)c(-c5ccccc5)c(-c5ccc(N(c6ccc(-c7ccccc7)cc6)c6ccccc6-c6ccccc6)cc5)c(-c5ccc(B6OC(C)(C)C(C)(C)O6)cc5)c4-c4ccccc4)c(-c4ccccc4)c3-c3ccc(N(c4ccc(-c5ccccc5)cc4)c4ccccc4-c4ccccc4)cc3)cc2)OC1(C)C] | 71% |
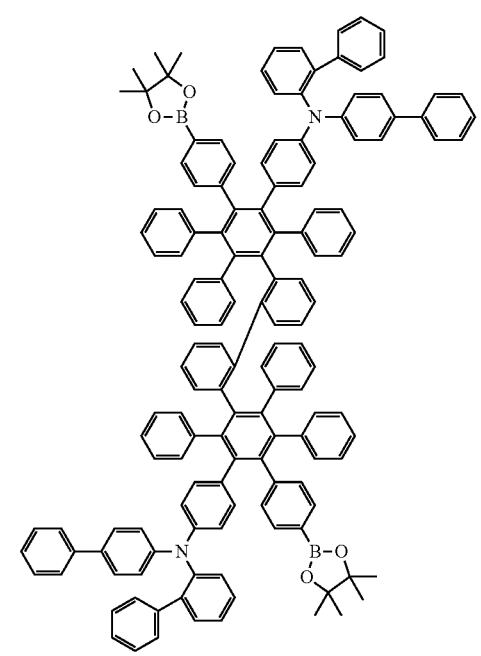 [SMILES: CC1(C)OB(c2ccc(-c3c(-c4ccccc4)c(-c4ccccc4)c(-c4ccccc4-c4ccccc4-c4c(-c5ccccc5)c(-c5ccccc5)c(-c5ccc(B6OC(C)(C)C(C)(C)O6)cc5)c(-c5ccc(N(c6ccc(-c7ccccc7)cc6)c6ccccc6-c6ccccc6)cc5)c4-c4ccccc4)c(-c4ccccc4)c3-c3ccc(N(c4ccc(-c5ccccc5)cc4)c4ccccc4-c4ccccc4)cc3)cc2)OC1(C)C]

| Ex. | Reactant | Product | Yield |
|---|---|---|---|

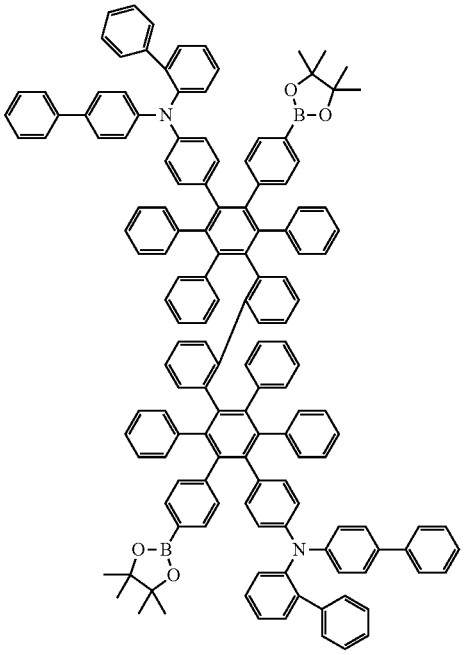

isomer mixture
210 mmol 73183-34-3

Example P1: Suzuki Coupling

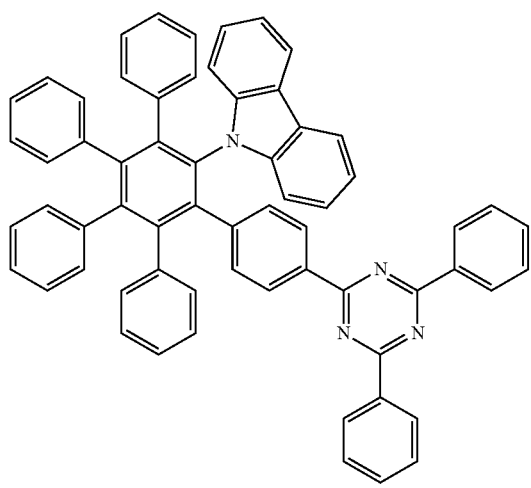 [SMILES: c1ccc(-c2nc(-c3ccccc3)nc(-c3ccc(-c4c(-c5ccccc5)c(-c5ccccc5)c(-c5ccccc5)c(-c5ccccc5)c4-n4c5ccccc5c5ccccc54)cc3)n2)cc1]

To a well-stirred mixture of 75.0 g (100 mmol) of S300, 28.1 g (105 mmol) of 1-chloro-3,5-diphenyltriazine [3842-55-5], 63.7 g (300 mmol) of tripotassium phosphate, 500 ml of toluene, 300 ml of dioxane, 500 ml of water are added 1.2 g (3 mmol) of S-Phos [657408-07-6] and 498 mg (2 mmol) of palladium(II) acetate, and then the mixture is heated under reflux for 16 h. After cooling, the organic phase is removed and washed twice with 300 ml each time of water and once with 300 ml of saturated sodium chloride solution, and then dried over magnesium sulfate. The desiccant is filtered off through a Celite bed in the form of a toluene slurry, the bed is washed through with 300 ml of toluene, the filtrate is concentrated to dryness and the residue is crystallized twice from dimethylacetamide. Further purification is effected by repeated hot extraction with n-butyl acetate, followed by fractional sublimation (p about $10^{-5}$ mbar, T about 330° C.). Yield: 47.9 g (56 mmol), 56%; purity: 99.9% by $^1$H NMR.

In an analogous manner, it is possible to prepare the following compounds, with products of molar mass greater than 1200 g/mol typically being freed of residual solvents by heating under high vacuum:

| Ex. | Reactant | Product | Yield |
|---|---|---|---|
| P2 | S101<br>1215596-23-6 | 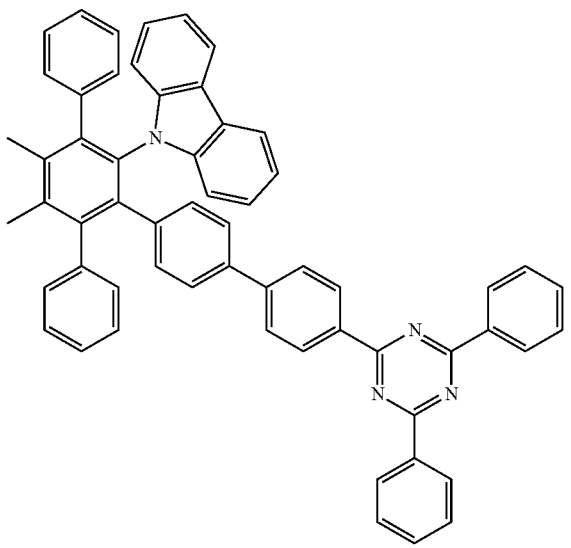 [SMILES: Cc1c(C)c(-c2ccccc2)c(-n2c3ccccc3c3ccccc32)c(-c2ccc(-c3ccc(-c4nc(-c5ccccc5)nc(-c5ccccc5)n4)cc3)cc2)c1-c1ccccc1] | 54% |
| P3 | S102<br>1613163-88-4 | 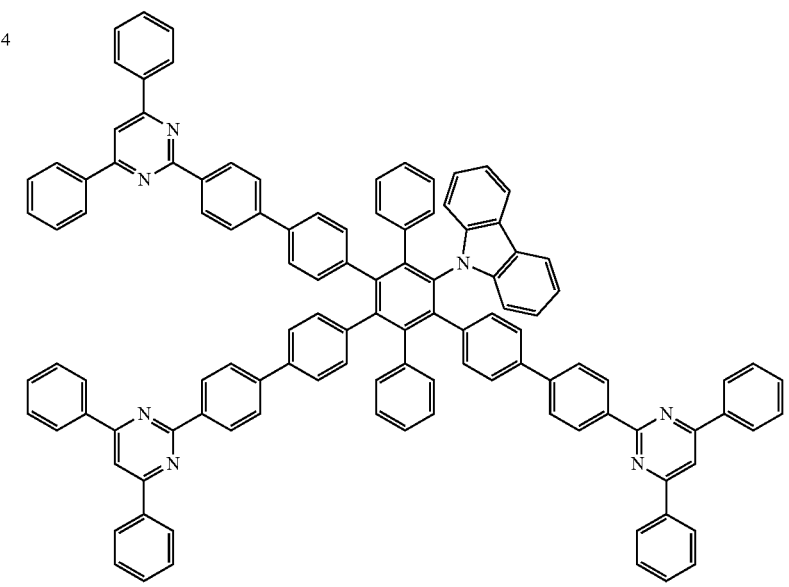<br>315 mmol 1613163-88-4<br>6 mmol S-Phos/4 mmol Pd(ac)$_2$ | 49% |

| Ex. | Reactant | Product | Yield |
|---|---|---|---|
| P4 | S303<br>2915-16-4 | 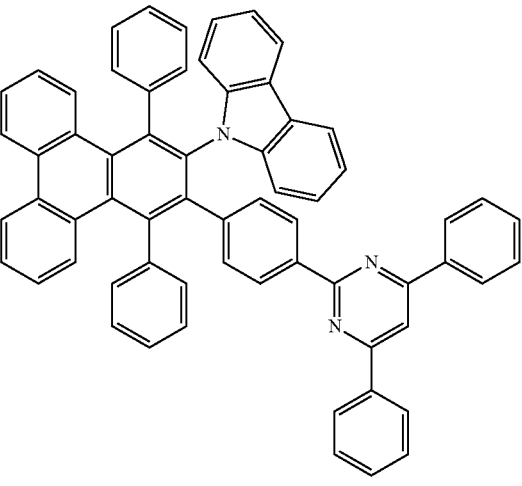 [SMILES: c1ccc(-c2cc(-c3ccccc3)nc(-c3ccc(-c4c(-n5c6ccccc6c6ccccc65)c(-c5ccccc5)c5c6ccccc6c6ccccc6c5c4-c4ccccc4)cc3)n2)cc1] | 59% |
| P5 | S304<br>3842-55-5 | 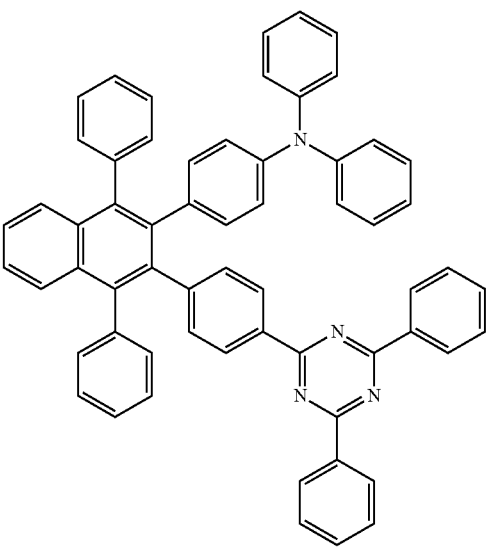 [SMILES: c1ccc(-c2nc(-c3ccccc3)nc(-c3ccc(-c4c(-c5ccc(N(c6ccccc6)c6ccccc6)cc5)c(-c5ccccc5)c5ccccc5c4-c4ccccc4)cc3)n2)cc1] | 57% |

| Ex. | Reactant | Product | Yield |
|---|---|---|---|
| P6 | S305<br>2915-16-4 | 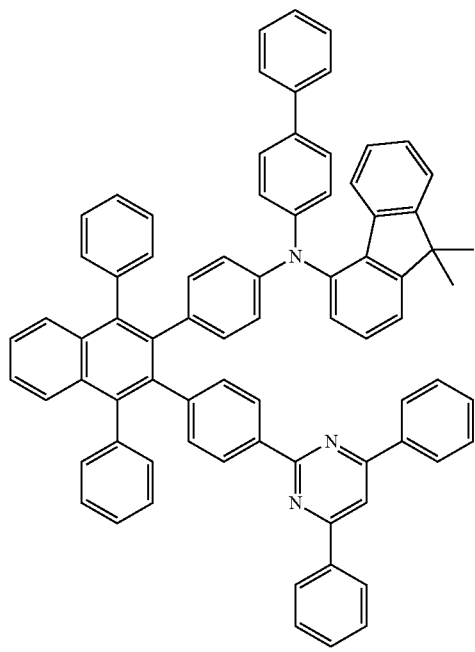 [SMILES: CC1(C)c2ccccc2-c2c(N(c3ccc(-c4ccccc4)cc3)c3ccc(-c4c(-c5ccc(-c6nc(-c7ccccc7)cc(-c7ccccc7)n6)cc5)c(-c5ccccc5)c5ccccc5c4-c4ccccc4)cc3)cccc21] | 53% |
| P7 | S306<br>29874-83-7 | 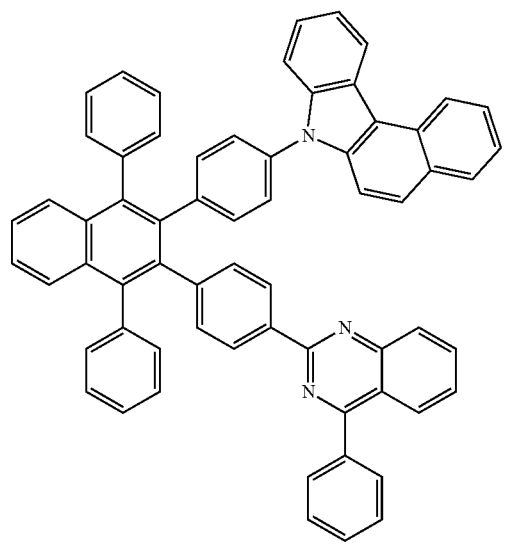 [SMILES: c1ccc(-c2nc(-c3ccc(-c4c(-c5ccc(-n6c7ccccc7c7c8ccccc8ccc76)cc5)c(-c5ccccc5)c5ccccc5c4-c4ccccc4)cc3)nc3ccccc23)cc1] | 55% |

| Ex. | Reactant | Product | Yield |
|---|---|---|---|
| P8 | S307<br>1300115-09-6 | 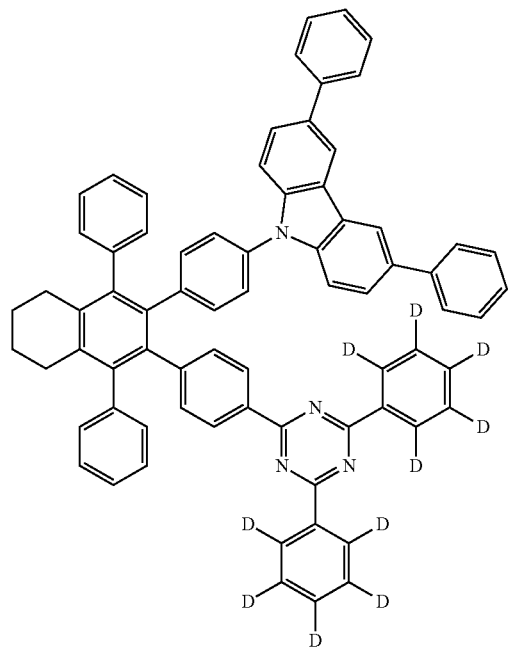 [SMILES: [2H]c1c([2H])c([2H])c(-c2nc(-c3ccc(-c4c(-c5ccccc5)c5c(c(-c6ccccc6)c4-c4ccc(-n6c7ccc(-c8ccccc8)cc7c7cc(-c8ccccc8)ccc76)cc4)CCCC5)cc3)nc(-c3c([2H])c([2H])c([2H])c([2H])c3[2H])n2)c([2H])c1[2H]] | 51% |
| P9 | S308<br>6484-25-9 | 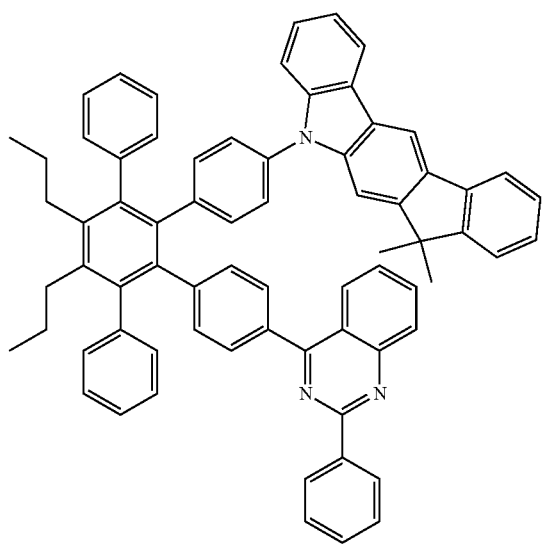 [SMILES: CCCc1c(CCC)c(-c2ccccc2)c(-c2ccc(-n3c4ccccc4c4cc5c(cc43)C(C)(C)c3ccccc3-5)cc2)c(-c2ccc(-c3nc(-c4ccccc4)nc4ccccc34)cc2)c1-c1ccccc1] | 49% |

-continued
| Ex. | Reactant | Product | Yield |
|---|---|---|---|
| P10 | S309<br>24547-45-3 | 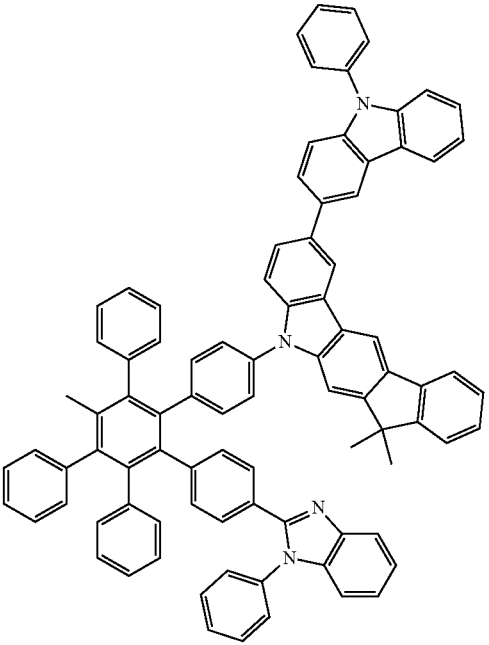 [SMILES: Cc1c(-c2ccccc2)c(-c2ccccc2)c(-c2ccc(-c3nc4ccccc4n3-c3ccccc3)cc2)c(-c2ccc(-n3c4ccc(-c5ccc6c(c5)c5ccccc5n6-c5ccccc5)cc4c4cc5c(cc43)C(C)(C)c3ccccc3-5)cc2)c1-c1ccccc1] | 38% |
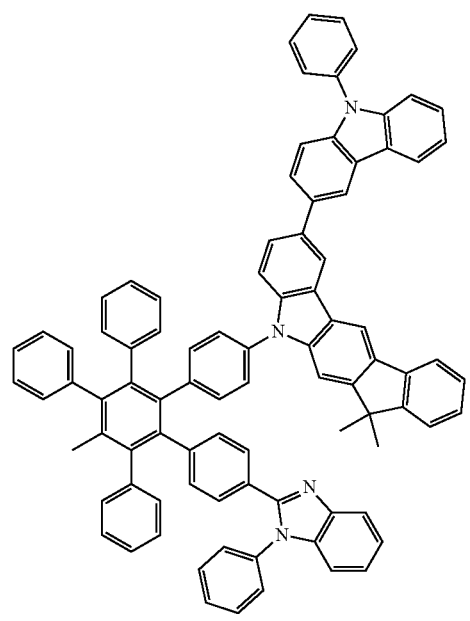
isomer mixture -continued
| Ex. | Reactant | Product | Yield |
|---|---|---|---|
| P11 | S310<br>23449-08-3 | 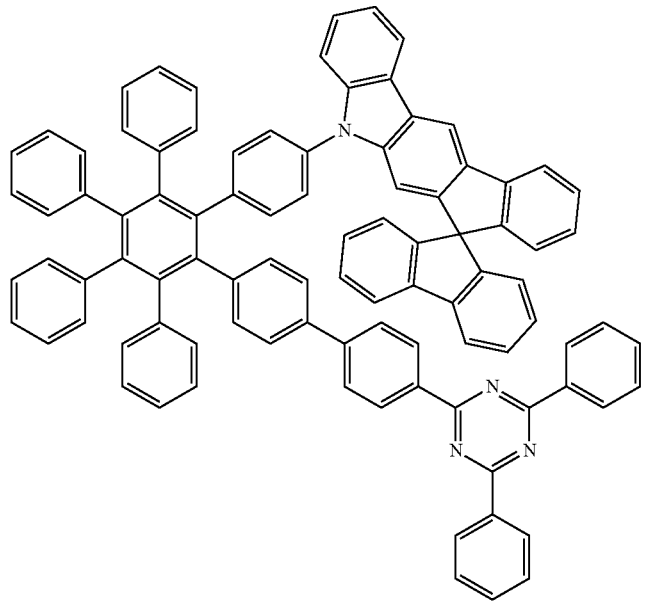 [SMILES: c1ccc(-c2nc(-c3ccccc3)nc(-c3ccc(-c4ccc(-c5c(-c6ccccc6)c(-c6ccccc6)c(-c6ccccc6)c(-c6ccccc6)c5-c5ccc(-n6c7ccccc7c7cc8c(cc76)C6(c7ccccc7-c7ccccc76)c6ccccc6-8)cc5)cc4)cc3)n2)cc1] | 55% |
| P12 | S311<br>864377-31-1 | 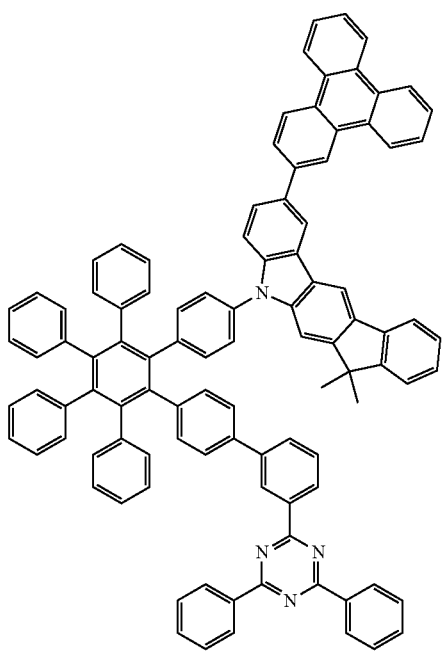 [SMILES: CC1(C)c2ccccc2-c2cc3c4cc(-c5ccc6c7ccccc7c7ccccc7c6c5)ccc4n(-c4ccc(-c5c(-c6ccccc6)c(-c6ccccc6)c(-c6ccccc6)c(-c6ccccc6)c5-c5ccc(-c6cccc(-c7nc(-c8ccccc8)nc(-c8ccccc8)n7)c6)cc5)cc4)c3cc21] | 58% |

| Ex. | Reactant | Product | Yield |
|---|---|---|---|
| P13 | S312 1616231-57-2 | 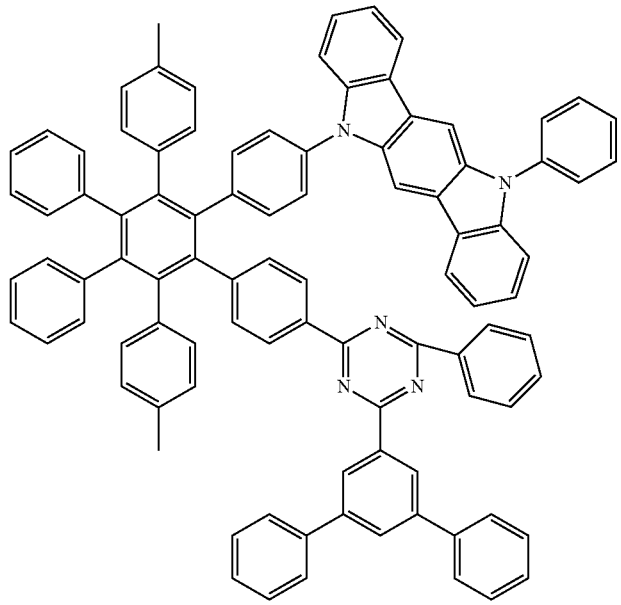 [SMILES: Cc1ccc(-c2c(-c3ccccc3)c(-c3ccccc3)c(-c3ccc(C)cc3)c(-c3ccc(-n4c5ccccc5c5cc6c(cc54)c4ccccc4n6-c4ccccc4)cc3)c2-c2ccc(-c3nc(-c4ccccc4)nc(-c4cc(-c5ccccc5)cc(-c5ccccc5)c4)n3)cc2)cc1] | 54% |
| P14 | S313 1689576-03-1 | 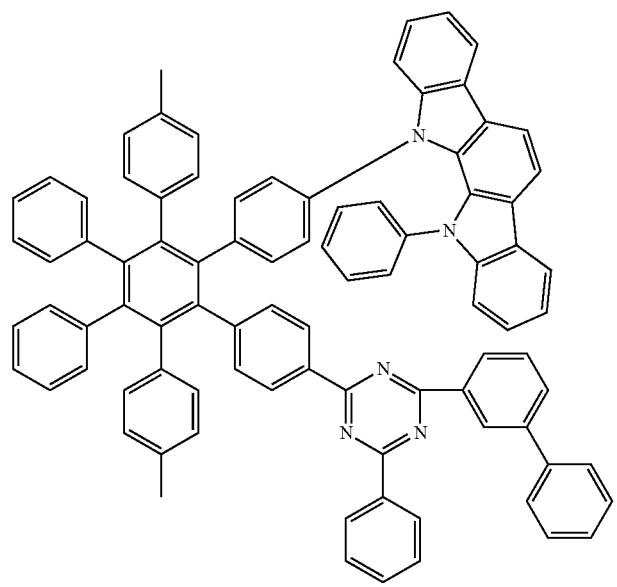 [SMILES: Cc1ccc(-c2c(-c3ccccc3)c(-c3ccccc3)c(-c3ccc(C)cc3)c(-c3ccc(-n4c5ccccc5c5ccc6c7ccccc7n(-c7ccccc7)c6c54)cc3)c2-c2ccc(-c3nc(-c4ccccc4)nc(-c4cccc(-c5ccccc5)c4)n3)cc2)cc1] | 50% |

| Ex. | Reactant | Product | Yield |
|---|---|---|---|
| P15 | S314<br>55635-65-9 | 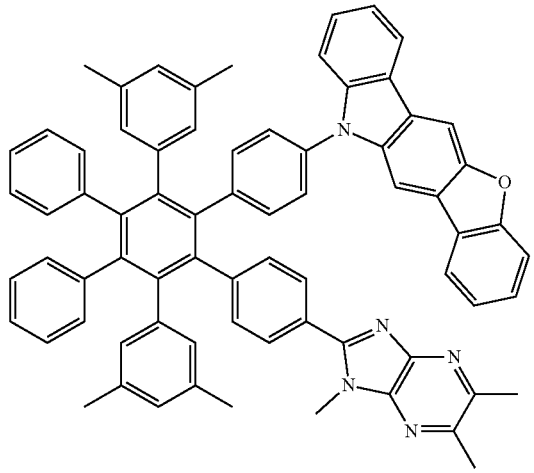 [SMILES: Cc1cc(C)cc(-c2c(-c3ccccc3)c(-c3ccccc3)c(-c3cc(C)cc(C)c3)c(-c3ccc(-n4c5ccccc5c5cc6oc7ccccc7c6cc54)cc3)c2-c2ccc(-c3nc4nc(C)c(C)nc4n3C)cc2)c1] | 57% |
| P16 | S315<br>1931136-94-5 | 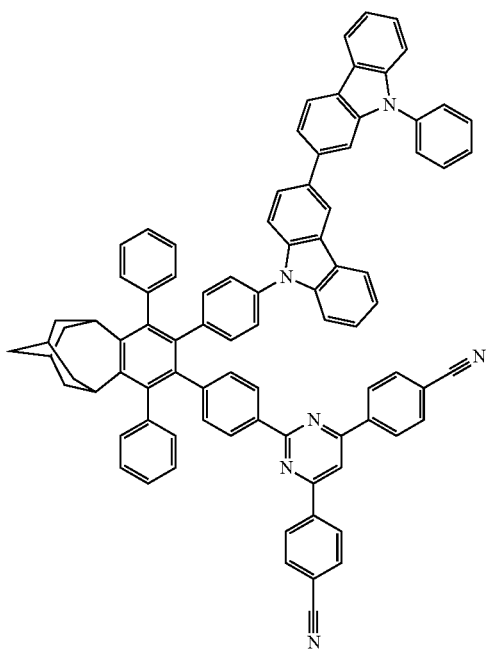 [SMILES: N#Cc1ccc(-c2cc(-c3ccc(C#N)cc3)nc(-c3ccc(-c4c(-c5ccc(-n6c7ccccc7c7cc(-c8ccc9c%10ccccc%10n(-c%10ccccc%10)c9c8)ccc76)cc5)c(-c5ccccc5)c5c(c4-c4ccccc4)C4CC6CC(C4)CC5C6)cc3)n2)cc1] | 51% |

| Ex. | Reactant | Product | Yield |
|---|---|---|---|
| P17 | S316<br>3842-55-5 | | 53% |
| P18 | S317<br>3842-55-5 | | 59% |

| Ex. | Reactant | Product | Yield |
|---|---|---|---|
| P19 | S318<br>1439929-51-7 | 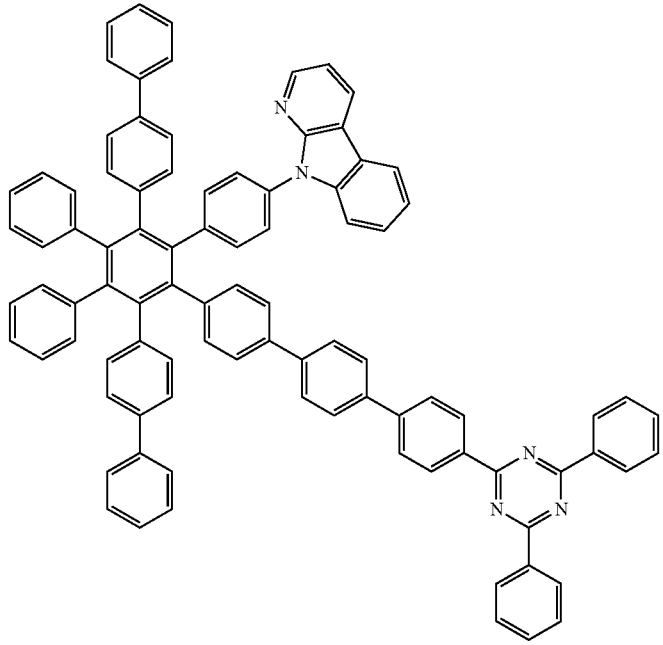 [SMILES: c1ccc(-c2ccc(-c3c(-c4ccccc4)c(-c4ccccc4)c(-c4ccc(-c5ccccc5)cc4)c(-c4ccc(-n5c6ccccc6c6cccnc65)cc4)c3-c3ccc(-c4ccc(-c5ccc(-c6nc(-c7ccccc7)nc(-c7ccccc7)n6)cc5)cc4)cc3)cc2)cc1] | 55% |
| P20 | S319<br>334-04-7 | 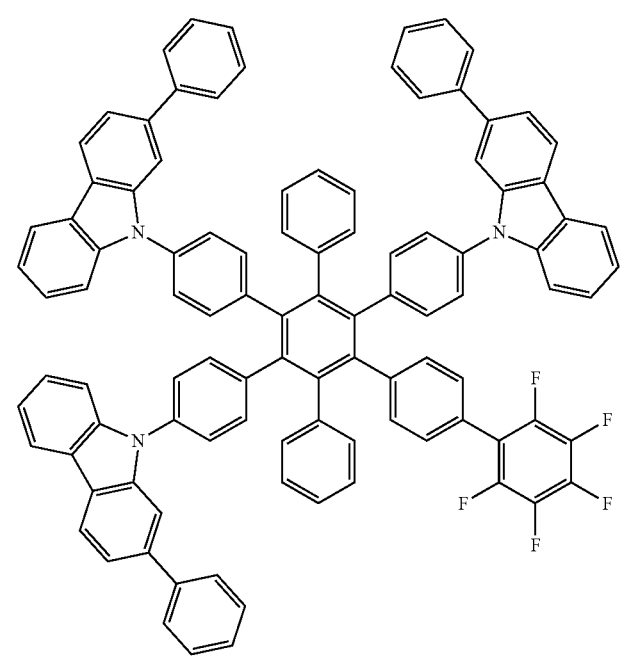 [SMILES: Fc1c(F)c(F)c(-c2ccc(-c3c(-c4ccccc4)c(-c4ccc(-n5c6ccccc6c6ccc(-c7ccccc7)cc65)cc4)c(-c4ccc(-n5c6ccccc6c6ccc(-c7ccccc7)cc65)cc4)c(-c4ccccc4)c3-c3ccc(-n4c5ccccc5c5ccc(-c6ccccc6)cc54)cc3)cc2)c(F)c1F] | 52% |

| Ex. | Reactant | Product | Yield |
|---|---|---|---|
| P21 | S320<br>371-88-6 | 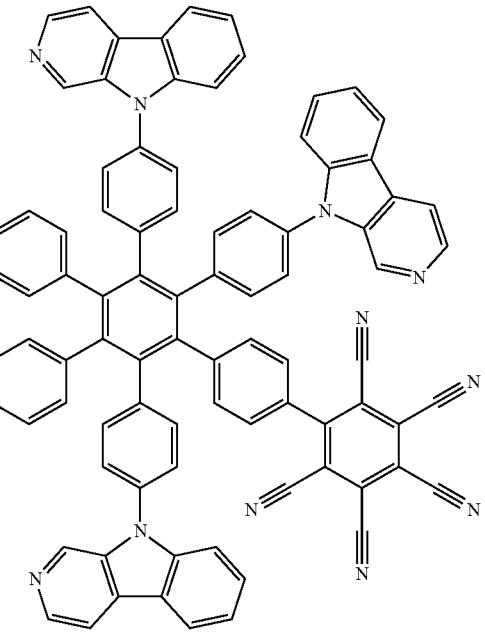 | 56% |
| P22 | S321<br>80587-76-4 | 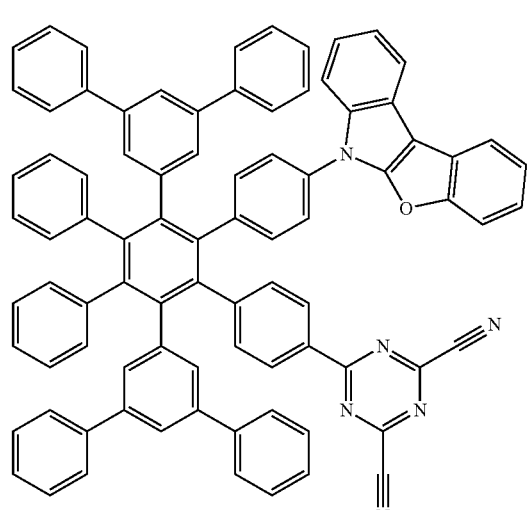 | 49% |
| P23 | S322<br>37084-03-4 | 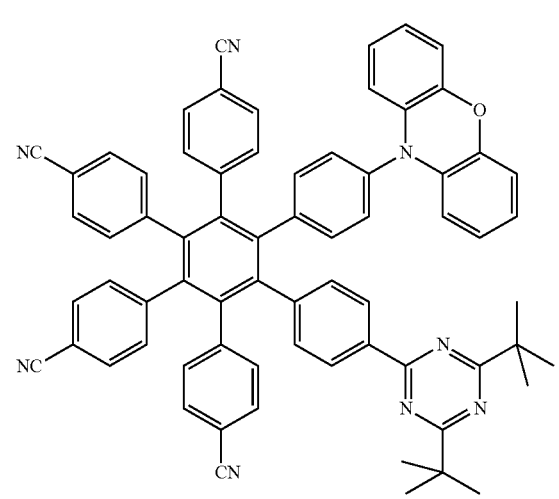 [SMILES: CC(C)(C)c1nc(-c2ccc(-c3c(-c4ccc(C#N)cc4)c(-c4ccc(C#N)cc4)c(-c4ccc(C#N)cc4)c(-c4ccc(C#N)cc4)c3-c3ccc(N4c5ccccc5Oc5ccccc54)cc3)cc2)nc(C(C)(C)C)n1] | 44% |

| Ex. | Reactant | Product | Yield |
|---|---|---|---|
| P24 | S323<br>334-04-7 | 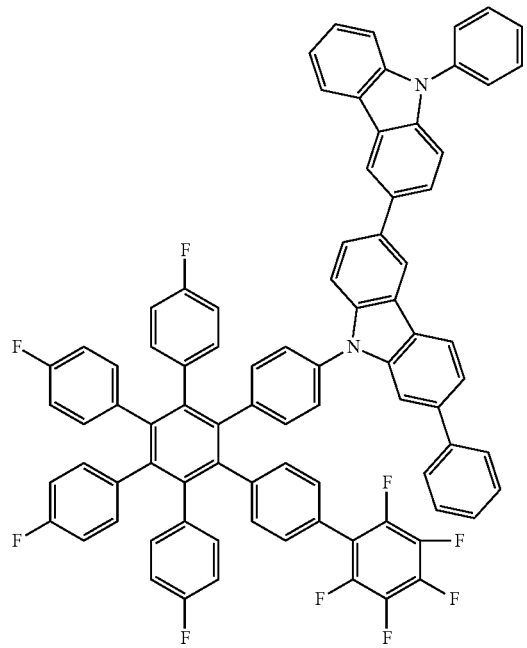 [SMILES: Fc1ccc(-c2c(-c3ccc(F)cc3)c(-c3ccc(F)cc3)c(-c3ccc(-n4c5ccc(-c6ccc7c(c6)c6ccccc6n7-c6ccccc6)cc5c5ccc(-c6ccccc6)cc54)cc3)c(-c3ccc(-c4c(F)c(F)c(F)c(F)c4F)cc3)c2-c2ccc(F)cc2)cc1] | 47% |
| P25 | S324<br>3842-55-5 | 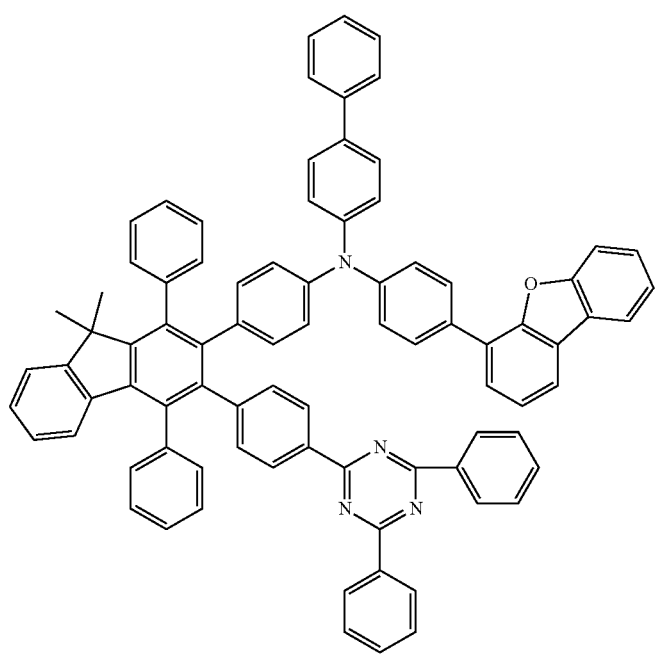 [SMILES: CC1(C)c2ccccc2-c2c(-c3ccccc3)c(-c3ccc(-c4nc(-c5ccccc5)nc(-c5ccccc5)n4)cc3)c(-c3ccc(N(c4ccc(-c5ccccc5)cc4)c4ccc(-c5cccc6c5oc5ccccc56)cc4)cc3)c(-c3ccccc3)c21] | 30% |

-continued
| Ex. | Reactant | Product | Yield |
|---|---|---|---|
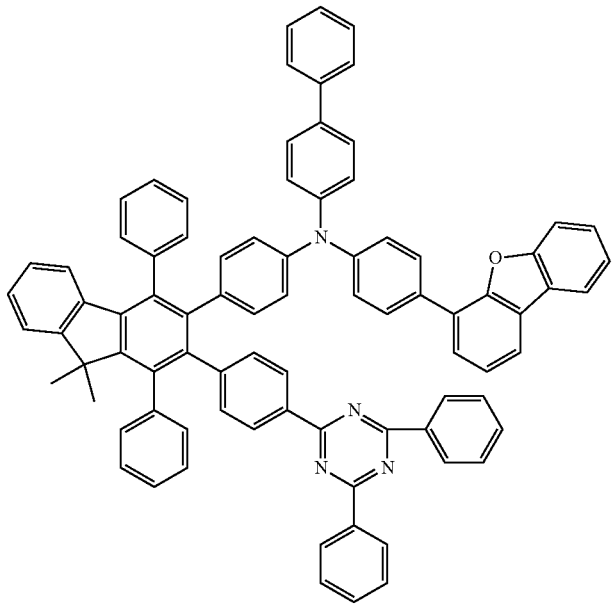
isomer mixture
| | | | |
|---|---|---|---|
| P26 | S325<br>3842-55-5 | | |
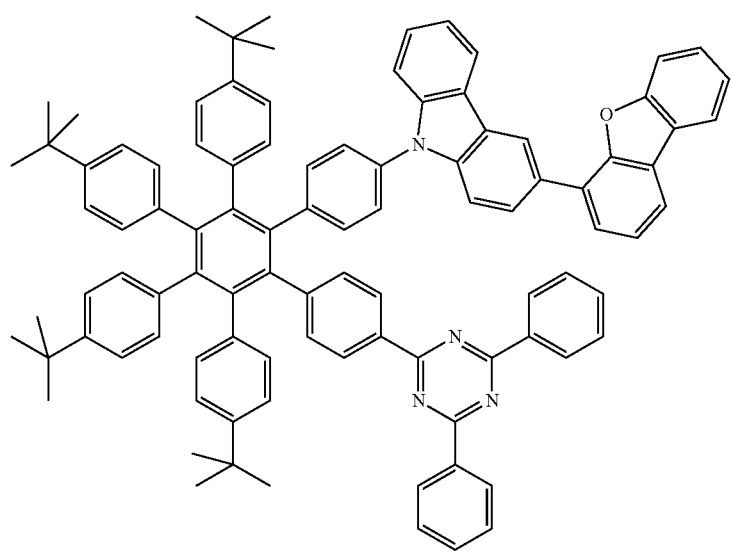 [SMILES: CC(C)(C)c1ccc(-c2c(-c3ccc(-c4nc(-c5ccccc5)nc(-c5ccccc5)n4)cc3)c(-c3ccc(-n4c5ccccc5c5cc(-c6cccc7c6oc6ccccc67)ccc54)cc3)c(-c3ccc(C(C)(C)C)cc3)c(-c3ccc(C(C)(C)C)cc3)c2-c2ccc(C(C)(C)C)cc2)cc1]

| Ex. | Reactant | Product | Yield |
|---|---|---|---|
| P27 | S326<br>15679-03-5 | 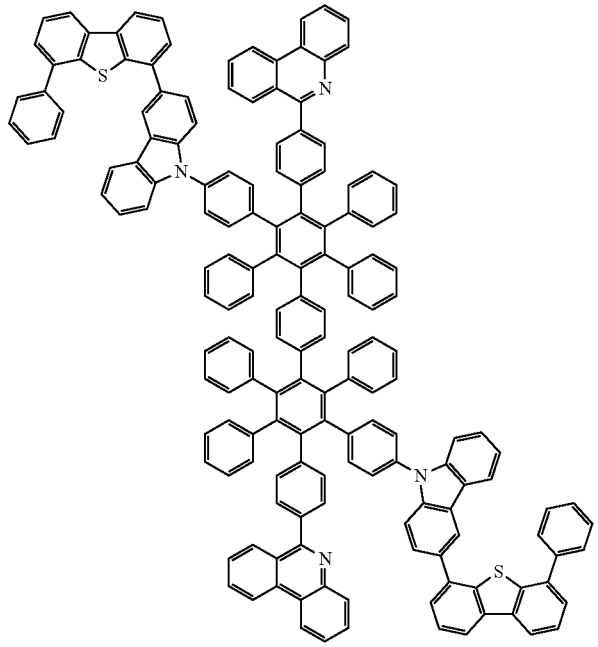 [SMILES: c1ccc(-c2c(-c3ccccc3)c(-c3ccc(-c4nc5ccccc5c5ccccc45)cc3)c(-c3ccc(-n4c5ccccc5c5cc(-c6cccc7c6sc6c(-c8ccccc8)cccc67)ccc54)cc3)c(-c3ccccc3)c2-c2ccc(-c3c(-c4ccccc4)c(-c4ccccc4)c(-c4ccc(-c5nc6ccccc6c6ccccc56)cc4)c(-c4ccc(-n5c6ccccc6c6cc(-c7cccc8c7sc7c(-c9ccccc9)cccc78)ccc65)cc4)c3-c3ccccc3)cc2)cc1] | 32% |
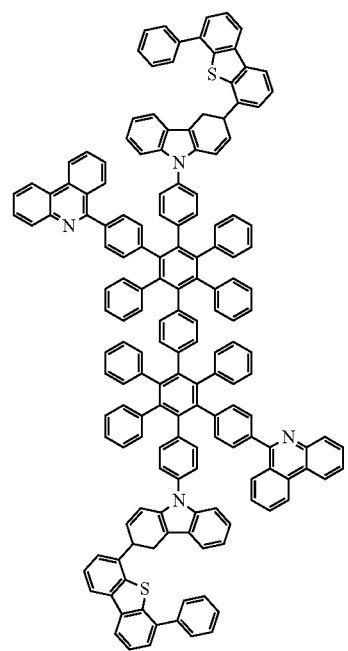 [SMILES: C1=CC(c2cccc3c2sc2c(-c4ccccc4)cccc23)Cc2c1n(-c1ccc(-c3c(-c4ccccc4)c(-c4ccccc4)c(-c4ccc(-c5c(-c6ccccc6)c(-c6ccccc6)c(-c6ccc(-n7c8c(c9ccccc97)CC(c7cccc9c7sc7c(-c%10ccccc%10)cccc79)C=C8)cc6)c(-c6ccc(-c7nc8ccccc8c8ccccc78)cc6)c5-c5ccccc5)cc4)c(-c4ccccc4)c3-c3ccc(-c4nc5ccccc5c5ccccc45)cc3)cc1)c1ccccc21]

-continued
| Ex. | Reactant | Product | Yield |
|---|---|---|---|
| | | 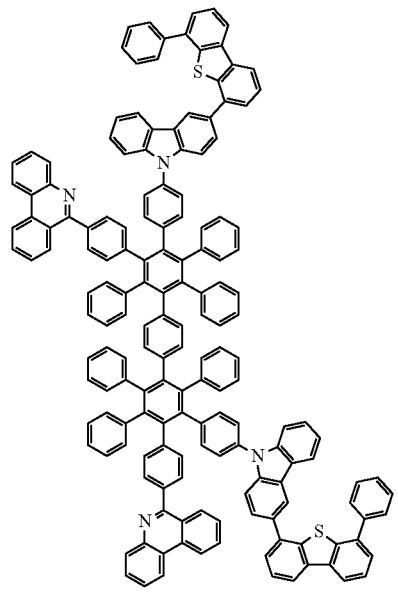<br>isomer mixture<br>210 mmol 73183-34-3 | |
| P28 | S327<br>3842-55-5 | 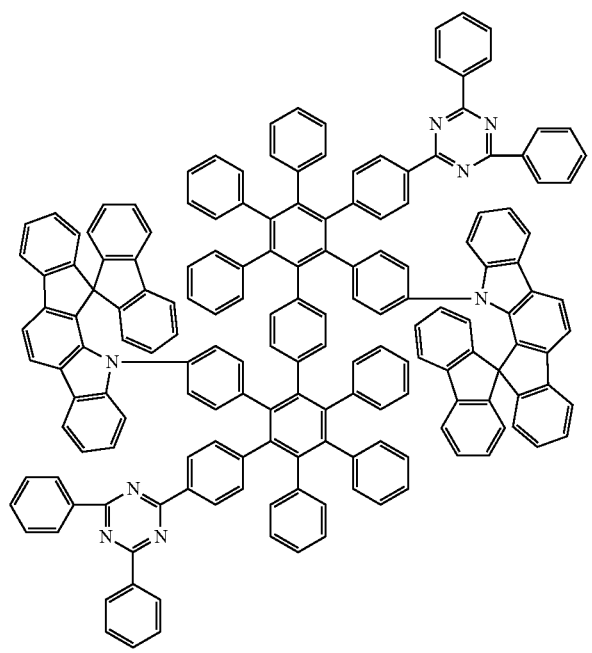 [SMILES: c1ccc(-c2nc(-c3ccccc3)nc(-c3ccc(-c4c(-c5ccccc5)c(-c5ccccc5)c(-c5ccccc5)c(-c5ccc(-c6c(-c7ccccc7)c(-c7ccccc7)c(-c7ccccc7)c(-c7ccc(-c8nc(-c9ccccc9)nc(-c9ccccc9)n8)cc7)c6-c6ccc(-n7c8ccccc8c8ccc9c(c87)C7(c8ccccc8-c8ccccc87)c7ccccc7-9)cc6)cc5)c4-c4ccc(-n5c6ccccc6c6ccc7c(c65)C5(c6ccccc6-c6ccccc65)c5ccccc5-7)cc4)cc3)n2)cc1] | 27% |

| Ex. | Reactant | Product | Yield |
|---|---|---|---|
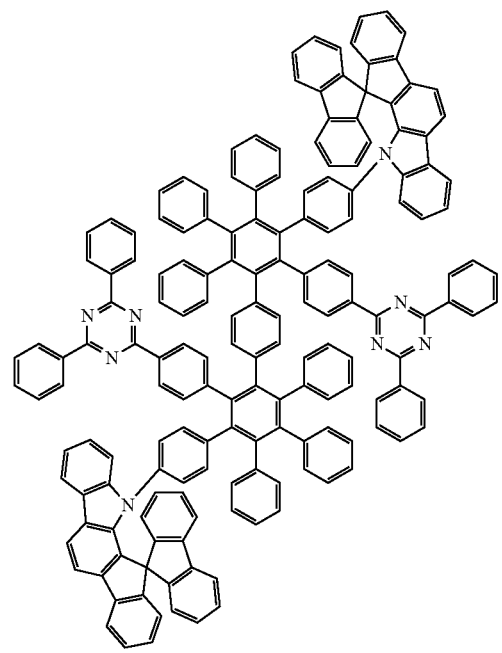 [SMILES: c1ccc(-c2nc(-c3ccccc3)nc(-c3ccc(-c4c(-c5ccc(-c6c(-c7ccccc7)c(-c7ccccc7)c(-c7ccccc7)c(-c7ccc(-n8c9ccccc9c9ccc%10c(c98)C8(c9ccccc9-c9ccccc98)c8ccccc8-%10)cc7)c6-c6ccc(-c7nc(-c8ccccc8)nc(-c8ccccc8)n7)cc6)cc5)c(-c5ccccc5)c(-c5ccccc5)c(-c5ccccc5)c4-c4ccc(-n5c6ccccc6c6ccc7c(c65)C5(c6ccccc6-c6ccccc65)c5ccccc5-7)cc4)cc3)n2)cc1]
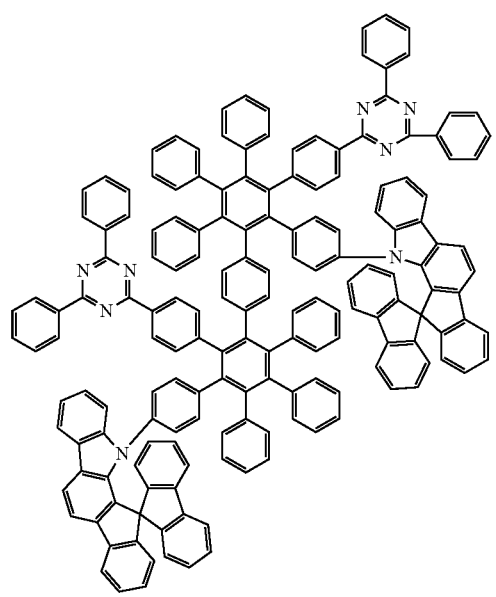
isomer mixture
210 mmol 73183-34-3

-continued
| Ex. | Reactant | Product | Yield |
|---|---|---|---|
| P29 | S328<br>3842-55-5 | 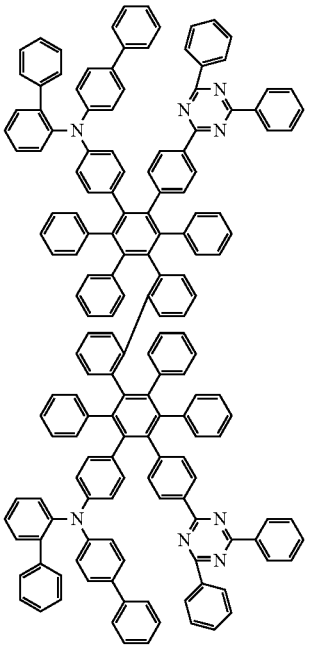 [SMILES: c1ccc(-c2ccc(N(c3ccc(-c4c(-c5ccccc5)c(-c5ccccc5)c(-c5ccccc5-c5ccccc5-c5c(-c6ccccc6)c(-c6ccccc6)c(-c6ccc(-c7nc(-c8ccccc8)nc(-c8ccccc8)n7)cc6)c(-c6ccc(N(c7ccc(-c8ccccc8)cc7)c7ccccc7-c7ccccc7)cc6)c5-c5ccccc5)c(-c5ccccc5)c4-c4ccc(-c5nc(-c6ccccc6)nc(-c6ccccc6)n5)cc4)cc3)c3ccccc3-c3ccccc3)cc2)cc1] | 29% |
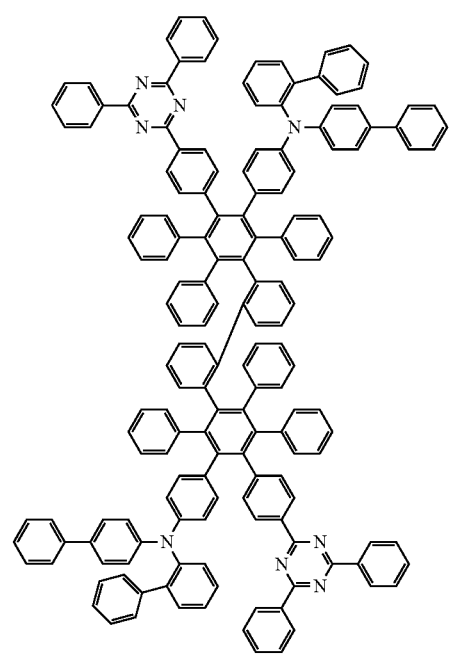 [SMILES: c1ccc(-c2ccc(N(c3ccc(-c4c(-c5ccc(-c6nc(-c7ccccc7)nc(-c7ccccc7)n6)cc5)c(-c5ccccc5)c(-c5ccccc5)c(-c5ccccc5-c5ccccc5-c5c(-c6ccccc6)c(-c6ccccc6)c(-c6ccc(-c7nc(-c8ccccc8)nc(-c8ccccc8)n7)cc6)c(-c6ccc(N(c7ccc(-c8ccccc8)cc7)c7ccccc7-c7ccccc7)cc6)c5-c5ccccc5)c4-c4ccccc4)cc3)c3ccccc3-c3ccccc3)cc2)cc1]

| Ex. | Reactant | Product | Yield |
|---|---|---|---|

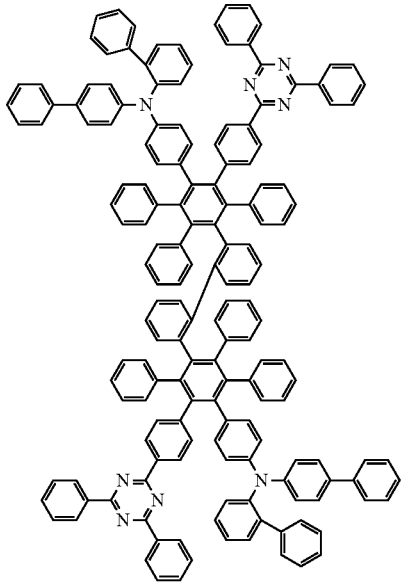

isomer mixture
210 mmol 73183-34-3

Example: Production of the OLEDs

1) Vacuum-Processed Devices:

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Glass plaques with structured ITO (50 nm, indium tin oxide) form the substrates to which the OLEDs are applied. The OLEDs basically have the following layer structure: substrate/hole transport layer 1 (HTL1) consisting of HTM doped with 5% NDP-9 (commercially available from Novaled), 20 nm/hole transport layer 2 (HTL2)/optional electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm.

First of all, vacuum-processed OLEDs are described. For this purpose, all the materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as M3:M2:Ir(L2) (55%:35%:10%) mean here that the material M3 is present in the layer in a proportion by volume of 55%, M2 in a proportion of 35% and Ir(L2) in a proportion of 10%. Analogously, the electron transport layer may also consist of a mixture of two materials. The exact structure of the OLEDs can be found in Table 1. The materials used for production of the OLEDs are shown in Table 4.

The OLEDs are characterized in a standard manner. For this purpose, the electroluminescence spectra, the power efficiency (measured in cd/A) and the voltage (measured at 1000 cd/m² in V) are determined from current-voltage-brightness characteristics (IUL characteristics). For selected experiments, the lifetime is determined. The lifetime is defined as the time after which the luminance has fallen from a particular starting luminance to a certain proportion. The figure LD50 means that the lifetime specified is the time at which the luminance has dropped to 50% of the starting luminance, i.e. from, for example, 1000 cd/m² to 500 cd/m². According to the emission colour, different starting brightnesses were selected. The values for the lifetime can be converted to a figure for other starting luminances with the aid of conversion formulae known to those skilled in the art. In this context, the lifetime for a starting luminance of 1000 cd/m² is a standard figure.

Use of Compounds of the Invention as Emitter Materials in Phosphorescent OLEDs

One use of the compounds of the invention is as emitter materials (TADF) in the emission layer in OLEDs.

They are also usable as matrix/host material for phosphorescent emitters. The compounds according to Table 4 are used as a comparison according to the prior art. The results for the OLEDs are collated in Table 2.

TABLE 1

Structure of the OLEDs

| Ex. | HTL2 thickness | EBL thickness | EML thickness | HBL thickness | ETL thickness |
|---|---|---|---|---|---|
| Ref.-D1 | HTM 40 nm | — | M1:IrRef1 (88%:12%) 35 nm | HBM1 10 nm | ETM1:ETM2 (50%:50%) 30 nm |
| D1 | HTM 40 nm | — | P1:IrRef1 (88%:12%) 35 nm | HBM1 10 nm | ETM1:ETM2 (50%:50%) 30 nm |

TABLE 1-continued

Structure of the OLEDs

| Ex. | HTL2 thickness | EBL thickness | EML thickness | HBL thickness | ETL thickness |
|---|---|---|---|---|---|
| D2 | HTM 40 nm | — | P4:IrRef1 (88%:12%) 35 nm | HBM1 10 nm | ETM1:ETM2 (50%:50%) 30 nm |
| D3 | HTM 40 nm | — | P4:IrRef1 (80%:20%) 35 nm | HBM1 10 nm | ETM1:ETM2 (50%:50%) 30 nm |
| D4 | HTM 40 nm | — | P4:M3:IrRef1 (60%:30%:10%) 35 nm | HBM1 10 nm | ETM1:ETM2 (50%:50%) 30 nm |
| D5 | HTM 40 nm | — | P18:M3 (60%:40%) 40 nm | HBM1 10 nm | ETM1:ETM2 (50%:50%) 30 nm |
| D6 | HTM 40 nm | — | P18:M3:SER1 (60%:35%:5%) 40 nm | HBM1 10 nm | ETM1:ETM2 (50%:50%) 30 nm |

TABLE 2

Results for the vacuum-processed OLEDs

| Ex. | EQE (%) | Voltage (V) | CIE x/y | LD50 (h) |
|---|---|---|---|---|
| | 1000 cd/m² | 1000 cd/m² | 1000 cd/m² | 1000 cd/m² |
| Ref.-D1 | 18.8 | 3.2 | 0.34/0.62 | 190000 |
| D1 | 18.9 | 3.0 | 0.33/0.62 | 240000 |
| D2 | 19.2 | 2.9 | 0.34/0.62 | 230000 |
| D3 | 19.4 | 2.9 | 0.33/0.63 | 340000 |
| D4 | 19.0 | 3.1 | 0.34/0.62 | 360000 |
| | 500 cd/m² | 500 cd/m² | 500 ccd/m² | 500 cd/m² |
| D5 | 12.3 | 3.4 | 0.26/0.54 | 20000 |
| D6 | 15.7 | 3.5 | 0.51/0.47 | 90000 |

Solution-Processed Devices:
From Soluble Functional Materials of Low Molecular Weight The iridium complexes of the invention may also be processed from solution and lead therein to OLEDs which are much simpler in terms of process technology compared to the vacuum-processed OLEDs, but nevertheless have good properties. The production of such components is based on the production of polymeric light-emitting diodes (PLEDs), which has already been described many times in the literature (for example in WO 2004/037887). The structure is composed of substrate/ITO/hole injection layer (60 nm)/interlayer (20 nm)/emission layer (60 nm)/hole blocker layer (10 nm)/electron transport layer (40 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in a cleanroom, a 20 nm hole injection layer is applied by spin-coating. The required spin rate depends on the degree of dilution and the specific spin-coater geometry. In order to remove residual water from the layer, the substrates are baked on a hotplate at 200° C. for 30 minutes. The interlayer used serves for hole transport; in this case, HL-X from Merck is used. The interlayer may alternatively also be replaced by one or more layers which merely have to fulfil the condition of not being leached off again by the subsequent processing step of EML deposition from solution. For production of the emission layer, the triplet emitters of the invention are dissolved together with the matrix materials in toluene or chlorobenzene. The typical solids content of such solutions is between 16 and 25 g/l when, as here, the layer thickness of 60 nm which is typical of a device is to be achieved by means of spin-coating. The solution-processed green type 1 devices contain an emission layer composed of P:M:IrRef2 (X %:Y %:Z %); the red type 2 devices contain an emission layer composed of P:M:IrRef2:IrRef3 (X %:Y %:Z %:5%); in other words, they contain two different Ir complexes. The emission layer is spun on in an inert gas atmosphere, argon in the present case, and baked at 160° C. for 10 min. Vapour-deposited above the latter are the hole blocker layer (10 nm ETM1) and the electron transport layer (40 nm ETM1 (50%)/ETM2 (50%)) (vapour deposition systems from Lesker or the like, typical vapour deposition pressure $5 \times 10^{-6}$ mbar). Finally, a cathode of aluminium (100 nm) (high-purity metal from Aldrich) is applied by vapour deposition. In order to protect the device from air and air humidity, the device is finally encapsulated and then characterized. The OLED examples cited are yet to be optimized; Table 3 summarizes the data obtained.

TABLE 3

Results with materials processed from solution

| Ex. | P:M:IrRef | EQE (%) 1000 cd/m² | Voltage (V) 1000 cd/m² | CIE x/y | LD50 (h) 1000 cd/m² |
|---|---|---|---|---|---|
| Red type 2 devices | | | | | |
| Sol-Ref-Red1 | M4:M5:IrRef2 30%:40%:25% | 17.4 | 6.2 | 0.66/0.34 | 240000 |
| Sol-RedD1 | P11:M5:IrRef2 70%:0%:25% | 18.3 | 5.8 | 0.66/0.34 | 290000 |
| Sol-RedD2 | P11:M5:IrRef2 50%:20%:25% | 18.6 | 5.9 | 0.66/0.34 | 320000 |
| Sol-RedD3 | P28:M5:IrRef2 70%:0%:25% | 18.8 | 6.1 | 0.66/0.34 | 370000 |
| Green type 1 devices | | | | | |
| Sol-Ref-Green1 | M4:M5:IrRef2 20%:60%:20% | 20.1 | 5.3 | 0.33/0.62 | 200000 |
| Sol-GreenD1 | P10:M5:IrRef2 80%:0%20% | 20.6 | 54 | 0.33/0.62 | 230000 |
| Sol-GreenD2 | P10:M5:IrRef2 50%:30%:20% | 20.9 | 5.3 | 0.33/0.62 | 220000 |
| Sol-GreenD3 | P11:M5:IrRef2 60%:20%:20% | 20.8 | 5.1 | 0.33/0.62 | 240000 |
| Sol-GreenD4 | P13:M5:IrRef2 50%:30%:25% | 20.5 | 5.2 | 0.33/0.62 | 240000 |
| Sol-GreenD5 | P14:M4:IrRef2 45%:30%:25% | 20.2 | 5.0 | 0.34/0.61 | 250000 |
| Sol-GreenD6 | P18:M3:IrRerf2 50%:35%:15% | 20.0 | 52 | 0.32/0.63 | 310000 |
| Sol-GreenD7 | P25:M5:IrRef2 80%:0%:20% | 19.9 | 5.1 | 0.33/0.62 | 260000 |
| Sol-GreenD8 | P28:M5:IrRef2 75%:0%:25% | 20.3 | 5.0 | 0.32/0.62 | 240000 |

TABLE 4
Structural formulae of the materials used
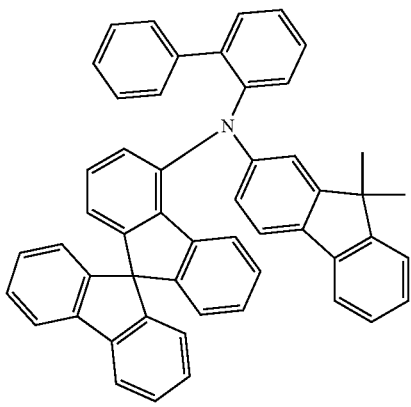
HTM = M9
1450933-44-4
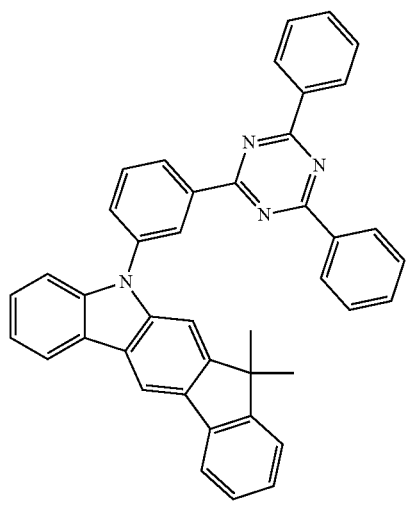
M1
1257248-13-7
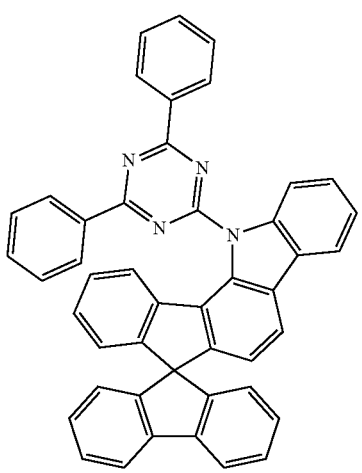
M2
1615703-29-1
TABLE 4-continued
Structural formulae of the materials used
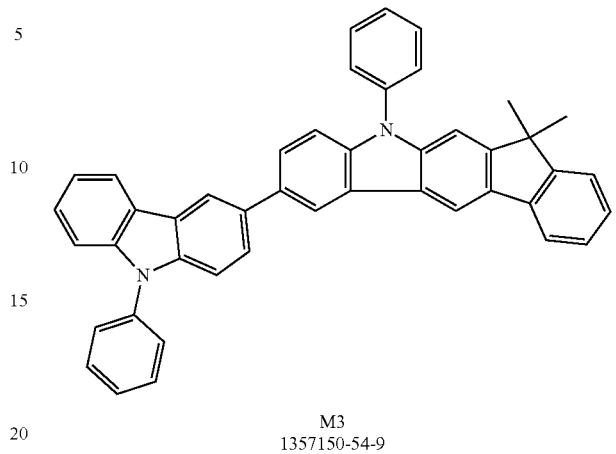
M3
1357150-54-9
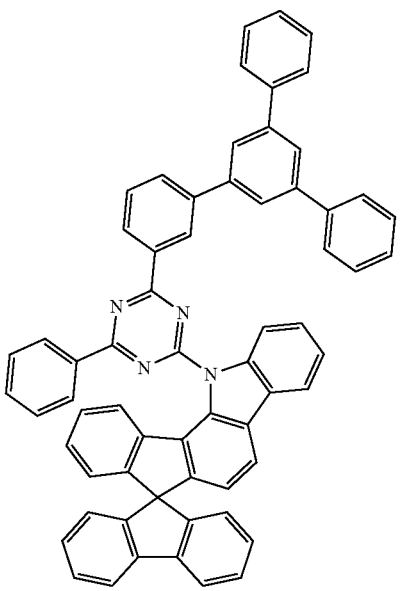
M4
1616231-60-7
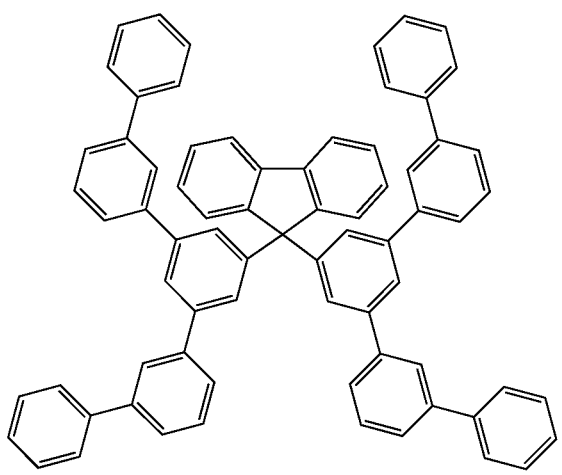
M5
1246496-85-4

TABLE 4-continued
Structural formulae of the materials used
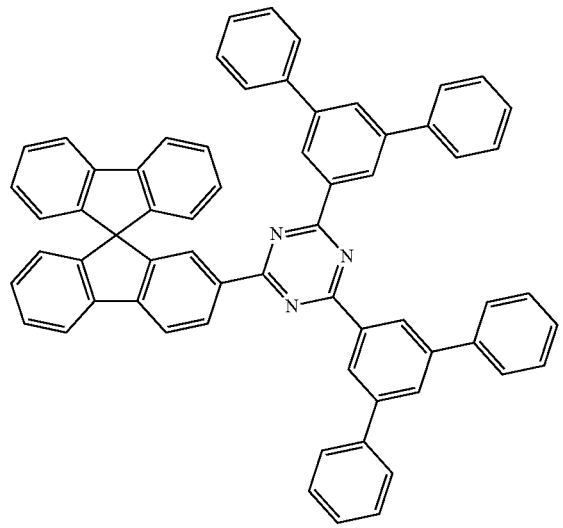
ETM1 = HBM1 = M10
1233200-52-6
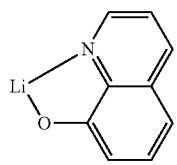
ETM2
25387-93-3
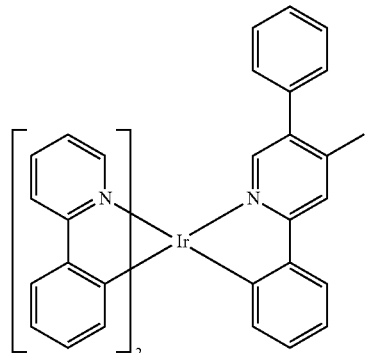
IrRef1
1215692-34-4
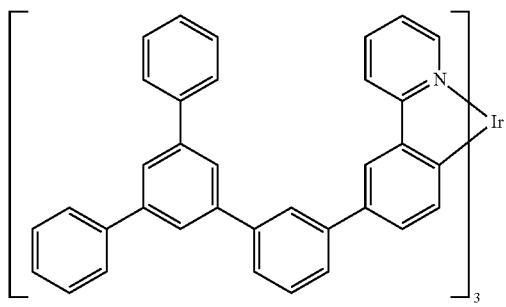
IrRef2
1269508-30-6
TABLE 4-continued
Structural formulae of the materials used
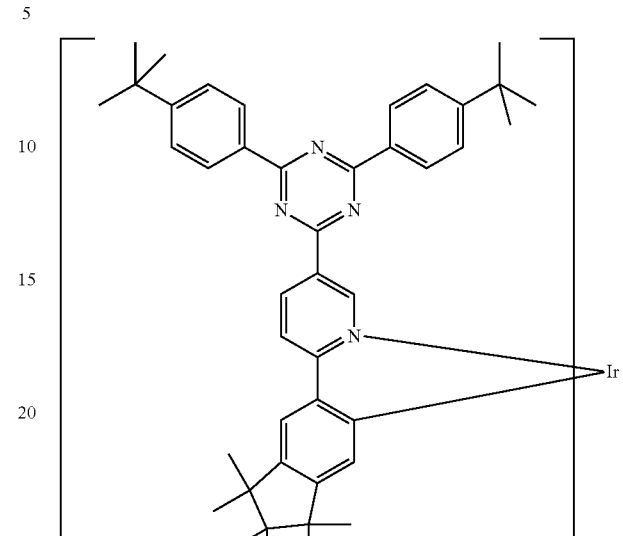
IrRef3
1870013-87-8
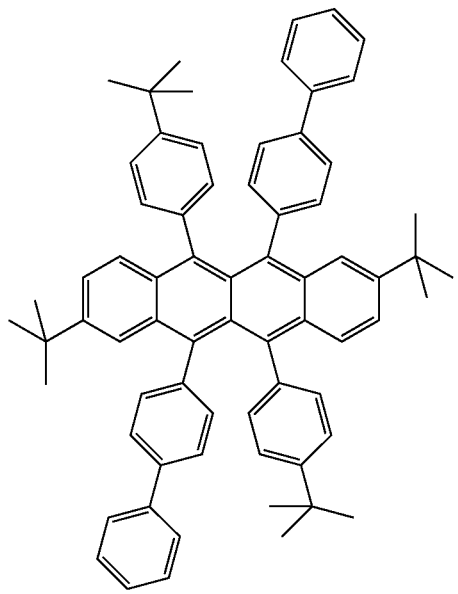
SER1
850797-15-8

The invention claimed is:
1. A compound comprising at least one structure of the formula (I):

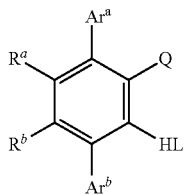

Formula (I)

where the symbols used are as follows:
Q is an acceptor that is represented by the formula (QL), $Q^1$-$L^1$-    Formula (QL)

in which $L^1$ represents an aromatic or heteroaromatic ring system which has 5 to 60 aromatic ring atoms and may be substituted by one or more $R^1$ radicals;
$Q^1$ is an electron-withdrawing group;
HL is a donor group;
$Ar^a$, $Ar^b$ is the same or different and is an aromatic or heteroaromatic ring system which has 5 to 60 aromatic ring atoms and may be substituted by one or more $R^1$ radicals;
$R^a$ and $R^b$ represent an aryl or heteroaryl radical, where $R^a$ and $R^b$ are joined by a ring closure effected by a bond between $R^a$ and $R^b$;
$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $S_1(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by —$R^2C=CR^2$—, —C≡C—, $Si(R^2)_2$, $Ge(R^2)_2$, $Sn(R^2)_2$, C=O, C=S, C=Se, C=$NR^2$, $NR^2$, $P(=O)(R^2)$, —C(=O)O—, —C(=O)$NR^2$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a mono- or polycyclic, aliphatic, heteroaliphatic, aromatic or heteroaromatic ring system;
$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $S_1(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by —$R^3C=CR^3$—, —C≡C—, $Si(R^3)_2$, $Ge(R^3)_2$, $Sn(R^3)_2$, C=O, C=S, C=Se, C=$NR^3$, $NR^3$, $P(=O)(R^3)$, —C(=O)O—, —C(=O)$NR^3$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy or heteroaryloxy group which has 5 to 60 aromatic ring atoms and may be substituted by one or more $R^3$ radicals, or an aralkyl or heteroaralkyl group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more $R^2$ substituents together may also form a mono- or polycyclic, aliphatic, heteroaliphatic, aromatic or heteroaromatic ring system; and
$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a mono- or polycyclic, aliphatic, heteroaliphatic, aromatic or heteroaromatic ring system.
2. The compound according to claim 1, wherein the $Ar^a$ and/or $Ar^b$ group in formula (I) is different from a donor group as per symbol HL.
3. The compound according to claim 1, wherein the donor group HL comprises a group selected from the formulae (H-1) to (H-3)

Formula (H-1)

Formula (H-2)

Formula (H-3)

where the dotted bond marks the attachment position and
$Ar^2$, $Ar^3$, $Ar^4$ are each independently an aryl group having 6 to 40 carbon atoms or a heteroaryl group having 3 to 40 carbon atoms, each of which may be substituted by one or more $R^1$ radicals;
P is 0, 1, 2, 3, 4, 5 or 6;
Z is $C(R^1)_2$, $Si(R^1)_2$, C=O, N—$Ar^1$, $BR^1$, $PR^1$, $POR^1$, SO, $SO_2$, Se, O or S;
$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $NR^2$, $P(=O)(R^2)$, $-C(=O)O-$, $-C(=O)NR^2-$, $-O-$, $-S-$, $SO$ or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a mono- or polycyclic, aliphatic, heteroaliphatic, aromatic or heteroaromatic ring system;

$R^2$ is the same or different at each instance and is H, D, F, Cl, Br, I, $B(OR^3)_2$, CHO, $C(=O)R^3$, $CR^3=C(R)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Ge(R^3)_2$, $Sn(R^3)_2$, $C=O$, $C=S$, $C=Se$, $C=NR^3$, $NR^3$, $P(=O)(R^3)$, $-C(=O)O-$, $-C(=O)NR^3-$, $-O-$, $-S-$, $SO$ or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy or heteroaryloxy group which has 5 to 60 aromatic ring atoms and may be substituted by one or more $R^3$ radicals, or an aralkyl or heteroaralkyl group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more $R^2$ substituents together may also form a mono- or polycyclic, aliphatic, heteroaliphatic, aromatic or heteroaromatic ring system;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a mono- or polycyclic, aliphatic, heteroaliphatic, aromatic or heteroaromatic ring system; and $Ar^1$ represents an aromatic or heteroaromatic ring system which has 5 to 60 aromatic ring atoms and may be substituted in each case by one or more $R^1$ radicals, an aryloxy group which has 5 to 60 aromatic ring atoms and may be substituted in each case by one or more $R^1$ radicals, or an aralkyl group which has 5 to 60 aromatic ring atoms and may be substituted in each case by one or more $R^1$ radicals, where it is optionally possible for two or more, $R^1$ substituents to form a mono- or polycyclic, aliphatic, heteroaliphatic, aromatic or heteroaromatic ring system which may be substituted by one or more $R^3$ radicals.

4. The compound according to claim 1, wherein the donor group HL comprises a group selected from the formulae (H-4) to (H-26)

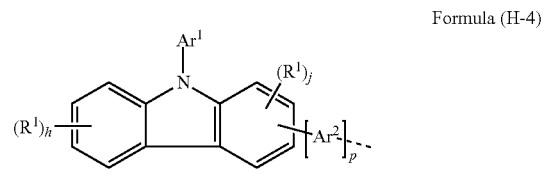

Formula (H-4)

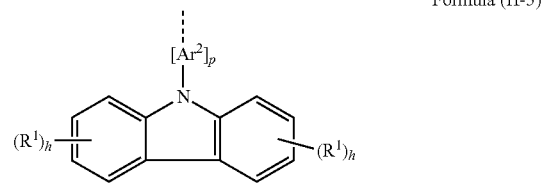

Formula (H-5)

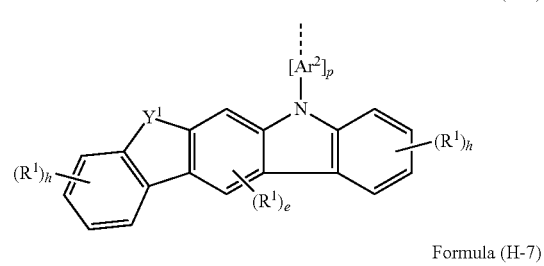

Formula (H-6)

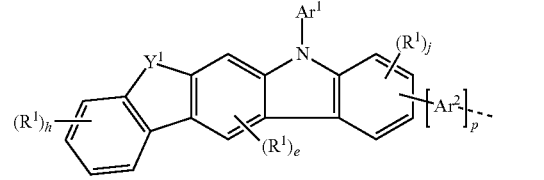

Formula (H-7)

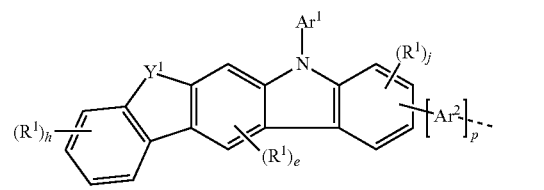

Formula (H-8)

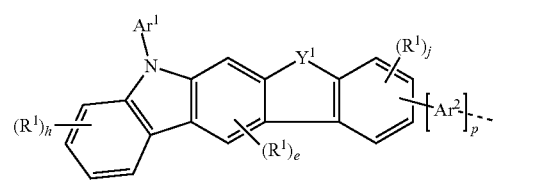

Formula (H-9)

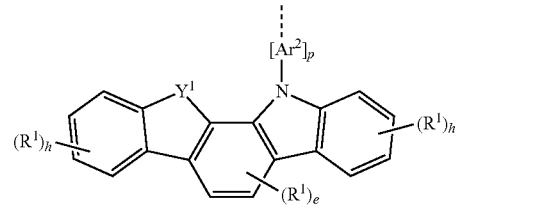

Formula (H-10)
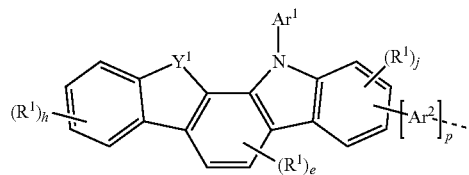
Formula (H-11)
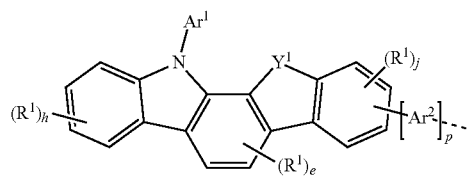
Formula (H-12)
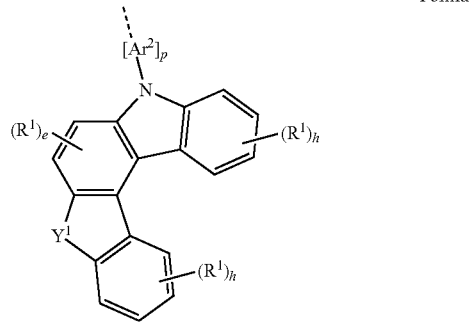
Formula (H-13)
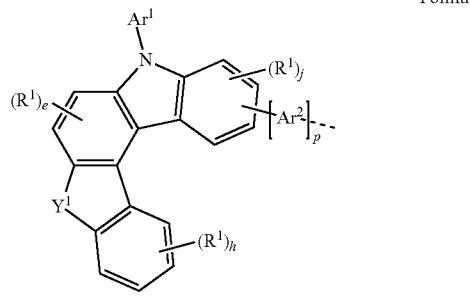
Formula (H-14)
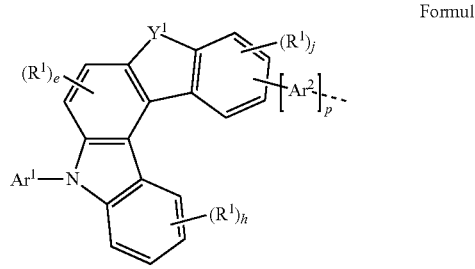
Formula (H-15)
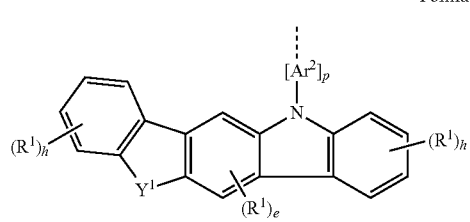
Formula (H-16)
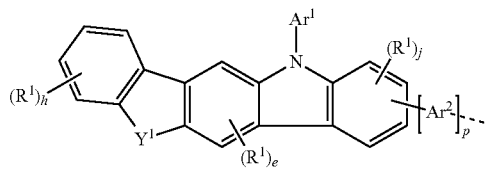
Formula (H-17)
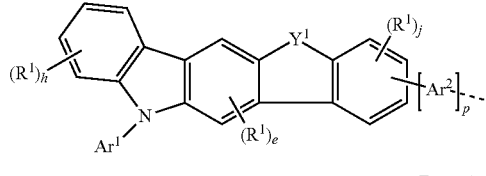
Formula (H-18)
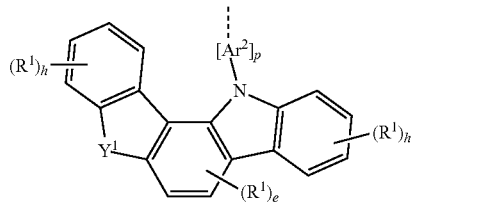
Formula (H-19)
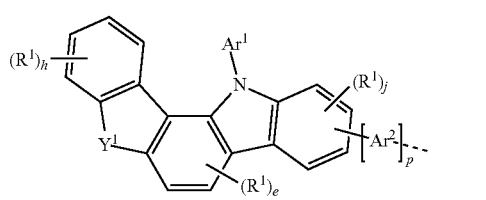
Formula (H-20)
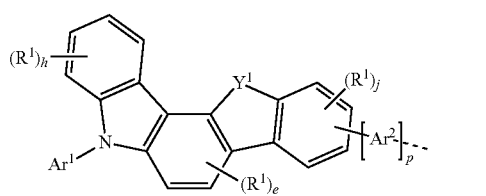
Formula (H-21)
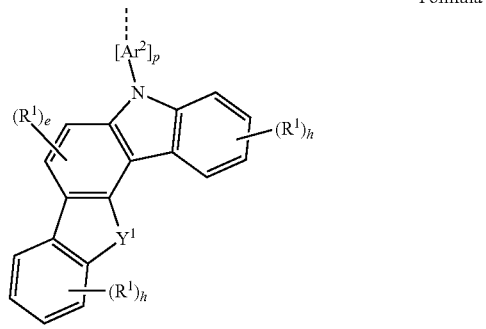

Formula (H-22)

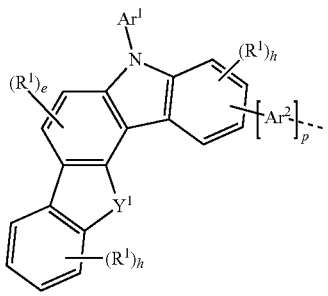

Formula (H-23)

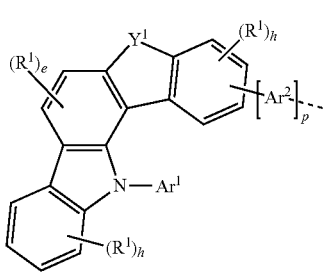

Formula (H-24)

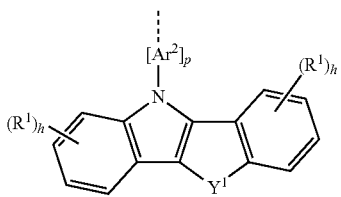

Formula (H-25)

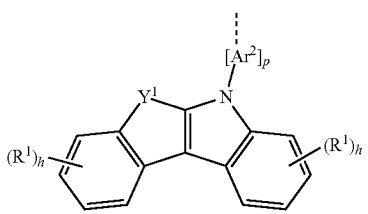

Formula (H-26)

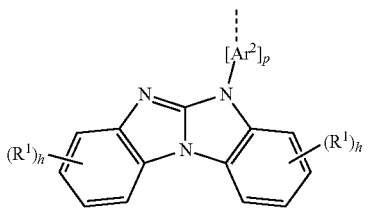

wherein $Y^1$ represents O, S, $C(R^1)_2$ or $NAr^1$;

the dotted bond marks the attachment position;

e is 0, 1 or 2;

j is 0, 1, 2 or 3;

h is 0, 1, 2, 3 or 4;

p is 0, 1, 2, 3, 4, 5 or 6;

$Ar^1$ represents an aromatic or heteroaromatic ring system which has 5 to 60 aromatic ring atoms and may be substituted in each case by one or more $R^1$ radicals, an aryloxy group which has 5 to 60 aromatic ring atoms and may be substituted in each case by one or more $R^1$ radicals, or an aralkyl group which has 5 to 60 aromatic ring atoms and may be substituted in each case by one or more RI radicals, where it is optionally possible for two or more, $R^1$ substituents to form a mono- or polycyclic, aliphatic, heteroaliphatic, aromatic or heteroaromatic ring system which may be substituted by one or more $R^3$ radicals;

$Ar^2$ is an aryl group having 6 to 40 carbon atoms or a heteroaryl group having 3 to 40 carbon atoms, each of which may be substituted by one or more $R^1$ radicals;

$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by —$R^2C=CR^2$—, —C≡C—, $Si(R^2)_2$, $Ge(R^2)_2$, $Sn(R^2)_2$, C=O, C=S, C=Se, C=$NR^2$, $NR^2$, $P(=O)(R^2)$, —C(=O)O—, —C(=O)$NR^2$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a mono- or polycyclic, aliphatic, heteroaliphatic, aromatic or heteroaromatic ring system;

$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by —$R^3C=CR^3$—, —C≡C—, $Si(R^3)_2$, $Ge(R^3)_2$, $Sn(R^3)_2$, C=O, C=S, C=Se, C=$NR^3$, $NR^3$, $P(=O)(R^3)$, —C(=O)O—, —C(=O)$NR^3$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy or heteroaryloxy group which has 5 to 60 aromatic ring atoms and may be substituted by one or more $R^3$ radicals, or an aralkyl or heteroaralkyl group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more $R^2$ substituents together may also form a mono- or polycyclic, aliphatic, heteroaliphatic, aromatic or heteroaromatic ring system; and $R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a mono- or polycyclic, aliphatic, heteroaliphatic, aromatic or heteroaromatic ring system.

5. The compound according to claim 3, wherein the $Ar^2$ group is a connecting structure of the formula (LAr-1)

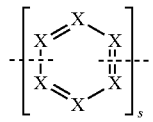

Formula (LAr-1)

where X is the same or different at each instance and is N or $CR^1$, or C if a group binds to X; the dotted bond marks the attachment position;

s is 0, 1, 2, 3, 4, 5 or 6;

$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $NR^2$, $P(=O)(R^2)$, $-C(=O)O-$, $-C(=O)NR^2-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a mono- or polycyclic, aliphatic, heteroaliphatic, aromatic or heteroaromatic ring system;

$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Ge(R^3)_2$, $Sn(R^3)_2$, $C=O$, $C=S$, $C=Se$, $C=NR^3$, $NR^3$, $P(=O)(R^3)$, $-C(=O)O-$, $-C(=O)NR^3-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy or heteroaryloxy group which has 5 to 60 aromatic ring atoms and may be substituted by one or more $R^3$ radicals, or an aralkyl or heteroaralkyl group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more $R^2$ substituents together may also form a mono- or polycyclic, aliphatic, heteroaliphatic, aromatic or heteroaromatic ring system; and $R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a mono- or polycyclic, aliphatic, heteroaliphatic, aromatic or heteroaromatic ring system.

6. The compound according to claim 3, wherein $Ar^2$ group is a connecting structure of the formula (LAr-2)

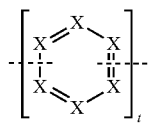

Formula (LAr-2)

where X is the same or different at each instance and is N or $CR^1$, or C if a group binds to X; the dotted bond marks the attachment position and t is 0, 1, 2, 3, 4, 5 or 6;

$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $NR^2$, $P(=O)(R^2)$, $-C(=O)O-$, $-C(=O)NR^2-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a mono- or polycyclic, aliphatic, heteroaliphatic, aromatic or heteroaromatic ring system;

$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R³ radicals, where one or more nonadjacent CH₂ groups may be replaced by —R³C=CR³—, —C≡C—, Si(R³)₂, Ge(R³)₂, Sn(R³)₂, C=O, C=S, C=Se, C=NR³, NR³, P(=O)(R³), —C(=O)O—, —C(=O)NR³—, —O—, —S—, SO or SO₂ and where one or more hydrogen atoms may be replaced by D, F, Cl, Br, I, CN or NO₂, or an aromatic or heteroaromatic ring system which has 5 to 60 aromatic ring atoms and may be substituted in each case by one or more R³ radicals, or an aryloxy or heteroaryloxy group which has 5 to 60 aromatic ring atoms and may be substituted by one or more R³ radicals, or an aralkyl or heteroaralkyl group which has 5 to 60 aromatic ring atoms and may be substituted by one or more R³ radicals, or a diarylamino group, diheteroarylamino group or arylheteroarylamino group which has 10 to 40 aromatic ring atoms and may be substituted by one or more R³ radicals, or a combination of these systems; at the same time, two or more R² substituents together may also form a mono- or polycyclic, aliphatic, heteroaliphatic, aromatic or heteroaromatic ring system; and R³ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more R³ substituents together may also form a mono- or polycyclic, aliphatic, heteroaliphatic, aromatic or heteroaromatic ring system.

7. The compound according to claim 3, wherein the group is selected from structures of the formulae (Q-1), (Q-2), (Q-3), (Q-4), (Q-5), (Q-6), (Q-7), (Q-8), (Q-9) and/or (Q-10)

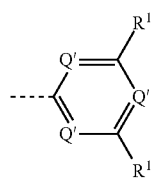

Formula (Q-1)

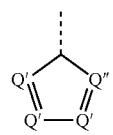

Formula (Q-2)

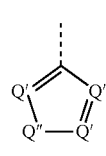

Formula (Q-3)

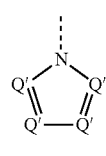

Formula (Q-4)

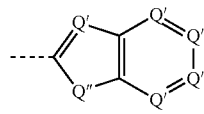

Formula (Q-5)

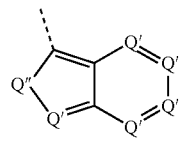

Formula (Q-6)

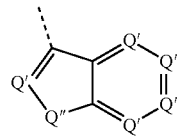

Formula (Q-7)

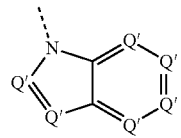

Formula (Q-8)

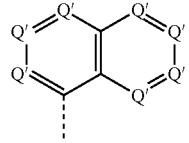

Formula (Q-9)

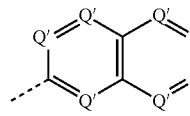

Formula (Q-10)

where the dotted bond marks the attachment position;
Q' is the same or different at each instance and represents CR¹ or N;
Q" represents NR', O or S;
where at least one Q' is N and/or at least one Q" is NW;
R¹ is the same or different at each instance and is H, D, F, Cl, Br, I, B(OR²)₂, CHO, C(=O)R², CR²=C(R²)₂, CN, C(=O)OR², C(=O)N(R²)₂, Si(R²)₃, N(R²)₂, NO₂, P(=O)(R²)₂, OSO₂R², OR², S(=O)R², S(=O)₂R², a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R² radicals, where one or more nonadjacent CH₂ groups may be replaced by —R²C=CR²—, —C≡C—, Si(R²)₂, Ge(R²)₂, Sn(R²)₂, C=O, C=S, C=Se, C=NR², NR², P(=O)(R²), —C(=O)O—, —C(=O)NR²—, —O—, —S—, SO or SO₂ and where one or more hydrogen atoms may be replaced by D, F, Cl, Br, I, CN or NO₂, or an aromatic or heteroaromatic ring system which has 5 to 60 aromatic ring atoms and may be substituted in each case by one or more R² radicals, or an aryloxy or heteroaryloxy group which has 5 to 60 aromatic ring atoms and may be substituted by one or more R² radicals, or an aralkyl or heteroaralkyl group which has 5 to 60 aromatic ring atoms and may be substituted by one or more R² radicals, or a diarylamino group, diheteroarylamino group or arylheteroarylamino group which has 10 to 40 aromatic ring atoms and may be substituted by one or more R² radicals; or a combination of these systems; at the same time, two or more R¹ radicals together may form a mono- or polycyclic, aliphatic, heteroaliphatic, aromatic or heteroaromatic ring system;

R² is the same or different at each instance and is H, D, F, Cl, Br, I, B(OR³)₂, CHO, C(=O)R³, CR³=C(R³)₂, CN, C(=O)OR³, C(=O)N(R³)₂, Si(R³)₃, N(R³)₂, NO₂, P(=O)(R³)₂, OSO₂R³, OR³, S(=O)R³, S(=O)₂R³, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R³ radicals, where one or more nonadjacent CH₂ groups may be replaced by —R³C=CR³—, —C≡C—, Si(R³)₂, Ge(R³)₂, Sn(R³)₂, C=O, C=S, C=Se, C=NR³, NR³, P(=O)(R³), —C(=O)O—, —C(=O)NR³—, —O—, —S—, SO or SO₂ and where one or more hydrogen atoms may be replaced by D, F, Cl, Br, I, CN or NO₂, or an aromatic or heteroaromatic ring system which has 5 to 60 aromatic ring atoms and may be substituted in each case by one or more R³ radicals, or an aryloxy or heteroaryloxy group which has 5 to 60 aromatic ring atoms and may be substituted by one or more R³ radicals, or an aralkyl or heteroaralkyl group which has 5 to 60 aromatic ring atoms and may be substituted by one or more R³ radicals, or a diarylamino group, diheteroarylamino group or arylheteroarylamino group which has 10 to 40 aromatic ring atoms and may be substituted by one or more R³ radicals, or a combination of these systems; at the same time, two or more R² substituents together may also form a mono- or polycyclic, aliphatic, heteroaliphatic, aromatic or heteroaromatic ring system; and R³ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more R³ substituents together may also form a mono- or polycyclic, aliphatic, heteroaliphatic, aromatic or heteroaromatic ring system.

8. The compound according to claim 3, wherein the Q¹ group is selected from structures of the formulae (Q-11), (Q-12), (Q-13), (Q-14) and/or (Q-15)

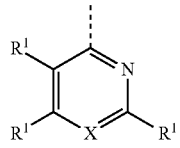

Formula (Q-11)

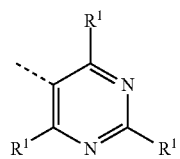

Formula (Q-12)

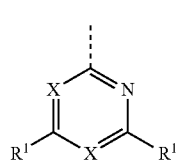

Formula (Q-13)

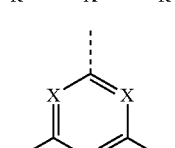

Formula (Q-14)

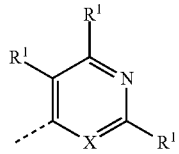

Formula (Q-15)

wherein

R¹ is the same or different at each instance and is H, D, F, Cl, Br, I, B(OR²)₂, CHO, C(=O)R², CR²=C(R²)₂, CN, C(=O)OR², C(=O)N(R²)₂, Si(R²)₃, N(R²)₂, NO₂, P(=O)(R²)₂, OSO₂R², OR², S(=O)R², S(=O)₂R², a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R² radicals, where one or more nonadjacent CH₂ groups may be replaced by —R²C=CR²—, —C≡C—, Si(R²)₂, Ge(R²)₂, Sn(R²)₂, C=O, C=S, C=Se, C=NR², NR², P(=O)(R²), —C(=O)O—, —C(=O)NR²—, —O—, —S—, SO or SO₂ and where one or more hydrogen atoms may be replaced by D, F, Cl, Br, I, CN or NO₂, or an aromatic or heteroaromatic ring system which has 5 to 60 aromatic ring atoms and may be substituted in each case by one or more R² radicals, or an aryloxy or heteroaryloxy group which has 5 to 60 aromatic ring atoms and may be substituted by one or more R² radicals, or an aralkyl or heteroaralkyl group which has 5 to 60 aromatic ring atoms and may be substituted by one or more R² radicals, or a diarylamino group, diheteroarylamino group or arylheteroarylamino group which has 10 to 40 aromatic ring atoms and may be substituted by one or more R² radicals; or a combination of these systems; at the same time, two or more R¹ radicals together may form a mono- or polycyclic, aliphatic, heteroaliphatic, aromatic or heteroaromatic ring system;

R² is the same or different at each instance and is H, D, F, Cl, Br, I, B(OR³)₂, CHO, C(=O)R³, CR³=C(R³)₂, CN, C(=O)OR³, C(=O)N(R³)₂, Si(R³)₃, N(R³)₂, NO₂, P(=O)(R³)₂, OSO₂R³, OR³, S(=O)R³, S(=O)₂R³, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R³ radicals, where one or more nonadjacent CH₂ groups may be replaced by —R³C=CR³—, —C≡C—, Si(R³)₂, Ge(R³)₂, Sn(R³)₂, C=O, C=S, C=Se, C=NR³, NR³, P(=O)(R³), —C(=O)O—, —C(=O)NR³—, —O—, —S—, SO or SO₂ and where one or more hydrogen atoms may be replaced by D, F, Cl, Br, I, CN or NO₂, or an aromatic or heteroaromatic ring system which has 5 to 60 aromatic ring atoms and may be substituted in each case by one or more R³ radicals, or an aryloxy or heteroaryloxy group which has 5 to 60 aromatic ring atoms and may be substituted by one or more R³ radicals, or an aralkyl or heteroaralkyl group which has 5 to 60 aromatic ring atoms and may be substituted by one or more R³ radicals, or a diarylamino group, diheteroarylamino group or arylheteroarylamino group which has 10 to 40 aromatic ring atoms and may be substituted by one or more R³ radicals, or a combination of these systems; at the same time, two or more R² substituents together may also form a mono- or polycyclic, aliphatic, heteroaliphatic, aromatic or heteroaromatic ring system;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a mono- or polycyclic, aliphatic, heteroaliphatic, aromatic or heteroaromatic ring system;

X is N or $CR^1$ and the dotted bond marks the attachment position.

9. The compound according to claim 3, wherein the $Q^1$ group is selected from structures of the formulae (Q-16), (Q-17), (Q-28), (Q-29) and/or (Q-30)

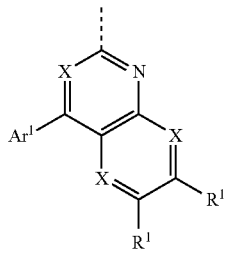

Formula (Q-16)

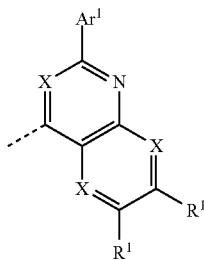

Formula (Q-17)

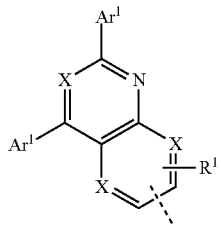

Formula (Q-28)

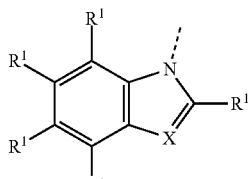

Formula (Q-29)

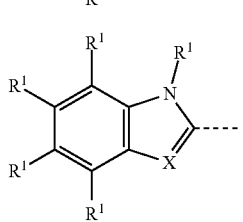

Formula (Q-30)

wherein

X is N or $CR^1$;

$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by $-R^2C=CR^2-$, $-C\equiv C-$, $Si(R^2)_2$, $Ge(R^2)_2$, $Sn(R^2)_2$, C=O, C=S, C=Se, $C=NR^2$, $NR^2$, $P(=O)(R^2)$, $-C(=O)O-$, $-C(=O)NR^2-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a mono- or polycyclic, aliphatic, heteroaliphatic, aromatic or heteroaromatic ring system;

$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by $-R^3C=CR^3-$, $-C\equiv C-$, $Si(R^3)_2$, $Ge(R^3)_2$, $Sn(R^3)_2$, C=O, C=S, C=Se, $C=NR^3$, $NR^3$, $P(=O)(R^3)$, $-C(=O)O-$, $-C(=O)NR^3-$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy or heteroaryloxy group which has 5 to 60 aromatic ring atoms and may be substituted by one or more $R^3$ radicals, or an aralkyl or heteroaralkyl group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more $R^2$ substituents together may also form a mono- or polycyclic, aliphatic, heteroaliphatic, aromatic or heteroaromatic ring system;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a mono- or polycyclic, aliphatic, heteroaliphatic, aromatic or heteroaromatic ring system;

the dotted bond marks the attachment position, and $Ar^1$ represents an aromatic or heteroaromatic ring system which has 5 to 60 aromatic ring atoms and may be substituted in each case by one or more $R^1$ radicals, an aryloxy group which has 5 to 60 aromatic ring atoms and may be substituted by one or more $R^1$ radicals, or an aralkyl group which has 5 to 60 aromatic ring atoms and may be substituted in each case by one or more $R^1$ radicals, where it is optionally possible for two or more.

10. The compound according to claim 3, wherein the electron-withdrawing $Q^1$ group is an aromatic or heteroaromatic ring system which has 5 to 60 aromatic ring atoms and has one or more electron-withdrawing substituents.

11. The compound according to claim 10, wherein the electron-withdrawing substituent is selected from F, fluorinated alkyl groups, $CF_3$, $C_nF_{2n+1}$, $C(=O)OR^1$, $C(=O)N(R^1)_2$, $NO_2$, CHO, $C(=O)R^1$, $S(=O)R^1$, $S(=O)_2R^1$ and/or CN;

$R^1$ is the same or different at each instance and is H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent $CH_2$ groups may be replaced by —$R^2C=CR^2$—, —C≡C—, $Si(R^2)_2$, $Ge(R^2)_2$, $Sn(R^2)_2$, C=O, C=S, C=Se, C=$NR^2$, $NR^2$, $P(=O)(R^2)$, —C(=O)O—, —C(=O)$NR^2$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; or a combination of these systems; at the same time, two or more $R^1$ radicals together may form a mono- or polycyclic, aliphatic, heteroaliphatic, aromatic or heteroaromatic ring system;

$R^2$ is the same or different at each instance and is H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent $CH_2$ groups may be replaced by —$R^3C=CR^3$—, —C≡C—, $Si(R^3)_2$, $Ge(R^3)_2$, $Sn(R^3)_2$, C=O, C=S, C=Se, C=$NR^3$, $NR^3$, $P(=O)(R^3)$, —C(=O)O—, —C(=O)$NR^3$—, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy or heteroaryloxy group which has 5 to 60 aromatic ring atoms and may be substituted by one or more $R^3$ radicals, or an aralkyl or heteroaralkyl group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of these systems; at the same time, two or more $R^2$ substituents together may also form a mono- or polycyclic, aliphatic, heteroaliphatic, aromatic or heteroaromatic ring system;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more $R^3$ substituents together may also form a mono- or polycyclic, aliphatic, heteroaliphatic, aromatic or heteroaromatic ring system; and n represents an integer in the range from 1 to 20.

12. The compound according to claim 5, wherein $Ar^2$ group is a connecting structure of the formula (LAr-1) or (LAr-2)

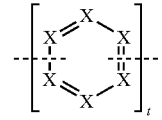

Formula (LAr-2)

where X is the same or different at each instance and is N or $CR^1$, or C if a group binds to X; the dotted bond marks the attachment position and t is 0, 1, 2, 3, 4, 5 or 6;

$R^1$ is defined in claim 5, and the difference between the index s in formula (LAr-1) and the index t in formula (LAr-2) is not more than 2.

13. An oligomer, polymer or dendrimer containing one or more compounds according to claim 1, wherein, rather than a hydrogen atom or a substituent, there are one or more bonds of the compounds to the polymer, oligomer or dendrimer.

14. A composition comprising at least one compound according to claim 1 and at least one further compound selected from the group consisting of fluorescent emitters, phosphorescent emitters, host materials, matrix materials, electron transport materials, electron injection materials, hole conductor materials, hole injection materials, electron blocker materials and hole blocker materials.

15. A formulation comprising at least one compound according to claim 1 and at least one solvent.

16. A TADF material, host material, electron transport material or hole conductor material which comprises the compound according to claim 1.

17. A process for preparing a compound according to claim 1 which comprises joining a compound comprising at least one donor group to an acceptor group in a coupling reaction.

18. An electronic device comprising at least one compound according to claim 1, wherein the electronic device is selected from the group consisting of organic integrated circuits, organic field-effect transistors, organic thin-film transistors, organic solar cells, organic optical detectors, organic photoreceptors, organic field-quench devices, organic electroluminescent devices.

19. The electronic device as claimed in claim 18, wherein the device is an organic electroluminescent device selected from the group of the organic light-emitting transistors, organic light-emitting diodes, organic light-emitting electrochemical cells and organic laser diodes.

* * * * *